US008232455B2

(12) United States Patent
Thompson et al.

(10) Patent No.: US 8,232,455 B2

(45) Date of Patent: Jul. 31, 2012

(54) POLYNUCLEOTIDES ENCODING CANOLA DHS AND ANTISENSE POLYNUCLEOTIDES THEREOF

(75) Inventors: John E. Thompson, Waterloo (CA); Tzann-Wei Michael Wang, Waterloo (BZ)

(73) Assignee: Senesco Technologies, Inc., Bridgewater, NJ (US)

( * ) Notice: Subject to any disclaimer, the term of this patent is extended or adjusted under 35 U.S.C. 154(b) by 934 days.

(21) Appl. No.: 12/026,483

(22) Filed: Feb. 5, 2008

(65) Prior Publication Data

US 2009/0288221 A1 Nov. 19, 2009

Related U.S. Application Data

(60) Division of application No. 10/862,440, filed on Jun. 8, 2004, now Pat. No. 7,358,418, which is a continuation-in-part of application No. 09/725,019, filed on Nov. 29, 2000, now Pat. No. 6,878,860, which is a continuation-in-part of application No. 09/597,771, filed on Jun. 19, 2000, now Pat. No. 6,538,182, which is a continuation-in-part of application No. 09/348,675, filed on Jul. 6, 1999, now abandoned.

(60) Provisional application No. 60/479,968, filed on Jun. 20, 2003, provisional application No. 60/479,969, filed on Jun. 20, 2003, provisional application No. 60/570,833, filed on May 14, 2004, provisional application No. 60/570,835, filed on May 14, 2004.

(51) Int. Cl.

| | |
|---|---|
| ***C12N 15/29*** | (2006.01) |
| ***C12N 15/82*** | (2006.01) |
| ***C12N 5/04*** | (2006.01) |
| ***A01H 5/00*** | (2006.01) |

(52) U.S. Cl. ..................... 800/298; 435/419; 435/252.3; 435/320.1; 536/23.6

(58) Field of Classification Search ........................ None
See application file for complete search history.

(56) References Cited

U.S. PATENT DOCUMENTS

| | | | |
|---|---|---|---|
| 5,328,999 | A | 7/1994 | Bennett et al. |
| 5,530,190 | A | 6/1996 | Grierson et al. |
| 5,763,742 | A | 6/1998 | Morrison et al. |
| 5,767,364 | A | 6/1998 | de Silva et al. |
| 2002/0023281 | A1 | 2/2002 | Gorlach et al. |

FOREIGN PATENT DOCUMENTS

WO WO 01/02592 1/2001

OTHER PUBLICATIONS

Wang et al (2005, Plant Physiology 138(3):1372-1382.*
Bowie et al, Science 247:1306-1310, 1990.*
McConnell et al, Nature 411 (6838):709-713, 2001.*
Bate et al., "Expression of Nuclear and Chloroplast Photosynthesis-Specific Genes During Leaf Senescence," *Journal of Experimental Botany*, vol. 42, No. 239:801-811 (1991).
Bevec, D. et al., "Molecular characterization of cDNA encoding function human deoxyhypusine synthase and chromosomal mapping of the corresponding gene locus," FEB Lett., vol. 378:195-198 (1996).
Bevec et al., "Eukarylotic Initiation Factor 5A Activity and HIV-1 Rev Function," *Biological Signals*, vol. 6:124-133 (1997).
Bird et al., "Manipulation of Plant Gene Expression by Antisense RNA," *Biotechnology and Genetic Engineering Reviews*, vol. 9:207-227 (1991).
Bork et al., "Cloning and Expression of the CBL1 Gene Encoding Cystathionine-Beta-Lyase from *Arabidopsis thaliana*," Database EMBL 'Online! Reieved from EBI, Database accession No. AB004823 XP002227363, Jul. 1997.
Bowie et al., "Deciphering the Message in Protein Sequences: Tolerance to Amino Acid Substitutions", Science, vol. 247:1306-1310 (1990).
Brach, Marion A., "The Mitogenic Response to Tumor Necrosis Factor Alpha Requires c-Jun/AP-1," *Molecular and Cellular Biology*, vol. 13, No. 7:4284-4290 (1993).
Buchanan-Wollaston, Vicky, "The molecular biology of leaf senescence," *Journal of Experimental Bothany*, vol. 48, No. 307:181-199 (1997).
Chamot, Danuta et. al., "Differential expression of genes encoding the hypusine-containing translation initiation factor, eIF-5A in tobacco," *Nucleic Acids Research*, vol. 20, No. 4:665-669 (1992).
Chen, Kuang Yu et al., "Biochemistry and Function of Hypusine Formation on Eukaryotic Initiation Factor 5A," *Biological Signals*, vol. 6:105-109 (1997).
Chory, Joanne et al., "A role for Cytokinins in De-Etiolation in Arabidopsis, det Mutants Have an Altered Response to Cytokinins," *Plant Physiol.*, vol. 104:339-347 (1994).
Cohen, Saymore S., "Growth of Studies on Hypusine in Biological Systems," Biol Signals, vol. 6:110-114 (1997).
Corpet, Florence, "Multiple sequence alignment of hierachical clustering," Nucleic Acids Research, vol. 16, No. 22:10880-10890 (1988).
Database Geneseq 'Online, "*Arabidopsis thaliana* expressed polynucleotide SEQ ID No. 886, "XP002319520, retrieved from EBI accession No. GSN:ABN99118, Abstract (Aug. 1, 2002).
Dresselhaus et al., "A transcript encoding translation initiation factor eif-5a is stored in unfertilized egg cells of maize," *Plant Molecular Biology*, vol. 39:1063-1071 (1999).
Evans, Philip T. et al., "Do Polyamines Have Roles in Plant Development," *Annu. Rev. Plant Physiol. Plant Mol. Biol.*, vol. 40:235-269 (1989).
Fobert, Pierre R. et al., "T-DNA tagging of a seed coat-specific cryptic promoter in tobacco," *The Plant Journal*, vol. 6, No. 4:567-577 (1994).
Fourgoux-Nicol et al., "Isolation of rapessed genes expressed early and specifically during development of the male gametophyte," *Plant Molecular Biology*, vol. 40:857-872 (1999).

(Continued)

*Primary Examiner* — Stuart F. Baum
(74) *Attorney, Agent, or Firm* — Morgan Lewis & Bockius LLP

(57) ABSTRACT

The present invention relates to unique isoforms of eukaryotic initiation Factor 5A ("eIF-5A"): senescence-induced eIF-5A; wounding-induced eIF-5A; and growth eIF-5A, as well as polynucleotides that encode these three factors. The present invention also relates to methods involving modulating the expression of these factors. The present invention also relates to deoxyhypusine synthase ("DHS"), polynucleotides that encode DHS, and methods involving modulating the expression of DHS.

8 Claims, 119 Drawing Sheets

OTHER PUBLICATIONS

Fromm, Michael E. et al., "Stable transformation of maize after gene transfer by electroporation," *Letters To Nature*, vol. 319:791-793 (1986).

Gallie, Daniel R., "A tale of two termi: A functional interaction between the termini of an mRNA is a prerequisite for efficient translation initiation," *Gene*, vol. 216:1-11 (1998).

Galston, Arthur W. et al., Polyamines in Plant Physiology[1],*Plant. Physiol*, vol. 94:406-410 (1990).

Gan, Susheng et al., Making Sense of Sensescence1, *Plant. Physiol.*, vol. 113:313-319 (1997).

Goyns, M.H., "The Role of Polyamines in Animal Cell Physiology," *J. theor. Biol.*, vol. 97:577-589 (1982).

Hensel, Linda L. et al., "Developmental and Age-Related Processes The Influence the Longevity and Senescence of Photosynthetic Tissues in *Arabidopsis*," *The Plant Cell*, vol. 5:553-564 (1993).

Igarashi, Kazuei et al., "Increase of Fidelity of Polypeptide synthesis by Spemidine in Eukarytoc Cell-Free Systems," *Eur. J. Biochem*, vol. 128:597-604 (1982).

Joe, Young Ae et al., "Cloning and Expression of Human Deoxyhypusine Synthase cDNA: Structure-Function Studies with the Recombinant Enzyme and Mutant Proteins," *The Journal of Biological Chemistry*, vol. 270, No. 38:22386-22392 (1995).

Klein, T. M. et al., "Factors Influencing Gene Delivery into Zea Mays Cells by High-Velocity Microprojectiles," *Bio/Technology*, vol. 6:559-563 (1988).

Kuipers, Anja G.J. et al., "Factors affecting the inhibition of antisense RNA if granule-bound starch synthase gene expression in potato," *Mol Gen Genet*, vol. 246:745-755 (1995).

Merlo, Ann Owens et al., "Ribozymes Targeted to Stearoyl-ACP Δ9 Desaturase mRNA Produce Heritable Increases of Stearic Acid in Transgenic Maize Leaves," *The Plant Cell*, vol. 10:1603-1621 (1998).

Miki, B. L. et al., "Procedures for Introducing Foreign DNA into Plants," *CRC Press Inc.*, pp. 67-88 (1993).

Moonan, F. et al., "Analyses of Genotypic Diversity among North, South, and Central American Isolates of Sugarcane Yellow Leaf Virus: Evidence for Columbian Origins and for Intraspecific Spatial Phylogenetic Variation," *Journal of virology*, vol. 76:1339-1348 (2002).

Morton, R. et al., "Gene Replacement," Molecular Breeding, vol. 1:123-132 (1995).

Murphey, Roberta J. et al., "Hypusine Formation in Protein by a Two-step Process in Cell Lysates," *The Journal of Biological Chemistry*, vol. 262, No. 31:15033-15036 (1987).

Murphey, Robert J. et al., "Hypusine Biosynthesis in Protein and its Biological Consequences," *Proceedings of the International Symposium on Polyamines in Biochemical and Clinical Research*, pp. 449-458 (1988).

Nierlich, Donald P. et al., "Molecular Mechanisms in the Control of Gene Expression," *ICN-UCLA Sumposia on Molecular and Cellular Biology*, vol. 5 (1976).

Ober et al., "Deoxyhypusine Synthase from Tobacco: cDNA Isolation, Characterization, and Bacterial Expression of an Enzyme with Extended Substrate Specificity" 1999, *Journal of biological Chemistry* 274:32040-32047.

Palauqui, Jean-Christophe et al., "Frequencies, Timing, and Spatial Patterns of Co-Suppression of Nitrate Reductase and Nitrite Reductase in Transgenic Tobacco Plants," *Plant Physiol.*, vol. 112:1447-1456 (1996).

Park, Myung Hee et al., "identification of hypusine, an unusual amino acid, in a protein from human lymphocytes and of spermidine as its biosynthetic precursor," *Proc. Natl. Acad. Sci. USA*, vol. 78, No. 5:2869-2873 (1981).

Park, Myung Hee et al., "The Biosynthesis protein-bound of Hypusine (N*(4-Amino-2-hydroxybuthyl)lysine); Lysine as the Amino Acid Precursor and the Intermediate Role of Deoxyhypusine(N*-4-Amino-2-hydroxybuthyl)lysine)," *The Journal of Biological Chemistry*, vol. 257, No. 12:7217-7222 (1982).

Park, Myung Hee et al., "The Biosymthesis of Hypusine (N*-(4-Amino-2-hydroxbutyl)lysine); Alignment of the Butylamine Segment and Source of the Secondary Amino Nitrogen," The Journal of Biological Chemistry, vol. 259, No. 19:12123-12127 (1984).

Park, Myung Hee et al., "Cell-free Synthesis of Deoxythypusine; Separation of Protein Substrate and Enzyme and Identification of 1,3-Diaminopropane as a Product of Spermidine Cleavage," *The Journal of Biological Chemistry*, vol. 263, No. 30:15264-15269 (1988).

Park, Myung Hee et al., "Comparision of the Activities of Variant Forms of elF-4D; The Requirement for Hypusine or Deoxyhypusine," *The Journal of Biological Chemistry*, vol. 266, No. 13:7988-7994 (1991).

Park, Myung Hee et al., "Hypusine: its post-translational formation in eukaryotic initiation factor 5A and its potential role in cellular regulation," *BioFactors*, vol. 4, No. 2:95-104 (1993).

Park, M.H. et al., "Is hypusine essential for eukaryotic cell proliferation?" *TIBS*, vol. 18:475-479 (1993).

Park Myung Hee et al., "Hypusine Is Essential for Eukaryotic Cell Proliferation," *Biological Signals*, vol. 6:115-123 (1997).

Park, Myung Hee et al., Deoxyhpusine Synthase Activity Is Essential for Cell Viability in the Yeast *Saccharomyces cerevisiae, The Jouranl of Biological Chemistry*, vol. 273, No. 3:1677-1683 (1998).

Paszkowski, Jerzy et al., "Direct gene transfer to plant," *The EMBO Journal*, vol. 3, No. 12:2717-2722 (1984).

Pay et al., Database EMBL 'Online!, "Isolation and Sequence Determination of the Plant Homologue of the Eukaryotic Initiation Factor 4D cDNA from Alfalfa Medicago Sativa," Retrieved from EBI, Database accession No. XP002227364, Nov. 1991.

Pena, A. de la et al., Transgenic rye plants obtained by injecting DNA into young floral tillers, *Nature*, vol. 325:274-276 (1987).

Ranu, Rajinder Singh et al., Regulation of Protein Synthesis in Rabbit Reticulocyte Lysates: Preparation of Efficient Protein Synthesis Lysates and the Purification and Characterization of the Heme-Regulated Translational Inhibitory Protein Kinase[1], *Methods in Enzymology*, vol. LX:459-484 (1979).

Reich, T.J. et al., "Efficient Transformation of Alfalfa Protoplasts by the Intranuclear Microinjection of Ti Plasmids," Bio/Technology, vol. 4:1001-1004 (1986).

Rhoads, Robert E., "Regulation of Eukaryotic Protein Synthesis of Initiation Factors," *The Journal of biological Chemistry*, vol. 268, No. 5:3017-3020 (1993).

Ruhl, Michael et al., "Eukaryotic Initiation Factor 5A is a Cellular Target of the Human Immunodeficiency Virus Type 1 Rev Activation Domain Mediating Trans-Activation" *Journal of Cell Biology*, vol. 123, No. 6:1309-1320 (1993).

Sandler, Steven J. et al., "Inhibition of gene expression in transformed plants by antisense RNA," *Plant Molecular Biology*, vol. 11:301-310 (1988).

Smith, C. J. S. et al., "Antisense RNA inhibition of polygalacturonase gene expression in transgenic tomatoes," *Letters to Nature*, vol. 334:724-726 (1988).

Thomas, Howard et al., "Leaf Senescence in a Non-Yellowing Mutant of *Festuca pratensis*, Transcripts and Translation Products," *J. Plant Physiol.*, vol. 139:403-412 (1992).

Tome, Margaret E. et al., "Cellular Eukaryotic Initiation Factor 5A Content as a Mediator of Polyamine Effects on Growth and Apoptosis," *Biological Signals*, vol. 6:150-156 (1997).

Tome, Margaret E. et al., "Excess putrescine accumulation inhibits the formation of modified eukaryotic initiation faction 5A (elf-5A) and induces apoptosis," *Biochem. J.*, vol. 328:847-854 (1997).

Wang, Tzann-Wei et al., "Isolation and Characterization of Senescence-induced cDNAs Encoding Deoxyhypusine Synthase and Eucartotic Translation Initiation Factor 5A from Tomato," *Journal of Biological Chemistry*, vol. 276, No. 20:17541-17549 (May 18, 2001).

Wang, Tzann-Wei et al., "Antisense suppression of deoxyhypusine synthase delays *Arabidopsis thaliana* leaf senescence and confers increased tolerance to environmental stress," Joint annual Meeting of the American Society of Plant Biologists and the Canadian Society of Plant Physiologists (Abstract #754), Jul. 21-25, 2001.

Wang, Tzann-Wei et al., "Pleiotropic effects of suppressing deoxyhypusine synthase expression in *Arabidopsis thaliana*," Plant Molecular Biology, vol. 52, No. 6:1223-1235, XP-002319519, ISSN:0167-4412 (Aug. 2003).
Wolff, Edith C. et al., Cleavage of spemidine as the first step in deoxyhypusine synthesis. The role of $Nad^+$, *The Journal of Biological Chemistry*, vol. 265, No. 9:4793-4799 (1990).
Wright, Michael, "The Effect of Chilling on Ethylene Production, Membrane Permeability and Water Loss of Leaves of *Phaseolus vugaris," Planta*, vol. 120:63-69 (1974).
Yan, Yong Ping et al., "Molecular cloning and functional expression of human deoxyhypusine synthase cDNA based on expressed sequence tag information," *Biochem. J.*, vol. 315:429-434 (1996).
Zuk, Dorit et al., "A single amino acid substitution in yeast eIF-5A results in MRNA stabilization," *the EMBO Journal*, vol. 17, No. 10:2914-2925 (1998).
Colliever et al., "Plant Mol. Biol.," vol. 35:509-522 (1997).
Emery et al., "Current Biology," vol. 13:1768-1774 (2003).

* cited by examiner

```
1 MSDEEHHFESSDAGASKTYPQQAGTIRKNGYIVIKNRPCKVVEVSTSKTGKHGHAKCHFV
2 MSDDEHHFEASESGASKTYPQSAGNIRKGGHIVIKNRPCKVVEVSTSKTGKHGHAKCHFV
3 MSDDEHHFESSDAGASKTYPQQAGNIRKGGHIVIKGRPCKVVEVSTSKTGKHGHAKCHFV

1 AIDIFTSKKLEDIVPSSHNCDVPHVNRTDYQLIDISEDGYVSLLTDNGSTKDDLKLPNDD
2 AIDIFTAKKLEDIVPSSHNCDVPHVNRVDYQLIDITEDGFVSLLTDSGGTKDDLKLPTDD
3 AIDIFTSKKLEDIVPSSHNCDVPHVNRVDYQLIDLSEDGFVSLLTDNGSTKDDLKLPTDE

1 TLLQQIKSGFDDGKDLVVSVMSAMGEEQINALKDIGPK
2 GLTAQMRLGFDEGKDIVVSVMSSMGEEQICAMKEVGGGK
3 ALLTQLKNGFEEGKDIVVSVMSAMGEEQMCALKEVGPK
```

Alignment of amino acid sequences of the three isoforms of eIF-5A in *Arabidopsis thaliana*. Identical amino acids are highlighted by dashed lines (----) and the regions that were used for peptide design are indicated by the solid lines (——). Each peptide contains eleven amino acids from the eIF-5A sequences as well as additional cysteine residue at the N-terminus, in order for conjugation to occur with KLH.

FIG. 1

```
1 ATGTCCGACGAGGAGCATCACTTTGAGTCCAGTGACGCCGGAGCGTCCAAAACCTACCCTCAACAAGCTGGAACCATCC
2 ATGTCTGACGACGAGCACCACTTTGAGGCCAGCGAATCCGGAGCTTCCAAGACCTATCCTCAATCAGCCGGTAACATCC
3 ATGTCAGACGACGAGCATCACTTCGAATCCAGCGACGCCGGAGCTTCTAAGACTTATCCTCAACAAGCCGGTAACATTC

1 GTAAGAATGGTTACATCGTCATCAAAAATCGTCCCTGCAAGGTTGTTGAGGTTTCAACCTCGAAGACTGGCAAGCATGG
2 GTAAAGGTGGTCACATCGTCATCAAAAACCGTCCCTGCAAGGTTGTTGAGGTTTCGACTTCCAAAACTGGCAAGCACGG
3 GTAAAGGTGGTCACATCGTCATCAAGGGACGTCCCTGCAAGGTGGTTGAGGTATCGACTTCGAAGACTGGGAAGCATGG

1 TCATGCTAAATGTCATTTTGTAGCTATTGATATCTTCACCAGCAAGAAACTCGAAGATATTGTTCCTTCTTCCCACAAT
2 TCACGCCAAATGTCACTTTGTTGCTATTGATATCTTCACTGCTAAGAAGCTTGAAGATATTGTTCCATCTTCCCACAAT
3 TCACGCCAAGTGTCACTTTGTTGCCATTGATATCTTTACTTCTAAGAAGCTTGAAGATATCGTTCCTTCTTCCCACAAT

1 TGTGATGTTCCTCATGTCAACCGTACTGATTATCAGCTGATTGACATTTCTGAAGATGGATATGTCAGTTTGTTGACTG
2 TGTGATGTTCCACATGTGAACCGTGTTGATTACCAGTTGATTGATATCACTGAGGATGGCTTCGTGAGCCTTCTCACTG
3 TGTGATGTTCCACATGTGAATCGTGTTGATTATCAGTTGATTGATATCTCTGAAGATGGCTTTGTTAGTCTTCTTACTG

1 ATAACGGTAGTACCAAGGATGACCTTAAGCTCCCTAATGATGACACTCTGCTCCAACAGATCAAGAGTGGGTTTGATGA
2 ACAGTGGTGGCACCAAGGATGATCTCAAGCTTCCCACCGATGATGGTCTCACCGCCCAGATGAGGCTTGGATTCGATGA
3 ATAATGGTAGCACTAAGGATGATCTGAAGCTGCCAACAGATGAAGCTTTACTCACACAGCTCAAGAATGGATTTGAGGA

1 TGGAAAAGATCTAGTGGTGAGTGTGATGTCAGCTATGGGAGAGGAACAGATCAATGCTCTTAAGGACATCGGTCCCAAG
2 GGGAAAGGATATTGTGGTGTCTGTCATGTCTTCCATGGGAGAGGAGCAGATCTGTGCCGTCAAGGAAGTTGGTGGTGGC
3 GGGTAAGGATATTGTTGTGTCTGTCATGTCTGCAATGGGAGAGGAGCAGATGTGTGCTCTCAAGGAAGTTGGTCCCAAG

1 ---TGA
2 AAGTAA
3 ---TAA
```

Alignment of the coding region of the three isoforms of eIF-5A in *Arabidopsis thaliana*. Base pairs that are identical in all three isoforms are indicated in boxes. The sequences only include the coding region from the methionine (ATG) to the stop codon.

1 = Senescence – induced eIF-5A
2 = Wounding – induced eIF-5A
3 = Growth eIF-5A

FIG. 2

```
ACAATAAGGCTTTAAAGCCCATAAAACCCTTAAATATATCAAAGCCCAAAAGAAACGCCTTT
TGCGCTTTCCCGATCGTGGTCAACTTCCTCTGTTACCAAAAAATCTGTACCGCAAAATCCTC
GTCGAAGCTCGCTGCTGCAACCATGTCCGACGAGGAGCATCACTTTGAGTCCAGTGACGCCG
GAGCGTCCAAAACCTACCCTCAACAAGCTGGAACCATCCGTAAGAATGGTTACATCGTCATC
AAAAATCGTCCCTGCAAGGTTTCGTTCTCAAACATTTCTCCACTCTCTTCCTCTGATCTTAT
TAGATCTGTTCATTACTTAGATTCCTCAGATTCTTTTTTTTGTCACCTCCACGATGTTCGAC
TGATATTTGTTCTTGTCATCATTGTTAAATTCACATTTTATTGCACTTTTGTTTTAGCGAAA
TTATTAAATTGGTCATCTTCAGTTTTGTTCGATTAGATAAGTTTTAGGATTTTTTCTTACAC
AAGTTACTGGATCAGCTGCTAAATGTCATTTTGTGTCGCAGGTTGTTGAGGTTTCAACCTCG
AAGACTGGCAAGCATGGTCATGCTAAATGTCATTTTGTAGCTATTGATATCTTCACCAGCAA
GAAACTCGAAGATATTGTTCCTTCTTCCCACAATTGTGATGTATGTGAAAAAAGCTCCTTTG
ATCACTTTCATTTCTTGTTTGTTTCTTTCAAGTCCCATTTGAGATTTTGTTTTTGTTGAATT
GGGTTTCAGGTTCCTCATGTCAACCGTACTGATTATCAGCTGATTGACATTTCTGAAGATGG
ATATGTATGTGTTCTTAAATAGCACTTGTTCCTTTATATGGTTTAGTTACTTGTTCTGTTTT
GTAATCATTTTGCAGGTCAGTTTGTTGACTGATAACGGTAGTACCAAGGATGACCTTAAGCT
CCCTAATGATGACACTCTGCTCCAACAGGTTAAGTTTTGCATGTTCATCACATTAAATGTTG
CTAGTTAATTAAAATCAACTCTATGTCGATTTCTGAAAATGGAAGAAAAAGTGCAGAGTAAT
GAGTGACCTGATTGTGTTAATGAAACAGATCAAGAGTGGGTTTGATGATGGAAAAGATCTAG
TGGTGAGTGTGATGTCAGCTATGGGAGAGGAACAGATCAATGCTCTTAAGGACATCGGTCCC
AAGTGAGACTAACAAAGCCTCCCCTTTGTTATGAGATTCTTCTTCTTCTTCTGTAGGCTTCC
ATTACTCATCGGAGATTATCTTGTTTTTGGGTGACTCCTATTTTGGATATTTAAACTTTTGT
TAATAATGCCATCTTCTTCAACCTTTTCCTTCTAGATGGTTTTTATACTTCTTCTAATTGAT
TGATTCTTTATGGTTGTCCAAGTGTCAAAGTGTTCCACCCATATGATTCTAACCTTTTGATG
AGCGAAGTCTTTACTCGTGCCGTTATGTAGAGACGTAGAAGCAATACCACAAAAGAGTATAAT
```

Genomic sequence of senescence-induced At-eIF-5A1. The dashed underscore (----) indicates the areas in which the primers were designed against. The 5' end primer also contained a HindIII restriction site and the 3' end primer contained a SacI restriction site to ensure proper orientation when ligated into the binary vector. The boxed area indicates the 3' end used as probe for Northern blots.

FIG.3

```
AGGATAATAATACAGTAACCCTAGAAAGGTTTCCTCCACCTTCCTCTTCCCCTCCTATATAAA
AAAAATCGACATCGCTTTTGCTCACTTCTCTCTCTTAGGTTTTTTTTCCCTTCTCCCAATCTC
ATCTTCTCCGAAAACCTTTCTTCTCTCAAATTTCTGTGAAAACATGTCTGACGACGAGCACCA
CTTTGAGGCCAGCGAATCCGGAGCTTCCAAGACCTATCCTCAATCAGCCGGTAACATCCGTAA
AGGTGGTCACATCGTCATCAAAAACCGTCCCTGCAAGGTCTGATTTCTATTTCATCATCAAAC
ATCGTTCTCGATCTCTTTTTCCTGATTCTAGATCTCGTCTCTGTATAGTAGCTCCTTGATTTT
GTTTTTATCCTCGGATTTGACCTGGTTCTGTTTAGTTTGAATTTTTCTTATAGATCGCTACTT
AGATGAATATGATGAATCTTATCCTGTTATTTTGATGGTGGTACCTCTCTAGATTCGTGGAAT
TTTGGGAAATGAAAATGAAAAATGGATAGAAATCAAGCAATATCAGACGACGCCTTTTGTGAT
TTTGAATCTAAGTAGTCTATTGATTGATTTGATTTAAACGTTTATGGAGAACATAGATTTGAT
TTTGATATTTTGGTTTTGATTAGGTTGTTGAGGTTTCGACTTCCAAAACTGGCAAGCACGGTC
ACGCCAAATGTCACTTTGTTGCTATTGATATCTTCACTGCTAAGAAGCTTGAAGATATTGTTC
CATCTTCCCACAATTGTGATGTAAGTTACTACACAAACTATGTAGATTCATTTTCACAGTATT
TGATATGATTGTGTGATCTGACTCAAATATTGTTCCTTTCTCTTTTTTTCTCAGGTTCCACAT
GTGAACCGTGTTGATTACCAGTTGATTGATATCACTGAGGATGGCTTCGTATGTTTTTCTTTA
TACTCACTTTCCTCATCACTCCAGCTTTATTTATCTATTCTTGCCATAACTTTTGTACTTGTT
TACATTATAGGTGAGCCTTCTCACTGACAGTGGTGGCACCAAGGATGATCTCAAGCTTCCCAC
CGATGATGGTCTCACCGCCCAGGTTATTTTCTTGTCTTTTCATACTCGCACACAAATGACTTG
ACTTTGTATTCATCTCTCGAATTGTGATATTGAAAACAGTTGTTGTGTTTTGTTAATGCAGAT
GAGGCTTGGATTCGATGAGGGAAAGGATATTGTGGTGTCTGTCATGTCCCGGATGGGAGAGGA
GCAGATCTGTGCCGTCAAGGAAGTTGGTGGTGGCAAGTAAACAAGTATCATTCGATATATTAT
TACCAGTTTGACAACGGACGTCAATGTTATAAGAACCAAAAGATGTTTTTCTTTTTCCTAATT
TAGACCCTTTGTGTGTGTTTCTTGTTGCAAGACAACCATATCTATTGGTTTTGGATTGTTGGA
AAAGTTTGTGTTGAAACATTCAAAGTTTCTTATGAGATGTTATTCTTAAAACCACTTTTTGTT
TGTTCACTGGATATGTTTGTTCATGAAGCTTGTTTTAAGCAACTCTTTACATGA
```

Genomic sequence of wounding-induced At-elF-5A. The dashed underscore (-----) indicates the areas in which the primers were designed against. The 5' end primer also contained a XhoI restriction site and the 3' end primer contained a SacI restriction site to ensure proper orientation when ligated into binary vector. The boxed area indicates the 3' end used as probe for Northern blots.

FIG.4

ACCCTAGATCGCTTTCTTCAGTGTTCTATAAAAACTAAACTCCATTCGCTGACTTCGCAAAG
AAGAACACTTTCTCTCTGAAATCTCAAATTCATCTCTTCTCTTCCGATTTCGCTGAATCATG
TCAGACGACGAGCATCACTTCGAATCCAGCGACGCCGGAGCTTCTAAGACTTATCCTCAACA
AGCCGGTAACATTCGTAAAGGTGGTCACATCGTCATCAAGGGACGTCCCTGCAAGGTTTTGT
CTCTGATTTGATTATTATTGATTTTAGAGGAATCATCTTCATGGATTGTATTAAAGCAGTGT
TCCGTTACCTGATCGTTGTGAATTTTTGAGGTTTAGTGATTCTGGATTGTGATCTGGTGTTT
AGTGTTGAGAAAAACCTCTGTTTTTGAAGTTTATGGATTTATAGGGTTTTTAAATCTATAAT
AGGGTTTAATTCAATTGGTGATATGTGGGGTTTATGATATAGGTGGTTGAGGTATCGACTTC
GAAGACTGGGAAGCATGGTCACGCCAAGTGTCACTTTGTTGCCATTGATATCTTTACTTCTA
AGAAGCTTGAAGATATCGTTCCTTCTTCCCAATTGTGATGTGAGTCTTGTGTGAATGGATTA
GAAACGTTATACAAAGTCTATAATTTTTGACTCACAACACAAAACTGTTTCCTTTTTATTGG
CACAGGTTCCACATGTGAATCGTGTTGATTATCAGTTGATTGATATCTCTGAAGATGGCTTT
GTATGTCATCTTCTTTTTCACTAGTTCAGCTTTGTGTTTTGTCTTTGCCCATATGGTTGAAT
TAGAGGGTTTTGTTCTTTGATTACATTTACAGGTTAGTCTTCTTACTGATAATGGTAGCACT
AAGGATGATCTGAAGCTGCCAACAGATGAAGCTTTACTCACACAGCTCAAGAATGGATTTGA
GGAGGGTAAGGATATTGTTGTGTCTGTCATGTCTGCAATGGGAGAGGAGCAGATGTGTGCTC
TCAAGGAAGTTGGTCCCAAGTANTAATAATAAGTAAGCATTCTCTCTTTTACAGAGGCTATG
TATTATCAAGTTTGACAGAGTCAAATGTTATAAGAACAAAGTTTGGTCCTTTTTTTTGGTCT
TCTTAGTATAATTTAAGCCCACATGTGTTTCCCATGCAAGACACTCTTATTTACTAGTAT
ATCTTACTATTGGTTTTGGTTGTGGAGAAGTTACTGTTGACAGTTCCAAACCTCTAC

Genomic sequence of growth At-elF-5A. The dashed underscore (-----) indicates the areas in which the primers were designed against. The 5' end primer also contained a xhol restriction site and the 3' end primer contained a SacI restriction site to ensure proper orientation when ligated into the binary vector. The boxed area indicates the 3' end used as probe for Northern blots.

FIG.5

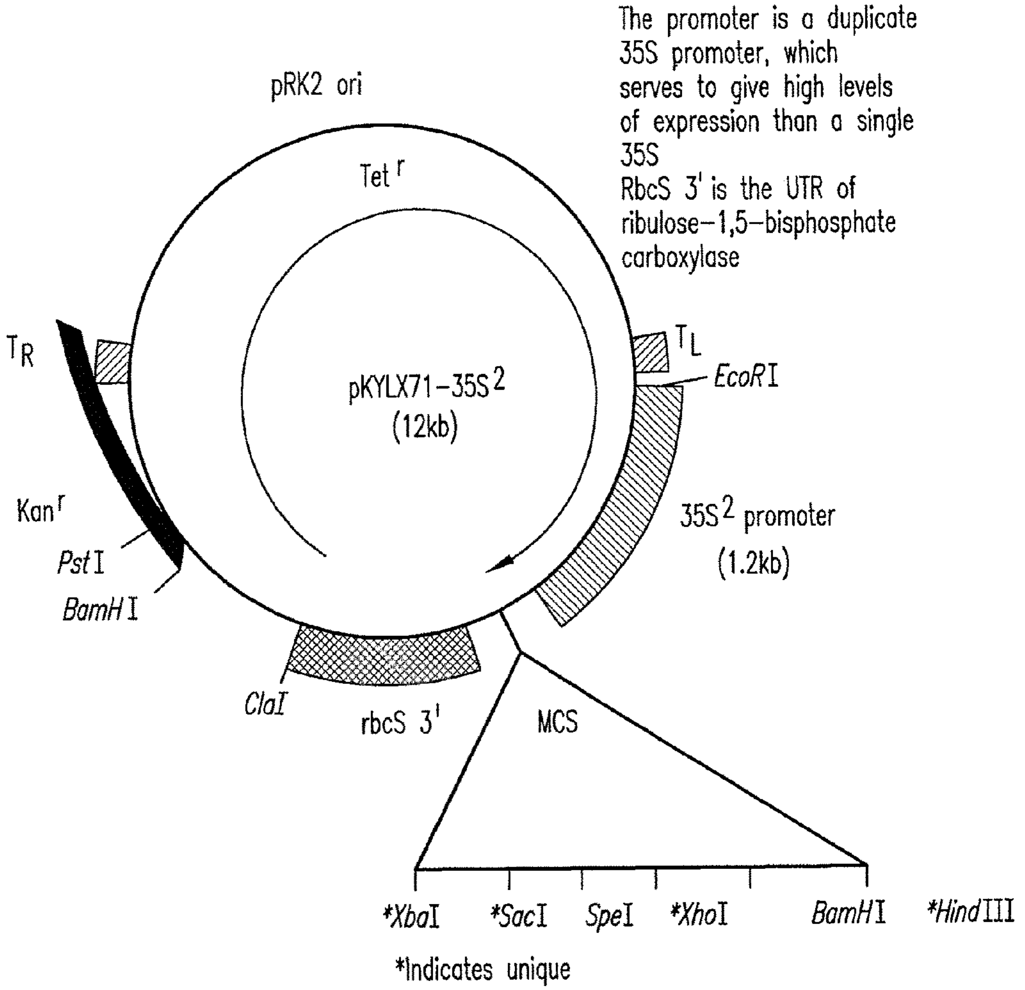

*Indicates unique

PKYLX71 multicoloning sites and primers pKFY4 -> pKYF3 -> p-KYF2 -> pKYF1 ->

5'- AAGACGTTCC AACCACGTCT TCAAAGCAAG TGGATTGATG TGATATCTCC ACTGACGTAA GGGATGACGC ACAATCCCAC TATCCTTCGC AAGACCCTTC
3'- TTCTGCAAGG TTGGTGCAGA AGTTTCGTTC ACCTAACTAC ACTATAGAGG TGACTGCATT CCCTACTGCG TGTTAGGGTG ATAGGAAGCG TTCTGGGAAG pKYU->
(<- 35S²) HindIII XhoI SacI CTCTATATAA GGAAGTTCAT TTCATTTGGA GAGGACACGC TGAAATCACC AGTCTCTCTC TCAAGCTTGG ATCCTCGAGT ACTAGTTCAG GGAGCTCGAA
GAGATATATT CCTTCAAGTA AAGTAAACCT CTCCTGTGCG ACTTTAGTGG TCAGAGAGAG AGTTCGAACC TAGGAGCTCA TGATCAAGTC CCTCGAGCTT XbaI (3'-rbcS ->)

TTGATCCTCT AGAGCTTTCG TTCGTATCAT CGGTTTCGAC AACGTTCGTC AAGTTCAATG CATCAGTTTC ATTGCGCACA CACCAGAATC CTACTGAGTT
AACTAGGAGA TCTCGAAAGC AAGCATAGTA GCCAAAGCTG TTGCAAGCAG TTCAAGTTAC GTAGTCAAAG TAACGCGTGT GTGGTCTTAG GATGACTCAA

<- pKYD <- pKYD1 <- pKYD2 < - pKYD3

TGAGTATTAT GGCATTGGG -3'
ACTCATAATA CCGTAACCC -5'

Map of binary vector pKYLX71-35S². The binary vector pKYLX71-35S² contains tetracycline resistance for transformant selection in *E. coli*, and Kanamycin resistance for seed transformant selection on MS plates containing kanamycin.

FIG.6

Map of binary vector pGEM®-T Easy Vector. The T overhangs in the middle of the multiple cloning sites provide the insertion site of PCR products. The $Amp^r$ gene is useful for screening transformants based on growth in the presence of ampicillin.

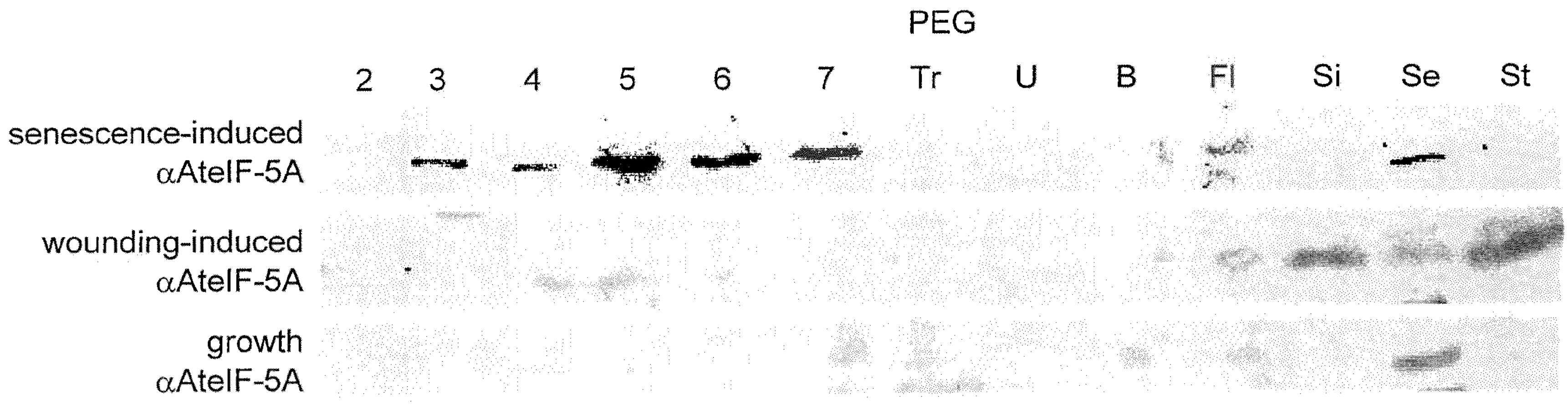

Western blots of different tissues of *Arabidopsis thaliana* wild type of the Columbia ecotype. The lane descriptions are a follows: lanes labelled 2, 3, 4, 5, 6, 7 are the total rosette leaves collected at 2, 3, 4, 5, 6, 7 weeks of age, Tr are leaves from plants treated with 5% PEG, U are leaves from the PEG control plants watered with water, B are closed unopened flower buds, Fl are flowers of all ages ranging from closed buds to senescent flowers, Si are siliques that were collected at 6 weeks, Se are seeds that were imbibed for 1 day and St are stems collected at 6 week.

FIG.8

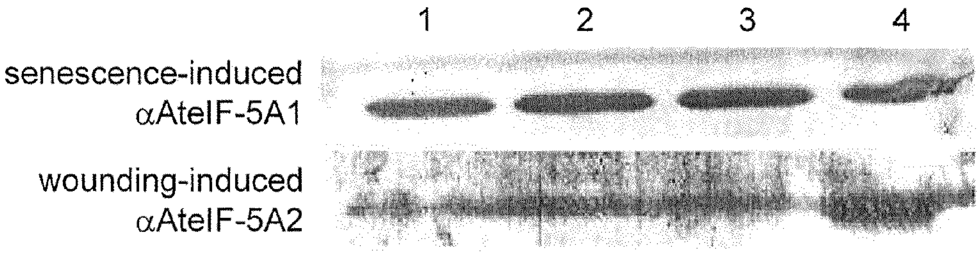

Western blots of infected leaves after 72 hours of *Arabidopsis thaliana* wild type of the Columbia ecotype. Lane 1: Control plant (untreated), Lane 2: Mock treated, Lane 3: Avr treated, Lane 4: Vir treated. The expression level of senescence-induced AteIF-5A remains constant as these plants are all 4 weeks old. The expression of wounding-induced AteIF-5A increases in the virulent treated plants. The expression of growth AteIF-5A was not detectable and thus not included in the figure.

FIG.9

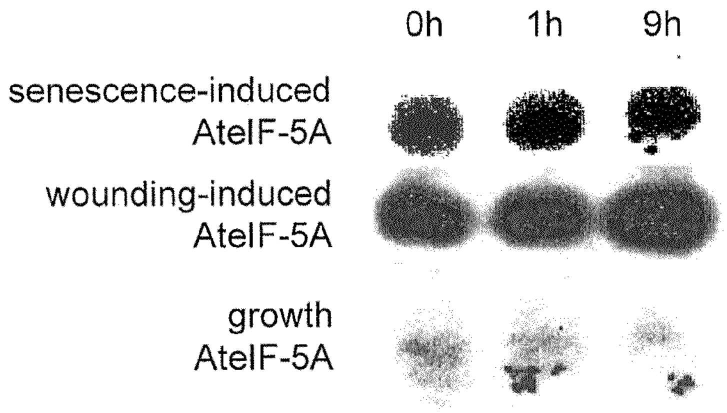

Northern blots of wounded leaves after 72 hours of *Arabidopsis thaliana* wild type of the Columbia ecotype. Leaves were wounded with a hemostat and collected at Ohours, immediately after treatment, 1 hours after wounding and 9 hours after wounding. The expression of wounding-induced AteIF-5A transcript is the only one that increases at 9 hours post wounding. The expression of growth AteIF-5A though low to begin with decreases in the event of wounding.

FIG.10

PCR products from genomic DNA of senescence-induced AteIF-5A, wounding-induced eIF-5A, and growth eIF-5A in lanes 1, 2 and 3 respectively. The single top band was excised and purified for ligation into pGEM.

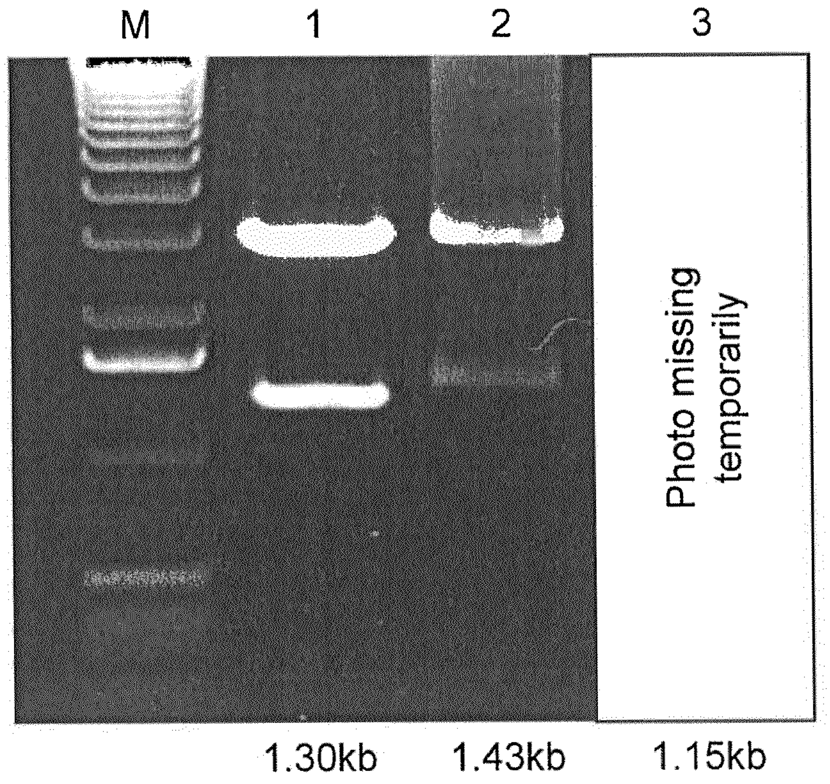

Agarose gel with senescence-induced AteIF-5A, wounding-induced eIF-5A, growth eIF-5A, genomic sequences in pGEM in lanes 1, 2, and 3 respectively. The pGEM: senescence-induced AteIF5A, pGEM: wounding-induced AteIF5A, and pGEM: growth AteIF5A were digested with EcoRI for to identify positive transformant colonies that contain inserts of the proper size. These clones were then sent for sequencing to confirm sequence suitability for over expression *in planta*.

FIG.12

Agarose gel with wounding-induced eIF-5A AteIF-5A2, growth eIF-5A, genomic sequences in pKYLX71. The colonies that were able to grow on tetracycline containing plates were screened for either the wounding-induced AteIF-5A insert or the growth AteIF-5A insert through both double digestion (D) with appropriate enzymes and PCR (P) with the corresponding primers.

T1 plate for plants transformed with construct having Sense wounding-induced AteIF-5A. Two transformants on this plate are circled in black and correspond to lines 13 and 14. The wild type controls are circled in white.

T1 plants for Sense wounding-induced AteIF-5A at 4 weeks of age. The transgenic lines are indicated by the P tags, the wildtype plants are indicated by the W tags and the binary vector control plants are indicated by the Y tags. Lines 6, 8, 10, 13 and 14 did not produce seeds.

T1 plants for sense wounding-induced AteIF-5A at 5.5 weeks of age. Just the lines that were very small are included in this figure. Lines 1, 4, and 12 all produced seed and the rest died eventually without producing seed.

T2 plants for Sense wounding-induced AteIF-5A at 10 days post seeding. All the T2 lines remain heterozygous as indicated by the mix of kanamycin resistant (dark plants) and non-transformants lacking kanamycin resistance (light plants). Wild type control plants are indicated in the white circles. Line 12 in not included in this figure as it only had one transformant grow and has yet to be transplanted.

FIG.17

T1 plants for Sense growth AteIF-5A at 10 days post seeding. Three transformants are indicated in black circles for this plate and correspond to lines 6, 7 and 8. Wild type control plants are indicated in the white circle.

T1 plants for Sense growth AteIF-5A at 4 weeks of age. The transformant lines are indicated by the B tags and wild type control by the W tags or the lack of tags. The empty binary control (Y tags) in included at the bottom of the figure showing that it looks no different than wild type.

Western blot of T2 Sense growth AteIF-5A lines. A representative of each mother line was used to determine the general level of expression in each line.

T2 plants of Sense growth AteIF-5A Line 1A-1D at 4 weeks of age (top), 5 weeks of age (bottom left) and 6 weeks of age (bottom right). The transformant lines are indicated by the B tags (grey circles) and wild type control by the W tags (white ellipse). The empty binary control are indicated by Y tags (black circles). Line 1A (indicated in the black box) will be carried through to T3.

T2 plants of Sense growth AteIF-5A Line 2A-1D at 4 weeks of age (top), 5 weeks of age (bottom left) and 6 weeks of age (bottom right). The transformant lines are indicated by the B tags (grey circles) and wild type control by the W tags (white ellipse). The empty binary control are indicated by Y tags (black circles). Line 2D (indicated in the black box) will be carried through to T3.

T2 plants of Sense growth AteIF-5A Line 4A-D at 4 weeks of age (top), 5 weeks of age (bottom left) and 6 weeks of age (bottom right). The transformant lines are indicated by the B tags (grey Circles) and wild type control by the W tags (white ellipse). The empty binary control are indicated by Y tags (black circle). Line 4D (indicated in the black box) will be carried through to T3.

T2 plants of Sense growth AteIF-5A Line 15A-D at 4 weeks of age (top), 5 weeks of age (bottom left) and 6 weeks of age (bottom right). The transformant lines are indicated by the B tags (grey circles) and wild type control by the W tags (white ellipse). The empty binary control are indicated by Y tags (black circles). Line 15A (indicated in the black box) will be carried through to T3.

T2 plants of Sense growth AteIF-5A Line 8A-D at 4 weeks of age (top), 5 weeks of age (bottom left) and 6 weeks of age (bottom right). The transformant lines are indicated by the B tags (grey circles) and wild type control by the W tags (white ellipse). The empty binary control are indicated by Y tags (black circles). Line 8D (indicated in the black box) will be carried through to T3.

T2 plants of Sense growth AteIF-5A Line 9E-H at 4 weeks of age (top), 5 weeks of age (bottom left) and 6 weeks of age (bottom right). The transformant lines are indicated by the B tags (grey circles) and wild type control by the W tags (white ellipse). The empty binary control are indicated by Y tags (black circles). Line 9H (indicated in the black box) will be carried through to T3.

T2 plants of Sense growth AteIF-5A Line 11A-D at 4 weeks of age (top), 5 weeks of age (bottom left) and 6 weeks of age (bottom right). The transformant lines are indicated by the blue tags and wild type control by the white tags. The empty binary control are indicated by yellow tags. Line 11C (indicated in the blue box) will be carried through to T3.

T2 plants of Sense growth AteIF-5A Line 16A-D at 4 weeks of age (top), 5 weeks of age (bottom left) and 6 weeks of age (bottom right). The transformant lines are indicated by the B tags (grey circles) and wild type control by the W tags (white ellipse). The empty binary control are indicated by Y tags (black circles). Line 16C (indicated in the black box) will be carried through to T3.

Photographs of wild type (WT), binary control (Binary), and lines 11c, 16C, 2D, 2H from T3 Sense growth AteIF-5A seeds. Lines 11C and 16C are only 88 and 87% of the average wild type seed size, whereas lines 2D and 2H are 273 and 299% larger than wild type respectively.

Average seed size (nm$^3$) for each T3 subline of Sense Growth AtelF-5A. Each line has sublines A-H not labeled separately in the figure. The binary control and the wild type controls correspond to the last two bars. The standard errors as represented by the error bars were calculated with n=10.

Average individual seed weight (mg) for each T3 subline of Sense Growth AtelF-5A. Each line has sublines A-H. The binary control and the wild type controls correspond to the last two bars.

The relationship between the weight of the individual seeds vs. the volume size of individual seeds.

Seed yield per plant (mg) for each T3 subline of Sense Growth AteIF-5A. Each line has sublines A-H. The binary control and the wild type controls correspond to the last two bars.

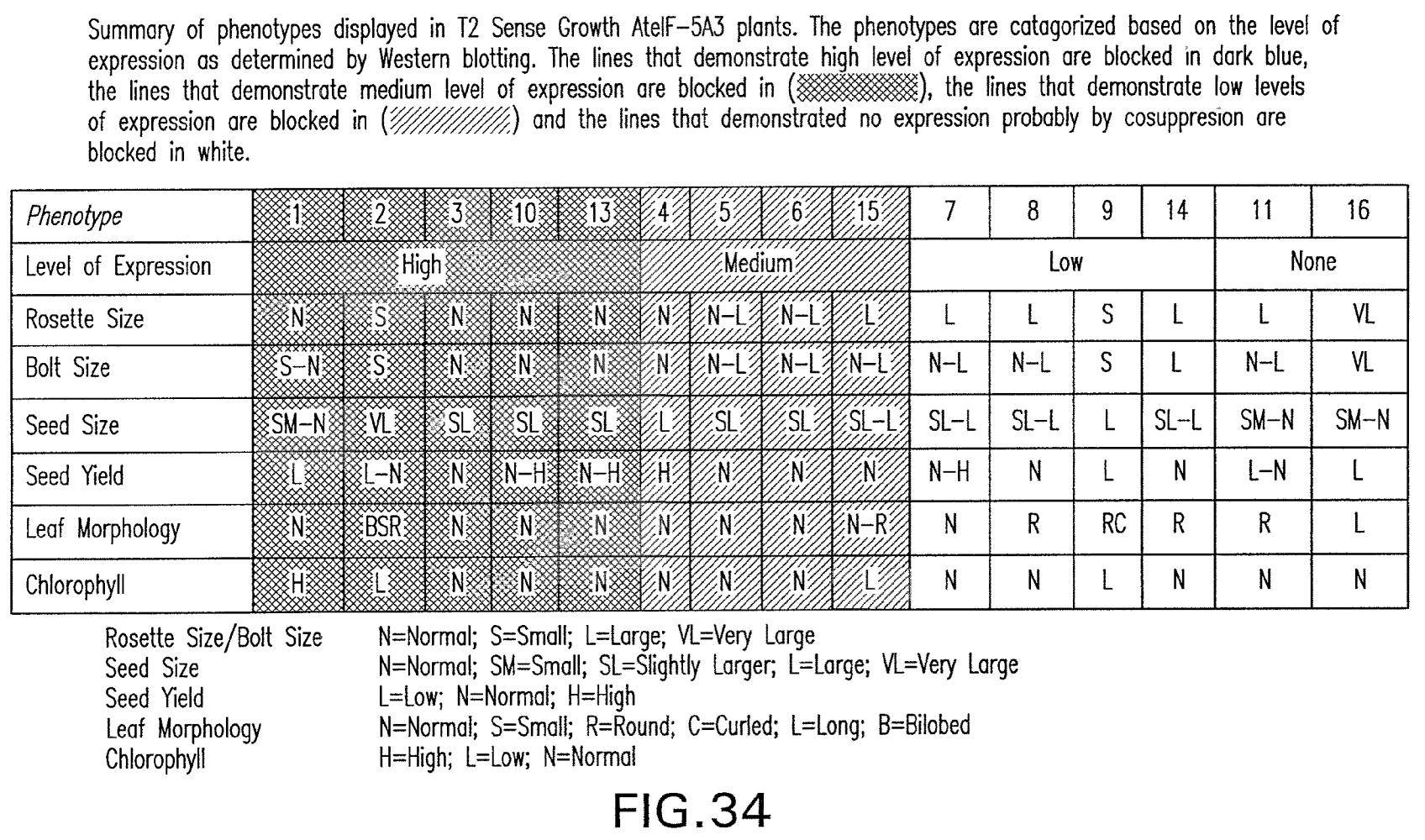

Summary of phenotypes displayed in T2 Sense Growth AtelF-5A3 plants. The phenotypes are catagorized based on the level of expression as determined by Western blotting. The lines that demonstrate high level of expression are blocked in dark blue, the lines that demonstrate medium level of expression are blocked in ( ), the lines that demonstrate low levels of expression are blocked in ( ) and the lines that demonstrated no expression probably by cosuppresion are blocked in white.

| *Phenotype* | 1 | 2 | 3 | 10 | 13 | 4 | 5 | 6 | 15 | 7 | 8 | 9 | 14 | 11 | 16 |
|---|---|---|---|---|---|---|---|---|---|---|---|---|---|---|---|
| Level of Expression | High | | | | | Medium | | | | Low | | | | None | |
| Rosette Size | N | S | N | N | N | N | N-L | N-L | L | L | L | S | L | L | VL |
| Bolt Size | S-N | S | N | N | N | N | N-L | N-L | N-L | N-L | N-L | S | L | N-L | VL |
| Seed Size | SM-N | VL | SL | SL | SL | L | SL | SL | SL-L | SL-L | SL-L | L | SL-L | SM-N | SM-N |
| Seed Yield | L | L-N | N | N-H | N-H | H | N | N | N | N-H | N | L | N | L-N | L |
| Leaf Morphology | N | BSR | N | N | N | N | N | N | N-R | N | R | RC | R | R | L |
| Chlorophyll | H | L | N | N | N | N | N | N | L | N | N | L | N | N | N |

Rosette Size/Bolt Size N=Normal; S=Small; L=Large; VL=Very Large
Seed Size N=Normal; SM=Small; SL=Slightly Larger; L=Large; VL=Very Large
Seed Yield L=Low; N=Normal; H=High
Leaf Morphology N=Normal; S=Small; R=Round; C=Curled; L=Long; B=Bilobed
Chlorophyll H=High; L=Low; N=Normal

FIG. 34

Phenotype of 11-week-old *Arabidopsis* SAG12 - antisense full-length senescence-induced eIF-5A plant (on left) versus wild-type plant (on right): Transgenic plant is dwarfed, has an increased number of small rosette leaves, and exhibits delayed senescence Week 7 Wildtype Week 7 Wildtype Wild Type Antisense growth eIF-5A Antisense growth eIF-5A 7 Weeks of Age Arabidopsis Primers used to construct "Antisense Arabidopsis (*Arabidopsis thaliana*) 31DHS in pTA7001"

Forward Primer. 5' - GGGAGGGACTAGTGTGCACGCC - 3'
(underlined portion: the recognition sequence for the restriction-enzyme *Spe*I)

Reverse Primer. 5'-GCGAAGCGGCCATGGCTCGAGTTTTTTTTTTTTTTTTT-3'
(underlined portion: includes recognition sequence for the restriction enzyme *Xho*I)

Portion of Arabidopsis (*Arabidopsis thaliana*) DHS gene amplified by the above primers (PCR product.- 521 bp)

GGGAGGGACTAGTGTGCACGCCCTGATGAAGCTGTGTCTTGGGGTAAAATTAGGGGTTCTGCTAAAACCGT
TAAGGTATACTGTGATGCTACCATAGCCTTCCCATTGTTGGTTGCAGAAACATTTGCCACAAAGAGAGACC
AAACCTGTGAGTCTAAGACTTAAGAACTGACTGGTTCGTACCTCTGGCCTCATCATCGATGTAGTACAAGA
TATCAGAGCTATGAACGGCGAAGCTGTCCATGCAAATCCTAAAAAGACAGGCGTTTTGGCCATGGATTCTT
AAAGATCGTTGCTTTTTGATTTTACACTGGAGTGACCATATAACACTCCACATTGATGTGGCTGTGACGCG
AATTGTCTTCTTGCGAATTGTACTTTAGTTTCTCTCAACCTAAAATGATTTGCAGATTGTGTTTTCGTTTA
FAACACAAGAGTCTTGTAGTCAATAATCCTTTGCCTTATAAAATTATTCAGTTCCAACAAAAAAAAAAAAA
AAACTCGAGCCATGGCCGCTTCGC

Portion of *Arabidopsis* (*Arabidopsis thaliana*) DHS gene amplified by the above primers, and gut with S*pe*I and X*ho*I, which was then ligated into the pTA7001 vector at the S*pe*I and X*ho*I cloning site CTAGTGTGCACGCCCTGATGAAGCTGTGTCTTGGGGTAAAATTAGGGGTTCTGCTAAAACCGTTAAGGTAT
ACTGTGATGCTACCATAGCCTTCCCATTGTTGGTTGCAGAAACATTTGCCACAAAGAGAGACCAAACCTGT
GAGTCTAAGACTTAAGAACTGACTGGTTCGTACCTCTGGCCTCATCATCGATGTAGTACAAGATATCAGAG
CTATGAACGGCGFAGCTGTCCATGCAAATCGTAAAAAGACAGGCGTTTTGGCCATGGATTCTTAAAGATCG
TTGCTTTTTGATTTTACACTGGAGTGACCATATAACACTCCACATTGAT3TGGCTGTGACGCGAATTGTCT
TCTTGCGAATTGTACTTTAGTTTCTCTCAACCTAAAATGATTTGCAGATTGTGTTTTCGTTTAAAACACAA
GAGTCTTGTAGTCAATAATCCTTTGCCTTATAAAATTATTCAGTTCCAACAAAAAAAAAAAAAAAACTCGA

FIG.39

The insert is the 3'-UTR of Antisense Arabidopsis DHS as described in Figure 40.

Arabidopsis (Wounding-induced) eIF-5A

TTTTTCCCTTCTCCCAATCTCATCTTCTCCGAAAACCTTTCTTCTCTCAAATTTCTGTGAAAACATGTCTGACGACG
AGCACCACTTTGAGGCCAGCGAATCCGGAGCTTCCAAGACCTATCCTCAATCAGCCGGTAACATCCGTAAAGGTGGT
CACATCGTCATCAAAAACCGTCCCTGCAAGGTTGTTGAGGTTTCGACTTCCAAAACTGGCAAGCACGGTCACGCCAA
ATGTCACTTTGTTGCTATTGATATCTTCACTGCTAAGAAGCTTGAAGATATTGTTCCATCTTCCCACAATTGTGATG
TTCCACATGTGAACCGTGTTGATTACCAGTTGATTGATATCACTGAGGATGGCTTCGTGAGCCTTCTCACTGACAGT
GGTGGCACCAAGGATGATCTCAAGCTTCCCACCGATGATGGTCTCACCGCCCAGATGAGGCTTGGATTCGATGAGGG
AAAGGATATTGTGGTGTCTGTCATGTCTTCCATGGGAGAGGAGCAGATCTGTGCCGTCAAGGAAGTTGGTGGTGGCA
AGTAAACAAGTATCATTCGATATATTATTACCAGTTTGACAACGGACGTCAATGTTATAAGAACCAAAAGATGTTTT
TCTTTTTCCTAATTTAGACCCTTTGTGTGTGTTTCTTGTTGCAAGACAACCATATCTATTGGTTTTGGATTGTTGGA
AAAGTTTGTGTTGAAACATTCAAAGTTTCTTATGAGATGTTATTCTTAAAACCACTTTTTGTTTGTTCACTGGATAT
GTTTGTTCATGAAGCTTGTTTTAAGCAACTCTTTACATGATATTCATTGCTATTTGCACGATTCAAGAGTGAAATAT
ACATTTTATTTAAC

Amino Acid (159 a.a.)

MSDDEHHFEASESGASKTYPQSAGNIRKGGHIVIKNRPCKVVEVSTSKTGKHGHAKCHFVAIDIFTAKKLEDIVPSS
HNCDVPHVNRVDYQLIDITEDGFVSLLTDSGGTKDDLKLPTDDGLTAQMRLGFDEGKDIVVSVMSSMGEEQICAVKE
VGGGK

Underline is the portion for antisense 3 -UTR.

Primers·
Upstream primer:
CTCGAGAAGAATAACATCTCATAAGAAAC
XhoI

Downstream primer.
GAGCTCGGCAAGTAAACAAGTATCATTCG
SacI

The PCR fragment was sucloned into pGEM-T (Promega) vector for sequence The fragment was then cut with XhoI/SacI from pGEM-T and sucloned into Pkylx71

FIG.41 pKYLX71-antisense-3 -UTR-Arabidopsis-wounding-induced eIF-5A

CACTGAATCAAAGGCCATGGAGTCAAAGATTCAAATAGAGGACCTAACAGAACTCGCCGTAAAGACTGGCGAACAGTTCATACAGAGTCTCT
TACGACTCAATGACAAGAAGAAAATCTTCGTC{AACATGGTGGAGCACGACACGCTTGTCTACCTCCAAAAATATCAAAGATACAGTCTCAG
AAGACCAAAGGGAATTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTCTGCCGACAGTGGTCCC
AAAGATGGACCCCCACCCACGAGGAGCATCGTGGAAAAAGAAGACGTTCCAACCACGTCTTCAAAGCAAGTGGATTGATGTGAT}[AACATG
GTGGAGCACGACACGCTTGTCTACCTCCAAAAATATCAAAGATACAGTCTCAGAAGACCAAAGGGAATTGAGACTTTTCAACAAAGGGTAAT
ATCCGGAAACCTCCTCGGATTCCATTGCCCAGCTATCTGTCACTTTATTGTGAAGATAGTGGAAAAGGAAGGTGGCTCCTACAAATGCCATC
ATTGCGATAAAGGAAAGGCCATCGTTGAAGATGCCTCTGCCGACAGTGGTCCCAAAGATGGACCCCCACCCACGAGGAGCATCGTGGAAAAA
GAAGACGTTCCAACCACGTCTTCAAAGCAAGTGGATTGATGTGAT]ATCTCCACTGACGTAAGUGATGACGCACAATCCCACTATCCTTCGC
AAAACCCTTCCTCTATATAAGGAAGTTCATTTCATTTGGAGAGGACACGCTGAAATCACCAGTCTCTCTCTAAGCTTGGATC

← pKYLX71-double 35S promoter

CTCGAG (XhoI)
AAGAATAACATCTCATAAGAAACTTTGAATGTTTCAACACAAACTTTTCCAACAATCCAAAACCAATAGATATGGTTGTCTTGCAACAAGAA
ACACACACAAAGGGTCTAAAETAGGAAAAAGAAAAACATCTTTTGGTTCTTATAACATTGACGTCCGTTGTCAACTGGTAATAATATATCG
AATGATACTTGTTTACTTGCC

(SacI) GAGCTC → rbcS-terminater

GAATTGATCCTCTAGAGCTTTCGTTCGTATCATCGGTTTCGACAACGTTCGTCAAGTTCAATGCATCAGTTTCATTGCGCACACACCAGAAT
CCTACTGAGTTCGAGTATTATGGCATTGGGAAAACTGTTTTTCTTGTACCATTTGTTGTGCTTGTAATTTACTGTGTTTTTTATTCGGTTTT
CGCTATCGAACTGTGAAATGGAAATGGATGGAGAAGAGTTAATGAATGATATGGTCCTTTTGTTCATTCTCAAATTAATATTATTTGTTTTT
TCTCTTATTTGTTGTGTGTTGAATTTGAAATTATAAGAGATATGCAAACATTTTGTTTTGAGTAAAAATGTGTCAAATCGTGGCCTCTAATG
ACCGAAGTTAATATGAGGAGTAAAACACTTGTAGTTGTACCATTATGCTTATTCACTAGGCAACAAATATATTTTCAGACCTAGAAAAGCTG
CAAATGTTACTGAATACAAGTATGTCCTCTTGTGTTTTAGACATTTATGAACTTTCCTTTATGTAATTTTCCAGAATCCTTGTCAGATTCTA
ATCATTGCTTTATAATTATAGTTATACTCATGGATTTGTAGTTGAGTATGAAAATATTTTTTAATGCATTTTATGACTTGCCAATTGATTGA
CAACATGCATCAATCGAT

FIG.42

Infection of antisense DHS A. thaliana with Pseudomonas syringae

Table 1: Standard plate counts of A. thaliana leaf discs inoculated with virulent or avirulent Pseudomonas syringae.

| Plant Line | Time | Treatment | CFU per Leaf Disc | SD |
|---|---|---|---|---|
| WT | 0 | Mock | 0 | |
| | 24 | Mock | 5.56E−01 | 9.62E−01 |
| | 48 | Mock | 1.67E+00 | 1.666667 |
| | 72 | Mock | 5.56E−01 | 0.96225 |
| | 0 | Avirulent | 1.11E+04 | 9622.504 |
| | 24 | Avirulent | 3.89E+04 | 9622.504 |
| | 48 | Avirulent | 3.89E+04 | 9622.504 |
| | 72 | Avirulent | 0 | 0 |
| | 0 | Virulent | 5.56E+03 | 9622.504 |
| | 24 | Virulent | 5.00E+05 | 33333.33 |
| | 48 | Virulent | 5.28E+05 | 58531.41 |
| | 72 | Virulent | 5.78E+05 | 48112.52 |
| Dex | 0 | Mock | 5.56E−01 | 0.96225 |
| | 24 | Mock | 0 | 0 |
| | 48 | Mock | 5.56E−01 | 0.96225 |
| | 72 | Mock | 0.00E+00 | 0 |
| | 0 | Avirulent | 0.00E+00 | 0 |
| | 24 | Avirulent | 5.56E+04 | 25458.75 |
| | 48 | Avirulent | 6.11E+04 | 9622.504 |
| | 72 | Avirulent | 6.11E+04 | 9622.504 |
| | 0 | Virulent | 0.00E+00 | 0 |
| | 24 | Virulent | 0.00E+00 | 0 |
| | 48 | Virulent | 5.56E+04 | 9622.504 |
| | 72 | Virulent | 1.78E+05 | 69388.87 |

FIG.43

Tomato Leaf DHS cDNA sequence

```
CGCAGAAACTCGCGGCGGCAGTCTTGTTCCGTACATAATCTTGGTCTGCAATAATGGGAGAAGCTCTGAAGTACAGTATCATGGAC
                                                       M  G  E  A  L  K  Y  S  I  M  D

TCAGTAAGATCGGTAGTTTTCAAAGAATCCGAAAATCTAGAAGGTTCTTGCACTAAAATCGAGGGCTACGACTTCAATAAAGGCGT
 S  V  R  S  V  V  F  K  E  S  E  N  L  E  G  S  C  T  K  I  E  G  Y  D  F  N  K  G  V

TAACTATGCTGAGCTGATCAAGTCCATGGTTTCCACTGGTTTCCAAGCATCTAATCTTGGTGACGCCATTGCAATTGTTAATCAAA
 N  Y  A  E  L  I  K  S  M  V  S  T  G  F  Q  A  S  N  L  G  D  A  I  A  I  V  N  Q

TGCTAGATTGGAGGCTTTCACATGAGCTGCCCACGGAGGATTGCAGTGAAGAAGAAAGAGATGTTGCATACAGAGAGTCGGTAACC
M  L  D  W  R  L  S  H  E  L  P  T  E  D  C  S  E  E  E  R  D  V  A  Y  R  E  S  V  T

TGCAAAATCTTCTTGGGGTTCACTTCAAACCTTGTTTCTTCTGGTGTTAGAGACACTGTCCGCTACCTTGTTCAGCACCGGATGGT
 C  K  I  F  L  G  F  T  S  N  L  V  S  S  G  V  R  D  T  V  R  Y  L  V  Q  H  R  M  V

TGATGTTGTGGTTACTACAGCTGGTGGTATTGAAGAGGATCTCATAAAGTGCCTCGCACCAACCTACAAGGGGGACTTCTCTTTAC
 D  V  V  V  T  T  A  G  G  I  E  E  D  L  I  K  C  L  A  P  T  Y  K  G  D  F  S  L

CTGGAGCTTCTCTACGATCGAAAGGATTGAACCGTATTGGTAACTTATTGGTTCCTAATGACAACTACTGCAAATTTGAGAATTGG
P  G  A  S  L  R  S  K  G  L  N  R  I  G  N  L  L  V  P  N  D  N  Y  C  K  F  E  N  W

ATCATCCCAGTTTTTGACCAAATGTATGAGGAGCAGATTAATGAGAAGGTTCTATGGACACCATCTAAAGTCATTGCTCGTCTGGG
 I  I  P  V  F  D  Q  M  Y  E  E  Q  I  N  E  K  V  L  W  T  P  S  K  V  I  A  R  L  G
```

FIG.45A

```
TAAAGAAATTAATGATGAAACCTCATACTTGTATTGGGCTTACAAGAACCGGATTCCTGTCTTCTGTCCTGGCTTGACGGATGGAT
 K  E  I  N  D  E  T  S  Y  L  Y  W  A  Y  K  N  R  I  P  V  F  C  P  G  L  T  D  G

CACTTGGTGACATGCTATACTTCCATTCTTTCAAAAAGGGTGATCCAGATAATCCAGATCTTAATCCTGGTCTAGTCATAGACATT
S  L  G  D  M  L  Y  F  H  S  F  K  K  G  D  P  D  N  P  D  L  N  P  G  L  V  I  D  I

GTAGGAGATATTAGGGCCATGAATGGTGAAGCTGTCCATGCTGGTTTGAGGAAGACAGGAATGATTATACTGGGTGGAGGGCTGCC
 V  G  D  I  R  A  M  N  G  E  A  V  H  A  G  L  R  K  T  G  M  I  I  L  G  G  G  L  P

TAAGCACCATGTTTGCAATGCCAATATGATGCGCAATGGTGCAGATTTTGCCGTCTTCATTAACACCGCACAAGAGTTTGATGGTA
 K  H  H  V  C  N  A  N  M  M  R  N  G  A  D  F  A  V  F  I  N  T  A  Q  E  F  D  G

GTGACTCTGGTGCCCGTCCTGATGAAGCTGTATCATGGGGAAAGATACGTGGTGGTGCCAAGACTGTGAAGGTGCATTGTGATGCA
S  D  S  G  A  R  P  D  E  A  V  S  W  G  K  I  R  G  G  A  K  T  V  K  V  H  C  D  A

ACCATTGCATTTCCCATATTAGTAGCTGAGACATTTGCAGCTAAGAGTAAGGAATTCTCCCAGATAAGGTGCCAAGTTTGAACATT
 T  I  A  F  P  I  L  V  A  E  T  F  A  A  K  S  K  E  F  S  Q  I  R  C  Q  V

GAGGAAGCTGTCCTTCCGACCACACATATGAATTGCTAGCTTTTGAAGCCAACTTGCTAGTGTGCAGCACCATTTATTCTGCAAAA
CTGACTAGAGAGCAGGGTATATTCCTCTACCCCGAGTTAGACGACATCCTGTATGGTTCAAATTAATTATTTTTCTCCCCTTCACA
CCATGTTATTTAGTTCTCTTCCTCTTCGAAAGTGAAGAGCTTAGATGTTCATAGGTTTTGAATTATGTTGGAGGTTGGTGATAACT
GACTAGTCCTCTTACCATATAGATAATGTATCCTTGTACTATGAGATTTTGGGTGTGTTTGATACCAAGGAAAAATGTTTATTTGG
AAAACAATTGGATTTTTAATTTATTTTTTCTTGTTT
```

FIG.45B

Arabidopsis DeoxyHypusine Synthase
(DHS) Predicted Sequence

```
GAACTCCCAAAACCCTCTACTACTACACTTTCAGATCCAAGGAAATCAATTTTGTCATTCGAGCAACATGG
                                                                     M
AGGATGATCGTGTTTTCTCTTCGGTTCACTCAACAGTTTTCAAAGAATCCGAATCATTGGAAGGAAAGTGT
E  D  D  R  V  F  S  S  V  H  S  T  V  F  K  E  S  E  S  L  E  G  K  C
GATAAAATCGAAGGATACGATTTCAATCAAGGAGTAGATTACCCAAAGCTTATGCGATCCATGCTCACCAC
 D  K  I  E  G  Y  D  F  N  Q  G  V  D  Y  P  K  L  M  R  S  M  L  T  T
CGGATTTCAAGCCTCGAATCTCGGCGAAGCTATTGATGTCGTCAATCAAATGGTTCGTTTCTCGAATTCAT
  G  F  Q  A  S  N  L  G  E  A  I  D  V  V  N  Q  M
CAAAAATAAAAATTCCTTCTTTTTGTTTTCCTTTGTTTTGGGTGAATTAGTAATGACAAAGAGTTTGAATT
                                                            F  E  F
TGTATTGAAGCTAGATTGGAGACTGGCTGATGAAACTACAGTAGCTGAAGACTGTAGTGAAGAGGAGAAGA
  V  L  K  L  D  W  R  L  A  D  E  T  T  V  A  E  D  C  S  E  E  E  K
ATCCATCGTTTAGAGAGTCTGTCAAGTGTAAAATCTTTCTAGGTTTCACTTCAAATCTTGTTTCATCTGGT
N  P  S  F  R  E  S  V  K  C  K  I  F  L  G  F  T  S  N  L  V  S  S  G
GTTAGAGATACTATTCGTTATCTTGTTCAGCATCATATGGTTTGTGATTTTTGCTTTATCACCCTGCTTTT
 V  R  D  T  I  R  Y  L  V  Q  H  H  M
TTATAGATGTTAAAATTTTCGAGCTTTAGTTTTGATTTCAATGGTTTTTCTGCAGGTTGATGTTATAGTCA
                                                      V  D  V  I  V
CGACAACTGGTGGTGTTGAGGAAGATCTCATAAAATGCCTTGCACCTACATTTAAAGGTGATTTCTCTCTA
T  T  T  G  G  V  E  E  D  L  I  K  C  L  A  P  T  F  K  G  D  F  S  L
CCTGGAGCTTATTTAAGGTCAAAGGGATTGAACCGAATTGGGAATTTGCTGGTTCCTAATGATAACTACTG
 P  G  A  Y  L  R  S  K  G  L  N  R  I  G  N  L  L  V  P  N  D  N  Y  C
CAAGTTTGAGGATTGGATCATTCCCATCTTTGACGAGATGTTGAAGGAACAGAAAGAAGAGGTATTGCTTT
  K  F  E  D  W  I  I  P  I  F  D  E  M  L  K  E  Q  K  E  E
ATCTTTCCTTTTTATATGATTTGAGATGATTCTGTTTGTGCGTCACTAGTGGAGATAGATTTTGATTCCTC
TCTTGCATCATTGACTTCGTTGGTGAATCCTTCTTTCTCTGGTTTTTCCTTGTAGAATGTGTTGTGGACTC
                                                      N  V  L  W  T
CTTCTAAACTGTTAGCACGGCTGGGAAAAGAAATCAACAATGAGAGTTCATACCTTTATTGGGCATACAAG
P  S  K  L  L  A  R  L  G  K  E  I  N  N  E  S  S  Y  L  Y  W  A  Y  K
GTATCCAAAATTTTAACCTTTTTAGTTTTTTAATCATCCTGTGAGGAACTCGGGGATTTAAATTTTCCGCT
TCTTGTGGTGTTTGTAGATGAATATTCCAGTATTCTGCCCAGGGTTAACAGATGGCTCTCTTGGGGATATG
                  M  N  I  P  V  F  C  P  G  L  T  D  G  S  L  G  D  M
CTGTATTTTCACTCTTTTCGTACCTCTGGCCTCATCATCGATGTAGTACAAGGTACTTCTTTTACTCAATA
 L  Y  F  H  S  F  R  T  S  G  L  I  I  D  V  V  Q
AGTCAGTGTGATAAATATTCCTGCTACATCTAGTGCAGGAATATTGTAACTAGTAGTGCATTGTAGCTTTT
CCAATTCAGCAACGGACTTTACTGTAAGTTGATATCTAAAGGTTCAAACGGGAGCTAGGAGAATAGCATAG
GGGCATTCTGATTTAGGTTTGGGGCACTGGGTTAAGAGTTAGAGAATAATAATCTTGTTAGTTGTTTATCA
AACTCTTTGATGGTTAGTCTCTTGGTAATTTGAATTTTATCACAGTGTTTATGGTCTTTGAACCAGTTAAT
GTTTTATGAACAGATATCAGAGCTATGAACGGCGAAGCTGTCCATGCAAATCCTAAAAAGACAGGGATGAT
            D  I  R  A  M  N  G  E  A  V  H  A  N  P  K  K  T  G  M  I
AATCCTTGGAGGGGGCTTGCCAAAGCACCACATATGTAATGCCAATATGATGCGCAATGGTGCAGATTACG
  I  L  G  G  G  L  P  K  H  H  I  C  N  A  N  M  M  R  N  G  A  D  Y
CTGTATTTATAAACACCGGGCAAGAATTTGATGGGAGCGACTCGGGTGCACGCCCTGATGAAGCCGTGTCT
A  V  F  I  N  T  G  Q  E  F  D  G  S  D  S  G  A  R  P  D  E  A  V  S
TGGGGTAAAATTAGGGGTTCTGCTAAAACCGTTAAGGTCTGCTTTTTAATTTCTTCACATCCTAATTTATA
 W  G  K  I  R  G  S  A  K  T  V  K  V  C  F  L  I  S  S  H  P  N  L  Y
TCTCACTCAGTGGTTTTGAGTACATATTTAATATTGGATCATTCTTGCAGGTATACTGTGATGCTACCATA
  L  T  Q  W  F
GCCTTCCCATTGTTGGTTGCAGAAACATTTGCCACAAAGAGAGACCAAACCTGTGAGTCTAAGACTTAAGA
ACTGACTGGTCGTTTTGGCCATGGATTCTTAAAGATCGTTGCTTTTTGATTTTACACTGGAGTGACCATAT
AACACTCCACATTGATGTGGCTGTGACGCGAATTGTCTTCTTGCGAATTGTACTTTAGTTTCTCTCAACCT
AAAATGATTTGCAGATTGTGTTTTCGTTTAAAACACAAGAGTCTTGTAGTCAATAATCCTTTGCCTTATAA
AATTATTCAGTTCCAACAACACATTGTGATTCTGTGACAAGTCTCCCGTTGCCTATGTTCACTTCTCTGCG
```

FIG.46A

MEDDRVFSSVHSTVFKESESLEGKCDKIEGYDFNQGVDYPKLMRSMLTTGFQASNLGEAIDVVNQMFEFVLKLDWRLADETTV
AEDCSEEEKNPSFRESVKCKIFLGFTSNLVSSGVRDTIRYLVQHHMVDVIVTTTGGVEEDLIKCLAPTFKGDFSLPGAYLRSK
GLNRIGNLLVPNDNYCKFEDWIIPIFDEMLKEQKEENVLWTPSKLLARLGKEINNESSYLYWAYKMNIPVFCPGLTDGSLGDM
LYFHSFRTSGLIIDVVQDIRAMNGEAVHANPKKTGMIILGGGLPKHHICNANMMRNGADYAVFINTGQEFDGSDSGARPDEAV
SWGKIRGSAKTVKVCFLISSHPNLYLTQWF

FIG.46B

GGTGGTGTTGAGGAAGATCTCATAAAATGCCTTGCACCTACATTTAAAGGTGATTTCTCTCTACCTGGAGCTTATTTAAG
GTCAAAGGGATTGAACCGAATTGGGAATTTGCTGGTTCCTAATGATAACTACTGCAAGTTTGAGGATTGGATCATTCCCA
TCTTTGACGAGATGTTGAAGGAACAGAAAGAAGAGAATGTGTTGTGGACTCCTTCTAAACTGTTAGCACGGCTGGGAAAA
GAAATCAACAATGAGAGTTCATACCTTTATTGGGCATACAAGATGAATATTCCAGTATTCTGCCCAGGGTTAACAGATGG
CTCTCTTAGGGATATGCTGTATTTTCACTCTTTTCGTACCTCTGGCCTCATCATCGATGTAGTACAAGATATCAGAGCTA
TGAACGGCGAAGCTGTCCATGCAAATCCTAAAAAGACAGGGATGATAATCCTTGGAGGGGGCTTGCCAAAGCACCACATA
TGTAATGCCAATATGATGCGCAATGGTGCAGATTACGCTGTATTTATAAACACCGGGCAAGAATTTGATGGGAGCGACTC
GGGTGCACGCCCTGATGAAGC

FIG.46C

GGVEEDLIKCLAPTFKGDFSLPGAYLRSKGLNRIGNLLVPNDNYCKFEDWIIPIFDEMLKEQKEENVLWTPSKLLARLGKEIN
NESSYLYWAYKMNIPVFCPGLTDGSLRDMLYFHSFRTSGLIIDVVQDIRAMNGEAVHANPKKTGMIILGGGLPKHHICNANMM
RNGADYAVFINTGQEFDGSDSGARPDE

FIG.46D

Northern analysis of DHS on tomato flowers

Bud

Blossom and Senescence

RNA

Northern

NORTHERN ANALYSIS OF DHS ON DEVELOPMENTAL STAGES OF TOMATO FRUIT

NORTHERN ANALYSIS OF DHS
TOMATO LEAF CHILLING EFFECTS

Canation DHS cDNA Sequence

```
GTCATTACAATGCATAGGATCATTGCACATGCTACCTTCCTCATTGCACTTGAGCTTGCCATA
CTTTTGTTTTTGACGTTTGATAATAATACTATGAAAATATTATGTTTTTTCTTTTGTGTGTTG
GTGTTTTTGAAGTTGTTTTTGATAAGCAGAACCCAGTTGTTTTACACTTTTACCATTGAACTA
CTGCAATTCTAAAACTTTGTTTACATTTTAATTCCATCAAAGATTGAGTTCAGCATAGGAAAA
AGGATGGAGGATGCTAATCATGATAGTGTGGCATCTGCGCACTCTGCAGCATTCAAAAAGTCG
   M  E  D  A  N  H  D  S  V  A  S  A  H  S  A  A  F  K  K  S
GAGAATTTAGAGGGGAAAAGCGTTAAGATTGAGGGTTATGATTTTAATCAAGGTGTAAACTAT
 E  N  L  E  G  K  S  V  K  I  E  G  Y  D  F  N  Q  G  V  N  Y
TCCAAACTCTTGCAATCTTTCGCTTCTAATGGGTTTCAAGCCTCGAATCTTGGAGATGCCATT
 S  K  L  L  Q  S  F  A  S  N  G  F  Q  A  S  N  L  G  D  A  I
GAAGTAGTTAATCATATGCTAGATTGGAGTCTGGCAGATGAGGCACCTGTGGACGATTGTAGC
 E  V  V  N  H  M  L  D  W  S  L  A  D  E  A  P  V  D  D  C  S
GAGGAAGAGAGGGATCCTAAATTCAGAGAATCTGTGAAGTGCAAAGTGTTCTTGGGCTTTACT
 E  E  E  R  D  P  K  F  R  E  S  V  K  C  K  V  F  L  G  F  T
TCAAATCTTATTTCCTCTGGTGTTCGTGACACAATTCGGTATCTCGTGCAACATCATATGGTT
 S  N  L  I  S  S  G  V  R  D  T  I  R  Y  L  V  Q  H  H  M  V
GACGTGATAGTAACGACAACCGGAGGTATAGAAGAAGATCTAATAAAAGGAAGATCCATCAAG
 D  V  I  V  T  T  T  G  G  I  E  E  D  L  I  K  G  R  S  I  K
TGCCTTGCACCCACTTTCAAAGGCGATTTTGCCTTACCAGGAGCTCAATTACGCTCCAAAGGG
 C  L  A  P  T  F  K  G  D  F  A  L  P  G  A  Q  L  R  S  K  G
TTGAATCGAATTGGTAATCTGTTGGTTCCGAATGATAACTACTGTAAATTTGAGGATTGGATC
 L  N  R  I  G  N  L  L  V  P  N  D  N  Y  C  K  F  E  D  W  I
ATTCCAATTTTAGATAAGATGTTGGAAGAGCAAATTTCAGAGAAAATCTTATGGACACCATCG
 I  P  I  L  D  K  M  L  E  E  Q  I  S  E  K  I  L  W  T  P  S
AAGTTGATTGGTCGATTAGGAAGAGAAATAAACGATGAGAGTTCATACCTTTACTGGGCCTTC
 K  L  I  G  R  L  G  R  E  I  N  D  E  S  S  Y  L  Y  W  A  F
AAGAACAATATTCCAGTATTTTGCCCAGGTTTAACAGACGGCTCACTCGGAGACATGCTATAT
 K  N  N  I  P  V  F  C  P  G  L  T  D  G  S  L  G  D  M  L  Y
TTTCATTCTTTTCGCAATCCGGGTTTAATCGTCGATGTTGTGCAAGATATAAGAGCAGTAAAT
 F  H  S  F  R  N  P  G  L  I  V  D  V  V  Q  D  I  R  A  V  N
GGCGAGGCTGTGCACGCAGCGCCTAGGAAAACAGGCATGATTATACTCGGTGGAGGGTTGCCT
 G  E  A  V  H  A  A  P  R  K  T  G  M  I  I  L  G  G  G  L  P
AAGCACCACATCTGCAACGCAAACATGATGAGAAATGGCGCCGATTATGCTGTTTTCATCAAC
 K  H  H  I  C  N  A  N  M  M  R  N  G  A  D  Y  A  V  F  I  N
ACTGCCGAAGAGTTTGACGGCAGTGATTCTGGTGCTCGCCCCGATGAGGCTATTTCATGGGGC
 T  A  E  E  F  D  G  S  D  S  G  A  R  P  D  E  A  I  S  W  G
AAAATTAGCGGATCTGCTAAGACTGTGAAGGTGCATTGTGATGCCACGATAGCTTTCCCTCTA
 K  I  S  G  S  A  K  T  V  K  V  H  C  D  A  T  I  A  F  P  L
CTAGTCGCTGAGACATTTGCAGCAAAAAGAGAAAAAGAGAGGAAGAGCTGTTAAAACTTTTTT
 L  V  A  E  T  F  A  A  K  R  E  K  E  R  K  S  C
GATTGTTGAAAAATCTGTGTTATACAAGTCTCGAAATGCATTTTAGTAATTGACTTGATCTTA
TCATTTCAATGTGTTATCTTTGAAAATGTTGGTAATGAAACATCTCACCTCTTCTATACAACA
TTGTTGATCCATTGTACTCCGTATCTTGTAATTTTGGAAAAAAAAAACCGTCTATTGTTACGA
GAGAGTACATTTTTGAGGTAAAAATATAGGATTTTTGTGCGATGCAAATGCTGGTTATTCCCT
TGAAAAAAAAAAAAAAAAAAA
```

(1384 bps, not include Poly A tail and 5'end nocoding region.
373 Amino Acid.)

FIG.54

Northern Analysis of WT AT Aging Leaves

Northern Analysis of Canation Petal *(In Situ)* DHS

Tomato Senescence-induced eif5A

```
AAAGAATCCTAGAGAGAGAAAGGGAATCCTAGAGAGAGAAGCATGTCGGACGAAGAACAC
                                          M  S  D  E  E  H
CATTTTGAGTCAAAGGCAGATGCTGGTGCCTCAAAAACTTTCCCACAGCAAGCTGGAACC
H  F  E  S  K  A  D  A  G  A  S  K  T  F  P  Q  Q  A  G  T
ATCCGTAAGAATGGTTACATCGTTATCAAAGGCCGTCCCTGCAAGGTTGTTGAGGTCTCC
I  R  K  N  G  Y  I  V  I  K  G  R  P  C  K  V  V  E  V  S
ACTTCAAAAACTGGAAAACACGGACATGCTAAATGTCACTTTGTGGCAATTGACATTTTC
T  S  K  T  G  K  H  G  H  A  K  C  H  F  V  A  I  D  I  F
AATGGAAAGAAACTGGAAGATATCGTTCCGTCCTCCCACAATTGTGATGTGCCACATGTT
N  G  K  K  L  E  D  I  V  P  S  S  H  N  C  D  V  P  H  V
AACCGTACCGACTATCAGCTGATTGATATCTCTGAAGATGGTTTTGTCTCACTTCTTACT
N  R  T  D  Y  Q  L  I  D  I  S  E  D  G  F  V  S  L  L  T
GAAAGTGGAAACACCAAGGATGACCTCAGGCTTCCCACCGATGAAAATCTGCTGAAGCAG
E  S  G  N  T  K  D  D  L  R  L  P  T  D  E  N  L  L  K  Q
GTTAAAGATGGGTTCCAGGAAGGAAAGGATCTTGTGGTGTCTGTTATGTCTGCGATGGGC
V  K  D  G  F  Q  E  G  K  D  L  V  V  S  V  M  S  A  M  G
GAAGAGCAGATTAACGCCGTTAAGGATGTTGGTACCAAGAATTAGTTATGTCATGGCAGC
E  E  Q  I  N  A  V  K  D  V  G  T  K  N
ATAATCACTGCCAAAGCTTTAAGACATTATCATATCCTAATGTGGTACTTTGATATCACT
AGATTATAAACTGTGTTATTTGCACTGTTCAAAACAAAAGAAAGAAAACTGCTGTTATGG
CTAGAGAAAGTATTGGCTTTGAGCTTTTGACAGCACAGTTGAACTATGTGAAAATTCTAC
TTTTTTTTTTTTGGGTAAAATACTGCTCGTTTAATGTTTTGCAAAAAAAAAAAAAAAAAA
```

*764 bps, not: including Poly(A) tail, 160 amino acids*

FIG.57

Carnation Senescence-induced F5A

CTCTTTTACATCAATCGAAAAAAAATTAGGGTTCTTATTTTAGAGTGAGA

GGCGAAAAATCGAACGATGTCGGACGACGATCACCATTTCGAGTCATCGG
M S D D D H H F E S S A
CCGACGCCGGAGCATCCAAGACTTACCCTCAACAAGCTGGTACAATCCGC
D A G A S K T Y P Q Q A G T I R
AAGAGCGGTCACATCGTCATCAAAAATCGcCCtTGCAAGGtGGTTGAGGT
K S G H I V I K N R P C K V V E V
TTCTACCTCCAAGACTGGCAAGCACGGTCATGCCAAATGTCACTTTGTTG
S T S K T G K H G H A K C H F V A
CCATTGACATTTTCAACGGCAAGAAGCTGGAAGATATTGTCCCCTCATCC
I D I F N G K K L E D I V P S S
CACAATTGTGATGTTCCACATGTCAACCGTGTCGACTACCAGCTGCTTGA
H N C D V P H V N R V D Y Q L L D
TATCACTGAAGATGGCTTTCTTAGTCTGCTGACTGACAGTGGTGACACCA
I T E D G F V S L L T D S G D T K
AGGATGATCTGAAGCTTCCTGCTGATGAGGCCCTTGTGAAGCAGATGAAG
D D L K L P A D E A L V K Q M K
GAGGGATTTGAGGCGGGGAAAGACTTGATTCTGTCAGTCATGTGTGCAAT
E G F E A G K D L I L S V M C A M
GGGAGAAGAGCAGATCTGCGCCGTCAAGGACGTTAGTGGTGGCAAGTAGA
G E E Q I C A V K D V S G G K
AGCTTTTGATGAATCCAATACTACGCGGTGCAGTTGAAGCAATAGTAATC
TCGAGAACATTCTGAACCTTATATGTTGAATTGATGGTGCTTAGTTTGTT
TTGGAAATCTCTTTGCAATTAAGTTGTACCAAATCAATGGATGTAATGTC
TTGAATTTGTTTTATTTTTGTTTTGATGTTTGCTGtGATTGCATTATGCA
TTGTTATGAGTTATGACCTGTTATAACACAAGGTTTTGGTAAAAAAAAAA
AAAAAAAAAAAA

*790 bps, 160 amino acids*

FIG.58

Arabidopsis Senescence-induced eI-F5A

```
CTGTTACCAAAAAATCTGTACCGCAAAATCCTCGTCGAAGCTCGCTGCTGCAACCATGTC
                                                       M  S
CGACGAGGAGCATCACTTTGAGTCCAGTGACGCCGGAGCGTCCAAAACCTACCCTCAACA
 D  E  E  H  H  F  E  S  S  D  A  G  A  S  K  T  Y  P  Q  Q
AGCTGGAACCATCCGTAAGAATGGTTACATCGTCATCAAAAATCGTCCCTGCAAGGTTGT
 A  G  T  I  R  K  N  G  Y  I  V  I  K  N  R  P  C  K  V  V
TGAGGTTTCAACCTCGAAGACTGGCAAGCATGGTCATGCTAAATGTCATTTTGTAGCTAT
 E  V  S  T  S  K  T  G  K  H  G  H  A  K  C  H  F  V  A  I
TGATATCTTCACCAGCAAGAAACTCGAAGATATTGTTCCTTCTTCCCACAATTGTGATGT
 D  I  F  T  S  K  K  L  E  D  I  V  P  S  S  H  N  C  D  V
TCCTCATGTCAACCGTACTGATTATCAGCTGATTGACATTTCTGAAGATGGATATGTCAG
 P  H  V  N  R  T  D  Y  Q  L  I  D  I  S  E  D  G  Y  V  S
TTTGTTGACTGATAACGGTAGTACCAAGGATGACCTTAAGCTCCCTAATGATGACACTCT
 L  L  T  D  N  G  S  T  K  D  D  L  K  L  P  N  D  D  T  L
GCTCCAACAGATCAAGAGTGGGTTTGATGATGGAAAAGATCTAGTGGTGAGTGTAATGTC
 L  Q  Q  I  K  S  G  F  D  D  G  K  D  L  V  V  S  V  M  S
AGCTATGGGAGAGGAACAGATCAATGCTCTTAAGGACATCGGTCCCAAGTGAGACTAACA
 A  M  G  E  E  Q  I  N  A  L  K  D  I  G  P  K
AAGCCTCCCCTTTGTTATGAGATTCTTCTTCTTCTGTAGGCTTCCATTACTCGTCGGAGA
TTATCTTGTTTTTGGGTTACTCCTATTTTGGATATTTAAACTTTTGTTAATAATGCCATC
TTCTTCAACCTTTTCCTTCTAGATGGTTTTTATACTTCTTCT
```

*754 bps, not including Poly(A) tail, 158 amino acids*

FIG.59

Northern Analysis of WT AT DHS and senescence-induced eIF-5A

Northern Analysis of Ripening Tomato Fruit

Northern Analysis of sorbitol-treated tomato leaves

Northern Analysis of chill-injured tomato leaves 4.6 Weeks

α-3'DHS # 3

Wild-Type 6.1 Weeks

α-3'DHS # 7

Wild-Type

18 Days

Anti 3'-DHS

Wild type

32 Days

Anti 3'-DHS

Wild type

Arabidopsis 3'-end DHS for antisense

Nucleotide and derived amino acid sequence

TGCACGCCCTGATGAAGCTGTGTCTTGGGGTAAAATTAGGGGTTCTGCTAAAACCGTTAAGGTCTGCTTTT
A R P D E A V S W G K I R G S A K T V K V C F

TAATTTCTTCACATCCTAATTTATATCTCACTCAGTGGTTTTGAGTACATATTTAATATTGGATCATTCTT
L I S S H P N L Y L T Q W F

GCAGGTATACTGTGATGCTACCATAGCCTTCCCATTGTTGGTTGCAGAAACATTTGCCACAAAGAGAGACC
AAACCTGTGAGTCTAAGACTTAAGAACTGACTGGTCGTTTTGGCCATGGATTCTTAAAGATCGTTGCTTTT
TGATTTTACACTGGAGTGACCATATAACACTCCACATTGATGTGGCTGTGACGCGAATTGTCTTCTTGCGA
ATTGTACTTTAGTTTCTCTCAACCTAAAATGATTTGCAGATTGTGTTTTCGTTTAAAACACAAGAGTCTTG
TAGTCAATAATCCTTTGCCTTATAAAATTATTCAGTTCCAACAAAAAAAAAAAAAAAA

---

Nucleotide sequence

TGCACGCCCTGATGAAGCTGTGTCTTGGGGTAAAATTAGGGGTTCTGCTAAAACCGTTAAGGTCTGCTTTT
TAATTTCTTCACATCCTAATTTATATCTCACTCAGTGGTTTTGAGTACATATTTAATATTGGATCATTCTT
GCAGGTATACTGTGATGCTACCATAGCCTTCCCATTGTTGGTTGCAGAAACATTTGCCACAAAGAGAGACC
AAACCTGTGAGTCTAAGACTTAAGAACTGACTGGTCGTTTTGGCCATGGATTCTTAAAGATCGTTGCTTTT
TGATTTTACACTGGAGTGACCATATAACACTCCACATTGATGTGGCTGTGACGCGAATTGTCTTCTTGCGA
ATTGTACTTTAGTTTCTCTCAACCTAAAATGATTTGCAGATTGTGTTTTCGTTTAAAACACAAGAGTCTTG
TAGTCAATAATCCTTTGCCTTATAAAATTATTCAGTTCCAACAAAAAAAAAAAAAAAA

ARPDEAVSWGKIRGSAKTVKVCFLISSHPNLYLTQWF

FIG.80

Tomato 3'-end-Deoxyhupsine synthase used for antisense

Nucleotide and derived amino acid sequence
GGTGCTCGTCCTGATGAAGCTGTATCATGGGGAAAGATACGTGGTGGTGCCAAGACTGTGAAGGTGCATTGTGATGCAAC
G A R P D E A V S W G K I R G G A K T V K V H C D A T CATTGCATTTCCCATATTAGTAGCTGAGACATTTGCAGCTAAGAGTAAGGAATTCTCCCAGATAAGGTGCCAAGTTTGAA
I A F P I L V A E T F A A K S K E F S Q I R C Q V CATTGAGGAAGCTGTCCTTCCGACCACACATATGAATTGCTAGCTTTTGAAGCCAACTTGCTAGTGTGCAGCACCATTTA
TTCTGCAAAACTGACTAGAGAGCAGGGTATATTCCTCTACCCCGAGTTAGACGACATCCTGTATGGTTCAAATTAATTAT
TTTTCTCCCCTTCACACCATGTTATTTAGTTCTCTTCCTCTTCGAAAGTGAAGAGCTTAGATGTTCATAGGTTTTGAATT
ATGTTGGAGGTTGGTGATAACTGACTAGTCCTCTTACCATATAGATAATGTATCCTTGTACTATGAGATTTTGGGTGTGT
TTGATACCAAGGAAAAATGTTTATTTGGAAAACAATTGGATTTTTAATTTAAAAAAAATTGNTTAAAAAAAAAAAAAAA

-----------------------------

Nucleotide sequence
GGTGCTCGTCCTGATGAAGCTGTATCATGGGGAAAGATACGTGGTGGTGCCAAGACTGTGAAGGTGCATTGTGATGCAAC
CATTGCATTTCCCATATTAGTAGCTGAGACATTTGCAGCTAAGAGTAAGGAATTC TCCCAGATAAGGTGCCAAGTTTGAACATTGAGGAAGCTGTCCTTCCGACCACACATATGAATTGCTAGCTTTTGAAGCCA
ACTTGCTAGTGTGCAGCACCATTTATTCTGCAAAACTGACTAGAGAGCAGGGTATATTCCTCTACCCCGAGTTAGACGAC
ATCCTGTATGGTTCAAATTAATTATTTTTCTCCCCTTCACACCATGTTATTTAGTTCTCTTCCTCTTCGAAAGTGAAGAG
CTTAGATGTTCATAGGTTTTGAATTATGTTGGAGGTTGGTGATAACTGACTAGTCCTCTTACCATATAGATAATGTATCC
TTGTACTATGAGATTTTGGGTGTGTTTGATACCAAGGAAAAATGTTTATTTGGAAAACAATTGGATTTTTAATTTAAAAA
AAATTGNTTAAAAAAAAAAAAAAA

FIG.81

600 bp Arabidopsis Deoxyhypusine Synthase Probe

Primer1 (underlined)

GGTGGTGTTGAGGAAGATCTCATAAAATGCCTTGCACCTACATTTAAAGGTGATTTCTCTCTACCTGGAGC
TTATTTAAG
G G V E E D L I K C L A P T F K G D F S L P G A
Y L R
GTCAAAGGGATTGAACCGAATTGGGAATTTGCTGGTTCCTAATGATAACTACTGCAAGTTTGAGGATTGGA
TCATTCCCA
S K G L N R I G N L L V P N D N Y C K F E D W I
I P
TCTTTGACGAGATGTTGAAGGAACAGAAAGAAGAGAATGTGTTGTGGACTCCTTCTAAACTGTTAGCACGG
CTGGGAAAA
I F D E M L K E Q K E E N V L W T P S K L L A R
L G K
GAAATCAACAATGAGAGTTCATACCTTTATTGGGCATACAAGATGAATATTCCAGTATTCTGCCCAGGGTT
AACAGATGG
E I N N E S S Y L Y W A Y K M N I P V F C F G L
T D G
CTCTCTTAGGGATATGCTGTATTTTCACTCTTTTCGTACCTCTGGCCTCATCATCGATGTAGTACAAGATA
TCAGAGCTA

S L R D M L Y F H S F R T S G L I I D V V Q D I
R A
TGAACGGCGAAGCTGTCCATGCAAATCCTAAAAAGACAGGGATGATAATCCTTGGAGGGGGCTTGCCAAAG
CACCACATA
M N G E A V H A N P K K T G M I I L G G G L P K
H H I
TGTAATGCCAATATGATGCGCAATGGTGCAGATTACGCTGTATTTATAAACACCGGGCAAGAATTTGATGG
GAGCGACTC
C N A N M M R N G A D Y A V F I N T G Q E F D G
S D S
GGGTGCACGCCCTGATGAAGC
G A R P D E
Primer 2 (underlined)

FIG.82

483 bp Carnation Deoxyhypusine Synthase Probe

GAAGATCCATCAAGTGCCTTGCACCCACTTTCAAAGGCGATTTTGCCTTACCAGGAGCTCAATTACGCTCC
AAAGGGT
R R S I K C L A P T F K G D F A L P G A Q L R S
K G

TGAATCGAATTGGTAATCTGTTGGTTCCGAATGATAACTACTGTAAATTTGAGGATTGGATCATTCCAATT
TTAGATA
L N R I G N L L V P N D N Y C K F E D W I I P I
L D

AGATGTTGGAAGAGCAAATTTCAGAGAAAATCTTATGGACACCATCGAAGTTGATTGGTCGATTAGGAAGA
GAAATAA
K M L E E Q I S E K I L W T P S K L I G R L G R
E I

ACGATGAGAGTTCATACCTTTACTGGGCCTTCAAGAACAATATTCCAGTATTTTGCCCAGGTTTAACAGAC
GGCTCAC
N D E S S Y L Y W A F K N N I P V F C P G L T D
G S

TCGGAGACATGCTATATTTTCATTCTTTTCGCAATCCGGGTTTAATCATCGATGTTGTGCAAGATATAAGA
GCAGTAA
L G D M L Y F H S F R N P G L I I D V V Q D I R
A V

ATGGCGAGGCTGTGCACGCAGCGCCTAGGAAAACAGGCATGATTATACTCGGTGGAGGGTTGCCTAAGCAC
CACATCT
N G E A V H A A P R K T G M I I L G G G L P K H
H I

GCAACGCAAACATGATGAGAAATGGCGCCGATTATGCTGTTTTCATCAACACCG
C N A N M M R N G A D Y A V F I N T

A full-length cDNA clone was obtained by screening a carnation senescing petal cDNA library with this probe.

FIG.83

Hypusine conserve sequence

| | * TGKHGH |
|---|---|
| AT Senescence | CKVVEVSTSKTGKHGHAKCHFV |
| AT wounding | CKVVEVSTSKTGKHGHAKCHFV |
| AT growth | CKVVEVSTSKTGKHGHAKCHFV |
| Canola | CKVVEVSTSKTGKHGHAKCHFV |
| carnation | CKVVEVSTSKTGKHGHAKCHFV |
| Tomato growth | CKVVEVSTSKTGKHGHAKCHFV |
| Tomato wounding | CKVVEVSTSKTGKHGHAKCHFV |
| Tomato senescence | CKVVEVSTSKTGKHGHAKCHFV |
| alfalfa-1 | CKVVEVSTSKTGKHGHAKCHFV |
| alfalfa-2 | CKVVEVSTSKTGKHGHAKCHFV |
| alfalfa-4 | CKVVEVSTSKTGKHGHAKCHFV |
| Lettucel | CKVVEVSTSKTGKHGHAKCHFV |
| treel | CKVVEVSTSKTGKHGHAKCHFV |
| tree3 | CKVVEVSTSKTGKHGHAKCHFV |
| tree4 | CKVVEVSTSKTGKHGHAKCHFV |

Nucleotide

| | |
|---|---|
| AT Senescence | TGCAAGGTTGTTGAGGTTTCAACCTCGAAGACTGGCAAGCATGGTCATGCTAAATGTCATTTTGTA |
| AT wounding | TGCAAGGTTGTTGAGGTTTCGACTTCCAAAACTGGCAAGCACGGTCACGCCAAATGTCATTTTGTT |
| AT growth | TGCAAGGTGGTTGAGGTATCGACTTCGAAGACTGGGAAGCATGGTCACGCCAAGTGTCACTTTGTT |
| Canola | TGCAAGGTTGTTGAGGTTTCGACTTCGAAGACTGGGAAGCACGGTCACGCAAAGTGTCACTTTGTT |
| carnation | TGCAAGGTGGTTGAGGTTTCTACCTCCAAGACTGGCAAGCACGGTCATGCCAAATGTCACTTTGTT |
| Tomato growth | TGCAAGGTGGTTGAGGTTTCAACTTCCAAGACAGGCAAGCACGGTCATGCTAAATGTCACTTTGTT |
| Tomato wounding | TGCAAGGTTGTGGAAGTCTCTACATCCAAAACTGGCAAGCACGGTCACGCCAAATGTCATTTCGTT |
| Tomato senescence | TGCAAGGTTGTTGAGGTCTCCACTTCCAAAACTGGCAAGCATGGACATGCAAAATGTCACTTTGTG |
| alfalfa-1 | TGCAAGGTGGTTGAAGTTTCGACTTCGAAGACCGGGAAGCATGGACATGCCAAGTGTCATTTTGTT |
| alfalfa-2 | TGCAAGGTTGTTGAGGTTTCTACTTCAAAAACAGGAAAACATGGACATGCAAAGTGTCACTTTGTT |
| alfalfa-4 | TGCAAGGTAGTTGAAGTTTCAACTTCTAAAACTGGAAAGCATGGACATGCAAAGTGTCACTTTGTT |
| Lettucel | TGCAAGGTTGTTGAAGTTTCTACCTCCAAGACTGGGAAGCATGGGCATGCTAAGTGTCACTTTGTC |
| treel | TGCAAGGTCGTGGAGGTTTCAACCTCTAAAACTGGCAAGCATGGCCATGCTAAATGTCACTTTGTT |
| tree2 | TGCAAGGTTGTTGAGGTTTCCACCTCAAAGACAGGCAAGCACGGACATGCTAAGTGCCACTTTGTG |
| tree3 | TGCAAGGTTGTGGAGGTTTCTACCTCTAAAACTGGCAAGCACGGCCATGCCAAATGTCACTTTGTT |
| tree4 | TGCAAGGTTGTTGAGGTTTCCACCTCAAAGACAGGCAAGCATGGACATGCTAAGTGCCACTTTGTG |

FIG.85

Tomato - eIF5A (Senescence)

TTCTCCACAGCAAACACAGAGAAGTTCATAGCAgAAGAAGAGAGAGATTTAGCTATGTCT
M S
GATGAAGAACaCCATTTTGAGTCCAAAGCTGATGCTGGTGCCTCAAAAACTTACCCTCAA
D E E H H F E S K A D A G A S K T Y P Q
CAAGCTGGTACTATTCGCAAGAATGGTTATATAGTTATCAAAGGCAGACCTTGCAAGGTT
Q A G T I R K N G Y I V I K G R P C K V
GTTGAGGTCTCCACTTCCAAAACTGGCAAGCATGGACATGCAAAATGTCACTTTGTGGCA
V E V S T S K T G K H G H A K C H F V A
ATCGACATTTTCAATGCAAAAAAGCTTGAAGATATTGTTCCTTCATCCCACAATTGTGAT
I D I F N A K K L E D I V P S S H N C D
GTGCCACATGTCAATCGTACTGACTATCAGCTGATTGACATATCTGAAGATGGTTTTGTG
V P H V N R T D Y Q L I D I S E D G F V
TCTCTTCTTACTGAAAATGGAAACACCAAAGACGACCTCAGACTTCCCACCGATGACACC
S L L T E N G N T K D D L R L P T D D T
CTGTTGAACCAGGTTAAAGGTGGATTTGAGGAAGGAAAGGATCTCGTTCTGTCTGTGATG
L L N Q V K G G F E E G K D L V L S V M
TCTGCAATGGGTGAAGAGCAGATCTGTGCTGTGAAGGACATTGGTACCAAGACCTAGTTG
S A M G E E Q I C A V K D I G T K T *
TGTGCATTCTGCAGCATAAATAATTGCTTTTTAGCGAAGACGTTTTATATCTTGTTATCG
TGGTACCTTTGCAATCTGTTTTATCGTGAAAACACCTTATATCTATTGGCATGGCTTGAA
TAGTTGAAACTCTAATAGTTTCTGTTTGGCATAAGGCAATGAACTGGATTTGATAGCAGA
AGTAATCTACATGTCACTTTTTTTT

TTCTCCACAGCAAACACAGAGAAGTTCATAGCAgAAGAAGAGAGAGATTTAGCTATGTCTGATGAAGAA
CaCCATTTTGAGTCCAAAGCTGATGCTGGTGCCTCAAAAACTTACCCTCAACAAGCTGGTACTATTCGC
AAGAATGGTTATATAGTTATCAAAGGCAGACCTTGCAAGGTTGTTGAGGTCTCCACTTCCAAAACTGGC
AAGCATGGACATGCAAAATGTCACTTTGTGGCAATCGACATTTTCAATGCAAAAAAGCTTGAAGATATT
GTTCCTTCATCCCACAATTGTGATGTGCCACATGTCAATCGTACTGACTATCAGCTGATTGACATATCT
GAAGATGGTTTTGTGTCTCTTCTTACTGAAAATGGAAACACCAAAGACGACCTCAGACTTCCCACCGAT
GACACCCTGTTGAACCAGGTTAAAGGTGGATTTGAGGAAGGAAAGGATCTCGTTCTGTCTGTGATGTCT
GCAATGGGTGAAGAGCAGATCTGTGCTGTGAAGGACATTGGTACCAAGACCTAGTTGTGTGCATTCTGC
AGCATAAATAATTGCTTTTTAGCGAAGACGTTTTATATCTTGTTATCGTGGTACCTTTGCAATCTGTTT
TATCGTGAAAACACCTTATATCTATTGGCATGGCTTGAATAGTTGAAACTCTAATAGTTTCTGTTTGGC
ATAAGGCAATGAACTGGATTTGATAGCAGAAGTAATCTACATGTCACTTTTTTTT (745 bps)

AA Sequence (164 aa)

MSDEEHHFESKADAGASKTYPQQAGTIRKNGYIVIKGRPCKVVEVSTSKTGKHGHAKCHFVAIDIFNAK
KLEDIVPSSHNCDVPHVNRTDYQLIDISEDGFVSLLTENGNTKDDLRLPTDDTLLNQVKGGFEEGKDLV
LSVMSAMGEEQICAVKDIGTKT

FIG.86

Construction of Double 35S Promoter::Sense-Senescence eIF5A 1.pKYLX71-sense-Arabidopsis-SENESCENCE-eIF-5A
Primers:
Upstream primer:
GAAGCTCGAGGCTGCAACCATGTCC
XhoI Downstream primer:
GGGGAGCTCTTGTTAGTCTCACTTGG
SacI CACTGAATCAAAGGCCATGGAGTCAAAGATTCAAATAGAGGACCTAACAGAACTCGCCGTAAAGACTGG
CGAACAGTTCATACAGAGTCTCTTACGACTCAATGACAAGAAGAAAATCTTCGTC{AACATGGTGGAGC
ACGACACGCTTGTCTACCTCCAAAAATATCAAAGATACAGTCTCAGAAGACCAAAGGGAATTGAGACTT
TTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAG
ATGCCTCTGCCGACAGTGGTCCCAAAGATGGACCCCCACCCACGAGGAGCATCGTGGAAAAAGAAGACG
TTCCAACCACGTCTTCAAAGCAAGTGGATTGATGTGAT}[AACATGGTGGAGCACGACACGCTTGTCTA
CCTCCAAAAATATCAAAGATACAGTCTCAGAAGACCAAAGGGAATTGAGACTTTTCAACAAAGGGTAAT
ATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAG
TGGTCCCAAAGATGGACCCCCACCCACGAGGAGCATCGTGGAAAAAGAAGACGTTCCAACCACGTCTTC
AAAGCAAGTGGATTGATGTGAT]ATCTCCACTGACGTAAGGGATGACGCACAATCCCACTATCCTTCGC
AAGACCCTTCCTCTATATAAGGAAGTTCATTTCATTTGGAGAGGACACGCTGAAATCACCAGTCTCTCT
CTAAGCTTGGATC ← pKYLX71-double 35S promoter
CTCGAG(XhoI)
**GCTGCAACCATGTCCGACGAGGAGCATCACTTTGAGTCCAGTGACGCCGGAGCGTCCAAAACCTACCCTCAACAAGCTGGAAC
CATCCGTAAGAATGGTTACATCGTCATCAAAAATCGTCCCTGCAAGGTTGTTGAGGTTTCAACCTCGAAGACTGGCAAGCATG
GTCATGCTAAATGTCATTTTGTAGCTATTGATATCTTCACCAGCAAGAAACTCGAAGATATTGTTCCTTCTTCCCACAATTGT
GATGTTCCTCATGTCAACCGTACTGATTATCAGCTGATTGACATTTCTGAAGATGGATATGTCAGTTTGTTGACTGATAACGG
TAGTACCAAGGATGACCTTAAGCTCCCTAATGATGACACTCTGCTCCAACAGATCAAGAGTGGGTTTGATGATGGAAAAGATC
TAGTGGTGAGTGTAATGTCAGCTATGGGAGAGGAACAGATCAATGCTCTTAAGGACATCGGTCCCAAGTGAGACTAACAA**

(SacI) GAGCTC → rbcS-terminater
GAATTGATCCTCTAGAGCTTTCGTTCGTATCATCGGTTTCGACAACGTTCGTCAAGTTCAATGCATCAG
TTTCATTGCGCACACACCAGAATCCTACTGAGTTCGAGTATTATGGCATTGGGAAAACTGTTTTTCTTG
TACCATTTGTTGTGCTTGTAATTTACTGTGTTTTTTATTCGGTTTTCGCTATCGAACTGTGAAATGGAA
ATGGATGGAGAAGAGTTAATGAATGATATGGTCCTTTTGTTCATTCTCAAATTAATATTATTTGTTTTT
TCTCTTATTTGTTGTGTGTTGAATTTGAAATTATAAGAGATATGCAAACATTTTGTTTTGAGTAAAAAT
GTGTCAAATCGTGGCCTCTAATGACCGAAGTTAATATGAGGAGTAAAACACTTGTAGTTGTACCATTAT
GCTTATTCACTAGGCAACAAATATATTTTCAGACCTAGAAAAGCTGCAAATGTTACTGAATACAAGTAT
GTCCTCTTGTGTTTTAGACATTTATGAACTTTCCTTTATGTAATTTTCCAGAATCCTTGTCAGATTCTA
ATCATTGCTTTATAATTATAGTTATACTCATGGATTTGTAGTTGAGTATGAAAATATTTTTTAATGCAT
TTTATGACTTGCCAATTGATTGACAACATGCATCAATCGAT

FIG.87 pK-YLX71-

GCG<u>CTCGAG</u>CTATGTCTGATGAAGAACaCC
XhoI

TTT<u>GAGCTC</u>CAGAATGCACACAACTAGG
SacI

CACTGAATCAAAGGCCATGGAGTCAAAGATTCAAATAGAGGACCTAACAGAACTCGCCGTAAAGACTGG
CGAACAGTTCATACAGAGTCTCTTACGACTCAATGACAAGAAGAAAATCTTCGTC{AACATGGTGGAGC
ACGACACGCTTGTCTACCTCCAAAAATATCAAAGATACAGTCTCAGAAGACCAAAGGGAATTGAGACTT
TTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAG
ATGCCTCTGCCGACAGTGGTCCCAAAGATGGACCCCCACCCACGAGGAGCATCGTGGAAAAAGAAGACG
TTCCAACCACGTCTTCAAAGCAAGTGGATTGATGTGAT}[AACATGGTGGAGCACGACACGCTTGTCTA
CCTCCAAAAATATCAAAGATACAGTCTCAGAAGACCAAAGGGAATTGAGACTTTTCAACAAAGGGTAAT
ATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAG
TGGTCCCAAAGATGGACCCCCACCCACGAGGAGCATCGTGGAAAAAGAAGACGTTCCAACCACGTCTTC
AAAGCAAGTGGATTGATGTGAT]ATCTCCACTGACGTAAGGGATGACGCACAATCCCACTATCCTTCGC
AAGACCCTTCCTCTATATAAGGAAGTTCATTTCATTTGGAGAGGACACGCTGAAATCACCAGTCTCTCT
CTAAGCTTGGATC

FIG.88A

<--- pKYLX71-double 35S promoter

CTCGAG (XhoI)

CTATGTCTGATGAAGAACaCCATTTTGAGTCCAAAGCTGATGCTGGTGCCTCAAAAACTTACCCTCAACAAGCTGGTACTATT
CGCAAGAATGGTTATATAGTTATCAAAGGCAGACCTTGCAAGGTTGTTGAGGTCTCCACTTCCAAAACTGGCAAGCATGGACA
TGCAAAATGTCACTTTGTGGCAATCGACATTTTCAATGCAAAAAAGCTTGAAGATATTGTTCCTTCATCCCACAATTGTGATG
TGCCACATGTCAATCGTACTGACTATCAGCTGATTGACATATCTGAAGATGGTTTTGTGTCTCTTCTTACTGAAAATGGAAAC
ACCAAAGACGACCTCAGACTTCCCACCGATGACACCCTGTTGAACCAGGTTAAAGGTGGATTTGAGGAAGGAAAGGATCTCGT
TCTGTCTGTGATGTCTGCAATGGGTGAAGAGCAGATCTGTGCTGTGAAGGACATTGGTACCAAGACCTAGTTGTGTGCATTCT
G (SacI) GAGCTC -> rbcS-terminater GAATTGATCCTCTAGAGCTTTCGTTCGTATCATCGGTTTCGACAACGTTCGTCAAGTTCAATGCATCAG
TTTCATTGCGCACACACCAGAATCCTACTGAGTTCGAGTATTATGGCATTGGGAAAACTGTTTTTCTTG
TACCATTTGTTGTGCTTGTAATTTACTGTGTTTTTTATTCGGTTTTCGCTATCGAACTGTGAAATGGAA
ATGGATGGAGAAGAGTTAATGAATGATATGGTCCTTTTGTTCATTCTCAAATTAATATTATTTGTTTTT
TCTCTTATTTGTTGTGTGTTGAATTTGAAATTATAAGAGATATGCAAACATTTTGTTTTGAGTAAAAAT
GTGTCAAATCGTGGCCTCTAATGACCGAAGTTAATATGAGGAGTAAAACACTTGTAGTTGTACCATTAT
GCTTATTCACTAGGCAACAAATATATTTTCAGACCTAGAAAAGCTGCAAATGTTACTGAATACAAGTAT
GTCCTCTTGTGTTTTAGACATTTATGAACTTTCCTTTATGTAATTTTCCAGAATCCTTGTCAGATTCTA
ATCATTGCTTTATAATTATAGTTATACTCATGGATTTGTAGTTGAGTATGAAAATATTTTTTAATGCAT
TTTATGACTTGCCAATTGATTGACAACATGCATCAATCGAT

FIG.88B

Comparison of control and At-eIF5A1-transgenic plants (5 weeks old). Whole Plants.

Comparison of control and At-eIF5A1-transgenic plants (5 weeks old). Inflorescence stems.

Cross sections of inflorescence stems
Control with promoter 35S only.
The xylem zones were stained grey with
phlorogucinol-HCl, bar=100 μm.

Cross sections of inflorescence stems
Transgenic with promoter 35S::At-eIF5A1
The xylem zones were stained grey with
phlorogucinol-HCl, bar=100 μm.

Cross sections of inflorescence stems
Control with promoter 35S only.
The xylem zones were stained grey with phlorogucinol-HCl, bar=100 μm.

Cross sections of inflorescence stems
Transgenic with promoter 35S::T-eIF5A4.
The xylem zones were stained grey with phlorogucinol-HCl, bar=100 μm.

Comparison of control and T-eIF5A4-transgenic plants (5 weeks old). Inflorescence stems.

Comparison of control and T-eIF5A4-transgenic plants (5 weeks old). Whole Plants.

Comparison of areas of different tissues between control and the TeIF-5A senescence transgenic inflorescence stems Canolla eIF-5A (growth)

ATGTCTGACGAGGAGCACCACTTCGAGTCCAGCGACGCCGGAGCTTCCAAAACCTACCCTCAGCAGGCTGGTA
ACATCCGCAAGGGTGGTCACATCGTCATCAAGGGCCGTCCCTGCAAGGTTGTTGAGGTTCGACTTTCGAAGAC
TGGGAAGCACGGTCACGCAAAGTGTCACTTTGTTGCTATCGACATCTTCACTGCTAAGAAGCTCGAGGATATT
GTTCCCTCTTCCCACAATTGTGATGTTCCCCATGTGAACCGTATTGACTACCAGTTGATTGATATCTCTGAGA
ATGGCTTTGTTAGCCTTTTGACCGACAGTGGTGGCACCAAGGACGACCTCAAGCTTCCCACCGATGATAATCT
CAGCGCTCTGATGAAGAGTGGATTCGAGGAGGGAAAGGATGTGGTGGTGTCTGTCATGTCTTCCATGGGAGAG
GAGCAGATCTGTGCCGTCAAGGAAGTTGGTGGTGGCAAGTAAAACCCATTCTCTGAGAGAGGATAATCTTATT
ACCAGTGGTCAATGTTATAAGAACAAGAACTTGTTTTTTTTCCTTTTTCTAATTTAGATCATTTGTGTTGTGT
TTCTTTGTTGCAAGACAACCATTATCTATTATTGGTTTTGGATTGTTTAAAAAAAAAAAAAAAAAAAAAAAAA
A (658 bp)

MSDEEHHFESSDAGASKTYPQQAGNIRKGGHIVIKGRPCKVVEVSTSKTGKHGHAKCHFVAIDIFTAKKLEDI
VPSSHNCDVPHVNRIDYQLIDISENGFVSLLTDSGGTKDDLKLPTDDNLSALMKSGFEEGKDVVVSVMSSMGE
EQICAVKEVGGGK (159 amino aids)

ATGTCTGACGAGGAGCACCACTTCGAGTCCAGCGACGCCGGAGCTTCCAAAACCTACCCTCAGCAGGCTGGT
M S D E E H H F E S S D A G A S K T Y P Q Q A G
AACATCCGCAAGGGTGGTCACATCGTCATCAAGGGCCGTCCCTGCAAGGTTGTTGAGGTTTCGACTTCGAAG
N I R K G G H I V I K G R P C K V V E V S T S K
ACTGGGAAGCACGGTCACGCAAAGTGTCACTTTGTTGCTATCGACATCTTCACTGCTAAGAAGCTCGAGGAT
T G K H G H A K C H F V A I D I F T A K K L E D
ATTGTTCCCTCTTCCCACAATTGTGATGTTCCCCATGTGAACCGTATTGACTACCAGTTGATTGATATCTCT
I V P S S H N C D V P H V N R I D Y Q L I D I S
GAGAATGGCTTTGTTAGCCTTTTGACCGACAGTGGTGGCACCAAGGACGACCTCAAGCTTCCCACCGATGAT
E N G F V S L L T D S G G T K D D L K L P T D D
AATCTCAGCGCTCTGATGAAGAGTGGATTCGAGGAGGGAAAGGATGTGGTGGTGTCTGTCATGTCTTCCATG
N L S A L M K S G F E E G K D V V V S V M S S M
GGAGAGGAGCAGATCTGTGCCGTCAAGGAAGTTGGTGGTGGCAAGTAAAACCCATTCTCTGAGAGAGGATAA
G E E Q I C A V K E V G G G K
TCTTATTACCAGTGGTCAATGTTATAAGAACAAGAACTTGTTTTTTTTCCTTTTTCTAATTTAGATCATTTG
TGTTGTGTTTCTTTGTTGCAAGACAACCATTATCTATTATTGGTTTTGGATTGTTTPAAAAAAAAAAAAAAA
AAAAAAAAAA

FIG.95

Primer.
GCATGTCGACATGTCTGACGAGGAGCACC
SalI pKYLX71-sense-Canola-growth-eIF-5A
CACTGAATCAAAGGCCATGGAGTCAAAGATTCAAATAGAGGACCTAACAGAACTCGCCGTAAAGACTGGCGAACAGTTCATACAGAG
TCTCTTACGACTCAATGACAAGAAGAAAATCTTCGTC{AACATGGTGGAGCACGACACGCTTGTCTACCTCCAAAAATATCAAAGAT
ACAGTCTCAGAAGACCAAAGGGAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTCTTCAAAGC
AAGTGGATTGATGTGAT}[AACATGGTGGAGCACGACACGCTTGTCTACCTCCAAAAATATCAAAGATACAGTCTCAGAAGACCAAA
GGGAATTGAGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGACAGTGGTCC
CAAAGATGGACCCCCACCCACGAGGAGCATCGTGGAAAAAGAAGACGTTCCAACCACGTCTTCAAAGCAAGTGGATTGATGTGAT]A
TCTCCACTGACGTAAGGGATGACGCACAATCCCACTATCCTTCGCAAGACCCTTCCTCTATATAAGGAAGTTCATTTCATTTGGAGA
GGACACGCTGAAATCACCAGTCTCTCTCTAAGCTTGGATC
← pKYLX71-double 35S promoter
CTCGAC(XhoI/SalI combination)
TCGACATGTCTGACGAGGAGCACCACTTCGAGTCCAGCGACGCCGGAGCTTCCAAAACCTACCCTCAGCAGGCTGGTAACATCCGCA
AGGGTGGTCACATCGTCATCAAGGGCCGTCCCTGCAAGGTTGTTGAGGTTTCGACTTCGAAGACTGGGAAGCACGGTCACGCAAAGT
GTCACTTTGTTGCTATTGACATCTTCACTGCTAAGAAGCTCGAGGATATTGTTCCCTCTTCCCACAATTGTGATGTTCCCCATGTGA
ACCGTATTGACTACCAGTTGATTGATATCTCTGAGAATGGCTTTGTTAGCCTTTTGACCGACAGTGGTGGCACCAAGGACGACCTCA
AGCTTCCCACCGATGATAATCTCAGCGCTCTGATGAAGAGTGGATTCGAGGAGGGAAAGGATGTGGTGGTGTCTGTCATGTCTTCCA
TGGGAGAGGAGCAGATCTGTGCCGTCAAGGAAGTTGGTGGTGGCAAGTAAAACCCATTCTCTGAGAGAGGATAATCTTATTACCAGT
GGTCAATGTTATAAGAACAAGAACTTGTTTTTTTTCCTTTTTCTAATTTAGATCATTTGTGTTGTGTTTCTTTGTTGCAAGACAACC
ATTATCTATTATTGGTTTTGGATTGTTTAAAAAAAAAAAAAAAAAAAAAAAA
(SacI) GAGCTC → rbcS-terminater
GAATTGATCCTCTAGAGCTTTCGTTCGTATCATCGGTTTCGACAACGTTCGTCAAGTTCAATGCATCAGTTTCATTGCGCACACACC
AGAATCCTACTGAGTTCGAGTATTATGGCATTGGGAAAACTGTTTTTCTTGTACCATTTGTTGTGCTTGTAATTTACTGTGTTTTTT
ATTCGGTTTTCGCTATCGAACTGTGAAATGGAAATGGATGGAGAAGAGTTAATGAATGATATGGTCCTTTTGTTCATTCTCAAATTA
ATATTATTTGTTTTTTCTCTTATTTGTTGTGTGTTGAATTTGAAATTATAAGAGATATGCAAACATTTTGTTTTGAGTAAAAATGTG
TCAAATCGTGGCCTCTAATGACCGAAGTTAATATGAGGAGTAAAACACTTGTAGTTGTACCATTATGCTTATTCACTAGGCAACAAA
TATATTTTCAGACCTAGAAAAGCTGCAAATGTTACTGAATACAAGTATGTCCTCTTGTGTTTTAGACATTTATGAACTTTCCTTTAT
GTAATTTTCCAGAATCCTTGTCAGATTCTAATCATTGCTTTATAATTATAGTTATACTCATGGATTTGTAGTTGAGTATGAAAATAT
TTTTTAATGCATTTTATGACTTGCCAATTGATTGACAACATGCATCAATCGAT

FIG.96

Canola-DHS

```
          CTTGCTAGAACCCTAAAACTCCCTCCCAAAACTCTCCACATCTTCCGAGAAAGAAGATGGAGG
                                                                  M  E
AGGATCGTGTTCTCTCGTCTGTCCACTCAACGGTCTTCAAGGAATCCGAATCGTTGGAAGGAAAGTGCGACA
E  D  R  V  L  S  S  V  H  S  T  V  F  K  E  S  E  S  L  E  G  K  C  D
AAATCGAAGGATACGATTTCAACCAAGGAGTAAACTACCCGAAGCTCCTCCGATCCATGCTCACAACCGGCT
K  I  E  G  Y  D  F  N  Q  G  V  N  Y  P  K  L  L  R  S  M  L  T  T  G
TCCAAGCCTCAAACCTCGGCGACGTAATTGATGTCGTTAATCAAATGCTAGAGTGGAGACTCTCTGATGAAA
F  Q  A  S  N  L  G  D  V  I  D  V  V  N  Q  M  L  E  W  R  L  S  D  E
CTATAGCACCTGAAGACTGTAGTGAAGAGGAGAAGGATCCAGCGTATAGAGAGTCCGTGAAGTGTAAAATCT
T  I  A  P  E  D  C  S  E  E  E  K  D  P  A  Y  R  E  S  V  K  C  K  I
TTCTAGGCTTCACTTCGAATCTTGTTTCCTCTGGTGTTAGAGAGACTATTCGATACCTTGTTCAGCATCATA
F  L  G  F  T  S  N  L  V  S  S  G  V  R  E  T  I  R  Y  L  V  Q  H  H
TGGTTGATGTTATAGTTACTACAACTGGTGGCGTAGAGGAAGATCTCATCAAATGCCTTGCTCCTACTTTCA
M  V  D  V  I  V  T  T  T  G  G  V  E  E  D  L  I  K  C  L  A  P  T  F
AAGGTGATTTCTCTCTACCGGGTGCGTATCTTCGGTCAAAGGGATTGAACCGGATCGGGAACTTGCTTGTTC
K  G  D  F  S  L  P  G  A  Y  L  R  S  K  G  L  N  R  I  G  N  L  L  V
CTAATGATAACTACTGCAAGTTTGAGGATTGGATCATTCCCATCTTTGACCAGATGTTGAAGGAACAGAAAG
P  N  D  N  Y  C  K  F  E  D  W  I  I  P  I  F  D  Q  M  L  K  E  Q  K
AAGAGAGTGTGTTGTGGACGCCTTCTAAATTGTTAGCGCGGCTGGGGAAAGAAATAAATAATGAGAGTTCAT
E  E  S  V  L  W  T  P  S  K  L  L  A  R  L  G  K  E  I  N  N  E  S  S
ATCTTTATTGGGCATACAAGATGAATATTCCAGTGTTCTGCCGGGGGTTAACCGATGGCTCTCTCGGTGATA
Y  L  Y  W  A  Y  K  M  N  I  P  V  F  C  R  G  L  T  D  G  S  L  G  D
TGTTGTATTTTCACTCATTTCGTACCTCTGGCCTTGTCATCGATGTTGTGCAAGATATTAGAGCTATGAACG
M  L  Y  F  H  S  F  R  T  S  G  L  V  I  D  V  V  Q  D  I  R  A  M  N
GTGAAGCAGTCCATGCGACTCCAAGAAAGACAGGGATGATAATCCTTGGAGGGGGCTTGCCGAAGCACCACA
G  E  A  V  H  A  T  P  R  K  T  G  M  I  I  L  G  G  G  L  P  K  H  H
TATGTAATGCCAACATGATGCGTAACGGTGCGGATTACGCTGTGTTTATCAACACCGGGCAAGAGTTTGATG
I  C  N  A  N  M  M  R  N  G  A  D  Y  A  V  F  I  N  T  G  Q  E  F  D
GAAGTGACTCGGGTGCACGCCCTGATGAAGCAGTGTCTTGGGGTAAAATAAGGGGATCTGCTAAAACTGTCA
G  S  D  S  G  A  R  P  D  E  A  V  S  W  G  K  I  R  G  S  A  K  T  V
AGGTGTACTGTGATGCTACCATAGCCTTCCCTTTGTTGGTTGCTGAAACATTTGCCTCCAAGAGAGAACAAA
K  V  Y  C  D  A  T  I  A  F  P  L  L  V  A  E  T  F  A  S  K  R  E  Q
GCTGTGAGCACAAGACCTAAGCCCAAGAAAGCTTACGTCTCTTTTATCGGTTTGTTCTTCCATCTTGTTGTT
S  C  E  H  K  T  *
GTACCCTTTGTCCTGCTTTACATAACATTCATCTCTAAAACAATACTACCTCCTTTTGACAAAAAATAAAAA
AAATTGGAAAAATGGTTTCACAAGAATAAAAAAAAAAAAAAAAAAAA
```

FIG.97A

NT.
CTTGCTAGAACCCTAAAACTCCCTCCCAAAACTCTCCACATCTTCCGAGAAAGAAGATGGAGGAGGATCGTGTTCTCTCG
TCTGTCCACTCAACGGTCTTCAAGGAATCCGAATCGTTGGAAGGAAAGTGCGACAAAATCGAAGGATACGATTTCAACCA
AGGAGTAAACTACCCGAAGCTCCTCCGATCCATGCTCACAACCGGCTTCCAAGCCTCAAACCTCGGCGACGTAATTGATG
TCGTTAATCAAATGCTAGAGTGGAGACTCTCTGATGAAACTATAGCACCTGAAGACTGTAGTGAAGAGGAGAAGGATCCA
GCGTATAGAGAGTCCGTGAAGTGTAAAATCTTTCTAGGCTTCACTTCGAATCTTGTTTCCTCTGGTGTTAGAGAGACTAT
TCGATACCTTGTTCAGCATCATATGGTTGATGTTATAGTTACTACAACTGGTGGCGTAGAGGAAGATCTCATCAAATGCC
TTGCTCCTACTTTCAAAGGTGATTTCTCTCTACCGGGTGCGTATCTTCGGTCAAAGGGATTGAACCGGATCGGGAACTTG
CTTGTTCCTAATGATAACTACTGCAAGTTTGAGGATTGGATCATTCCCATCTTTGACCAGATGTTGAAGGAACAGAAAGA
AGAGAGTGTGTTGTGGACGCCTTCTAAATTGTTAGCGCGGCTGGGGAAAGAAATAAATAATGAGAGTTCATATCTTTATT
GGGCATACAAGATGAATATTCCAGTGTTCTGCCGGGGGTTAACCGATGGCTCTCTCGGTGATATGTTGTATTTTCACTCA
TTTCGTACCTCTGGCCTTGTCATCGATGTTGTGCAAGATATTAGAGCTATGAACGGTGAAGCAGTCCATGCGACTCCAAG
AAAGACAGGGATGATAATCCTTGGAGGGGGCTTGCCGAAGCACCACATATGTAATGCCAACATGATGCGTAACGGTGCGG
ATTACGCTGTGTTTATCAACACCGGGCAAGAGTTTGATGGAAGTGACTCGGGTGCACGCCCTGATGAAGCAGTGTCTTGG
GGTAAAATAAGGGGATCTGCTAAAACTGTCAAGGTGTACTGTGATGCTACCATAGCCTTCCCTTTGTTGGTTGCTGAAAC
ATTTGCCTCCAAGAGAGAACAAAGCTGTGAGCACAAGACCTAAGCCCAAGAAAGCTTACGTCTCTTTTATCGGTTTGTTC
TTCCATCTTGTTGTTGTACCCTTTGTCCTGCTTTACATAACATTCATCTCTAAAACAATACTACCTCCTTTTGACAAAAA
ATAAAAAAAAATTGGAAAAATGGTTTCACAAGAATAAAAAAAAAAAAAAAAAAAA (1335)

AA:
MEEDRVLSSVHSTVFKESESLEGKCDKIEGYDFNQGVNYPKLLRSMLTTGFQASNLGDVIDVVNQMLEWRLSDETIAPED
CSEEEKDPAYRESVKCKIFLGFTSNLVSSGVRETIRYLVQHHMVDVIVTTTGGVEEDLIKCLAPTFKGDFSLPGAYLRSK
GLNRIGNLLVPNDNYCKFEDWIIPIFDQMLKEQKEESVLWTPSKLLARLGKEINNESSYLYWAYKMNIPVFCRGLTDGSL
GDMLYFHSFRTSGLVIDVVQDIRAMNGEAVHATPRKTGMIILGGGLPKHHICNANMMRNGADYAVFINTGQEFDGSDSGA
RPDEAVSWGKIRGSAKTVKVYCDATIAFPLLVAETFASKREQSCEHKT (368)

FIG.97B

3'-UTR (SacI)
GGTGCACGCCCTGATGAAGCAGTGTCTTGGGGTAAAATAAGGGGATCTGCTAAAACTGTCAAGGTGTACTGTGATGCTAC
CATAGCCTTCCCTTTGTTGGTTGCTGAAACATTTGCCTCCAAGAGAGAACAAAGCTGTGAGCACAAGACCTAAGCCCAAG
AAAGCTTACGTCTCTTTTATCGGTTTGTTCTTCCATCTTGTTGTTGTACCCTTTGTCCTGCTTTACATAACATTCATCTC
TAAAACAATACTACCTCCTT'TTGACAAAAAATAAAAAAAATTGGAAAAATGGTTTCACAAGAATAAAAAAAAAAAAAA
AAAAA(XhoI)

pKYLX71-anti-3~-UTR-canola-DHS

CACTGAATCAAAGGCCATGGAGTCAAAGATTCAAATAGAGGACCTAACAGAACTCGCCGTAAAGACTGGCGAACAGTTCA
TACAGAGTCTCTTACGACTCAATGACAAGAAGAAAATCTTCGTC{AACATGGTGGAGCACGACACGCTTGTCTACCTCCA
AAAATATCAAAGATACAGTCTCAGAAGACCAAAGGGAATTGAGACTTTTCAACAAAGGGTAATATCCGGAAACCTCCTCG
GATTCCATTGCCCAGCTATCTGTCACTTTATTGTGAAGATAGTGGAAAAGGAAGGTGGCTCCTACAAATGCCATCATTGC
GATAAAGGAAAGGCCATCGTTGAAGATGCCTCTGCCGACAGTGGTCCCAAAGATGGACCCCCACCCACGAGGAGCATCGT
GGAAAAAGAAGACGTTCCAACCACGTCTTCAAAGCAAGTGGATTGATGTGAT}[AACATGGTGGAGCACGACACGCTTGT
CTACCTCCAAAAATATCAAAGATACAGTCTCAGAAGACCAAAGGGAATTGAGACTTTTCAACAAAGGGTAATATCCGGAA
ACCTCCTCGGATTCCATTGCCCAGCTATCTGTCACTTTATTGTGAAGATAGTGGAAAAGGAAGGTGGCTCCTACAAATGC
CATCATTGCGATAAAGGAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGAT]ATCTCCACTGACGTAAGG
GATGACGCACAATCCCACTATCCTTCGCAAGACCCTTCCTCTATATAAGGAAGTTCATTTCATTTGGAGAGGACACGCTG
AAATCACCAGTCTCTCTCTAAGCTTGGATC
← pKYLX71-double 35S promoter
CTCGAG(XhoI)
TTTTTTTTTTTTTTTTTTTTTTATTCTTGTGAAACCATTTTTCCAATTTTTTTTATTTTTTGTCAAAAGGAGGTAGTATTG
TTTTAGAGATGAATGTTATGTAAAGCAGGACAAAGGGTACAACAACAAGATGGAAGAACAAACCGATAAAAGAGACGTAA
GCTTTCTTGGGCTTAGGTCTTGTGCTCACAGCTTTGTTCTCTCTTGGAGGCAAATGTTTCAGCAACCAACAAAGGGAAGG
CTATGGTAGCATCACAGTACACCTTGACAGTTTTAGCAGATCCCCTTATTTTACCCCAAGACACTGCTTCATCAGGGCGT
GCACC
(SacI) GAGCTC → rbcS-terminater
GAATTGATCCTCTAGAGCTTTCGTTCGTATCATCGGTTTCGACAACGTTCGTCAAGTTCAATGCATCAGTTTCATTGCGC
ACACACCAGAATCCTACTGAGTTCGAGTATTATGGCATTGGGAAAACTGTTTTTCTTGTACCATTTGTTGTGCTTGTAAT
TTACTGTGTTTTTTATTCGGTTTTCGCTATCGAACTGTGAAATGGAAATGGATGGAGAAGAGTTAATGAATGATATGGTC
CTTTTGTTCATTCTCAAATTAATATTATTTGTTTTTTCTCTTATTTGTTGTGTGTTGAATTTGAAATTATAAGAGATATG
CAAACATTTTGTTTTGAGTAAAPATGTGTCAAATCGTGGCCTCTAATGACCGAAGTTAATATGAGGAGTAAAACACTTGT
AGTTGTACCATTATGCTTATTCACTAGGCAACAAATATATTTTCAGACCTAGAAAAGCTGCAAATGTTACTGAATACAAG
TATGTCCTCTTGTGTTTTAGACATTTATGAACTTTCCTTTATGTAATTTTCCAGAATCCTTGTCAGATTCTAATCATTGC
TTTATAATTATAGTTATACTCATGGATTTGTAGTTGAGTATGAAAATATTTTTTAATGCATTTTATGACTTGCCAATTGA
TTGACAACATGCATCAATCGAT

FIG.98

Tomato eIF-5A1 (Growth)

AAATTTCTCCTTCTCCTTAATCCTCTCCACCGGCGAACCGGCGAAGATCAAAACGATGTCGGACGAAGAGCACC
ACTTCGAATCCAAGGCCGATGCCGGAGCTTCAAAGACGTATCCTCAACAAGCTGGTACTATTCGTAAAGGTGGT
CACATCGTCATAAAAAATCGTCCTTGCAAGGTGGTTGAAGTTTCAACTTCCAAGACAGGCAAGCACGGTCATGC
TAAATGTCACTTCGTGGCAATTGACATTTTCACTGGAAAGAAACTTGAGGATATTGTTCCCTCTTCTCACAATT
GTGATGTTCCTCATGTGAATAGGACTGATTATCAACTTATTGATATCTCTGAGGATGGCTTTGTGAGTCTGTTG
ACTGAAAATGGTAACACCAAGGATGACTTGAGACTCCCAACTGATGATACTCTTCTGGCTCAGGTCAAAGATGG
TTTTGCTGAGGGGAAAGACCTGGTTCTATCAGTGATGTCTGCCATGGGAGAGGAGCAGATTTGTGGTATCAAGG
ACATTGGCCCTAAGTAGCTGCAGATGGTATTGGTGTATGTTTACAgagTTTCTATAAAAGATGTATTAAGAACC
AAAACTTCTTTACTTTCTCTTGCAGTTGCTCTATATAACTGCCATTTAACTATTATTatatgtgttgtgattag
attcttgtctcactacagtatttcctttactctg AA Sequence (159aa)

MSDEEHHFESIZADAGASKTYPQQAGTIRKGGHIVIKNRPCKWEVSTSKTGKHGHAKCHFVAIDIFTGKKLEDI
VPSSHNCDVPHVNRTDYQLIDTSEDGFVSLLTENGNTKDDLRLPTDDTLLAQVKDGFAEGKDLVLSVMSAMGEE
QICGIKDIGPK

AAATTTCTCCTTCTCCTTAATCCTCTCCACCGGCGAACCGGCGAAGATCAAAACGATGTCGGACGAAGAGCA
M S D E E H
CCACTTCGAATCCAAGGCCGATGCCGGAGCTTCAAAGACGTATCCTCAACAAGCTGGTACTATTCGTAAAGG
H F E S K A D A G A S K T Y P Q Q A G T I R K G
TGGTCACATCGTCATAAAAAATCGTCCTTGCAAGGTGGTTGAAGTTTCAACTTCCAAGACAGGCAAGCACGG
G H I V I K N R P C K V V E V S T S K T G K H G
TCATGCTAAATGTCACTTCGTGGCAATTGACATTTTCACTGGAAAGAAACTTGAGGATATTGTTCCCTCTTC
H A K C H F V A I D I F T G K K L E D I V P S S
TCACAATTGTGATGTTCCTCATGTGAATAGGACTGATTATCAACTTATTGATATCTCTGAGGATGGCTTTGT
H N C D V P F V N R T D Y Q L I D I S E D G F V
GAGTCTGTTGACTGAAAATGGTAACACCAAGGATGACTTGAGACTCCCAACTGATGATACTCTTCTGGCTCA
S L L T E N G N T K D D L R L P T D D T L L A Q
GGTCAAAGATGGTTTTGCTGAGGGGAAAGACCTGGTTCTATCAGTGATGTCTGCCATGGGAGAGGAGCAGAT
V K D G F A E G K D L V L S V M S A M G E E Q I
TTGTGGTATCAAGGACATTGGCCCTAAGTAGCTGCAGATGGTATTGGTGTATQTTTACAgagTTTCTATAAA
C G I K D I G P K *
AGATGTATTAAGAACCAAAACTTCTTTACTTTCTCTTGCAGTTGCTCTATATAACTGCCATTTAACTATTAT
Tatatgtgttgtgattagattcttgtctcactacagtatttcctttactctg

FIG.101

Primers:
Upstream primer:
AAGCTCGAGATGTCGGACGAAGAGCACC
XhoI

Downstream primer:
GTAGAGCTCCACCAATACCATCTGCAGC
SacI pKYLX71-sense-Tomato-growth-eIF-5A CACTGAATCAAAGGCCATGGAGTCAAAGATTCAAATAGAGGACCTAACAGAACTCGCCGTAAAGACTGGCGAACAGTTCATACAGAGTC
TCTTACGACTCAATGACAAGAAGAAAATCTTCGTC{AACATGGTGGAGCACGACACGCTTGTCTACCTCCAAAAATATCAAAGATACAG
TCTCAGAAGACCAAAGGGAATTGAGACTTTTCAACAAAGGGTAATATCCGGAAACCTCCTCGGATTCCATTGCCCAGCTATCTGTCACT
TTATTGTGAAGATAGTGGAAAAGGAAGGTGGCTCCTACAAATGCCATCATTGCGATAAAGGAAAGGCCATCGTTGAAGATGCCTCTGCC
GACAGTGGTCCCAAAGATGGACCCCCACCCACGAGGAGCATCGTGGAAAAAGAAGACGTTCCAACCACGTCTTCAAAGCAAGTGGATTG
ATGTGAT}[AACATGGTGGAGCACGACACGCTTGTCTACCTCCAAAAATATCAAAGATACAGTCTCAGAAGACCAAAGGGAATTGAGAC
TTTTCAACAAAGGGTAATATCCGGAAACCTCCTCGGATTCCATTGCCCAGCTATCTGTCACTTTATTGTGAAGATAGTGGAAAAGGAAG
GTGGCTCCTACAAATGCCATCATTGCGATAAAGGAAAGGCCATCGTTGAAGATGCCTCTGCCGACAGTGGTCCCAAAGATGGACCCCCA
CCCACGAGGAGCATCGTGGAAAAAGAAGACGTTCCAACCACGTCTTCAAAGCAAGTGGATTGATGTGAT]ATCTCCACTGACGTAAGGG
ATGACGCACAATCCCACTATCCTTCGCAAGACCCTTCCTCTATATAAGGAAGTTCATTTCATTTGGAGAGGACACGCTGAAATCACCAG
TCTCTCTCTAAGCTTGGATC

FIG.102A

← pKYLX71-double 35S promoter

<u>CTCGAG</u> (XhoI)

ATGTCGGACGAAGAGCACCACTTCGAATCCAAGGCCGATGCCGGAGCTTCAAAGACGTATCCTCAACAAGCTGGTACTATTCGTAAAGG
TGGTCACATCGTCATAAAAAATCGTCCTTGCAAGGTGGTTGAAGTTTCAACTTCCAAGACAGGCAAGCACGGTCATGCTAAATGTCACT
TCGTGGCAATTGACATTTTCACTGGAAAGAAACTTGAGGATATTGTTCCCTCTTCTCACAATTGTGATGTTCCTCATGTGAATAGGACT
GATTATCAACTTATTGATATCTCTGAGGATGGCTTTGTGAGTCTGTTGACTGAAAATGGTAACACCAAGGATGACTTGAGACTCCCAAC
TGATGATACTCTTCTGGCTCAGGTCAAAGATGGTTTTGCTGAGGGGAAAGACCTGGTTCTATCAGTGATGTCTGCCATGGGAGAGGAGC
AGATTTGTGGTATCAAGGACATTGGCCCTAAGTAGCTGCAGATGGTATTGGTG (SacI) <u>GAGCTC</u> → rbcS-terminater GAATTGATCCTCTAGAGCTTTCGTTCGTATCATCGGTTTCGACAACGTTCGTCAAGTTCAATGCATCAGTTTCATTGCGCACACACCAG
AATCCTACTGAGTTCGAGTATTATGGCATTGGGAAAACTGTTTTTCTTGTACCATTTGTTGTGCTTGTAATTTACTGTGTTTTTTATTC
GGTTTTCGCTATCGAACTGTGAAATGGAAATGGATGGAGAAGAGTTAATGAATGATATGGTCCTTTTGTTCATTCTCAAATTAATATTA
TTTGTTTTTTCTCTTATTTGTTGTGTGTTGAATTTGAAATTATAAGAGATATGCAAACATTTTGTTTTGAGTAAAAATGTGTCAAATCG
TGGCCTCTAATGACCGAAGTTAATATGAGGAGTAAAACACTTGTAGTTGTACCATTATGCTTATTCACTAGGCAACAAATATATTTTCA
GACCTAGAAAAGCTGCAAATGTTACTGAATACAAGTATGTCCTCTTGTGTTTTAGACATTTATGAACTTTCCTTTATGTAATTTTCCAG
AATCCTTGTCAGATTCTAATCATTGCTTTATAATTATAGTTATACTCATGGATTTGTAGTTGAGTATGAAAATATTTTTTAATGCATTT
TATGACTTGCCAATTGATTGACAACATGCATCAATCGAT

FIG.102B

TeIF-5A3 (Wounding)

CTTCCTGAATTTTTCTCcTTCTCCTTCTCCGTTCAATCGAATTTTTCAGCCATGTCTGACGAGG
AGCATCAATTTGAGTCTAAGGCTGATGCCGGAGCATCAAAAACTTACCCTCAACAAGCTGGTAC
TATTCGTAAGAACGGTTATATCGTCATCAAAGGCCGTCCATGCAAGGTTGTGGAAGTCTCTACA
TCCAAAACTGGCAAGCACGGTCACGCCAAATGTCATTTCGTTGCTATTGACATCTTCACTGGGA
AGAAGCTTGAGGATATTGTCCCCTCTTCACACAATTGTGATGTGCCCCATGTTAATCGTACAGA
TTATCAGCTTATTGACATCTCTGAAGATGGATTTGTGAGTCTGCTTACTGACAATGGTAACACC
AAGGATGACCTCAGGCTTCCTACTGATGAAAATCTGCTTTCACTGATCAAGGACGGGTTTGCCG
AGGGTAAGGACCTCGTTGTGTCTGTTATGTCAGCTATGGGTGAGGAACAGATTAATGCTTTGAA
GGATATTGGCCCCAAGTGATCTCTTGATTGGATGGATTGCTTGACGCGATGGTTCTTTACGACC
TTGAGTGAGATAGATATTTATAGTCATGGAAAAAAATTGTGATCTTATGGAATATTCGTATCAT
GATTTATGGACCATTGTGAGTTAGATTTTTATTTATGTTGTTTTAAATTGTGGTATTC (698 bps)

AA Sequence (159aa)

MSDEEHQFESKADAGASKTYPQQAGTIRKNGYIVIKGRPCKVVEVSTSKTGKHGHAKCHFVAID
IFTGKKLEDIVPSSHNCDVPHVNRTDYQLIDISEDGFVSLLTDNGNTKDDLRLPTDENLLSLIK
DGFAEGKDLWSVMSAMGEEQINALKDIGPK

CTTCCTGAATTTTTCTCcTTCTCCTTCTCCGTTCAATCGAATTTTTCAGCCATGTCTGAC
M S D
GAGGAGCATCAATTTGAGTCTAAGGCTGATGCCGGAGCATCAAAAACTTACCCTCAACAA
E E H Q F E S K A D A G A S K T Y P Q Q
GCTGGTACTATTCGTAAGAACGGTTATATCGTCATCAAAGGCCGTCCATGCAAGGTTGTG
A G T I R K N G Y I V I K G R P C K V V
GAAGTCTCTACATCCAAAACTGGCAAGCACGGTCACGCCAAATGTCATTTCGTTGCTATT
E V S T S K T G K H G H A K C H F V A I
GACATCTTCACTGGGAAGAAGCTTGAGGATATTGTCCCCTCTTCACACAATTGTGATGTG
D I F T G K K L E D I V P S S H N C D V
CCCCATGTTAATCGTACAGATTATCAGCTTATTGACATCTCTGAAGATGGATTTGTGAGT
P H V N R T D Y Q L I D I S E D G F V S
CTGCTTACTGACAATGGTAACACCAAGGATGACCTCAGGCTTCCTACTGATGAAAATCTG
L L T D N G N T K D D L R L P T D E N L
CTTTCACTGATCAAGGACGGGTTTGCCGAGGGTAAGGACCTCGTTGTGTCTGTTATGTCA
L S L I K D G F A E G K D L V V S V M S
GCTATGGGTGAGGAACAGATTAATGCTTTGAAGGATATTGGCCCCAAGTGATCTCTTGAT
A M G E E Q I N A L K D I G P K *
TGGATGGATTGCTTGACGCGATGGTTCTTTACGACCTTGAGTGAGATAGATATTTATAGT
CATGGAAAAAAATTGTGATCTTATGGAATATTCGTATCATGATTTATGGACCATTGTGAG
TTAGATTTTTATTTATGTTGTTTTAAATTGTGGTATTC

FIG. 103

Primers
Upstream primer·
CGACTCGAGCAGCCATGTCTGACGAGG
XhoI

Downstream primer.
ATCGAGCTCATCACTTGGGGCCAATATCC
SacI pKYLX71-sense-Tomato-wounding-eIF-5A CACTGAATCAAAGGCCATGGAGTCAAAGATTCAAATAGAGGACCTAACAGAACTCGCCGTAAAG
ACTGGCGAACAGTTCATACAGAGTCTCTTACGACTCAATGACAAGAAGAAAATCTTCGTC{AAC
ATGGTGGAGCACGACACGCTTGTCTACCTCCAAAAATATCAAAGATACAGTCTCAGAAGACCAA
AGGGAATTGAGACTTTTCAACAAAGGGTAATATCCGGAAACCTCCTCGGATTCCATTGCCCAGC
TATCTGTCACTTTATTGTGAAGATAGTGGAAAAGGAAGGTGGCTCCTACAAATGCCATCATTGC
GATAAAGGAAAGGCCATCGTTGAAGATGCCTCTGCCGACAGTGGTCCCAAAGATGGACCCCCAC
CCACGAGGAGCATCGTGGAAAAAGAAGACGTTCCAACCACGTCTTCAAAGCAAGTGGATTGATG
TGAT}[AACATGGTGGAGCACGACACGCTTGTCTACCTCCAAAAATATCAAAGATACAGTCTCA
GAAGACCAAAGGGAATTGAGACTTTTCAACAAAGGGTAATATCCGGAAACCTCCTCGGATTCCA
TTGCCCAGCTATCTGTCACTTTATTGTGAAGATAGTGGAAAAGGAAGGTGGCTCCTACAAATGC
CATCATTGCGATAAAGGAAAGGCCATCGTTGAAGATGCCTCTGCCGACAGTGGTCCCAAAGATG
GACCCCCACCCACGAGGAGCATCGTGGAAAAAGAAGACGTTCCAACCACGTCTTCAAAGCAAGT
GGATTGATGTGAT]ATCTCCACTGACGTAAGGGATGACGCACAATCCCACTATCCTTCGCAAGA
CCCTTCCTCTATATAAGGAAGTTCATTTCATTTGGAGAGGACACGCTGAAATCACCAGTCTCTC
TCTAAGCTTGGATC
← pKYLX71-double 35S promoter
CTCGAG (Xho I)
CAGCCATGTCTGACGAGGAGCATCAATTTGAGTCTAAGGCTGATGCCGGAGCATCAAAAACTTA
CCCTCAACAAGCTGGTACTATTCGTAAGAACGGTTATATCGTCATCAAAGGCCGTCCATGCAAG
GTTGTGGAAGTCTCTACATCCAAAACTGGCAAGCACGGTCACGCCAAATGTCATTTCGTTGCTA
TTGACATCTTCACTGGGAAGAAGCTTGAGGATATTGTCCCCTCTTCACACAATTGTGATGTGCC
CCATGTTAATCGTACAGATTATCAGCTTATTGACATCTCTGAAGATGGATTTGTGAGTCTGCTT
ACTGACAATGGTAACACCAAGGATGACCTCAGGCTTCCTACTGATGAAAATCTGCTTTCACTGA
TCAAGGACGGGTTTGCCGAGGGTAAGGACCTCGTTGTGTCTGTTATGTCAGCTATGGGTGAGGA
ACAGATTAATGCTTTGAAGGATATTGGCCCCAAGTGAT

FIG.104A (SacI) GAGCTC → rbcS-terminater

GAATTGATCCTCTAGAGCTTTCGTTCGTATCATCGGTTTCGACAACGTTCGTCAAGTTCAATGC
ATCAGTTTCATTGCGCACACACCAGAATCCTACTGAGTTCGAGTATTATGGCATTGGGAAAACT
GTTTTTCTTGTACCATTTGTTGTGCTTGTAATTTACTGTGTTTTTTATTCGGTTTTCGCTATCG
AACTGTGAAATGGAAATGGATGGAGAAGAGTTAATGAATGATATGGTCCTTTTGTTCATTCTCA
AATTAATATTATTTGTTTTTTCTCTTATTTGTTGTGTGTTGAATTTGAAATTATAAGAGATATG
CAAACATTTTGTTTTGAGTAAAAATGTGTCAAATCGTGGCCTCTAATGACCGAAGTTAATATGA
GGAGTAAAACACTTGTAGTTGTACCATTATGCTTATTCACTAGGCAACAAATATATTTTCAGAC
CTAGAAAAGCTGCAAATGTTACTGAATACAAGTATGTCCTCTTGTGTTTTAGACATTTATGAAC
TTTCCTTTATGTAATTTTCCAGAATCCTTGTCAGATTCTAATCATTGCTTTATAATTATAGTTA
TACTCATGGATTTGTAGTTGAGTATGAAAATATTTTTTAATGCATTTTATGACTTGCCAATTGA
TTGACAACATGCATCAATCGAT

FIG. 104B

Lettuce

Primers used to construct "Antisense Lettuce (*Lactuca sativa*) 3'DHS in pTA7001"

Forward Primer: 5'-CACTGCTCACTAGTTTGATGGC-3'
(underlined portion: the recognition sequence for the restriction enzyme *Spe*I)

Reverse Primer: 5'-GCGAAGCGGCCATGGCTCGAGTTTTTTTTTTTTTTTTT-3'
(underlined portion: includes recognition sequence for the restriction enzyme *Xho*I)

Portion of Lettuce *(Lactuca sativa)* DAIS gene amplified by the above primers (PCR product: 413 bp)

CACTGCTCACTAGTTTGATGGCAGTGATTCTGGTGCTCGACCTGATGAAGCTGTCTCCT
GGGGGAAAATACGTGGTTCTGCTAAATCTGTCAAGGTGCACTGTGATGCAACTATCGCG
TTCCCTTTACTTGTTGCAGAAACATTTGCTGCAAAGAGAGAGGGGGAGATGAAAAATGT
TGAGTCAACCAAAGCTTTGGTTTAAAAAGGTGGAACAGTGTAGGACAGGGACTCATTTT
TGATATTTTGTTTGCTAAAAAATGGTCTTTGGAAGAATATTGATGCACACAAACAAGGA
GACAATGTTACTGATCTTGGAGAGTGTACATGTAAAATGTCTAAATAATTTCAAAGCTT
CTCACAACAAATCAAACTTAAAAAAAAAAAAAAAAAACTCGAGCCATGGCCGCTTCGC

Portion of Lettuce *(Lactuca sativa)* DHS gene amplified by the above primers, and cut with *Spe*I and *Xho*I, which was then ligated into the pTA7001 vector at the *Spe*I and *Xho*I cloning site

CTAGTTTGATGGCAGTGATTCTGGTGCTCGACCTGATGAAGCTGTCTCCTGGGGGAAAA
TACGTGGTTCTGCTAAATCTGTCAAGGTGCACTGTGATGCAACTATCGCGTTCCCTTTA
CTTGTTGCAGAAACATTTGCTGCAAAGAGAGAGGGGGAGATGAAAAATGTTGAGTCAAC
CAAAGCTTTGGTTTAAAAKGGTGGAACAGTGTAGGACAGGGACTCATTTTTGATATTTT
GTTTGCTAAAAAATGGTCTTTGGAAGAATATTGATGCACACAAACAAGGAGACAATGTT
ACTGATCTTGGAGAGTGTACATGTAAAATGTCTAAATAATTTCAAAGCTTCTCACAACA
AATCAAACTTAAAAAAAAAAAAAAAAAACTCGA

FIG. 105

The insert is the 3'-UTR of Antisense Lettuce DHS

Alfalfa DHS cDNA

```
GAAACCTTCTTCTTCTGGAGCAAAGTCGCCATTCCCTACCTCCTTCTTCATTCTTATTCT
CTATAACAAACGGTCCGACCGGATCCAAGTTGCACCGGTTCGAACCGCTTTAGTTACTAC
TAACGGTTCGAACCGTTATTTTTCAACCCGTGACAAACGTGGAAGGCTTCGTTGTTTCTT
CTTCTTCTTCTTAATTACCATGCGTTTTTGTTTTTCTTTTGAGTCATTGAAGTCTTGTTT
TTTGTCGTGTTTCTGTCTTGAGACCGTGAAAGAGAAAACAAAGAGTACGAGAATGAGTGA
                                                        M  S  E
AACAAAGCAAGAAGATGATACAATTATGTCCTCAGTTCACTCCACTGTCTTCAAAGAATC
  T  K  Q  E  D  D  T  I  M  S  S  V  H  S  T  V  F  K  E  S
CGAAAATCTCGCAGGAAAGTGTGTCCAAATCGAGGGTTATGATTTCAACCGCGGCGTCGA
  E  N  L  A  G  K  C  V  Q  I  E  G  Y  D  F  N  R  G  V  D
TTATCAACAGCTTCTCAAATCAATGCTCACAACTGGTTTTCAAGCTTCCAACTTTGGTGA
  Y  Q  Q  L  L  K  S  M  L  T  T  G  F  Q  A  S  N  F  G  D
TGCCGTTAAAGTCGTTAATCAAATGCTAGATTGGAGGTTGGTTGATGAACCAATTGATGA
  A  V  K  V  V  N  Q  M  L  D  W  R  L  V  D  E  P  I  D  E
GGATTGTGATGAAGATAAGAAGGATTTGGAGTATAGGAAATCTGTTACATGCAAAGTGTT
  D  C  D  E  D  K  K  D  L  E  Y  R  K  S  V  T  C  K  V  F
TTTGGGTTTCACTTCTAATCTTATCTCTTCTGGTGTTAGAGATGTTGTTCGTTACCTTTG
  L  G  F  T  S  N  L  I  S  S  G  V  R  D  V  V  R  Y  L  C
TCAGCATCACATGGTTCATGTAGTTGTTACAACTACAGGTGGTATTGAAGAAGATCTTAT
  Q  H  H  M  V  H  V  V  V  T  T  T  G  G  I  E  E  D  L  I
AAAGTGCCTTGCACCAACATATAAAGGAGAGTTCTCTTTGCCCGGAGCTTATCTTCGCTC
  K  C  L  A  P  T  Y  K  G  E  F  S  L  P  G  A  Y  L  R  S
AAAAGGATTGAATCGAATCGGTAATTTATTGGTCCCTAATGAAAATTATTGCAAATTTGA
  K  G  L  N  R  I  G  N  L  L  V  P  N  E  N  Y  C  K  F  E
GGACTGGATTATTCCTATTTTTGATCAAATGTTGAAGGAGCAAAAGGAAGAGAAAGTGCT
  D  W  I  I  P  I  F  D  Q  M  L  K  E  Q  K  E  E  K  V  L
GTGGACACCGTCTAAGTTAATAGCTCGATTGGGAAAAGAGATCAACAATGAAAACTCCTA
  M  T  P  S  K  L  I  A  R  L  G  K  E  I  N  N  E  N  S  Y
CCTTTACTGGGCATATAAGAACAATATTCCAGTTTATTGTCCAGGATTAACCGATGGCTC
  L  Y  W  A  Y  K  N  N  I  P  V  Y  C  P  G  L  T  D  G  S
ACTGGGTGACATGCTGTACTTCCATTCCTTCCACAACCCTGGTCTGATTGTGGACATAGT
  L  G  D  M  L  Y  F  H  S  F  H  N  P  G  L  I  V  D  I  V
GCAAGATATAAGGGCCATGAATGGTGAAGCTGTACATGCAAATCCTAGCAAGACGGGCAT
  Q  D  I  R  A  M  N  G  E  A  V  H  A  N  P  S  K  T  G  M
GATTATTTTAGGAGGCGGCCTTCCAAAACATCACATTTGCAATGCCAATATGATGCGCAA
  I  I  L  G  G  G  L  P  K  H  H  I  C  N  A  N  M  M  R  N
TGGTGCAGACTATGCGGTTTTTATTAATACTGCACAAGAATTTGATGGAAGTGATTCTGG
  G  A  D  Y  A  V  F  I  N  T  A  Q  E  F  D  G  S  D  S  G
AGCTCGTCCAGATGAGGCTGTTTCATGGGGGAAAATACGAGGATCTGCTAAAACTGTTAA
  A  R  P  D  E  A  V  S  W  G  K  I  R  G  S  A  K  T  V  K
GGTACATTGTGATGCAACGATAGCATTCCCTCTGCTGGTTGCTGAAACATTTGCCTCAAG
  V  H  C  D  A  T  I  A  F  P  L  L  V  A  E  T  F  A  S  R
AACGTCACCCCTTAATTGATAAAGGTCCACCGTCAAAAGTAAAAGGTGTGGCTGGGAAGT
  T  S  P  L  N  *
GTTTTACCGCAGCTCCACTTGTGAGTGCCAAATGTTTTGGTATGTAACTTATAAGACCAA
GGTCGGCTGTATGTCATACTTGAGTTGAGGTCAAAGTTCATTTGCAATGCAGTGTGTTTG
AGGATCTTGATGGACCAGTTTGCCATTGACTTTTAATTTGACTGTCTTGTTATTCGCAAG
GTCCACATAACAAGCATTTTTACCATTTAGAAACAATTTATTAGTCCTGAAGGAATTGAG
AGTCATGAATTCAGATGTAAATTATGCAATGCTAACTATATTTTTTTGGAACTGTGGTTT
CTCTTAGATTTGAGGTGTTGAAAACTGTAATATCTAGAGCAAATAAGACTAGAAAAGTTT
ATCAACTATTACTGATCAGTTATAGTATCTTCAATATTTTCCAGAAAAAAAAAAAAAAAA
A
```

FIG.107A

Alfalfa

Nucleic acid (1861 bp)

GAAACCTTCTTCTTCTGGAGCAAAGTCGCCATTCCCTACCTCCTTCTTCATTCTTATTCTCTATAACAAACGGTCCG
ACCGGATCCAAGTTGCACCGGTTCGAACCGCTTTAGTTACTACTAACGGTTCGAACCGTTATTTTTCAACCCGTGAC
AAACGTGGAAGGCTTCGTTGTTTCTTCTTCTTCTTCTTAATTACCATGCGTTTTTGTTTTTCTTTTGAGTCATTGAA
GTCTTGTTTTTTGTCGTGTTTCTGTCTTGAGACCGTGAAAGAGAAAACAAAGAGTACGAGAATGAGTGAAACAAAGC
AAGAAGATGATACAATTATGTCCTCAGTTCACTCCACTGTCTTCAAAGAATCCGAAAATCTCGCAGGAAAGTGTGTC
CAAATCGAGGGTTATGATTTCAACCGCGGCGTCGATTATCAACAGCTTCTCAAATCAATGCTCACAACTGGTTTTCA
AGCTTCCAACTTTGGTGATGCCGTTAAAGTCGTTAATCAAATGCTAGATTGGAGGTTGGTTGATGAACCAATTGATG
AGGATTGTGATGAAGATAAGAAGGATTTGGAGTATAGGAAATCTGTTACATGCAAAGTGTTTTTGGGTTTCACTTCT
AATCTTATCTCTTCTGGTGTTAGAGATGTTGTTCGTTACCTTTGTCAGCATCACATGGTTCATGTAGTTGTTACAAC
TACAGGTGGTATTGAAGAAGATCTTATAAAGTGCCTTGCACCAACATATAAAGGAGAGTTCTCTTTGCCCGGAGCTT
ATCTTCGCTCAAAAGGATTGAATCGAATCGGTAATTTATTGGTCCCTAATGAAAATTATTGCAAATTTGAGGACTGG
ATTATTCCTATTTTTGATCAAATGTTGAAGGAGCAAAAGGAAGAGAAAGTGCTGTGGACACCGTCTAAGTTAATAGC
TCGATTGGGAAAAGAGATCAACAATGAAAACTCCTACCTTTACTGGGCATATAAGAACAATATTCCAGTTTATTGTC
CAGGATTAACCGATGGCTCACTGGGTGACATGCTGTACTTCCATTCCTTCCACAACCCTGGTCTGATTGTGGACATA
GTGCAAGATATAAGGGCCATGAATGGTGAAGCTGTACATGCAAATCCTAGCAAGACGGGCATGATTATTTTAGGAGG
CGGCCTTCCAAAACATCACATTTGCAATGCCAATATGATGCGCAATGGTGCAGACTATGCGGTTTTTATTAATACTG
CACAAGAATTTGATGGAAGTGATTCTGGAGCTCGTCCAGATGAGGCTGTTTCATGGGGAAAATACGAGGATCTGCT
AAAACTGTTAAGGTACATTGTGATGCAACGATAGCATTCCCTCTGCTGGTTGCTGAAACATTTGCCTCAAGAACGTC
ACCCCTTAATTGATAAAGGTCCACCGTCAAAAGTAAAAGGTGTGGCTGGGAAGTGTTTTACCGCAGCTCCACTTGTG
AGTGCCAAATGTTTTGGTATGTAACTTATAAGACCAAGGTCGGCTGTATGTCATACTTGAGTTGAGGTCAAAGTTCA
TTTGCAATGCAGTGTGTTTGAGGATCTTGATGGACCAGTTTGCCATTGACTTTTAATTTGACTGTCTTGTTATTCGC
AAGGTCCACATAACAAGCATTTTTACCATTTAGAAACAATTTATTAGTCCTGAAGGAATTGAGAGTCATGAATTCAG
ATGTAAATTATGCAATGCTAACTATATTTTTTTGGAACTGTGGTTTCTCTTAGATTTGAGGTGTTGAAAACTGTAAT
ATCTAGAGCAAATAAGACTAGAAAAGTTTATCAACTATTACTGATCAGTTATAGTATCTTCAATATTTTCCAGAAAA
AAAAAAAAAAAAA

Amino acid (368)

MSETKQEDDTIMSSVHSTVFKESENLAGKCVQIEGYDFNRGVDYQQLLKSMLTTGFQASNFGDAVKVVNQMLDWRLV
DEPIDEDCDEDKKDLEYRKSVTCKVFLGFTSNLISSGVRDVVRYLCQHHMVHVVVTTTGGIEEDLIKCLAPTYKGEF
SLPGAYLRSKGLNRIGNLLVPNENYCKFEDWIIPIFDQMLKEQKEEKVLWTPSKLIARLGKEINNENSYLYWAYKNN
IPVYCPGLTDGSLGDMLYFHSFHNPGLIVDIVQDIRAMNGEAVHANPSKTGMIILGGGLPKHHICNANMMRNGADYA
VFINTAQEFDGSDSGARPDEAVSWGKIRGSAKTVKVHCDATIAFPLLVAETFASRTSPLN

FIG. 107B

Banana DHS cDNA

GGCACGAGCGCGCGGCGCCCGCAACGAATATTGCAGAGAGTAAGAAGGATCCTCGCCTTTGTCACCAAACC
CTTGGTTTCCAGCGAGGCGACATGGAAGGCGGCGCCGCGGGAGGGCAGCGAGACCGGGAAACCCTGGACGC
M E G G A A G G Q R D R E T L D A
GGTGCGGTCGGTGGTGTTTAAGCCTTCCGTATCCTTGGAGGAGAAGCGGTTCCCGAGGGTCCAGGGGTACG
V R S V V F K P S V S L E E K R F P R V Q G Y
ACTTCAACCGGGGTTGTGACCTCATCGGCCTCCTCGATTCCATCTCCTCTACCGGGTTCCAAGCTTCCAAC
D F N R G C D L I G L L D S I S S T G F Q A S N
CTCGGCGACGCCATCGATGTCATCAATCAGATGATTGACTGGAGGCTCTCCCATGATGCGCCCACGGAAGA
L G D A I D V I N Q M I D W R L S H D A P T E D
TTGCAGCGAGGAAGAGCGCAATCTGGCTTACAGGCAATCGGTCACGTGCAAGATCTTTCTGGGCTTCACTT
C S E E E R N L A Y R Q S V T C K I F L G F T
CGAACCTTGTATCTTCTGGCATCAGGGAGATAATTCGGTTTCTTGTGCAGCACCGAATGGTTGAAGTTTTA
S N L V S S G I R E I I R F L V Q H R M V E V L
GTCACAACTGCTGGCGGCATTGAAGAAGATTTAATCAAATGCCTTGCTCCAACATATAAGGGTGACTTTTC
V T T A G G I E E D L I K C L A P T Y K G D F S
TTTGCCTGGATCGTATCTGCGTTCAAAAGGATTGAATCGGATAGGAAACCTTCTTGTCCCTAATGACAATT
L P G S Y L R S K G L N R I G N L L V P N D N
ACTGCAAATTCGAGGACTGGATCATGCCAATTCTGGACCAGATGTTACTTGAACAGACTACAGAGAATGTA
Y C K F E D W I M P I L D Q M L L E Q T T E N V
GTTTGGACACCATCTAAAGTGATTGCGCGCCTTGGAAAAGAAATAAATGATGAAAGTTCATACCTGTACTG
V W T P S K V I A R L G K E I N D E S S Y L Y W
GGCATACAAGAACAATGTTTCTGTCTATTGCCCGGCATTGACTGATGGATCATTGGGGGATATGTTGTACT
A Y K N N V S V Y C P A L T D G S L G D M L Y
GCCATTCAGTGCGGAATCCTGGTTTACTTATTGATATTGTGCAAGACATACGAGCAATGAATGGAGAAGCT
C H S V R N P G L L I D I V Q D I R A M N G E A
GTACATGTGGGTCTGAGAAAGACTGGGGTCATAATTCTTGGTGGGGGCCTCCCAAAGCACCATATATGTAA
V H V G L R K T G V I I L G G G L P K H H I C N
TGCCAACATGTTTCGGAATGGTGCAGATTATGCTGTTTATGTCAACACTGCACAGGAATTTGATGGAAGTG
A N M F R N G A D Y A V Y V N T A Q E F D G S
ATTCTGGAGCAGAGCCTGATGAGGCGATTTCATGGGGAAAGATAAAAGGTTCTGCGAAGACTATTAAAGTT
D S G A E P D E A I S W G K I K G S A K T I K V
CATTGTGATGCAACTATTGCTTTTCCTCTATTGGTAGCTGCAACATTTGCAAGAAAGTTTCAGGAAAGAAA
H C D A T I A F P L L V A A T F A R K F Q E R N
CAACAAATTAGCCTGATGGGGGTGCAAAAGGTGATCATCTTATTTGGATTCPAATACCTTAATGTAATCTG
N K L A
CTAACATCTGCAGATGCTGTATTCTTGCAAACCAAAAATTTAATATTAGATAACCGAGAGCCTACAGAGGG
TCCTTTCAAAAAAA

FIG. 108A

Banana
Nucleic acid (1363 bp)

GGCACGAGCGCGCGGCGCCCGCAACGAATATTGCAGAGAGTAAGAAGGATCCTCGCCTTTGTCACCAAACCCTTGGT
TTCCAGCGAGGCGACATGGAAGGCGGCGCCGCGGGAGGGCAGCGAGACCGGGAAACCCTGGACGCGGTGCGGTCGGT
GGTGTTTAAGCCTTCCGTATCCTTGGAGGAGAAGCGGTTCCCGAGGGTCCAGGGGTACGACTTCAACCGGGGTTGTG
ACCTCATCGGCCTCCTCGATTCCATCTCCTCTACCGGQTTCCAAGCTTCCAACCTCGGCGACGCCATCGATGTCATC
AATCAGATGATTGACTGGAGGCTCTCCCATGATGCGCCCACGGAAGATTGCAGCGAGGAAGAGCGCAATCTGGCTTA
CAGGCAATCGGTCACGTGCAAGATCTTTCTGGGCTTCACTTCGAACCTTGTATCTTCTGGCATCAGGGAGATAATTC
GGTTTCTTGTGCAGCACCGAATGGTTGAAGTTTTAGTCACAACTGCTGGCGGCATTGAAGAAGATTTAATCAAATGC
CTTGCTCCAACATATAAGGGTGACTTTTCTTTGCCTGGATCGTATCTGCGTTCAAAAGGATTGAATCGGATAGGAAA
CCTTCTTGTCCCTAATGACAATTACTGCAAATTCGAGGACTGGATCATGCCAATTCTGGACCAGATGTTACTTGAAC
AGACTACAGAGAATGTAGTTTGGACACCATCTAAAGTGATTGCGCGCCTTGGAAAAGAAATAAATGATGAAAGTTCA
TACCTGTACTGGGCATACAAGAACAATGTTTCTGTCTATTGCCCGGCATTGACTGATGGATCATTGGGGGATATGTT
GTACTGCCATTCAGTGCGGAATCCTGGTTTACTTATTGATATTGTGCAAGACATACGAGCAATGAATGGAGAAGCTG
TACATGTGGGTCTGAGAAAGACTGGGGTCATAATTCTTGGTGGGGGCCTCCCAAAGCACCATATATGTAATGCCAAC
ATGTTTCGGAATGGTGCAGATTATGCTGTTTATGTCAACACTGCACAGGAATTTGATGGAAGTGATTCTGGAGCAGA
GCCTGATGAGGCGATTTCATGGGGAAAGATAAAAGGTTCTGCGAAGACTATTAAAGTTCATTGTGATGCAACTATTG
CTTTTCCTCTATTGGTAGCTGCAACATTTGCAAGAAAGTTTCAGGAAAGAAACAACAAATTAGCCTGATGGGGGTGC
AAAAGGTGATCATCTTATTTGGATTCAAATACCTTAATGTAATCTGCTAACATCTGCAGATGCTGTATTCTTGCAAA
CCAAAAATTTAATATTAGATAACCGAGAGCCTACAGAGGGTCCTTTCAAAAAAA

Amino acid (376)

MEGGAAGGQRDRETLDAVRSVVFKPSVSLEEKRFPRVQGYDFNRGCDLIGLLDSISSTGFQASNLGDAIDVINQMID
WRLSHDAPTEDCSEEERNLAYRQSVTCKIFLGFTSNLVSSGIREIIRFLVQHRMVEVLVTTAGGIEEDLIKCLAPTY
KGDFSLPGSYLRSKGLNRIGNLLVPNDNYCKFEDWIMPILDQMLLEQTTENVVWTPSKVIARLGKEINDESSYLYWA
YKNNVSVYCPALTDGSLGDMLYCHSVRNPGLLIDIVQDIRAMNGEAVHVGLRKTGVIILGGGLPKHHICNANMFRNG
ADYAVYVNTAQEFDGSDSGAEPDEAISWGKIKGSAKTIKVHCDATIAFPLLVAATFARKFQERNNKLA

FIG. 108B

Cottonwood DHS cDNA

```
GGGATTTATGACAGGCAAAAAACAATGGGAGGAAGATTTGCTATCATCAGTACGGACCAC
        M  T  G  K  K  Q  W  E  E  D  L  L  S  S  V  R  T  T
AGTGTTTAAAGAATCAGAAGCTCTTGATGGGAAATGCATTAAAATTGAAGGTTATGATTT
  V  F  K  E  S  E  A  L  D  G  K  C  I  K  I  E  G  Y  D  F
TAATCAAGGAGTGAACTACTCTAAGCTTCTCAAATCCATGGTCTCTACCGGGTTTCAAGC
  N  Q  G  V  N  Y  S  K  L  L  K  S  M  V  S  T  G  F  Q  A
TTCCAACCTTGGAGATGCCATTCAAGTTGTTAATAACATGCTAGACTGGAGGCTTGCTGA
  S  N  L  G  D  A  I  Q  V  V  N  N  M  L  D  W  R  L  A  D
TGAAGAGATAACAGAAGATTGTAGTGATGAGGAGAGGGAGTTGGCCTATAGAGAGTCTGT
  E  E  I  T  E  D  C  S  D  E  E  R  E  L  A  Y  R  E  S  V
GAGATGCAAACTGTTCTTGGGTTTTACATCAAATCTTGTTTCTTCAGGTGTCAGAGATAC
  R  C  K  L  F  L  G  F  T  S  N  L  V  S  S  G  V  R  D  T
AATTCGATATCTTGTTCAGCATCATATGGTTGATGTAGTGGTTACAACGGCAGGTGGCAT
  I  R  Y  L  V  Q  H  H  M  V  D  V  V  V  T  T  A  G  G  I
AGAAGAAGATCTTATAAAATGCCTGGCACCAACATACAAAGGTGACTTTTCTCTACCCGG
  E  E  D  L  I  K  C  L  A  P  T  Y  K  G  D  F  S  L  P  G
GGCTCAATTACGATCAAAAGGGTTGAATCGAATTGGTAACTTGTTGGTACCTAATGACAA
  A  Q  L  R  S  K  G  L  N  R  I  G  N  L  L  V  P  N  D  N
CTACTGCAAATTTGAGGATTGGATCATTCCAATCTTTGACCAAATGTTGAAGGAACAAAT
  Y  C  K  F  E  D  W  I  I  P  I  F  D  Q  M  L  K  E  Q  I
TGAAGAGAATATCACCTGGACACCTTCTAAATTAATAGCTCGCATGGGGAAAGAAATAAA
  E  E  N  I  T  W  T  P  S  K  L  I  A  R  M  G  K  E  I  N
TAATGAGAGTTCATACCTTTATTGGGCATATAAGAACGACATTCCAGTATTCTGTCCAGG
  N  E  S  S  Y  L  Y  W  A  Y  K  N  D  I  P  V  F  C  P  G
CTTAACAGATGGTTCTCTAGGGGACATGCTATACTTTCATTCCTTCCACAACCCTGGTCT
  L  T  D  G  S  L  G  D  M  L  Y  F  H  S  F  H  N  P  G  L
AATTGTTGCCATAGTCCAAGATATTAGAGCCATGAATGGTGAAGCTGTCCACGCAAGTCC
  I  V  A  I  V  Q  D  I  R  A  M  N  G  E  A  V  H  A  S  P
TAGAAAAACTGGTATCATCATTCTTGGAGGTGGGCTTCCTAAGCATCATATATGCAATGC
  R  K  T  G  I  I  I  L  G  G  G  L  P  K  H  H  I  C  N  A
CAATATGATGCGTAACGGTGCAGATTATGCTGTATTCATCAATACAGCACAAGAATTTGA
  N  M  M  R  N  G  A  D  Y  A  V  F  I  N  T  A  Q  E  F  D
TGGGAGTGATTCTGGAGCTCATCCTGATGAGGCTGTATCGTGGGGGAAAATACGAGGTTC
  G  S  D  S  G  A  H  P  D  E  A  V  S  W  G  K  I  R  G  S
TGCTAAAACTGTTAAGGTCCACTGTGATGCAACTATTGCTTTTCCTCTCCTAGTTGCTGA
  A  K  T  V  K  V  H  C  D  A  T  I  A  F  P  L  L  V  A  E
AACATTTGCCCCTAGGAGGAACAGATTCTGCAGCAGTACTGAAAGCTAGGGCTGTGTGCA
  T  F  A  P  R  R  N  R  F  C  S  S  T  Q  S  *
GTTCTTGGCCAGAAAATTGATTCATTTTTATTTGTATTATGACTGAACGATCCGCAGGAT
GGGTAGTGGGCTCCATTGATGCCATAAACTTCTTTTTTTTTCCCCTCAGAATTAAGGGAT
CCGCCAGAACACACTGCTCTCAGCCCCAAACCATTGTTGCCTCTACTGGGAGTAGCATAA
CCAATTGAATTGCGCTCCTCCAAGCAGCGCCTCTTAGTTGCGTTATTTATTGTAAGTAGC
GCAACCAACTAAATTATGCTAGTTCCCACATTTATTGACTGCTATTTTCAAAAGAAAAAA
AAAAAAAAAAA
```

FIG. 109A

Cottonwood
Nucleic acid:

GGGATTTATGACAGGCAAAAAACAATGGGAGGAAGATTTGCTATCATCAGTACGGACCACAGTGTTTAAAGAATCAG
AAGCTCTTGATGGGAAATGCATTAAAATTGAAGGTTATGATTTTAATCAAGGAGTGAACTACTCTAAGCTTCTCAAA
TCCATGGTCTCTACCGGGTTTCAAGCTTCCAACCTTGGAGATGCCATTCAAGTTGTTAATAACATGCTAGACTGGAG
GCTTGCTGATGAAGAGATAACAGAAGATTGTAGTGATGAGGAGAGGGAGTTGGCCTATAGAGAGTCTGTGAGATGCA
AACTGTTCTTGGGTTTTACATCAAATCTTGTTTCTTCAGGTGTCAGAGATACAATTCGATATCTTGTTCAGCATCAT
ATGGTTGATGTAGTGGTTACAACGGCAGGTGGCATAGAAGAAGATCTTATAAAATGCCTGGCACCAACATACAAAGG
TGACTTTTCTCTACCCGGGGCTCAATTACGATCAAAAGGGTTGAATCGAATTGGTAACTTGTTGGTACCTAATGACA
ACTACTGCAAATTTGAGGATTGGATCATTCCAATCTTTGACCAAATGTTGAAGGAACAAATTGAAGAGAATATCACC
TGGACACCTTCTAAATTAATAGCTCGCATGGGGAAAGAAATAAATAATGAGAGTTCATACCTTTATTGGGCATATAA
GAACGACATTCCAGTATTCTGTCCAGGCTTAACAGATGGTTCTCTAGGGGACATGCTATACTTTCATTCCTTCCACA
ACCCTGGTCTAATTGTTGCCATAGTCCAAGATATTAGAGCCATGAATGGTGAAGCTGTCCACGCAAGTCCTAGAAAA
ACTGGTATCATCATTCTTGGAGGTGGGCTTCCTAAGCATCATATATGCAATGCCAATATGATGCGTAACGGTGCAGA
TTATGCTGTATTCATCAATACAGCACAAGAATTTGATGGGAGTGATTCTGGAGCTCATCCTGATGAGGCTGTATCGT
GGGGGAAAATACGAGGTTCTGCTAAAACTGTTAAGGTCCACTGTGATGCAACTATTGCTTTTCCTCTCCTAGTTGCT
GAAACATTTGCCCCTAGGAGGAACAGATTCTGCAGCAGTACTCAAAGCTAGGGCTGTGTGCAGTTCTTGGCCAGAAA
ATTGATTCATTTTTATTTGTATTATGACTGAACGATCCGCAGGATGGGTAGTGGGCTCCATTGATGCCATAAACTTC
TTTTTTTTTCCCCTCAGAATTAAGGGATCCGCCAGAACACACTGCTCTCAGCCCCAAACCATTGTTGCCTCTACTGG
GAGTAGCATAACCAATTGAATTGCGCTCCTCCAAGCAGCGCCTCTTAGTTGCGTTATTTATTGTAAGTAGCGCAACC
AACTAAATTATGCTAGTTCCCACATTTATTGACTGCTATTTTCAAAAGAAAAAAAAAAAAAAAAA (1451 bp)

Amino acid

MTGKKQWEEDLLSSVRTTVFKESEALDGKCIKIEGYDFNQGVNYSKLLKSMVSTGFQASNLGDAIQVVNNMLDWRLA
DEEITEDCSDEERELAYRESVRCKLFLGFTSNLVSSGVRDTIRYLVQHHMVDVVVTTAGGIEEDLIKCLAPTYKGDF
SLPGAQLRSKGLNRIGNLLVPNDNYCKFEDWIIPIFDQMLKEQIEENITWTPSKLIARMGKEINNESSYLYWAYKND
IPVFCPGLTDGSLGDMLYFHSFHNPGLIVAIVQDIRAMNGEAVHASPRKTGIIILGGGLPKHHICNANMMRNGADYA
VFINTAQEFDGSDSGAHPDEAVSWGKIRGSAKTVKVHCDATIAFPLLVAETFAPRRNRFCSSTQS (373 aa)

FIG.109B

Fungus DHS (*Mycosphaerella fijiensis*)-- incomplete

Primer F2F/F2D
#183· GLNRIGNL
F2F. 5'- GGN TTR AAY CGN ATH GGN AAY TT -3' (23 mer)
#350 AEFDGSDQ
F2D· 5'- TGR TCG GAN CCR TCR AAY TCN GC -3' (23 mer)

CGCCAAGCTATTTAGGTGACACTATAGAATACTCAAGCTATGCATCCAACGCGTTGGGAGCTCTCCCATATGGTCGA
CCTGCAGGCGGCCGCGAATTCACTAGTGATT

GGGTTAAATCGTATTGGAAACTTCTTAGTGCCAAACGACAATTACTGCCGCTTTGAAGACTGGGTGATGCCAATCCT
CGACACAATGCTCGAAGAACAGGAAGCATGCAAGGGTTCGGGCGAAGCAATCCACTGGACTCCCAGCAAAATCATCA
ACCGGCTTGGCAAGGAGGTCAACGACGAATCGTCCGTGTACTACTGGGCATGGAAGAACGACATTCCAGTGTTCTGT
CCGGCGCTTACTGATGGCAGTCTCGGAGACATGCTGTACTTCCACACGTTCAAATCCTCACCGCAGCAGCTTCGAGT
CGACATTGTGGAAGACATCCGAAAGATCAACACCCTCGCCGTCCGAGCCAAGCGCACTGGCATGATCATTCTCGGAG
GCGGCATTGTCAAGCACCACATCGCAAATGCCAACCTGATGCGCAATGGCGCGGAAAGCGCAGTGTACATCAATACC
GCGCCGAATTCGACGGATCCGACCA

AATCGAATTCCCGCGGCCGCCATGGCGGCCGGGAGCATGCGACGTCGGGCCCAATTCGCCCTATAGTGAGTCGTATT
ACAATTCACTGGCCGTCGTTTTACAACGTCGTGACTGGGAAAACCCTGGCGGTACCCAACTTAATCGCCTTGCAGCAC
ATCCCCCTTTCGCCAGCTGGCGTAATAGCGAAGAGGCCCGCACCGATCGCCCTTCCAACA

```
GGGTTAAATCGTATTGGAAACTTCTTAGTGCCAAACGACAATTACTGCCGCTTTGAAGACTGGGTGATGCCA
 G  L  N  R  I  G  N  F  L  V  P  N  D  N  Y  C  R  F  E  D  W  V  M  P
ATCCTCGACACAATGCTCGAAGAACAGGAAGCATGCAAGGGTTCGGGCGAAGCAATCCACTGGACTCCCAGC
 I  L  D  T  M  L  E  E  Q  E  A  C  K  G  S  G  E  A  I  H  W  T  P  S
AAAATCATCAACCGGCTTGGCAAGGAGGTCAACGACGAATCGTCCGTGTACTACTGGGCATGGAAGAACGAC
 K  I  I  N  R  L  G  K  E  V  N  D  E  S  S  V  Y  Y  W  A  W  K  N  D
ATTCCAGTGTTCTGTCCGGCGCTTACTGATGGCAGTCTCGGAGACATGCTGTACTTCCACACGTTCAAATCC
 I  P  V  F  C  P  A  L  T  D  G  S  L  G  D  M  L  Y  F  H  T  F  K  S
TCACCGCAGCAGCTTCGAGTCGACATTGTGGAAGACATCCGAAAGATCAACACCCTCGCCGTCCGAGCCAAG
 S  P  Q  Q  L  R  V  D  I  V  E  D  I  R  K  I  N  T  L  A  V  R  A  K
CGCACTGGCATGATCATTCTCGGAGGCGGCATTGTCAAGCACCACATCGCAAATGCCAACCTGATGCGCAAT
 R  T  G  M  I  I  L  G  G  G  I  V  K  H  H  I  A  N  A  N  L  M  R  N
                                       GCNGARTTYGAYGGNTCCGAYCA (primer)
GGCGCGGAAAGCGCAGTGTACATCAATACCGCGCCGAATTCGACGGATCCGACCA
 G  A  E  S  A  V  Y  I  N  T  A  P  N  S  T  D  P  T
                                        A  E  F  D  G  S  D
```

Nucleic acid:

GGGTTAAATCGTATTGGAAACTTCTTAGTGCCAAACGACAATTACTGCCGCTTTGAAGACTGGGTGATGCCAATCCT
CGACACAATGCTCGAAGAACAGGAAGCATGCAAGGGTTCGGGCGAAGCAATCCACTGGACTCCCAGCAAAATCATCA
ACCGGCTTGGCAAGGAGGTCAACGACGAATCGTCCGTGTACTACTGGGCATGGAAGAACGACATTCCAGTGTTCTGT
CCGGCGCTTACTGATGGCAGTCTCGGAGACATGCTGTACTTCCACACGTTCAAATCCTCACCGCAGCAGCTTCGAGT
CGACATTGTGGAAGACATCCGAAAGATCAACACCCTCGCCGTCCGAGCCAAGCGCACTGGCATGATCATTCTCGGAG
GCGGCATTGTCAAGCACCACATCGCAAATGCCAACCTGATGCGCAATGGCGCGGAAAGCGCAGTGTACATCAATACC
GCGCCGGAATTCGACGGATCCGACCA (488 bp)

Amino acid

GLNRIGNFLVPNDNYCRFEDWVMPILDTMLEEQEACKGSGEAIHWTPSKIINRLGKEVNDESSVYYWAWKNDIPVFC
PALTDGSLGDMLYFHTFKSSPQQLRVDIVEDIRKINTLAVRAKRTGMIILGGGIVKHHIANANLMRNGAESAVYINT
AEFDGSD (163 aa)

FIG. 110

SEQUENCE LISTING

```
<160> NUMBER OF SEQ ID NOS: 165

<210> SEQ ID NO 1
<211> LENGTH: 1584
<212> TYPE: DNA
<213> ORGANISM: Lycopersicon esculentum
<220> FEATURE:
<221> NAME/KEY: CDS
<222> LOCATION: (54)..(1196)

<400> SEQUENCE: 1

cgcagaaact cgcggcggca gtcttgttcc gtacataatc ttggtctgca ata atg        56
                                                           Met
                                                            1

gga gaa gct ctg aag tac agt atc atg gac tca gta aga tcg gta gtt       104
Gly Glu Ala Leu Lys Tyr Ser Ile Met Asp Ser Val Arg Ser Val Val
            5                   10                  15

ttc aaa gaa tcc gaa aat cta gaa ggt tct tgc act aaa atc gag ggc       152
Phe Lys Glu Ser Glu Asn Leu Glu Gly Ser Cys Thr Lys Ile Glu Gly
        20                  25                  30

tac gac ttc aat aaa ggc gtt aac tat gct gag ctg atc aag tcc atg       200
Tyr Asp Phe Asn Lys Gly Val Asn Tyr Ala Glu Leu Ile Lys Ser Met
    35                  40                  45

gtt tcc act ggt ttc caa gca tct aat ctt ggt gac gcc att gca att       248
Val Ser Thr Gly Phe Gln Ala Ser Asn Leu Gly Asp Ala Ile Ala Ile
 50                  55                  60                  65

gtt aat caa atg cta gat tgg agg ctt tca cat gag ctg ccc acg gag       296
```

-continued

```
Val Asn Gln Met Leu Asp Trp Arg Leu Ser His Glu Leu Pro Thr Glu
                70                  75                  80

gat tgc agt gaa gaa gaa aga gat gtt gca tac aga gag tcg gta acc      344
Asp Cys Ser Glu Glu Glu Arg Asp Val Ala Tyr Arg Glu Ser Val Thr
            85                  90                  95

tgc aaa atc ttc ttg ggg ttc act tca aac ctt gtt tct tct ggt gtt      392
Cys Lys Ile Phe Leu Gly Phe Thr Ser Asn Leu Val Ser Ser Gly Val
        100                 105                 110

aga gac act gtc cgc tac ctt gtt cag cac cgg atg gtt gat gtt gtg      440
Arg Asp Thr Val Arg Tyr Leu Val Gln His Arg Met Val Asp Val Val
    115                 120                 125

gtt act aca gct ggt ggt att gaa gag gat ctc ata aag tgc ctc gca      488
Val Thr Thr Ala Gly Gly Ile Glu Glu Asp Leu Ile Lys Cys Leu Ala
130                 135                 140                 145

cca acc tac aag ggg gac ttc tct tta cct gga gct tct cta cga tcg      536
Pro Thr Tyr Lys Gly Asp Phe Ser Leu Pro Gly Ala Ser Leu Arg Ser
                150                 155                 160

aaa gga ttg aac cgt att ggt aac tta ttg gtt cct aat gac aac tac      584
Lys Gly Leu Asn Arg Ile Gly Asn Leu Leu Val Pro Asn Asp Asn Tyr
            165                 170                 175

tgc aaa ttt gag aat tgg atc atc cca gtt ttt gac caa atg tat gag      632
Cys Lys Phe Glu Asn Trp Ile Ile Pro Val Phe Asp Gln Met Tyr Glu
        180                 185                 190

gag cag att aat gag aag gtt cta tgg aca cca tct aaa gtc att gct      680
Glu Gln Ile Asn Glu Lys Val Leu Trp Thr Pro Ser Lys Val Ile Ala
    195                 200                 205

cgt ctg ggt aaa gaa att aat gat gaa acc tca tac ttg tat tgg gct      728
Arg Leu Gly Lys Glu Ile Asn Asp Glu Thr Ser Tyr Leu Tyr Trp Ala
210                 215                 220                 225

tac aag aac cgg att cct gtc ttc tgt cct ggc ttg acg gat gga tca      776
Tyr Lys Asn Arg Ile Pro Val Phe Cys Pro Gly Leu Thr Asp Gly Ser
                230                 235                 240

ctt ggt gac atg cta tac ttc cat tct ttc aaa aag ggt gat cca gat      824
Leu Gly Asp Met Leu Tyr Phe His Ser Phe Lys Lys Gly Asp Pro Asp
            245                 250                 255

aat cca gat ctt aat cct ggt cta gtc ata gac att gta gga gat att      872
Asn Pro Asp Leu Asn Pro Gly Leu Val Ile Asp Ile Val Gly Asp Ile
        260                 265                 270

agg gcc atg aat ggt gaa gct gtc cat gct ggt ttg agg aag aca gga      920
Arg Ala Met Asn Gly Glu Ala Val His Ala Gly Leu Arg Lys Thr Gly
    275                 280                 285

atg att ata ctg ggt gga ggg ctg cct aag cac cat gtt tgc aat gcc      968
Met Ile Ile Leu Gly Gly Gly Leu Pro Lys His His Val Cys Asn Ala
290                 295                 300                 305

aat atg atg cgc aat ggt gca gat ttt gcc gtc ttc att aac acc gca     1016
Asn Met Met Arg Asn Gly Ala Asp Phe Ala Val Phe Ile Asn Thr Ala
                310                 315                 320

caa gag ttt gat ggt agt gac tct ggt gcc cgt cct gat gaa gct gta     1064
Gln Glu Phe Asp Gly Ser Asp Ser Gly Ala Arg Pro Asp Glu Ala Val
            325                 330                 335

tca tgg gga aag ata cgt ggt ggt gcc aag act gtg aag gtg cat tgt     1112
Ser Trp Gly Lys Ile Arg Gly Gly Ala Lys Thr Val Lys Val His Cys
        340                 345                 350

gat gca acc att gca ttt ccc ata tta gta gct gag aca ttt gca gct     1160
Asp Ala Thr Ile Ala Phe Pro Ile Leu Val Ala Glu Thr Phe Ala Ala
    355                 360                 365

aag agt aag gaa ttc tcc cag ata agg tgc caa gtt tgaacattga          1206
Lys Ser Lys Glu Phe Ser Gln Ile Arg Cys Gln Val
370                 375                 380

ggaagctgtc cttccgacca cacatatgaa ttgctagctt ttgaagccaa cttgctagtg   1266
```

```
tgcagcacca tttattctgc aaaactgact agagagcagg gtatattcct ctaccccgag    1326

ttagacgaca tcctgtatgg ttcaaattaa ttatttttct ccccttcaca ccatgttatt    1386

tagttctctt cctctccgaa agtgaagagc ttagatgttc ataggttttg aattatgttg    1446

gaggttggtg ataactgact agtcctctta ccatatagat aatgtatcct tgtactatga    1506

gattttgggt gtgtttgata ccaaggaaaa atgtttattt ggaaaacaat tggattttta    1566

atttattttt tcttgttt                                                  1584

<210> SEQ ID NO 2
<211> LENGTH: 381
<212> TYPE: PRT
<213> ORGANISM: Lycopersicon esculentum

<400> SEQUENCE: 2
```

| Met | Gly | Glu | Ala | Leu | Lys | Tyr | Ser | Ile | Met | Asp | Ser | Val | Arg | Ser | Val |
|---|---|---|---|---|---|---|---|---|---|---|---|---|---|---|---|
| 1 | | | | 5 | | | | | 10 | | | | | 15 | |

| Val | Phe | Lys | Glu | Ser | Glu | Asn | Leu | Glu | Gly | Ser | Cys | Thr | Lys | Ile | Glu |
|---|---|---|---|---|---|---|---|---|---|---|---|---|---|---|---|
| | | | 20 | | | | | 25 | | | | | 30 | | |

| Gly | Tyr | Asp | Phe | Asn | Lys | Gly | Val | Asn | Tyr | Ala | Glu | Leu | Ile | Lys | Ser |
| | | 35 | | | | | 40 | | | | | 45 | | | |

| Met | Val | Ser | Thr | Gly | Phe | Gln | Ala | Ser | Asn | Leu | Gly | Asp | Ala | Ile | Ala |
| 50 | | | | | 55 | | | | | 60 | | | | | |

| Ile | Val | Asn | Gln | Met | Leu | Asp | Trp | Arg | Leu | Ser | His | Glu | Leu | Pro | Thr |
| 65 | | | | 70 | | | | | 75 | | | | | 80 | |

| Glu | Asp | Cys | Ser | Glu | Glu | Arg | Asp | Val | Ala | Tyr | Arg | Glu | Ser | Val |
| | | | | 85 | | | | | 90 | | | | | 95 |

| Thr | Cys | Lys | Ile | Phe | Leu | Gly | Phe | Thr | Ser | Asn | Leu | Val | Ser | Ser | Gly |
| | | | 100 | | | | | 105 | | | | | 110 | | |

| Val | Arg | Asp | Thr | Val | Arg | Tyr | Leu | Val | Gln | His | Arg | Met | Val | Asp | Val |
| | | 115 | | | | | 120 | | | | | 125 | | | |

| Val | Val | Thr | Thr | Ala | Gly | Gly | Ile | Glu | Glu | Asp | Leu | Ile | Lys | Cys | Leu |
| | 130 | | | | | 135 | | | | | 140 | | | | |

| Ala | Pro | Thr | Tyr | Lys | Gly | Asp | Phe | Ser | Leu | Pro | Gly | Ala | Ser | Leu | Arg |
| 145 | | | | | 150 | | | | | 155 | | | | | 160 |

| Ser | Lys | Gly | Leu | Asn | Arg | Ile | Gly | Asn | Leu | Leu | Val | Pro | Asn | Asp | Asn |
| | | | | 165 | | | | | 170 | | | | | 175 | |

| Tyr | Cys | Lys | Phe | Glu | Asn | Trp | Ile | Ile | Pro | Val | Phe | Asp | Gln | Met | Tyr |
| | | | 180 | | | | | 185 | | | | | 190 | | |

| Glu | Glu | Gln | Ile | Asn | Glu | Lys | Val | Leu | Trp | Thr | Pro | Ser | Lys | Val | Ile |
| | | 195 | | | | | 200 | | | | | 205 | | | |

| Ala | Arg | Leu | Gly | Lys | Glu | Ile | Asn | Asp | Glu | Thr | Ser | Tyr | Leu | Tyr | Trp |
| | 210 | | | | | 215 | | | | | 220 | | | | |

| Ala | Tyr | Lys | Asn | Arg | Ile | Pro | Val | Phe | Cys | Pro | Gly | Leu | Thr | Asp | Gly |
| 225 | | | | | 230 | | | | | 235 | | | | | 240 |

| Ser | Leu | Gly | Asp | Met | Leu | Tyr | Phe | His | Ser | Phe | Lys | Lys | Gly | Asp | Pro |
| | | | | 245 | | | | | 250 | | | | | 255 | |

| Asp | Asn | Pro | Asp | Leu | Asn | Pro | Gly | Leu | Val | Ile | Asp | Ile | Val | Gly | Asp |
| | | | 260 | | | | | 265 | | | | | 270 | | |

| Ile | Arg | Ala | Met | Asn | Gly | Glu | Ala | Val | His | Ala | Gly | Leu | Arg | Lys | Thr |
| | | 275 | | | | | 280 | | | | | 285 | | | |

| Gly | Met | Ile | Ile | Leu | Gly | Gly | Gly | Leu | Pro | Lys | His | His | Val | Cys | Asn |
| | 290 | | | | | 295 | | | | | 300 | | | | |

| Ala | Asn | Met | Met | Arg | Asn | Gly | Ala | Asp | Phe | Ala | Val | Phe | Ile | Asn | Thr |
| 305 | | | | | 310 | | | | | 315 | | | | | 320 |

```
Ala Gln Glu Phe Asp Gly Ser Asp Ser Gly Ala Arg Pro Asp Glu Ala
                325                 330                 335

Val Ser Trp Gly Lys Ile Arg Gly Gly Ala Lys Thr Val Lys Val His
            340                 345                 350

Cys Asp Ala Thr Ile Ala Phe Pro Ile Leu Val Ala Glu Thr Phe Ala
        355                 360                 365

Ala Lys Ser Lys Glu Phe Ser Gln Ile Arg Cys Gln Val
    370                 375                 380


<210> SEQ ID NO 3
<211> LENGTH: 369
<212> TYPE: PRT
<213> ORGANISM: Homo sapiens

<400> SEQUENCE: 3

Met Glu Gly Ser Leu Glu Arg Glu Ala Pro Ala Gly Ala Leu Ala Ala
  1               5                  10                  15

Val Leu Lys His Ser Ser Thr Leu Pro Pro Glu Ser Thr Gln Val Arg
             20                  25                  30

Gly Tyr Asp Phe Asn Arg Gly Val Asn Tyr Arg Ala Leu Leu Glu Ala
         35                  40                  45

Phe Gly Thr Thr Gly Phe Gln Ala Thr Asn Phe Gly Arg Ala Val Gln
     50                  55                  60

Gln Val Asn Ala Met Ile Glu Lys Lys Leu Glu Pro Leu Ser Gln Asp
 65                  70                  75                  80

Glu Asp Gln His Ala Asp Leu Thr Gln Ser Arg Arg Pro Leu Thr Ser
                 85                  90                  95

Cys Thr Ile Phe Leu Gly Tyr Thr Ser Asn Leu Ile Ser Ser Gly Ile
            100                 105                 110

Arg Glu Thr Ile Arg Tyr Leu Val Gln His Asn Met Val Asp Val Leu
        115                 120                 125

Val Thr Thr Ala Gly Gly Val Glu Glu Asp Leu Ile Lys Cys Leu Ala
    130                 135                 140

Pro Thr Tyr Leu Gly Glu Phe Ser Leu Arg Gly Lys Glu Leu Arg Glu
145                 150                 155                 160

Asn Gly Ile Asn Arg Ile Gly Asn Leu Leu Val Pro Asn Glu Asn Tyr
                165                 170                 175

Cys Lys Phe Glu Asp Trp Leu Met Pro Ile Leu Asp Gln Met Val Met
            180                 185                 190

Glu Gln Asn Thr Glu Gly Val Lys Trp Thr Pro Ser Lys Met Ile Ala
        195                 200                 205

Arg Leu Gly Lys Glu Ile Asn Asn Pro Glu Ser Val Tyr Tyr Trp Ala
    210                 215                 220

Gln Lys Asn His Ile Pro Val Phe Ser Pro Ala Leu Thr Asp Gly Ser
225                 230                 235                 240

Leu Gly Asp Met Ile Phe Phe His Ser Tyr Lys Asn Pro Gly Leu Val
                245                 250                 255

Leu Asp Ile Val Glu Asp Leu Arg Leu Ile Asn Thr Gln Ala Ile Phe
            260                 265                 270

Ala Lys Cys Thr Gly Met Ile Ile Leu Gly Gly Gly Val Val Lys His
        275                 280                 285

His Ile Ala Asn Ala Asn Leu Met Arg Asn Gly Ala Asp Tyr Ala Val
    290                 295                 300

Tyr Ile Asn Thr Ala Gln Glu Phe Asp Gly Ser Asp Ser Gly Ala Arg
305                 310                 315                 320
```

```
Pro Asp Glu Ala Val Ser Trp Gly Lys Ile Arg Val Asp Ala Gln Pro
                325                 330                 335

Val Lys Val Tyr Ala Asp Ala Ser Leu Val Phe Pro Leu Leu Val Ala
            340                 345                 350

Glu Thr Phe Ala Gln Lys Met Asp Ala Phe Met His Glu Lys Asn Glu
        355                 360                 365

Asp


<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      conserved peptide fragment

<400> SEQUENCE: 4

Thr Gly Lys His Gly His
  1               5


<210> SEQ ID NO 5
<211> LENGTH: 2272
<212> TYPE: DNA
<213> ORGANISM: Arabidopsis thaliana
<220> FEATURE:
<221> NAME/KEY: CDS
<222> LOCATION: (68)..(265)
<220> FEATURE:
<221> NAME/KEY: CDS
<222> LOCATION: (348)..(536)
<220> FEATURE:
<221> NAME/KEY: CDS
<222> LOCATION: (624)..(842)
<220> FEATURE:
<221> NAME/KEY: CDS
<222> LOCATION: (979)..(1065)
<220> FEATURE:
<221> NAME/KEY: CDS
<222> LOCATION: (1154)..(1258)
<220> FEATURE:
<221> NAME/KEY: CDS
<222> LOCATION: (1575)..(1862)

<400> SEQUENCE: 5

gaactcccaa aaccctctac tactacactt tcagatccaa ggaaatcaat tttgtcattc     60

gagcaac atg gag gat gat cgt gtt ttc tct tcg gtt cac tca aca gtt      109
        Met Glu Asp Asp Arg Val Phe Ser Ser Val His Ser Thr Val
          1               5                  10

ttc aaa gaa tcc gaa tca ttg gaa gga aag tgt gat aaa atc gaa gga      157
Phe Lys Glu Ser Glu Ser Leu Glu Gly Lys Cys Asp Lys Ile Glu Gly
 15                  20                  25                  30

tac gat ttc aat caa gga gta gat tac cca aag ctt atg cga tcc atg      205
Tyr Asp Phe Asn Gln Gly Val Asp Tyr Pro Lys Leu Met Arg Ser Met
                 35                  40                  45

ctc acc acc gga ttt caa gcc tcg aat ctc ggc gaa gct att gat gtc      253
Leu Thr Thr Gly Phe Gln Ala Ser Asn Leu Gly Glu Ala Ile Asp Val
             50                  55                  60

gtc aat caa atg gttcgtttct cgaattcatc aaaaataaaa attccttctt          305
Val Asn Gln Met
         65

tttgttttcc tttgttttgg gtgaattagt aatgacaaag ag ttt gaa ttt gta       359
                                              Phe Glu Phe Val
                                                          70

ttg aag cta gat tgg aga ctg gct gat gaa act aca gta gct gaa gac      407
Leu Lys Leu Asp Trp Arg Leu Ala Asp Glu Thr Thr Val Ala Glu Asp
```

-continued

```
                75                  80                  85

tgt agt gaa gag gag aag aat cca tcg ttt aga gag tct gtc aag tgt      455
Cys Ser Glu Glu Glu Lys Asn Pro Ser Phe Arg Glu Ser Val Lys Cys
            90                  95                 100

aaa atc ttt cta ggt ttc act tca aat ctt gtt tca tct ggt gtt aga      503
Lys Ile Phe Leu Gly Phe Thr Ser Asn Leu Val Ser Ser Gly Val Arg
        105                 110                 115

gat act att cgt tat ctt gtt cag cat cat atg gtttgtgatt tttgctttat    556
Asp Thr Ile Arg Tyr Leu Val Gln His His Met
    120                 125

caccctgctt ttttatagat gttaaaattt tcgagcttta gttttgattt caatggtttt    616

tctgcag gtt gat gtt ata gtc acg aca act ggt ggt gtt gag gaa gat      665
        Val Asp Val Ile Val Thr Thr Thr Gly Gly Val Glu Glu Asp
        130                 135                 140

ctc ata aaa tgc ctt gca cct aca ttt aaa ggt gat ttc tct cta cct      713
Leu Ile Lys Cys Leu Ala Pro Thr Phe Lys Gly Asp Phe Ser Leu Pro
    145                 150                 155

gga gct tat tta agg tca aag gga ttg aac cga att ggg aat ttg ctg      761
Gly Ala Tyr Leu Arg Ser Lys Gly Leu Asn Arg Ile Gly Asn Leu Leu
160                 165                 170                 175

gtt cct aat gat aac tac tgc aag ttt gag gat tgg atc att ccc atc      809
Val Pro Asn Asp Asn Tyr Cys Lys Phe Glu Asp Trp Ile Ile Pro Ile
                180                 185                 190

ttt gac gag atg ttg aag gaa cag aaa gaa gag gtattgcttt atctttcctt    862
Phe Asp Glu Met Leu Lys Glu Gln Lys Glu Glu
            195                 200

tttatatgat ttgagatgat tctgtttgtg cgtcactagt ggagatagat tttgattcct    922

ctcttgcatc attgacttcg ttggtgaatc cttctttctc tggtttttcc ttgtag aat    981
                                                              Asn

gtg ttg tgg act cct tct aaa ctg tta gca cgg ctg gga aaa gaa atc     1029
Val Leu Trp Thr Pro Ser Lys Leu Leu Ala Arg Leu Gly Lys Glu Ile
    205                 210                 215

aac aat gag agt tca tac ctt tat tgg gca tac aag gtatccaaaa          1075
Asn Asn Glu Ser Ser Tyr Leu Tyr Trp Ala Tyr Lys
220                 225                 230

ttttaacctt tttagttttt taatcatcct gtgaggaact cggggattta aattttccgc   1135

ttcttgtggt gtttgtag atg aat att cca gta ttc tgc cca ggg tta aca     1186
                    Met Asn Ile Pro Val Phe Cys Pro Gly Leu Thr
                                235                 240

gat ggc tct ctt ggg gat atg ctg tat ttt cac tct ttt cgt acc tct     1234
Asp Gly Ser Leu Gly Asp Met Leu Tyr Phe His Ser Phe Arg Thr Ser
        245                 250                 255

ggc ctc atc atc gat gta gta caa ggtacttctt ttactcaata agtcagtgtg    1288
Gly Leu Ile Ile Asp Val Val Gln
    260                 265

ataaatattc ctgctacatc tagtgcagga atattgtaac tagtagtgca ttgtagcttt   1348

tccaattcag caacggactt tactgtaagt tgatatctaa aggttcaaac gggagctagg   1408

agaatagcat aggggcattc tgatttaggt ttggggcact gggttaagag ttagagaata   1468

ataatcttgt tagttgttta tcaaactctt tgatggttag tctcttggta atttgaattt   1528

tatcacagtg tttatggtct ttgaaccagt taatgtttta tgaaca gat atc aga      1583
                                                   Asp Ile Arg

gct atg aac ggc gaa gct gtc cat gca aat cct aaa aag aca ggg atg     1631
Ala Met Asn Gly Glu Ala Val His Ala Asn Pro Lys Lys Thr Gly Met
270                 275                 280                 285

ata atc ctt gga ggg ggc ttg cca aag cac cac ata tgt aat gcc aat     1679
Ile Ile Leu Gly Gly Gly Leu Pro Lys His His Ile Cys Asn Ala Asn
```

-continued

```
                290                 295                 300

atg atg cgc aat ggt gca gat tac gct gta ttt ata aac acc ggg caa      1727
Met Met Arg Asn Gly Ala Asp Tyr Ala Val Phe Ile Asn Thr Gly Gln
            305                 310                 315

gaa ttt gat ggg agc gac tcg ggt gca cgc cct gat gaa gcc gtg tct      1775
Glu Phe Asp Gly Ser Asp Ser Gly Ala Arg Pro Asp Glu Ala Val Ser
        320                 325                 330

tgg ggt aaa att agg ggt tct gct aaa acc gtt aag gtc tgc ttt tta      1823
Trp Gly Lys Ile Arg Gly Ser Ala Lys Thr Val Lys Val Cys Phe Leu
    335                 340                 345

att tct tca cat cct aat tta tat ctc act cag tgg ttt tgagtacata       1872
Ile Ser Ser His Pro Asn Leu Tyr Leu Thr Gln Trp Phe
350                 355                 360

tttaatattg gatcattctt gcaggtatac tgtgatgcta ccatagcctt cccattgttg   1932

gttgcagaaa catttgccac aaagagagac caaacctgtg agtctaagac ttaagaactg   1992

actggtcgtt ttggccatgg attcttaaag atcgttgctt tttgatttta cactggagtg   2052

accatataac actccacatt gatgtggctg tgacgcgaat tgtcttcttg cgaattgtac   2112

tttagtttct ctcaacctaa aatgatttgc agattgtgtt ttcgtttaaa acacaagagt   2172

cttgtagtca ataatccttt gccttataaa attattcagt tccaacaaca cattgtgatt   2232

ctgtgacaag tctcccgttg cctatgttca cttctctgcg                          2272


<210> SEQ ID NO 6
<211> LENGTH: 362
<212> TYPE: PRT
<213> ORGANISM: Arabidopsis thaliana

<400> SEQUENCE: 6

Met Glu Asp Asp Arg Val Phe Ser Ser Val His Ser Thr Val Phe Lys
  1               5                  10                  15

Glu Ser Glu Ser Leu Glu Gly Lys Cys Asp Lys Ile Glu Gly Tyr Asp
             20                  25                  30

Phe Asn Gln Gly Val Asp Tyr Pro Lys Leu Met Arg Ser Met Leu Thr
         35                  40                  45

Thr Gly Phe Gln Ala Ser Asn Leu Gly Glu Ala Ile Asp Val Val Asn
     50                  55                  60

Gln Met Phe Glu Phe Val Leu Lys Leu Asp Trp Arg Leu Ala Asp Glu
 65                  70                  75                  80

Thr Thr Val Ala Glu Asp Cys Ser Glu Glu Glu Lys Asn Pro Ser Phe
                 85                  90                  95

Arg Glu Ser Val Lys Cys Lys Ile Phe Leu Gly Phe Thr Ser Asn Leu
            100                 105                 110

Val Ser Ser Gly Val Arg Asp Thr Ile Arg Tyr Leu Val Gln His His
        115                 120                 125

Met Val Asp Val Ile Val Thr Thr Thr Gly Gly Val Glu Glu Asp Leu
    130                 135                 140

Ile Lys Cys Leu Ala Pro Thr Phe Lys Gly Asp Phe Ser Leu Pro Gly
145                 150                 155                 160

Ala Tyr Leu Arg Ser Lys Gly Leu Asn Arg Ile Gly Asn Leu Leu Val
                165                 170                 175

Pro Asn Asp Asn Tyr Cys Lys Phe Glu Asp Trp Ile Ile Pro Ile Phe
            180                 185                 190

Asp Glu Met Leu Lys Glu Gln Lys Glu Glu Asn Val Leu Trp Thr Pro
        195                 200                 205

Ser Lys Leu Leu Ala Arg Leu Gly Lys Glu Ile Asn Asn Glu Ser Ser
```

```
    210                 215                 220

Tyr Leu Tyr Trp Ala Tyr Lys Met Asn Ile Pro Val Phe Cys Pro Gly
225                 230                 235                 240

Leu Thr Asp Gly Ser Leu Gly Asp Met Leu Tyr Phe His Ser Phe Arg
                245                 250                 255

Thr Ser Gly Leu Ile Ile Asp Val Val Gln Asp Ile Arg Ala Met Asn
            260                 265                 270

Gly Glu Ala Val His Ala Asn Pro Lys Lys Thr Gly Met Ile Ile Leu
        275                 280                 285

Gly Gly Gly Leu Pro Lys His His Ile Cys Asn Ala Asn Met Met Arg
    290                 295                 300

Asn Gly Ala Asp Tyr Ala Val Phe Ile Asn Thr Gly Gln Glu Phe Asp
305                 310                 315                 320

Gly Ser Asp Ser Gly Ala Arg Pro Asp Glu Ala Val Ser Trp Gly Lys
                325                 330                 335

Ile Arg Gly Ser Ala Lys Thr Val Lys Val Cys Phe Leu Ile Ser Ser
            340                 345                 350

His Pro Asn Leu Tyr Leu Thr Gln Trp Phe
        355                 360


<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

ggtggtgttg aggaagatc                                                19


<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

ggtgcacgcc ctgatgaagc                                               20


<210> SEQ ID NO 9
<211> LENGTH: 1660
<212> TYPE: DNA
<213> ORGANISM: Dianthus caryophyllus
<220> FEATURE:
<221> NAME/KEY: CDS
<222> LOCATION: (256)..(1374)

<400> SEQUENCE: 9

gtcattacaa tgcataggat cattgcacat gctaccttcc tcattgcact tgagcttgcc     60

atacttttgt ttttgacgtt tgataataat actatgaaaa tattatgttt tttcttttgt    120

gtgttggtgt ttttgaagtt gtttttgata agcagaaccc agttgtttta cacttttacc    180

attgaactac tgcaattcta aaactttgtt tacattttaa ttccatcaaa gattgagttc    240

agcataggaa aaagg atg gag gat gct aat cat gat agt gtg gca tct gcg     291
                 Met Glu Asp Ala Asn His Asp Ser Val Ala Ser Ala
                   1               5                  10

cac tct gca gca ttc aaa aag tcg gag aat tta gag ggg aaa agc gtt      339
His Ser Ala Ala Phe Lys Lys Ser Glu Asn Leu Glu Gly Lys Ser Val
```

-continued

```
        15                  20                  25

aag att gag ggt tat gat ttt aat caa ggt gta aac tat tcc aaa ctc      387
Lys Ile Glu Gly Tyr Asp Phe Asn Gln Gly Val Asn Tyr Ser Lys Leu
     30                  35                  40

ttg caa tct ttc gct tct aat ggg ttt caa gcc tcg aat ctt gga gat      435
Leu Gln Ser Phe Ala Ser Asn Gly Phe Gln Ala Ser Asn Leu Gly Asp
 45                  50                  55                  60

gcc att gaa gta gtt aat cat atg cta gat tgg agt ctg gca gat gag      483
Ala Ile Glu Val Val Asn His Met Leu Asp Trp Ser Leu Ala Asp Glu
                 65                  70                  75

gca cct gtg gac gat tgt agc gag gaa gag agg gat cct aaa ttc aga      531
Ala Pro Val Asp Asp Cys Ser Glu Glu Glu Arg Asp Pro Lys Phe Arg
             80                  85                  90

gaa tct gtg aag tgc aaa gtg ttc ttg ggc ttt act tca aat ctt att      579
Glu Ser Val Lys Cys Lys Val Phe Leu Gly Phe Thr Ser Asn Leu Ile
         95                 100                 105

tcc tct ggt gtt cgt gac aca att cgg tat ctc gtg caa cat cat atg      627
Ser Ser Gly Val Arg Asp Thr Ile Arg Tyr Leu Val Gln His His Met
    110                 115                 120

gtt gac gtg ata gta acg aca acc gga ggt ata gaa gaa gat cta ata      675
Val Asp Val Ile Val Thr Thr Thr Gly Gly Ile Glu Glu Asp Leu Ile
125                 130                 135                 140

aaa gga aga tcc atc aag tgc ctt gca ccc act ttc aaa ggc gat ttt      723
Lys Gly Arg Ser Ile Lys Cys Leu Ala Pro Thr Phe Lys Gly Asp Phe
                145                 150                 155

gcc tta cca gga gct caa tta cgc tcc aaa ggg ttg aat cga att ggt      771
Ala Leu Pro Gly Ala Gln Leu Arg Ser Lys Gly Leu Asn Arg Ile Gly
            160                 165                 170

aat ctg ttg gtt ccg aat gat aac tac tgt aaa ttt gag gat tgg atc      819
Asn Leu Leu Val Pro Asn Asp Asn Tyr Cys Lys Phe Glu Asp Trp Ile
        175                 180                 185

att cca att tta gat aag atg ttg gaa gag caa att tca gag aaa atc      867
Ile Pro Ile Leu Asp Lys Met Leu Glu Glu Gln Ile Ser Glu Lys Ile
    190                 195                 200

tta tgg aca cca tcg aag ttg att ggt cga tta gga aga gaa ata aac      915
Leu Trp Thr Pro Ser Lys Leu Ile Gly Arg Leu Gly Arg Glu Ile Asn
205                 210                 215                 220

gat gag agt tca tac ctt tac tgg gcc ttc aag aac aat att cca gta      963
Asp Glu Ser Ser Tyr Leu Tyr Trp Ala Phe Lys Asn Asn Ile Pro Val
                225                 230                 235

ttt tgc cca ggt tta aca gac ggc tca ctc gga gac atg cta tat ttt     1011
Phe Cys Pro Gly Leu Thr Asp Gly Ser Leu Gly Asp Met Leu Tyr Phe
            240                 245                 250

cat tct ttt cgc aat ccg ggt tta atc gtc gat gtt gtg caa gat ata     1059
His Ser Phe Arg Asn Pro Gly Leu Ile Val Asp Val Val Gln Asp Ile
        255                 260                 265

aga gca gta aat ggc gag gct gtg cac gca gcg cct agg aaa aca ggc     1107
Arg Ala Val Asn Gly Glu Ala Val His Ala Ala Pro Arg Lys Thr Gly
    270                 275                 280

atg att ata ctc ggt gga ggg ttg cct aag cac cac atc tgc aac gca     1155
Met Ile Ile Leu Gly Gly Gly Leu Pro Lys His His Ile Cys Asn Ala
285                 290                 295                 300

aac atg atg aga aat ggc gcc gat tat gct gtt ttc atc aac act gcc     1203
Asn Met Met Arg Asn Gly Ala Asp Tyr Ala Val Phe Ile Asn Thr Ala
                305                 310                 315

gaa gag ttt gac ggc agt gat tct ggt gct cgc ccc gat gag gct att     1251
Glu Glu Phe Asp Gly Ser Asp Ser Gly Ala Arg Pro Asp Glu Ala Ile
            320                 325                 330

tca tgg ggc aaa att agc gga tct gct aag act gtg aag gtg cat tgt     1299
Ser Trp Gly Lys Ile Ser Gly Ser Ala Lys Thr Val Lys Val His Cys
```

```
        335                 340                 345

gat gcc acg ata gct ttc cct cta cta gtc gct gag aca ttt gca gca     1347
Asp Ala Thr Ile Ala Phe Pro Leu Leu Val Ala Glu Thr Phe Ala Ala
    350                 355                 360

aaa aga gaa aaa gag agg aag agc tgt taaaactttt ttgattgttg           1394
Lys Arg Glu Lys Glu Arg Lys Ser Cys
365                 370

aaaaatctgt gttatacaag tctcgaaatg cattttagta attgacttga tcttatcatt   1454

tcaatgtgtt atctttgaaa atgttggtaa tgaaacatct cacctcttct atacaacatt   1514

gttgatccat tgtactccgt atcttgtaat tttggaaaaa aaaaaccgtc tattgttacg   1574

agagagtaca tttttgaggt aaaaatatag gatttttgtg cgatgcaaat gctggttatt   1634

cccttgaaaa aaaaaaaaaa aaaaaa                                        1660


<210> SEQ ID NO 10
<211> LENGTH: 373
<212> TYPE: PRT
<213> ORGANISM: Dianthus caryophyllus

<400> SEQUENCE: 10

Met Glu Asp Ala Asn His Asp Ser Val Ala Ser Ala His Ser Ala Ala
  1               5                  10                  15

Phe Lys Lys Ser Glu Asn Leu Glu Gly Lys Ser Val Lys Ile Glu Gly
            20                  25                  30

Tyr Asp Phe Asn Gln Gly Val Asn Tyr Ser Lys Leu Leu Gln Ser Phe
        35                  40                  45

Ala Ser Asn Gly Phe Gln Ala Ser Asn Leu Gly Asp Ala Ile Glu Val
     50                  55                  60

Val Asn His Met Leu Asp Trp Ser Leu Ala Asp Glu Ala Pro Val Asp
 65                  70                  75                  80

Asp Cys Ser Glu Glu Glu Arg Asp Pro Lys Phe Arg Glu Ser Val Lys
                 85                  90                  95

Cys Lys Val Phe Leu Gly Phe Thr Ser Asn Leu Ile Ser Ser Gly Val
            100                 105                 110

Arg Asp Thr Ile Arg Tyr Leu Val Gln His His Met Val Asp Val Ile
        115                 120                 125

Val Thr Thr Thr Gly Gly Ile Glu Glu Asp Leu Ile Lys Gly Arg Ser
    130                 135                 140

Ile Lys Cys Leu Ala Pro Thr Phe Lys Gly Asp Phe Ala Leu Pro Gly
145                 150                 155                 160

Ala Gln Leu Arg Ser Lys Gly Leu Asn Arg Ile Gly Asn Leu Leu Val
                165                 170                 175

Pro Asn Asp Asn Tyr Cys Lys Phe Glu Asp Trp Ile Ile Pro Ile Leu
            180                 185                 190

Asp Lys Met Leu Glu Glu Gln Ile Ser Glu Lys Ile Leu Trp Thr Pro
        195                 200                 205

Ser Lys Leu Ile Gly Arg Leu Gly Arg Glu Ile Asn Asp Glu Ser Ser
    210                 215                 220

Tyr Leu Tyr Trp Ala Phe Lys Asn Asn Ile Pro Val Phe Cys Pro Gly
225                 230                 235                 240

Leu Thr Asp Gly Ser Leu Gly Asp Met Leu Tyr Phe His Ser Phe Arg
                245                 250                 255

Asn Pro Gly Leu Ile Val Asp Val Val Gln Asp Ile Arg Ala Val Asn
            260                 265                 270

Gly Glu Ala Val His Ala Ala Pro Arg Lys Thr Gly Met Ile Ile Leu
```

```
        275                 280                 285

Gly Gly Gly Leu Pro Lys His His Ile Cys Asn Ala Asn Met Met Arg
    290                 295                 300

Asn Gly Ala Asp Tyr Ala Val Phe Ile Asn Thr Ala Glu Glu Phe Asp
305                 310                 315                 320

Gly Ser Asp Ser Gly Ala Arg Pro Asp Glu Ala Ile Ser Trp Gly Lys
                325                 330                 335

Ile Ser Gly Ser Ala Lys Thr Val Lys Val His Cys Asp Ala Thr Ile
            340                 345                 350

Ala Phe Pro Leu Leu Val Ala Glu Thr Phe Ala Ala Lys Arg Glu Lys
        355                 360                 365

Glu Arg Lys Ser Cys
    370


<210> SEQ ID NO 11
<211> LENGTH: 780
<212> TYPE: DNA
<213> ORGANISM: Lycopersicon esculentum
<220> FEATURE:
<221> NAME/KEY: CDS
<222> LOCATION: (43)..(522)

<400> SEQUENCE: 11

aaagaatcct agagagagaa agggaatcct agagagagaa gc atg tcg gac gaa        54
                                               Met Ser Asp Glu
                                                 1

gaa cac cat ttt gag tca aag gca gat gct ggt gcc tca aaa act ttc      102
Glu His His Phe Glu Ser Lys Ala Asp Ala Gly Ala Ser Lys Thr Phe
  5                  10                  15                  20

cca cag caa gct gga acc atc cgt aag aat ggt tac atc gtt atc aaa      150
Pro Gln Gln Ala Gly Thr Ile Arg Lys Asn Gly Tyr Ile Val Ile Lys
                 25                  30                  35

ggc cgt ccc tgc aag gtt gtt gag gtc tcc act tca aaa act gga aaa      198
Gly Arg Pro Cys Lys Val Val Glu Val Ser Thr Ser Lys Thr Gly Lys
             40                  45                  50

cac gga cat gct aaa tgt cac ttt gtg gca att gac att ttc aat gga      246
His Gly His Ala Lys Cys His Phe Val Ala Ile Asp Ile Phe Asn Gly
         55                  60                  65

aag aaa ctg gaa gat atc gtt ccg tcc tcc cac aat tgt gat gtg cca      294
Lys Lys Leu Glu Asp Ile Val Pro Ser Ser His Asn Cys Asp Val Pro
     70                  75                  80

cat gtt aac cgt acc gac tat cag ctg att gat atc tct gaa gat ggt      342
His Val Asn Arg Thr Asp Tyr Gln Leu Ile Asp Ile Ser Glu Asp Gly
 85                  90                  95                 100

ttt gtc tca ctt ctt act gaa agt gga aac acc aag gat gac ctc agg      390
Phe Val Ser Leu Leu Thr Glu Ser Gly Asn Thr Lys Asp Asp Leu Arg
                105                 110                 115

ctt ccc acc gat gaa aat ctg ctg aag cag gtt aaa gat ggg ttc cag      438
Leu Pro Thr Asp Glu Asn Leu Leu Lys Gln Val Lys Asp Gly Phe Gln
            120                 125                 130

gaa gga aag gat ctt gtg gtg tct gtt atg tct gcg atg ggc gaa gag      486
Glu Gly Lys Asp Leu Val Val Ser Val Met Ser Ala Met Gly Glu Glu
        135                 140                 145

cag att aac gcc gtt aag gat gtt ggt acc aag aat tagttatgtc           532
Gln Ile Asn Ala Val Lys Asp Val Gly Thr Lys Asn
    150                 155                 160

atggcagcat aatcactgcc aaagctttaa gacattatca tatcctaatg tggtactttg    592

atatcactag attataaact gtgttatttg cactgttcaa aacaaaagaa agaaaactgc    652

tgttatggct agagaaagta ttggctttga gcttttgaca gcacagttga actatgtgaa    712
```

```
aattctactt ttttttttt gggtaaaata ctgctcgttt aatgttttgc aaaaaaaaaa    772

aaaaaaaa                                                            780


<210> SEQ ID NO 12
<211> LENGTH: 160
<212> TYPE: PRT
<213> ORGANISM: Lycopersicon esculentum

<400> SEQUENCE: 12

Met Ser Asp Glu Glu His His Phe Glu Ser Lys Ala Asp Ala Gly Ala
  1               5                  10                  15

Ser Lys Thr Phe Pro Gln Gln Ala Gly Thr Ile Arg Lys Asn Gly Tyr
             20                  25                  30

Ile Val Ile Lys Gly Arg Pro Cys Lys Val Val Glu Val Ser Thr Ser
         35                  40                  45

Lys Thr Gly Lys His Gly His Ala Lys Cys His Phe Val Ala Ile Asp
     50                  55                  60

Ile Phe Asn Gly Lys Lys Leu Glu Asp Ile Val Pro Ser Ser His Asn
 65                  70                  75                  80

Cys Asp Val Pro His Val Asn Arg Thr Asp Tyr Gln Leu Ile Asp Ile
                 85                  90                  95

Ser Glu Asp Gly Phe Val Ser Leu Leu Thr Glu Ser Gly Asn Thr Lys
            100                 105                 110

Asp Asp Leu Arg Leu Pro Thr Asp Glu Asn Leu Leu Lys Gln Val Lys
        115                 120                 125

Asp Gly Phe Gln Glu Gly Lys Asp Leu Val Val Ser Val Met Ser Ala
    130                 135                 140

Met Gly Glu Glu Gln Ile Asn Ala Val Lys Asp Val Gly Thr Lys Asn
145                 150                 155                 160


<210> SEQ ID NO 13
<211> LENGTH: 812
<212> TYPE: DNA
<213> ORGANISM: Dianthus caryophyllus
<220> FEATURE:
<221> NAME/KEY: CDS
<222> LOCATION: (67)..(546)

<400> SEQUENCE: 13

ctcttttaca tcaatcgaaa aaaaattagg gttcttattt tagagtgaga ggcgaaaaat     60

cgaacg atg tcg gac gac gat cac cat ttc gag tca tcg gcc gac gcc       108
       Met Ser Asp Asp Asp His His Phe Glu Ser Ser Ala Asp Ala
         1               5                  10

gga gca tcc aag act tac cct caa caa gct ggt aca atc cgc aag agc      156
Gly Ala Ser Lys Thr Tyr Pro Gln Gln Ala Gly Thr Ile Arg Lys Ser
 15                  20                  25                  30

ggt cac atc gtc atc aaa aat cgc cct tgc aag gtg gtt gag gtt tct      204
Gly His Ile Val Ile Lys Asn Arg Pro Cys Lys Val Val Glu Val Ser
                 35                  40                  45

acc tcc aag act ggc aag cac ggt cat gcc aaa tgt cac ttt gtt gcc      252
Thr Ser Lys Thr Gly Lys His Gly His Ala Lys Cys His Phe Val Ala
             50                  55                  60

att gac att ttc aac ggc aag aag ctg gaa gat att gtc ccc tca tcc      300
Ile Asp Ile Phe Asn Gly Lys Lys Leu Glu Asp Ile Val Pro Ser Ser
         65                  70                  75

cac aat tgt gat gtt cca cat gtc aac cgt gtc gac tac cag ctg ctt      348
His Asn Cys Asp Val Pro His Val Asn Arg Val Asp Tyr Gln Leu Leu
     80                  85                  90
```

-continued

```
gat atc act gaa gat ggc ttt gtt agt ctg ctg act gac agt ggt gac      396
Asp Ile Thr Glu Asp Gly Phe Val Ser Leu Leu Thr Asp Ser Gly Asp
 95                 100                 105                 110

acc aag gat gat ctg aag ctt cct gct gat gag gcc ctt gtg aag cag      444
Thr Lys Asp Asp Leu Lys Leu Pro Ala Asp Glu Ala Leu Val Lys Gln
                115                 120                 125

atg aag gag gga ttt gag gcg ggg aaa gac ttg att ctg tca gtc atg      492
Met Lys Glu Gly Phe Glu Ala Gly Lys Asp Leu Ile Leu Ser Val Met
            130                 135                 140

tgt gca atg gga gaa gag cag atc tgc gcc gtc aag gac gtt agt ggt      540
Cys Ala Met Gly Glu Glu Gln Ile Cys Ala Val Lys Asp Val Ser Gly
        145                 150                 155

ggc aag tagaagcttt tgatgaatcc aatactacgc ggtgcagttg aagcaatagt       596
Gly Lys
    160

aatctcgaga acattctgaa ccttatatgt tgaattgatg gtgcttagtt tgttttggaa    656

atctctttgc aattaagttg taccaaatca atggatgtaa tgtcttgaat ttgttttatt    716

tttgttttga tgtttgctgt gattgcatta tgcattgtta tgagttatga cctgttataa    776

cacaaggttt tggtaaaaaa aaaaaaaaaa aaaaaa                              812


<210> SEQ ID NO 14
<211> LENGTH: 160
<212> TYPE: PRT
<213> ORGANISM: Dianthus caryophyllus

<400> SEQUENCE: 14

Met Ser Asp Asp Asp His His Phe Glu Ser Ser Ala Asp Ala Gly Ala
  1               5                  10                  15

Ser Lys Thr Tyr Pro Gln Gln Ala Gly Thr Ile Arg Lys Ser Gly His
             20                  25                  30

Ile Val Ile Lys Asn Arg Pro Cys Lys Val Val Glu Val Ser Thr Ser
         35                  40                  45

Lys Thr Gly Lys His Gly His Ala Lys Cys His Phe Val Ala Ile Asp
     50                  55                  60

Ile Phe Asn Gly Lys Lys Leu Glu Asp Ile Val Pro Ser Ser His Asn
 65                  70                  75                  80

Cys Asp Val Pro His Val Asn Arg Val Asp Tyr Gln Leu Leu Asp Ile
                 85                  90                  95

Thr Glu Asp Gly Phe Val Ser Leu Leu Thr Asp Ser Gly Asp Thr Lys
            100                 105                 110

Asp Asp Leu Lys Leu Pro Ala Asp Glu Ala Leu Val Lys Gln Met Lys
        115                 120                 125

Glu Gly Phe Glu Ala Gly Lys Asp Leu Ile Leu Ser Val Met Cys Ala
    130                 135                 140

Met Gly Glu Glu Gln Ile Cys Ala Val Lys Asp Val Ser Gly Gly Lys
145                 150                 155                 160


<210> SEQ ID NO 15
<211> LENGTH: 702
<212> TYPE: DNA
<213> ORGANISM: Arabidopsis thaliana
<220> FEATURE:
<221> NAME/KEY: CDS
<222> LOCATION: (56)..(529)

<400> SEQUENCE: 15

ctgttaccaa aaaatctgta ccgcaaaatc ctcgtcgaag ctcgctgctg caacc atg      58
                                                             Met
                                                               1
```

tcc gac gag gag cat cac ttt gag tcc agt gac gcc gga gcg tcc aaa 106
Ser Asp Glu Glu His His Phe Glu Ser Ser Asp Ala Gly Ala Ser Lys
5 10 15 acc tac cct caa caa gct gga acc atc cgt aag aat ggt tac atc gtc 154
Thr Tyr Pro Gln Gln Ala Gly Thr Ile Arg Lys Asn Gly Tyr Ile Val
20 25 30 atc aaa aat cgt ccc tgc aag gtt gtt gag gtt tca acc tcg aag act 202
Ile Lys Asn Arg Pro Cys Lys Val Val Glu Val Ser Thr Ser Lys Thr
35 40 45 ggc aag cat ggt cat gct aaa tgt cat ttt gta gct att gat atc ttc 250
Gly Lys His Gly His Ala Lys Cys His Phe Val Ala Ile Asp Ile Phe
50 55 60 65 acc agc aag aaa ctc gaa gat att gtt cct tct tcc cac aat tgt gat 298
Thr Ser Lys Lys Leu Glu Asp Ile Val Pro Ser Ser His Asn Cys Asp
70 75 80 gtt cct cat gtc aac cgt act gat tat cag ctg att gac att tct gaa 346
Val Pro His Val Asn Arg Thr Asp Tyr Gln Leu Ile Asp Ile Ser Glu
85 90 95 gat gga tat gtc agt ttg ttg act gat aac ggt agt acc aag gat gac 394
Asp Gly Tyr Val Ser Leu Leu Thr Asp Asn Gly Ser Thr Lys Asp Asp
100 105 110 ctt aag ctc cct aat gat gac act ctg ctc caa cag atc aag agt ggg 442
Leu Lys Leu Pro Asn Asp Asp Thr Leu Leu Gln Gln Ile Lys Ser Gly
115 120 125 ttt gat gat gga aaa gat cta gtg gtg agt gta atg tca gct atg gga 490
Phe Asp Asp Gly Lys Asp Leu Val Val Ser Val Met Ser Ala Met Gly
130 135 140 145 gag gaa cag atc aat gct ctt aag gac atc ggt ccc aag tgagactaac 539
Glu Glu Gln Ile Asn Ala Leu Lys Asp Ile Gly Pro Lys
150 155 aaagcctccc ctttgttatg agattcttct tcttctgtag gcttccatta ctcgtcggag 599 attatcttgt ttttgggtta ctcctatttt ggatatttaa acttttgtta ataatgccat 659 cttcttcaac cttttccttc tagatggttt ttatacttct tct 702

<210> SEQ ID NO 16
<211> LENGTH: 158
<212> TYPE: PRT
<213> ORGANISM: Arabidopsis thaliana

<400> SEQUENCE: 16

Met Ser Asp Glu Glu His His Phe Glu Ser Ser Asp Ala Gly Ala Ser
1 5 10 15

Lys Thr Tyr Pro Gln Gln Ala Gly Thr Ile Arg Lys Asn Gly Tyr Ile
20 25 30

Val Ile Lys Asn Arg Pro Cys Lys Val Val Glu Val Ser Thr Ser Lys
35 40 45

Thr Gly Lys His Gly His Ala Lys Cys His Phe Val Ala Ile Asp Ile
50 55 60

Phe Thr Ser Lys Lys Leu Glu Asp Ile Val Pro Ser Ser His Asn Cys
65 70 75 80

Asp Val Pro His Val Asn Arg Thr Asp Tyr Gln Leu Ile Asp Ile Ser
85 90 95

Glu Asp Gly Tyr Val Ser Leu Leu Thr Asp Asn Gly Ser Thr Lys Asp
100 105 110

Asp Leu Lys Leu Pro Asn Asp Asp Thr Leu Leu Gln Gln Ile Lys Ser
115 120 125

Gly Phe Asp Asp Gly Lys Asp Leu Val Val Ser Val Met Ser Ala Met

```
   130                 135                 140

Gly Glu Glu Gln Ile Asn Ala Leu Lys Asp Ile Gly Pro Lys
145                 150                 155


<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

aaarrycgmc cytgcaaggt                                                  20


<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

aatacgactc actatag                                                     17


<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: a, t, c or g

<400> SEQUENCE: 19

tcyttnccyt cmkctaahcc                                                  20


<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

attaaccctc actaaag                                                     17


<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

ctgttaccaa aaaatctgta cc                                               22


<210> SEQ ID NO 22
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 22

agaagaagta taaaaaccat c                                              21


<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

aaagaatcct agagagagaa agg                                            23


<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

ttttacatca atcgaaaa                                                  18


<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

accaaaacct gtgttataac tcc                                            23


<210> SEQ ID NO 26
<211> LENGTH: 581
<212> TYPE: DNA
<213> ORGANISM: Arabidopsis thaliana
<220> FEATURE:
<221> NAME/KEY: CDS
<222> LOCATION: (1)..(579)

<400> SEQUENCE: 26

ggt ggt gtt gag gaa gat ctc ata aaa tgc ctt gca cct aca ttt aaa       48
Gly Gly Val Glu Glu Asp Leu Ile Lys Cys Leu Ala Pro Thr Phe Lys
  1               5                  10                  15

ggt gat ttc tct cta cct gga gct tat tta agg tca aag gga ttg aac       96
Gly Asp Phe Ser Leu Pro Gly Ala Tyr Leu Arg Ser Lys Gly Leu Asn
             20                  25                  30

cga att ggg aat ttg ctg gtt cct aat gat aac tac tgc aag ttt gag      144
Arg Ile Gly Asn Leu Leu Val Pro Asn Asp Asn Tyr Cys Lys Phe Glu
         35                  40                  45

gat tgg atc att ccc atc ttt gac gag atg ttg aag gaa cag aaa gaa      192
Asp Trp Ile Ile Pro Ile Phe Asp Glu Met Leu Lys Glu Gln Lys Glu
     50                  55                  60

gag aat gtg ttg tgg act cct tct aaa ctg tta gca cgg ctg gga aaa      240
Glu Asn Val Leu Trp Thr Pro Ser Lys Leu Leu Ala Arg Leu Gly Lys
 65                  70                  75                  80

gaa atc aac aat gag agt tca tac ctt tat tgg gca tac aag atg aat      288
Glu Ile Asn Asn Glu Ser Ser Tyr Leu Tyr Trp Ala Tyr Lys Met Asn
                 85                  90                  95
```

```
att cca gta ttc tgc cca ggg tta aca gat ggc tct ctt agg gat atg      336
Ile Pro Val Phe Cys Pro Gly Leu Thr Asp Gly Ser Leu Arg Asp Met
            100                 105                 110

ctg tat ttt cac tct ttt cgt acc tct ggc ctc atc atc gat gta gta      384
Leu Tyr Phe His Ser Phe Arg Thr Ser Gly Leu Ile Ile Asp Val Val
        115                 120                 125

caa gat atc aga gct atg aac ggc gaa gct gtc cat gca aat cct aaa      432
Gln Asp Ile Arg Ala Met Asn Gly Glu Ala Val His Ala Asn Pro Lys
    130                 135                 140

aag aca ggg atg ata atc ctt gga ggg ggc ttg cca aag cac cac ata      480
Lys Thr Gly Met Ile Ile Leu Gly Gly Gly Leu Pro Lys His His Ile
145                 150                 155                 160

tgt aat gcc aat atg atg cgc aat ggt gca gat tac gct gta ttt ata      528
Cys Asn Ala Asn Met Met Arg Asn Gly Ala Asp Tyr Ala Val Phe Ile
                165                 170                 175

aac acc ggg caa gaa ttt gat ggg agc gac tcg ggt gca cgc cct gat      576
Asn Thr Gly Gln Glu Phe Asp Gly Ser Asp Ser Gly Ala Arg Pro Asp
            180                 185                 190

gaa gc                                                               581
Glu


<210> SEQ ID NO 27
<211> LENGTH: 523
<212> TYPE: DNA
<213> ORGANISM: Dianthus caryophyllus
<220> FEATURE:
<221> NAME/KEY: CDS
<222> LOCATION: (1)..(522)

<400> SEQUENCE: 27

mga aga tcc atc aag tgc ctt gca ccc act ttc aaa ggc gat ttt gcc       48
Arg Arg Ser Ile Lys Cys Leu Ala Pro Thr Phe Lys Gly Asp Phe Ala
  1               5                  10                  15

tta cca gga gct caa tta cgc tcc aaa ggg ttg aat cga att ggt aat       96
Leu Pro Gly Ala Gln Leu Arg Ser Lys Gly Leu Asn Arg Ile Gly Asn
            20                  25                  30

ctg ttg gtt ccg aat gat aac tac tgt aaa ttt gag gat tgg atc att      144
Leu Leu Val Pro Asn Asp Asn Tyr Cys Lys Phe Glu Asp Trp Ile Ile
        35                  40                  45

cca att tta gat aag atg ttg gaa gag caa att tca gag aaa atc tta      192
Pro Ile Leu Asp Lys Met Leu Glu Glu Gln Ile Ser Glu Lys Ile Leu
    50                  55                  60

tgg aca cca tcg aag ttg att ggt cga tta gga aga gaa ata aac gat      240
Trp Thr Pro Ser Lys Leu Ile Gly Arg Leu Gly Arg Glu Ile Asn Asp
 65                  70                  75                  80

gag agt tca tac ctt tac tgg gcc ttc aag aac aat att cca gta ttt      288
Glu Ser Ser Tyr Leu Tyr Trp Ala Phe Lys Asn Asn Ile Pro Val Phe
                 85                  90                  95

tgc cca ggt tta aca gac ggc tca ctc gga gac atg cta tat ttt cat      336
Cys Pro Gly Leu Thr Asp Gly Ser Leu Gly Asp Met Leu Tyr Phe His
            100                 105                 110

tct ttt cgc aat ccg ggt tta atc atc gat gtt gtg caa gat ata aga      384
Ser Phe Arg Asn Pro Gly Leu Ile Ile Asp Val Val Gln Asp Ile Arg
        115                 120                 125

gca gta aat ggc gag gct gtg cac gca gcg cct agg aaa aca ggc atg      432
Ala Val Asn Gly Glu Ala Val His Ala Ala Pro Arg Lys Thr Gly Met
    130                 135                 140

att ata ctc ggt gga ggg ttg cct aag cac cac atc tgc aac gca aac      480
Ile Ile Leu Gly Gly Gly Leu Pro Lys His His Ile Cys Asn Ala Asn
145                 150                 155                 160

atg atg aga aat ggc gcc gat tat gct gtt ttc atc aac acc g            523
```

```
Met Met Arg Asn Gly Ala Asp Tyr Ala Val Phe Ile Asn Thr
                165                 170


<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

ttgargaaga tycatmaart gcct                                        24


<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

ccatcaaayt cytgkgcrgt gtt                                         23


<210> SEQ ID NO 30
<211> LENGTH: 484
<212> TYPE: DNA
<213> ORGANISM: Arabidopsis thaliana
<220> FEATURE:
<221> NAME/KEY: CDS
<222> LOCATION: (2)..(112)

<400> SEQUENCE: 30

t gca cgc cct gat gaa gct gtg tct tgg ggt aaa att agg ggt tct gct     49
  Ala Arg Pro Asp Glu Ala Val Ser Trp Gly Lys Ile Arg Gly Ser Ala
    1               5                  10                  15

aaa acc gtt aag gtc tgc ttt tta att tct tca cat cct aat tta tat       97
Lys Thr Val Lys Val Cys Phe Leu Ile Ser Ser His Pro Asn Leu Tyr
             20                  25                  30

ctc act cag tgg ttt tgagtacata tttaatattg gatcattctt gcaggtatac      152
Leu Thr Gln Trp Phe
         35

tgtgatgcta ccatagcctt cccattgttg gttgcagaaa catttgccac aaagagagac    212

caaacctgtg agtctaagac ttaagaactg actggtcgtt ttggccatgg attcttaaag    272

atcgttgctt tttgatttta cactggagtg accatataac actccacatt gatgtggctg    332

tgacgcgaat tgtcttcttg cgaattgtac tttagtttct ctcaacctaa aatgatttgc    392

agattgtgtt ttcgtttaaa acacaagagt cttgtagtca ataatccttt gccttataaa    452

attattcagt tccaacaaaa aaaaaaaaaa aa                                  484


<210> SEQ ID NO 31
<211> LENGTH: 559
<212> TYPE: DNA
<213> ORGANISM: Lycopersicon esculentum
<220> FEATURE:
<221> NAME/KEY: CDS
<222> LOCATION: (1)..(156)
<220> FEATURE:
<221> NAME/KEY: modified_base
<222> LOCATION: (542)
<223> OTHER INFORMATION: a, t, c or g

<400> SEQUENCE: 31

ggt gct cgt cct gat gaa gct gta tca tgg gga aag ata cgt ggt ggt       48
```

-continued

```
Gly Ala Arg Pro Asp Glu Ala Val Ser Trp Gly Lys Ile Arg Gly Gly
  1               5                  10                  15

gcc aag act gtg aag gtg cat tgt gat gca acc att gca ttt ccc ata       96
Ala Lys Thr Val Lys Val His Cys Asp Ala Thr Ile Ala Phe Pro Ile
             20                  25                  30

tta gta gct gag aca ttt gca gct aag agt aag gaa ttc tcc cag ata      144
Leu Val Ala Glu Thr Phe Ala Ala Lys Ser Lys Glu Phe Ser Gln Ile
         35                  40                  45

agg tgc caa gtt tgaacattga ggaagctgtc cttccgacca cacatatgaa          196
Arg Cys Gln Val
     50

ttgctagctt ttgaagccaa cttgctagtg tgcagcacca tttattctgc aaaactgact    256

agagagcagg gtatattcct ctaccccgag ttagacgaca tcctgtatgg ttcaaattaa    316

ttatttttct ccccttcaca ccatgttatt tagttctctt cctcttcgaa agtgaagagc    376

ttagatgttc ataggttttg aattatgttg gaggttggtg ataactgact agtcctctta    436

ccatatagat aatgtatcct tgtactatga gattttgggt gtgtttgata ccaaggaaaa    496

atgtttattt ggaaaacaat tggattttta atttaaaaaa aattgnttaa aaaaaaaaaa    556

aaa                                                                  559


<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      conserved peptide fragment

<400> SEQUENCE: 32

Cys Lys Val Val Glu Val Ser Thr Ser Lys Thr Gly Lys His Gly His
  1               5                  10                  15

Ala Lys Cys His Phe Val
             20


<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

gagctcaaga ataacatctc ataagaaac                                       29


<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

ctcgagtgct cacttctctc tcttagg                                         27


<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 35

Cys Asn Asp Asp Thr Leu Leu Gln Gln Ile Lys Ser
1 5 10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Cys Thr Asp Asp Gly Leu Thr Ala Gln Met Arg Leu
1 5 10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Cys Thr Asp Glu Ala Leu Leu Thr Gln Leu Lys Asn
1 5 10

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
aagcttgatc gtggtcaact tcctctgtta cc 32

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gagctcagaa gaagtataaa aaccatc 27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ctcgagtgct cacttctctc tcttagg 27

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gagctcaaga ataacatctc ataagaaac 29

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
ctcgagctaa actccattcg ctgacttcgc 30

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
gagctctagt aaatataaga gtgtcttgc 29

<210> SEQ ID NO 44
<211> LENGTH: 353
<212> TYPE: PRT
<213> ORGANISM: Unknown
<220> FEATURE:
<223> OTHER INFORMATION: Description of Unknown: Fungi sequence

<400> SEQUENCE: 44

```
Met Ala Asp Asn Gln Ile Pro Ser Ser Val Ala Asp Ala Val Leu Val
  1               5                  10                  15

Lys Ser Ile Glu Met Pro Glu Gly Ser Gln Lys Val Glu Glu Leu Asp
             20                  25                  30

Phe Asn Lys Phe Lys Gly Arg Pro Ile Thr Val Asp Asp Leu Leu Gln
         35                  40                  45

Gly Met Lys His Met Gly Phe Gln Ala Ser Ser Met Cys Glu Ala Val
     50                  55                  60

Arg Ile Ile Asn Glu Met Arg Ala Tyr Arg Asp Pro Thr Thr Ser Glu
 65                  70                  75                  80

Lys Thr Thr Ile Phe Leu Gly Tyr Thr Ser Asn Leu Ile Ser Ser Gly
                 85                  90                  95

Leu Arg Gly Thr Leu Arg Tyr Leu Val Gln His Lys His Val Ser Ala
            100                 105                 110

Ile Val Thr Thr Ala Gly Gly Ile Glu Glu Asp Phe Ile Lys Cys Leu
        115                 120                 125

Gly Asp Thr Tyr Met Ser Ser Phe Ser Ala Val Gly Ala Asp Leu Arg
    130                 135                 140

Ser Lys Gly Leu Asn Arg Ile Gly Asn Leu Val Val Pro Asn Ser Asn
145                 150                 155                 160

Tyr Cys Ala Phe Glu Asp Trp Val Val Pro Ile Leu Asp Lys Met Leu
                165                 170                 175

Glu Glu Gln Glu Ala Ser Arg Gly Thr Glu Asn Glu Ile Asn Trp Thr
            180                 185                 190

Pro Ser Lys Val Ile His Arg Leu Gly Lys Glu Ile Asn Asp Glu Arg
        195                 200                 205
```

```
Ser Val Tyr Tyr Trp Ala Trp Lys Asn Asp Ile Pro Val Phe Cys Pro
    210                 215                 220

Ala Leu Thr Asp Gly Ser Leu Gly Asp Met Leu Tyr Phe His Thr Phe
225                 230                 235                 240

Lys Ala Ser Pro Glu Gln Leu Arg Ile Asp Ile Val Glu Asp Ile Arg
                245                 250                 255

Lys Ile Asn Thr Ile Ala Val Arg Ala Lys Arg Ala Gly Met Ile Ile
            260                 265                 270

Leu Gly Gly Gly Ile Val Lys His His Ile Ala Asn Ala Cys Leu Met
        275                 280                 285

Arg Asn Gly Ala Glu Ser Ala Val Tyr Ile Asn Thr Ala Gln Glu Phe
    290                 295                 300

Asp Gly Ser Asp Ala Gly Ala Arg Pro Asp Glu Ala Val Ser Trp Gly
305                 310                 315                 320

Lys Ile Lys Val Gly Ala Asp Ala Val Lys Val Tyr Met Glu Ala Thr
                325                 330                 335

Ala Ala Phe Pro Phe Ile Val Ala Asn Thr Phe Ala Lys Glu Asp Gly
            340                 345                 350

Leu
```

<210> SEQ ID NO 45
<211> LENGTH: 387
<212> TYPE: PRT
<213> ORGANISM: Unknown
<220> FEATURE:
<223> OTHER INFORMATION: Description of Unknown: Yeast sequence

<400> SEQUENCE: 45

```
Met Ser Asp Ile Asn Glu Lys Leu Pro Glu Leu Leu Gln Asp Ala Val
  1               5                  10                  15

Leu Lys Ala Ser Val Pro Ile Pro Asp Asp Phe Val Lys Val Gln Gly
             20                  25                  30

Ile Asp Tyr Ser Lys Pro Glu Ala Thr Asn Met Arg Ala Thr Asp Leu
         35                  40                  45

Ile Glu Ala Met Lys Thr Met Gly Phe Gln Ala Ser Ser Val Gly Thr
     50                  55                  60

Ala Cys Glu Ile Ile Asp Ser Met Arg Ser Trp Arg Gly Lys His Ile
 65                  70                  75                  80

Asp Glu Leu Asp Asp His Glu Lys Lys Gly Cys Phe Asp Glu Glu Gly
                 85                  90                  95

Tyr Gln Lys Thr Thr Ile Phe Met Gly Tyr Thr Ser Asn Leu Ile Ser
            100                 105                 110

Ser Gly Val Arg Glu Thr Leu Arg Tyr Leu Val Gln His Lys Met Val
        115                 120                 125

Asp Ala Val Val Thr Ser Ala Gly Gly Val Glu Glu Asp Leu Ile Lys
    130                 135                 140

Cys Leu Ala Pro Thr Tyr Leu Gly Glu Phe Ala Leu Lys Gly Lys Ser
145                 150                 155                 160

Leu Arg Asp Gln Gly Met Asn Arg Ile Gly Asn Leu Leu Val Pro Asn
                165                 170                 175

Asp Asn Tyr Cys Lys Phe Glu Glu Trp Ile Val Pro Ile Leu Asp Lys
            180                 185                 190

Met Leu Glu Glu Gln Asp Glu Tyr Val Lys Lys His Gly Ala Asp Cys
        195                 200                 205

Leu Glu Ala Asn Gln Asp Val Asp Ser Pro Ile Trp Thr Pro Ser Lys
```

-continued

```
    210                 215                 220

Met Ile Asp Arg Phe Gly Lys Glu Ile Asn Asp Glu Ser Ser Val Leu
225                 230                 235                 240

Tyr Trp Ala His Lys Asn Lys Ile Pro Ile Phe Cys Pro Ser Leu Thr
                245                 250                 255

Asp Gly Ser Ile Gly Asp Met Leu Phe Phe His Thr Phe Lys Ala Ser
            260                 265                 270

Pro Lys Gln Leu Arg Val Asp Ile Val Gly Asp Ile Arg Lys Ile Asn
        275                 280                 285

Ser Met Ser Met Ala Ala Tyr Arg Ala Gly Met Ile Ile Leu Gly Gly
    290                 295                 300

Gly Leu Ile Lys His His Ile Ala Asn Ala Cys Leu Met Arg Asn Gly
305                 310                 315                 320

Ala Asp Tyr Ala Val Tyr Ile Asn Thr Gly Gln Glu Tyr Asp Gly Ser
                325                 330                 335

Asp Ala Gly Ala Arg Pro Asp Glu Ala Val Ser Trp Gly Lys Ile Lys
            340                 345                 350

Ala Glu Ala Lys Ser Val Lys Leu Phe Ala Asp Val Thr Thr Val Leu
        355                 360                 365

Pro Leu Ile Val Ala Ala Thr Phe Ala Ser Gly Lys Pro Ile Lys Lys
    370                 375                 380

Val Lys Asn
385


<210> SEQ ID NO 46
<211> LENGTH: 370
<212> TYPE: PRT
<213> ORGANISM: Unknown
<220> FEATURE:
<223> OTHER INFORMATION: Description of Unknown: Archaebacterial
      sequence

<400> SEQUENCE: 46

Met Arg Asp Ile Lys Asp Asn Pro Ile Arg Arg Gly Ile Ala Glu Gln
  1               5                  10                  15

Ser Glu Ala Met His Pro Gly Tyr Thr Asn Arg Ala Lys Pro Tyr Gly
            20                  25                  30

Cys Lys Arg Asp Pro Lys Asp Ile Val Leu Lys Glu Ser Glu Asp Ile
        35                  40                  45

Glu Gly Ile Ala Ile Glu Gly Pro Trp Leu Glu Asp Asp Ile Ser Leu
     50                  55                  60

Glu Glu Ile Ile Lys Lys Tyr Tyr Leu Lys Ile Gly Phe Gln Ala Ser
 65                  70                  75                  80

His Ile Gly Lys Ala Ile Lys Ile Trp Lys His Ile Glu Glu Lys Arg
                 85                  90                  95

Lys Lys Gly Asp Glu Ile Thr Val Phe Phe Gly Tyr Thr Ser Asn Ile
            100                 105                 110

Val Ser Ser Gly Leu Arg Glu Ile Ile Ala Tyr Leu Val Lys His Lys
        115                 120                 125

Lys Ile Asp Ile Ile Val Thr Thr Ala Gly Gly Val Glu Glu Asp Phe
    130                 135                 140

Ile Lys Cys Leu Lys Pro Phe Ile Leu Gly Asp Trp Glu Val Asp Gly
145                 150                 155                 160

Lys Met Leu Arg Glu Lys Gly Ile Asn Arg Ile Gly Asn Ile Phe Val
                165                 170                 175

Pro Asn Asp Arg Tyr Ile Ala Phe Glu Glu Tyr Met Met Glu Phe Phe
```

```
            180                 185                 190

Glu Glu Ile Leu Asn Leu Gln Arg Glu Thr Gly Lys Ile Ile Thr Ala
        195                 200                 205

Ser Glu Phe Cys Tyr Lys Leu Gly Glu Phe Met Asp Lys Lys Leu Lys
    210                 215                 220

Ser Lys Glu Lys Glu Lys Ser Ile Leu Tyr Trp Ala Tyr Lys Asn Asn
225                 230                 235                 240

Ile Pro Ile Phe Cys Pro Ala Ile Thr Asp Gly Ser Ile Gly Asp Met
                245                 250                 255

Leu Tyr Phe Phe Lys Lys Tyr Asn Lys Asp Glu Glu Leu Lys Ile Asp
            260                 265                 270

Val Ala Asn Asp Ile Val Lys Leu Asn Asp Ile Ala Ile Asn Ser Lys
        275                 280                 285

Glu Thr Ala Cys Ile Val Leu Gly Gly Ser Leu Pro Lys His Ser Ile
    290                 295                 300

Ile Asn Ala Asn Leu Phe Arg Glu Gly Thr Asp Tyr Ala Ile Tyr Val
305                 310                 315                 320

Thr Thr Ala Leu Pro Trp Asp Gly Ser Leu Ser Gly Ala Pro Pro Glu
                325                 330                 335

Glu Gly Val Ser Trp Gly Lys Ile Gly Ala Lys Ala Asp Tyr Val Glu
            340                 345                 350

Ile Trp Gly Asp Ala Thr Ile Ile Phe Pro Leu Leu Val Tyr Cys Val
        355                 360                 365

Met Lys
    370


<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, t, c or g
<220> FEATURE:
<221> NAME/KEY: modified_base
<222> LOCATION: (15)
<223> OTHER INFORMATION: a, t, c or g

<400> SEQUENCE: 47

gcngarttyg ayggntccga yca                                              23


<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

ccgagctcct gttaccaaaa aatctgtacc                                       30


<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 49
acctcgagcg gccgcagaag aagtataaaa accatc 36

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
cgtcgacgat atctcttttt atattcaaac 30

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
cgtctagaca ttgttttagg aaagttaaat ga 32

<210> SEQ ID NO 52
<211> LENGTH: 1235
<212> TYPE: DNA
<213> ORGANISM: Arabidopsis thaliana

<400> SEQUENCE: 52
accctagatc gctttcttca gtgttctata aaaactaaac tccattcgct gacttcgcaa 60
agaagaacac tttctctctg aaatctcaaa ttcatctctt ctcttccgat ttcgctgaat 120
catgtcagac gacgagcatc acttcgaatc cagcgacgcc ggagcttcta agacttatcc 180
tcaacaagcc ggtaacattc gtaaaggtgg tcacatcgtc atcaagggac gtccctgcaa 240
ggttttgtct ctgatttgat tattattgat tttagaggaa tcatcttcat ggattgtatt 300
aaagcagtgt tccgttacct gatcgttgtg aatttttgag gtttagtgat tctggattgt 360
gatctggtgt ttagtgttga gaaaaacctc tgtttttgaa gtttatggat ttatagggtt 420
tttaaatcta taatagggtt taattcaatt ggtgatatgt ggggtttatg atataggtgg 480
ttgaggtatc gacttcgaag actgggaagc atggtcacgc caagtgtcac tttgttgcca 540
ttgatatctt tacttctaag aagcttgaag atatcgttcc ttcttcccac aattgtgatg 600
tgagtcttgt gaatggatta gaaacgttat acaaagtcta taatttttga ctcacaacac 660
aaaactgttt cctttttatt ggcacaggtt ccacatgtga atcgtgttga ttatcagttg 720
attgatatct ctgaagatgg ctttgtatgt catcttcttt ttcactagtt cagctttgtg 780
ttttgtcttt gcccatatgg ttgaattaga gggttttgtt ctttgattac atttacaggt 840
tagtcttctt actgataatg gtagcactaa ggatgatctg aagctgccaa cagatgaagc 900
tttactcaca cagctcaaga atggatttga ggagggtaag gatattgttg tgtctgtcat 960
gtctgcaatg ggagaggagc agatgtgtgc tctcaaggaa gttggtccca agtaataata 1020
ataagtaagc attctctctt ttacagaggc tatgtattat caagtttgac agagtcaaat 1080
gttataagaa caaagtttgg tccttttttt tggtcttctt agtataattt aagcccacat 1140
gtgtttccca tgcaagacac tcttatattt actagtatat cttactattg gttttggttg 1200
tggagaagtt actgttgaca gttccaaacc tctac 1235

<210> SEQ ID NO 53
<211> LENGTH: 161
<212> TYPE: PRT
<213> ORGANISM: Mycosphaerella fijiensis

<400> SEQUENCE: 53

```
Gly Leu Asn Arg Ile Gly Asn Phe Leu Val Pro Asn Asp Asn Tyr Cys
  1               5                  10                  15

Arg Phe Glu Asp Trp Val Met Pro Ile Leu Asp Thr Met Leu Glu Glu
             20                  25                  30

Gln Glu Ala Cys Lys Gly Ser Gly Glu Ala Ile His Trp Thr Pro Ser
         35                  40                  45

Lys Ile Ile Asn Arg Leu Gly Lys Glu Val Asn Asp Glu Ser Ser Val
     50                  55                  60

Tyr Tyr Trp Ala Trp Lys Asn Asp Ile Pro Val Phe Cys Pro Ala Leu
 65                  70                  75                  80

Thr Asp Gly Ser Leu Gly Asp Met Leu Tyr Phe His Thr Phe Lys Ser
                 85                  90                  95

Ser Pro Gln Gln Leu Arg Val Asp Ile Val Glu Asp Ile Arg Lys Ile
            100                 105                 110

Asn Thr Leu Ala Val Arg Ala Lys Arg Thr Gly Met Ile Ile Leu Gly
        115                 120                 125

Gly Gly Ile Val Lys His His Ile Ala Asn Ala Asn Leu Met Arg Asn
    130                 135                 140

Gly Ala Glu Ser Ala Val Tyr Ile Asn Thr Ala Glu Phe Asp Gly Ser
145                 150                 155                 160

Asp
```

<210> SEQ ID NO 54
<211> LENGTH: 861
<212> TYPE: DNA
<213> ORGANISM: Arabidopsis sp.

<400> SEQUENCE: 54

```
tttttccctt ctcccaatct catcttctcc gaaaaccttt cttctctcaa atttctgtga      60

aaacatgtct gacgacgagc accactttga ggccagcgaa tccggagctt ccaagaccta     120

tcctcaatca gccggtaaca tccgtaaagg tggtcacatc gtcatcaaaa accgtccctg     180

caaggttgtt gaggtttcga cttccaaaac tggcaagcac ggtcacgcca aatgtcactt     240

tgttgctatt gatatcttca ctgctaagaa gcttgaagat attgttccat cttcccacaa     300

ttgtgatgtt ccacatgtga accgtgttga ttaccagttg attgatatca ctgaggatgg     360

cttcgtgagc cttctcactg acagtggtgg caccaaggat gatctcaagc ttcccaccga     420

tgatggtctc accgcccaga tgaggcttgg attcgatgag ggaaaggata ttgtggtgtc     480

tgtcatgtct tccatgggag aggagcagat ctgtgccgtc aaggaagttg gtggtggcaa     540

gtaaacaagt atcattcgat atattattac cagtttgaca acggacgtca atgttataag     600

aaccaaaaga tgtttttctt tttcctaatt tagacccttt gtgtgtgttt cttgttgcaa     660

gacaaccata tctattggtt ttggattgtt ggaaaagttt gtgttgaaac attcaaagtt     720

tcttatgaga tgttattctt aaaaccactt tttgtttgtt cactggatat gtttgttcat     780

gaagcttgtt ttaagcaact ctttacatga tattcattgc tatttgcacg attcaagagt     840

gaaatataca ttttatttaa c                                               861
```

```
<210> SEQ ID NO 55
<211> LENGTH: 159
<212> TYPE: PRT
<213> ORGANISM: Arabidopsis thaliana

<400> SEQUENCE: 55

Met Ser Asp Asp Glu His His Phe Glu Ala Ser Glu Ser Gly Ala Ser
  1               5                  10                  15

Lys Thr Tyr Pro Gln Ser Ala Gly Asn Ile Arg Lys Gly Gly His Ile
             20                  25                  30

Val Ile Lys Asn Arg Pro Cys Lys Val Val Glu Val Ser Thr Ser Lys
         35                  40                  45

Thr Gly Lys His Gly His Ala Lys Cys His Phe Val Ala Ile Asp Ile
     50                  55                  60

Phe Thr Ala Lys Lys Leu Glu Asp Ile Val Pro Ser Ser His Asn Cys
 65                  70                  75                  80

Asp Val Pro His Val Asn Arg Val Asp Tyr Gln Leu Ile Asp Ile Thr
                 85                  90                  95

Glu Asp Gly Phe Val Ser Leu Leu Thr Asp Ser Gly Gly Thr Lys Asp
            100                 105                 110

Asp Leu Lys Leu Pro Thr Asp Asp Gly Leu Thr Ala Gln Met Arg Leu
        115                 120                 125

Gly Phe Asp Glu Gly Lys Asp Ile Val Val Ser Val Met Ser Ser Met
    130                 135                 140

Gly Glu Glu Gln Ile Cys Ala Val Lys Glu Val Gly Gly Gly Lys
145                 150                 155


<210> SEQ ID NO 56
<211> LENGTH: 698
<212> TYPE: DNA
<213> ORGANISM: Lycopersicon esculentum
<220> FEATURE:
<221> NAME/KEY: CDS
<222> LOCATION: (52)..(528)

<400> SEQUENCE: 56

cttcctgaat ttttctcctt ctccttctcc gttcaatcga atttttcagc c atg tct      57
                                                         Met Ser
                                                           1

gac gag gag cat caa ttt gag tct aag gct gat gcc gga gca tca aaa      105
Asp Glu Glu His Gln Phe Glu Ser Lys Ala Asp Ala Gly Ala Ser Lys
          5                  10                  15

act tac cct caa caa gct ggt act att cgt aag aac ggt tat atc gtc      153
Thr Tyr Pro Gln Gln Ala Gly Thr Ile Arg Lys Asn Gly Tyr Ile Val
     20                  25                  30

atc aaa ggc cgt cca tgc aag gtt gtg gaa gtc tct aca tcc aaa act      201
Ile Lys Gly Arg Pro Cys Lys Val Val Glu Val Ser Thr Ser Lys Thr
 35                  40                  45                  50

ggc aag cac ggt cac gcc aaa tgt cat ttc gtt gct att gac atc ttc      249
Gly Lys His Gly His Ala Lys Cys His Phe Val Ala Ile Asp Ile Phe
                 55                  60                  65

act ggg aag aag ctt gag gat att gtc ccc tct tca cac aat tgt gat      297
Thr Gly Lys Lys Leu Glu Asp Ile Val Pro Ser Ser His Asn Cys Asp
             70                  75                  80

gtg ccc cat gtt aat cgt aca gat tat cag ctt att gac atc tct gaa      345
Val Pro His Val Asn Arg Thr Asp Tyr Gln Leu Ile Asp Ile Ser Glu
         85                  90                  95

gat gga ttt gtg agt ctg ctt act gac aat ggt aac acc aag gat gac      393
Asp Gly Phe Val Ser Leu Leu Thr Asp Asn Gly Asn Thr Lys Asp Asp
    100                 105                 110
```

```
ctc agg ctt cct act gat gaa aat ctg ctt tca ctg atc aag gac ggg      441
Leu Arg Leu Pro Thr Asp Glu Asn Leu Leu Ser Leu Ile Lys Asp Gly
115                 120                 125                 130

ttt gcc gag ggt aag gac ctc gtt gtg tct gtt atg tca gct atg ggt      489
Phe Ala Glu Gly Lys Asp Leu Val Val Ser Val Met Ser Ala Met Gly
                135                 140                 145

gag gaa cag att aat gct ttg aag gat att ggc ccc aag tgatctcttg       538
Glu Glu Gln Ile Asn Ala Leu Lys Asp Ile Gly Pro Lys
            150                 155

attggatgga ttgcttgacg cgatggttct ttacgacctt gagtgagata gatatttata    598

gtcatggaaa aaaattgtga tcttatggaa tattcgtatc atgatttatg gaccattgtg    658

agttagattt ttatttatgt tgttttaaat tgtggtattc                          698


<210> SEQ ID NO 57
<211> LENGTH: 159
<212> TYPE: PRT
<213> ORGANISM: Lycopersicon esculentum

<400> SEQUENCE: 57

Met Ser Asp Glu Glu His Gln Phe Glu Ser Lys Ala Asp Ala Gly Ala
  1               5                  10                  15

Ser Lys Thr Tyr Pro Gln Gln Ala Gly Thr Ile Arg Lys Asn Gly Tyr
             20                  25                  30

Ile Val Ile Lys Gly Arg Pro Cys Lys Val Val Glu Val Ser Thr Ser
         35                  40                  45

Lys Thr Gly Lys His Gly His Ala Lys Cys His Phe Val Ala Ile Asp
     50                  55                  60

Ile Phe Thr Gly Lys Lys Leu Glu Asp Ile Val Pro Ser Ser His Asn
 65                  70                  75                  80

Cys Asp Val Pro His Val Asn Arg Thr Asp Tyr Gln Leu Ile Asp Ile
                 85                  90                  95

Ser Glu Asp Gly Phe Val Ser Leu Leu Thr Asp Asn Gly Asn Thr Lys
            100                 105                 110

Asp Asp Leu Arg Leu Pro Thr Asp Glu Asn Leu Leu Ser Leu Ile Lys
        115                 120                 125

Asp Gly Phe Ala Glu Gly Lys Asp Leu Val Val Ser Val Met Ser Ala
    130                 135                 140

Met Gly Glu Glu Gln Ile Asn Ala Leu Lys Asp Ile Gly Pro Lys
145                 150                 155


<210> SEQ ID NO 58
<211> LENGTH: 158
<212> TYPE: PRT
<213> ORGANISM: Arabidopsis thaliana

<400> SEQUENCE: 58

Met Ser Asp Glu Glu His His Phe Glu Ser Ser Asp Ala Gly Ala Ser
  1               5                  10                  15

Lys Thr Tyr Pro Gln Gln Ala Gly Thr Ile Arg Lys Asn Gly Tyr Ile
             20                  25                  30

Val Ile Lys Asn Arg Pro Cys Lys Val Val Glu Val Ser Thr Ser Lys
         35                  40                  45

Thr Gly Lys His Gly His Ala Lys Cys His Phe Val Ala Ile Asp Ile
     50                  55                  60

Phe Thr Ser Lys Lys Leu Glu Asp Ile Val Pro Ser Ser His Asn Cys
 65                  70                  75                  80

Asp Val Pro His Val Asn Arg Thr Asp Tyr Gln Leu Ile Asp Ile Ser
```

```
                85                  90                  95

Glu Asp Gly Tyr Val Ser Leu Leu Thr Asp Asn Gly Ser Thr Lys Asp
            100                 105                 110

Asp Leu Lys Leu Pro Asn Asp Asp Thr Leu Leu Gln Gln Ile Lys Ser
        115                 120                 125

Gly Phe Asp Asp Gly Lys Asp Leu Val Val Ser Val Met Ser Ala Met
    130                 135                 140

Gly Glu Glu Gln Ile Asn Ala Leu Lys Asp Ile Gly Pro Lys
145                 150                 155


<210> SEQ ID NO 59
<211> LENGTH: 159
<212> TYPE: PRT
<213> ORGANISM: Arabidopsis thaliana

<400> SEQUENCE: 59

Met Ser Asp Asp Glu His His Phe Glu Ala Ser Glu Ser Gly Ala Ser
  1               5                  10                  15

Lys Thr Tyr Pro Gln Ser Ala Gly Asn Ile Arg Lys Gly Gly His Ile
             20                  25                  30

Val Ile Lys Asn Arg Pro Cys Lys Val Val Glu Val Ser Thr Ser Lys
         35                  40                  45

Thr Gly Lys His Gly His Ala Lys Cys His Phe Val Ala Ile Asp Ile
     50                  55                  60

Phe Thr Ala Lys Lys Leu Glu Asp Ile Val Pro Ser Ser His Asn Cys
 65                  70                  75                  80

Asp Val Pro His Val Asn Arg Val Asp Tyr Gln Leu Ile Asp Ile Thr
                 85                  90                  95

Glu Asp Gly Phe Val Ser Leu Leu Thr Asp Ser Gly Gly Thr Lys Asp
            100                 105                 110

Asp Leu Lys Leu Pro Thr Asp Asp Gly Leu Thr Ala Gln Met Arg Leu
        115                 120                 125

Gly Phe Asp Glu Gly Lys Asp Ile Val Val Ser Val Met Ser Ser Met
    130                 135                 140

Gly Glu Glu Gln Ile Cys Ala Val Lys Glu Val Gly Gly Gly Lys
145                 150                 155


<210> SEQ ID NO 60
<211> LENGTH: 158
<212> TYPE: PRT
<213> ORGANISM: Arabidopsis thaliana

<400> SEQUENCE: 60

Met Ser Asp Asp Glu His His Phe Glu Ser Ser Asp Ala Gly Ala Ser
  1               5                  10                  15

Lys Thr Tyr Pro Gln Gln Ala Gly Asn Ile Arg Lys Gly Gly His Ile
             20                  25                  30

Val Ile Lys Gly Arg Pro Cys Lys Val Val Glu Val Ser Thr Ser Lys
         35                  40                  45

Thr Gly Lys His Gly His Ala Lys Cys His Phe Val Ala Ile Asp Ile
     50                  55                  60

Phe Thr Ser Lys Lys Leu Glu Asp Ile Val Pro Ser Ser His Asn Cys
 65                  70                  75                  80

Asp Val Pro His Val Asn Arg Val Asp Tyr Gln Leu Ile Asp Ile Ser
                 85                  90                  95

Glu Asp Gly Phe Val Ser Leu Leu Thr Asp Asn Gly Ser Thr Lys Asp
            100                 105                 110
```

```
Asp Leu Lys Leu Pro Thr Asp Glu Ala Leu Leu Thr Gln Leu Lys Asn
        115                 120                 125

Gly Phe Glu Glu Gly Lys Asp Ile Val Val Ser Val Met Ser Ala Met
    130                 135                 140

Gly Glu Glu Gln Met Cys Ala Leu Lys Glu Val Gly Pro Lys
145                 150                 155


<210> SEQ ID NO 61
<211> LENGTH: 477
<212> TYPE: DNA
<213> ORGANISM: Arabidopsis thaliana

<400> SEQUENCE: 61

atgtccgacg aggagcatca ctttgagtcc agtgacgccg gagcgtccaa aacctaccct     60

caacaagctg gaaccatccg taagaatggt tacatcgtca tcaaaaatcg tccctgcaag    120

gttgttgagg tttcaacctc gaagactggc aagcatggtc atgctaaatg tcattttgta    180

gctattgata tcttcaccag caagaaactc gaagatattg ttccttcttc ccacaattgt    240

gatgttcctc atgtcaaccg tactgattat cagctgattg acatttctga agatggatat    300

gtcagtttgt tgactgataa cggtagtacc aaggatgacc ttaagctccc taatgatgac    360

actctgctcc aacagatcaa gagtgggttt gatgatggaa aagatctagt ggtgagtgtg    420

atgtcagcta tgggagagga acagatcaat gctcttaagg acatcggtcc caagtga       477


<210> SEQ ID NO 62
<211> LENGTH: 480
<212> TYPE: DNA
<213> ORGANISM: Arabidopsis thaliana

<400> SEQUENCE: 62

atgtctgacg acgagcacca ctttgaggcc agcgaatccg gagcttccaa gacctatcct     60

caatcagccg gtaacatccg taaaggtggt cacatcgtca tcaaaaaccg tccctgcaag    120

gttgttgagg tttcgacttc caaaactggc aagcacggtc acgccaaatg tcactttgtt    180

gctattgata tcttcactgc taagaagctt gaagatattg ttccatcttc ccacaattgt    240

gatgttccac atgtgaaccg tgttgattac cagttgattg atatcactga ggatggcttc    300

gtgagccttc tcactgacag tggtggcacc aaggatgatc tcaagcttcc caccgatgat    360

ggtctcaccg cccagatgag gcttggattc gatgagggaa aggatattgt ggtgtctgtc    420

atgtcttcca tgggagagga gcagatctgt gccgtcaagg aagttggtgg tggcaagtaa    480


<210> SEQ ID NO 63
<211> LENGTH: 477
<212> TYPE: DNA
<213> ORGANISM: Arabidopsis thaliana

<400> SEQUENCE: 63

atgtcagacg acgagcatca cttcgaatcc agcgacgccg gagcttctaa gacttatcct     60

caacaagccg gtaacattcg taaaggtggt cacatcgtca tcaagggacg tccctgcaag    120

gtggttgagg tatcgacttc gaagactggg aagcatggtc acgccaagtg tcactttgtt    180

gccattgata tctttacttc taagaagctt gaagatatcg ttccttcttc ccacaattgt    240

gatgttccac atgtgaatcg tgttgattat cagttgattg atatctctga agatggcttt    300

gttagtcttc ttactgataa tggtagcact aaggatgatc tgaagctgcc aacagatgaa    360

gctttactca cacagctcaa gaatggattt gaggagggta aggatattgt tgtgtctgtc    420
```

```
atgtctgcaa tgggagagga gcagatgtgt gctctcaagg aagttggtcc caagtaa       477


<210> SEQ ID NO 64
<211> LENGTH: 700
<212> TYPE: DNA
<213> ORGANISM: Lycopersicon esculentum
<220> FEATURE:
<221> NAME/KEY: CDS
<222> LOCATION: (56)..(532)

<400> SEQUENCE: 64

aaatttctcc ttctccttaa tcctctccac cggcgaaccg gcgaagatca aaacg atg      58
                                                             Met
                                                               1

tcg gac gaa gag cac cac ttc gaa tcc aag gcc gat gcc gga gct tca      106
Ser Asp Glu Glu His His Phe Glu Ser Lys Ala Asp Ala Gly Ala Ser
              5                  10                  15

aag acg tat cct caa caa gct ggt act att cgt aaa ggt ggt cac atc      154
Lys Thr Tyr Pro Gln Gln Ala Gly Thr Ile Arg Lys Gly Gly His Ile
         20                  25                  30

gtc ata aaa aat cgt cct tgc aag gtg gtt gaa gtt tca act tcc aag      202
Val Ile Lys Asn Arg Pro Cys Lys Val Val Glu Val Ser Thr Ser Lys
     35                  40                  45

aca ggc aag cac ggt cat gct aaa tgt cac ttc gtg gca att gac att      250
Thr Gly Lys His Gly His Ala Lys Cys His Phe Val Ala Ile Asp Ile
 50                  55                  60                  65

ttc act gga aag aaa ctt gag gat att gtt ccc tct tct cac aat tgt      298
Phe Thr Gly Lys Lys Leu Glu Asp Ile Val Pro Ser Ser His Asn Cys
                 70                  75                  80

gat gtt cct cat gtg aat agg act gat tat caa ctt att gat atc tct      346
Asp Val Pro His Val Asn Arg Thr Asp Tyr Gln Leu Ile Asp Ile Ser
              85                  90                  95

gag gat ggc ttt gtg agt ctg ttg act gaa aat ggt aac acc aag gat      394
Glu Asp Gly Phe Val Ser Leu Leu Thr Glu Asn Gly Asn Thr Lys Asp
        100                 105                 110

gac ttg aga ctc cca act gat gat act ctt ctg gct cag gtc aaa gat      442
Asp Leu Arg Leu Pro Thr Asp Asp Thr Leu Leu Ala Gln Val Lys Asp
    115                 120                 125

ggt ttt gct gag ggg aaa gac ctg gtt cta tca gtg atg tct gcc atg      490
Gly Phe Ala Glu Gly Lys Asp Leu Val Leu Ser Val Met Ser Ala Met
130                 135                 140                 145

gga gag gag cag att tgt ggt atc aag gac att ggc cct aag              532
Gly Glu Glu Gln Ile Cys Gly Ile Lys Asp Ile Gly Pro Lys
                150                 155

tagctgcaga tggtattggt gtatgtttac agagtttcta taaaagatgt attaagaacc    592

aaaacttctt tactttctct tgcagttgct ctatataact gccatttaac tattattata    652

tgtgttgtga ttagattctt gtctcactac agtatttcct ttactctg                 700


<210> SEQ ID NO 65
<211> LENGTH: 159
<212> TYPE: PRT
<213> ORGANISM: Lycopersicon esculentum

<400> SEQUENCE: 65

Met Ser Asp Glu Glu His His Phe Glu Ser Lys Ala Asp Ala Gly Ala
  1               5                  10                  15

Ser Lys Thr Tyr Pro Gln Gln Ala Gly Thr Ile Arg Lys Gly Gly His
             20                  25                  30

Ile Val Ile Lys Asn Arg Pro Cys Lys Val Val Glu Val Ser Thr Ser
         35                  40                  45
```

```
Lys Thr Gly Lys His Gly His Ala Lys Cys His Phe Val Ala Ile Asp
     50                  55                  60

Ile Phe Thr Gly Lys Lys Leu Glu Asp Ile Val Pro Ser Ser His Asn
 65                  70                  75                  80

Cys Asp Val Pro His Val Asn Arg Thr Asp Tyr Gln Leu Ile Asp Ile
                 85                  90                  95

Ser Glu Asp Gly Phe Val Ser Leu Leu Thr Glu Asn Gly Asn Thr Lys
            100                 105                 110

Asp Asp Leu Arg Leu Pro Thr Asp Asp Thr Leu Leu Ala Gln Val Lys
        115                 120                 125

Asp Gly Phe Ala Glu Gly Lys Asp Leu Val Leu Ser Val Met Ser Ala
    130                 135                 140

Met Gly Glu Glu Gln Ile Cys Gly Ile Lys Asp Ile Gly Pro Lys
145                 150                 155


<210> SEQ ID NO 66
<211> LENGTH: 658
<212> TYPE: DNA
<213> ORGANISM: Brassica napus
<220> FEATURE:
<221> NAME/KEY: CDS
<222> LOCATION: (1)..(477)

<400> SEQUENCE: 66

atg tct gac gag gag cac cac ttc gag tcc agc gac gcc gga gct tcc       48
Met Ser Asp Glu Glu His His Phe Glu Ser Ser Asp Ala Gly Ala Ser
  1               5                  10                  15

aaa acc tac cct cag cag gct ggt aac atc cgc aag ggt ggt cac atc       96
Lys Thr Tyr Pro Gln Gln Ala Gly Asn Ile Arg Lys Gly Gly His Ile
             20                  25                  30

gtc atc aag ggc cgt ccc tgc aag gtt gtt gag gtt tcg act tcg aag      144
Val Ile Lys Gly Arg Pro Cys Lys Val Val Glu Val Ser Thr Ser Lys
         35                  40                  45

act ggg aag cac ggt cac gca aag tgt cac ttt gtt gct atc gac atc      192
Thr Gly Lys His Gly His Ala Lys Cys His Phe Val Ala Ile Asp Ile
     50                  55                  60

ttc act gct aag aag ctc gag gat att gtt ccc tct tcc cac aat tgt      240
Phe Thr Ala Lys Lys Leu Glu Asp Ile Val Pro Ser Ser His Asn Cys
 65                  70                  75                  80

gat gtt ccc cat gtg aac cgt att gac tac cag ttg att gat atc tct      288
Asp Val Pro His Val Asn Arg Ile Asp Tyr Gln Leu Ile Asp Ile Ser
                 85                  90                  95

gag aat ggc ttt gtt agc ctt ttg acc gac agt ggt ggc acc aag gac      336
Glu Asn Gly Phe Val Ser Leu Leu Thr Asp Ser Gly Gly Thr Lys Asp
            100                 105                 110

gac ctc aag ctt ccc acc gat gat aat ctc agc gct ctg atg aag agt      384
Asp Leu Lys Leu Pro Thr Asp Asp Asn Leu Ser Ala Leu Met Lys Ser
        115                 120                 125

gga ttc gag gag gga aag gat gtg gtg gtg tct gtc atg tct tcc atg      432
Gly Phe Glu Glu Gly Lys Asp Val Val Val Ser Val Met Ser Ser Met
    130                 135                 140

gga gag gag cag atc tgt gcc gtc aag gaa gtt ggt ggt ggc aag          477
Gly Glu Glu Gln Ile Cys Ala Val Lys Glu Val Gly Gly Gly Lys
145                 150                 155

taaaacccat tctctgagag aggataatct tattaccagt ggtcaatgtt ataagaacaa    537

gaacttgttt tttttccttt ttctaattta gatcatttgt gttgtgtttc tttgttgcaa    597

gacaaccatt atctattatt ggttttggat tgtttaaaaa aaaaaaaaaa aaaaaaaaaa    657

a                                                                     658
```

<210> SEQ ID NO 67
<211> LENGTH: 159
<212> TYPE: PRT
<213> ORGANISM: Brassica napus

<400> SEQUENCE: 67

```
Met Ser Asp Glu Glu His His Phe Glu Ser Ser Asp Ala Gly Ala Ser
  1               5                  10                  15

Lys Thr Tyr Pro Gln Gln Ala Gly Asn Ile Arg Lys Gly Gly His Ile
             20                  25                  30

Val Ile Lys Gly Arg Pro Cys Lys Val Val Glu Val Ser Thr Ser Lys
         35                  40                  45

Thr Gly Lys His Gly His Ala Lys Cys His Phe Val Ala Ile Asp Ile
     50                  55                  60

Phe Thr Ala Lys Lys Leu Glu Asp Ile Val Pro Ser Ser His Asn Cys
 65                  70                  75                  80

Asp Val Pro His Val Asn Arg Ile Asp Tyr Gln Leu Ile Asp Ile Ser
                 85                  90                  95

Glu Asn Gly Phe Val Ser Leu Leu Thr Asp Ser Gly Gly Thr Lys Asp
            100                 105                 110

Asp Leu Lys Leu Pro Thr Asp Asp Asn Leu Ser Ala Leu Met Lys Ser
        115                 120                 125

Gly Phe Glu Glu Gly Lys Asp Val Val Val Ser Val Met Ser Ser Met
    130                 135                 140

Gly Glu Glu Gln Ile Cys Ala Val Lys Glu Val Gly Gly Gly Lys
145                 150                 155
```

<210> SEQ ID NO 68
<211> LENGTH: 8
<212> TYPE: PRT
<213> ORGANISM: Mycosphaerella fijiensis

<400> SEQUENCE: 68

```
Gly Leu Asn Arg Ile Gly Asn Leu
  1               5
```

<210> SEQ ID NO 69
<211> LENGTH: 8
<212> TYPE: PRT
<213> ORGANISM: Mycosphaerella fijiensis

<400> SEQUENCE: 69

```
Ala Glu Phe Asp Gly Ser Asp Gln
  1               5
```

<210> SEQ ID NO 70
<211> LENGTH: 1335
<212> TYPE: DNA
<213> ORGANISM: Brassica napus
<220> FEATURE:
<221> NAME/KEY: CDS
<222> LOCATION: (57)..(1160)

<400> SEQUENCE: 70

```
cttgctagaa ccctaaaact ccctcccaaa actctccaca tcttccgaga aagaag atg      59
                                                              Met
                                                                1

gag gag gat cgt gtt ctc tcg tct gtc cac tca acg gtc ttc aag gaa       107
Glu Glu Asp Arg Val Leu Ser Ser Val His Ser Thr Val Phe Lys Glu
             5                  10                  15

tcc gaa tcg ttg gaa gga aag tgc gac aaa atc gaa gga tac gat ttc       155
```

```
Ser Glu Ser Leu Glu Gly Lys Cys Asp Lys Ile Glu Gly Tyr Asp Phe
        20                  25                  30

aac caa gga gta aac tac ccg aag ctc ctc cga tcc atg ctc aca acc      203
Asn Gln Gly Val Asn Tyr Pro Lys Leu Leu Arg Ser Met Leu Thr Thr
    35                  40                  45

ggc ttc caa gcc tca aac ctc ggc gac gta att gat gtc gtt aat caa      251
Gly Phe Gln Ala Ser Asn Leu Gly Asp Val Ile Asp Val Val Asn Gln
 50                  55                  60                  65

atg cta gag tgg aga ctc tct gat gaa act ata gca cct gaa gac tgt      299
Met Leu Glu Trp Arg Leu Ser Asp Glu Thr Ile Ala Pro Glu Asp Cys
                 70                  75                  80

agt gaa gag gag aag gat cca gcg tat aga gag tcc gtg aag tgt aaa      347
Ser Glu Glu Glu Lys Asp Pro Ala Tyr Arg Glu Ser Val Lys Cys Lys
             85                  90                  95

atc ttt cta ggc ttc act tcg aat ctt gtt tcc tct ggt gtt aga gag      395
Ile Phe Leu Gly Phe Thr Ser Asn Leu Val Ser Ser Gly Val Arg Glu
        100                 105                 110

act att cga tac ctt gtt cag cat cat atg gtt gat gtt ata gtt act      443
Thr Ile Arg Tyr Leu Val Gln His His Met Val Asp Val Ile Val Thr
    115                 120                 125

aca act ggt ggc gta gag gaa gat ctc atc aaa tgc ctt gct cct act      491
Thr Thr Gly Gly Val Glu Glu Asp Leu Ile Lys Cys Leu Ala Pro Thr
130                 135                 140                 145

ttc aaa ggt gat ttc tct cta ccg ggt gcg tat ctt cgg tca aag gga      539
Phe Lys Gly Asp Phe Ser Leu Pro Gly Ala Tyr Leu Arg Ser Lys Gly
                150                 155                 160

ttg aac cgg atc ggg aac ttg ctt gtt cct aat gat aac tac tgc aag      587
Leu Asn Arg Ile Gly Asn Leu Leu Val Pro Asn Asp Asn Tyr Cys Lys
            165                 170                 175

ttt gag gat tgg atc att ccc atc ttt gac cag atg ttg aag gaa cag      635
Phe Glu Asp Trp Ile Ile Pro Ile Phe Asp Gln Met Leu Lys Glu Gln
        180                 185                 190

aaa gaa gag agt gtg ttg tgg acg cct tct aaa ttg tta gcg cgg ctg      683
Lys Glu Glu Ser Val Leu Trp Thr Pro Ser Lys Leu Leu Ala Arg Leu
    195                 200                 205

ggg aaa gaa ata aat aat gag agt tca tat ctt tat tgg gca tac aag      731
Gly Lys Glu Ile Asn Asn Glu Ser Ser Tyr Leu Tyr Trp Ala Tyr Lys
210                 215                 220                 225

atg aat att cca gtg ttc tgc cgg ggg tta acc gat ggc tct ctc ggt      779
Met Asn Ile Pro Val Phe Cys Arg Gly Leu Thr Asp Gly Ser Leu Gly
                230                 235                 240

gat atg ttg tat ttt cac tca ttt cgt acc tct ggc ctt gtc atc gat      827
Asp Met Leu Tyr Phe His Ser Phe Arg Thr Ser Gly Leu Val Ile Asp
            245                 250                 255

gtt gtg caa gat att aga gct atg aac ggt gaa gca gtc cat gcg act      875
Val Val Gln Asp Ile Arg Ala Met Asn Gly Glu Ala Val His Ala Thr
        260                 265                 270

cca aga aag aca ggg atg ata atc ctt gga ggg ggc ttg ccg aag cac      923
Pro Arg Lys Thr Gly Met Ile Ile Leu Gly Gly Gly Leu Pro Lys His
    275                 280                 285

cac ata tgt aat gcc aac atg atg cgt aac ggt gcg gat tac gct gtg      971
His Ile Cys Asn Ala Asn Met Met Arg Asn Gly Ala Asp Tyr Ala Val
290                 295                 300                 305

ttt atc aac acc ggg caa gag ttt gat gga agt gac tcg ggt gca cgc     1019
Phe Ile Asn Thr Gly Gln Glu Phe Asp Gly Ser Asp Ser Gly Ala Arg
                310                 315                 320

cct gat gaa gca gtg tct tgg ggt aaa ata agg gga tct gct aaa act     1067
Pro Asp Glu Ala Val Ser Trp Gly Lys Ile Arg Gly Ser Ala Lys Thr
            325                 330                 335

gtc aag gtg tac tgt gat gct acc ata gcc ttc cct ttg ttg gtt gct     1115
```

```
Val Lys Val Tyr Cys Asp Ala Thr Ile Ala Phe Pro Leu Leu Val Ala
        340                 345                 350

gaa aca ttt gcc tcc aag aga gaa caa agc tgt gag cac aag acc         1160
Glu Thr Phe Ala Ser Lys Arg Glu Gln Ser Cys Glu His Lys Thr
    355                 360                 365

taagcccaag aaagcttacg tctcttttat cggtttgttc ttccatcttg ttgttgtacc   1220

ctttgtcctg ctttacataa cattcatctc taaaacaata ctacctcctt ttgacaaaaa   1280

ataaaaaaaa ttggaaaaat ggtttcacaa gaataaaaaa aaaaaaaaaa aaaaa        1335


<210> SEQ ID NO 71
<211> LENGTH: 368
<212> TYPE: PRT
<213> ORGANISM: Brassica napus

<400> SEQUENCE: 71

Met Glu Glu Asp Arg Val Leu Ser Ser Val His Ser Thr Val Phe Lys
  1               5                  10                  15

Glu Ser Glu Ser Leu Glu Gly Lys Cys Asp Lys Ile Glu Gly Tyr Asp
             20                  25                  30

Phe Asn Gln Gly Val Asn Tyr Pro Lys Leu Leu Arg Ser Met Leu Thr
         35                  40                  45

Thr Gly Phe Gln Ala Ser Asn Leu Gly Asp Val Ile Asp Val Val Asn
     50                  55                  60

Gln Met Leu Glu Trp Arg Leu Ser Asp Glu Thr Ile Ala Pro Glu Asp
 65                  70                  75                  80

Cys Ser Glu Glu Glu Lys Asp Pro Ala Tyr Arg Glu Ser Val Lys Cys
                 85                  90                  95

Lys Ile Phe Leu Gly Phe Thr Ser Asn Leu Val Ser Ser Gly Val Arg
            100                 105                 110

Glu Thr Ile Arg Tyr Leu Val Gln His His Met Val Asp Val Ile Val
        115                 120                 125

Thr Thr Thr Gly Gly Val Glu Glu Asp Leu Ile Lys Cys Leu Ala Pro
    130                 135                 140

Thr Phe Lys Gly Asp Phe Ser Leu Pro Gly Ala Tyr Leu Arg Ser Lys
145                 150                 155                 160

Gly Leu Asn Arg Ile Gly Asn Leu Leu Val Pro Asn Asp Asn Tyr Cys
                165                 170                 175

Lys Phe Glu Asp Trp Ile Ile Pro Ile Phe Asp Gln Met Leu Lys Glu
            180                 185                 190

Gln Lys Glu Glu Ser Val Leu Trp Thr Pro Ser Lys Leu Leu Ala Arg
        195                 200                 205

Leu Gly Lys Glu Ile Asn Asn Glu Ser Ser Tyr Leu Tyr Trp Ala Tyr
    210                 215                 220

Lys Met Asn Ile Pro Val Phe Cys Arg Gly Leu Thr Asp Gly Ser Leu
225                 230                 235                 240

Gly Asp Met Leu Tyr Phe His Ser Phe Arg Thr Ser Gly Leu Val Ile
                245                 250                 255

Asp Val Val Gln Asp Ile Arg Ala Met Asn Gly Glu Ala Val His Ala
            260                 265                 270

Thr Pro Arg Lys Thr Gly Met Ile Ile Leu Gly Gly Gly Leu Pro Lys
        275                 280                 285

His His Ile Cys Asn Ala Asn Met Met Arg Asn Gly Ala Asp Tyr Ala
    290                 295                 300

Val Phe Ile Asn Thr Gly Gln Glu Phe Asp Gly Ser Asp Ser Gly Ala
305                 310                 315                 320
```

```
Arg Pro Asp Glu Ala Val Ser Trp Gly Lys Ile Arg Gly Ser Ala Lys
            325                 330                 335

Thr Val Lys Val Tyr Cys Asp Ala Thr Ile Ala Phe Pro Leu Leu Val
        340                 345                 350

Ala Glu Thr Phe Ala Ser Lys Arg Glu Gln Ser Cys Glu His Lys Thr
    355                 360                 365


<210> SEQ ID NO 72
<211> LENGTH: 1862
<212> TYPE: DNA
<213> ORGANISM: Medicago sativa
<220> FEATURE:
<221> NAME/KEY: CDS
<222> LOCATION: (293)..(1396)

<400> SEQUENCE: 72

gaaaccttct tcttctggag caaagtcgcc attccctacc tccttcttca ttcttattct      60

ctataacaaa cggtccgacc ggatccaagt tgcaccggtt cgaaccgctt tagttactac     120

taacggttcg aaccgttatt tttcaacccg tgacaaacgt ggaaggcttc gttgtttctt     180

cttcttcttc ttaattacca tgcgtttttg tttttctttt gagtcattga agtcttgttt     240

tttgtcgtgt ttctgtcttg agaccgtgaa agagaaaaca aagagtacga ga atg agt     298
                                                          Met Ser
                                                            1

gaa aca aag caa gaa gat gat aca att atg tcc tca gtt cac tcc act      346
Glu Thr Lys Gln Glu Asp Asp Thr Ile Met Ser Ser Val His Ser Thr
          5                  10                  15

gtc ttc aaa gaa tcc gaa aat ctc gca gga aag tgt gtc caa atc gag      394
Val Phe Lys Glu Ser Glu Asn Leu Ala Gly Lys Cys Val Gln Ile Glu
     20                  25                  30

ggt tat gat ttc aac cgc ggc gtc gat tat caa cag ctt ctc aaa tca      442
Gly Tyr Asp Phe Asn Arg Gly Val Asp Tyr Gln Gln Leu Leu Lys Ser
 35                  40                  45                  50

atg ctc aca act ggt ttt caa gct tcc aac ttt ggt gat gcc gtt aaa      490
Met Leu Thr Thr Gly Phe Gln Ala Ser Asn Phe Gly Asp Ala Val Lys
                 55                  60                  65

gtc gtt aat caa atg cta gat tgg agg ttg gtt gat gaa cca att gat      538
Val Val Asn Gln Met Leu Asp Trp Arg Leu Val Asp Glu Pro Ile Asp
             70                  75                  80

gag gat tgt gat gaa gat aag aag gat ttg gag tat agg aaa tct gtt      586
Glu Asp Cys Asp Glu Asp Lys Lys Asp Leu Glu Tyr Arg Lys Ser Val
         85                  90                  95

aca tgc aaa gtg ttt ttg ggt ttc act tct aat ctt atc tct tct ggt      634
Thr Cys Lys Val Phe Leu Gly Phe Thr Ser Asn Leu Ile Ser Ser Gly
    100                 105                 110

gtt aga gat gtt gtt cgt tac ctt tgt cag cat cac atg gtt cat gta      682
Val Arg Asp Val Val Arg Tyr Leu Cys Gln His His Met Val His Val
115                 120                 125                 130

gtt gtt aca act aca ggt ggt att gaa gaa gat ctt ata aag tgc ctt      730
Val Val Thr Thr Thr Gly Gly Ile Glu Glu Asp Leu Ile Lys Cys Leu
                135                 140                 145

gca cca aca tat aaa gga gag ttc tct ttg ccc gga gct tat ctt cgc      778
Ala Pro Thr Tyr Lys Gly Glu Phe Ser Leu Pro Gly Ala Tyr Leu Arg
            150                 155                 160

tca aaa gga ttg aat cga atc ggt aat tta ttg gtc cct aat gaa aat      826
Ser Lys Gly Leu Asn Arg Ile Gly Asn Leu Leu Val Pro Asn Glu Asn
        165                 170                 175

tat tgc aaa ttt gag gac tgg att att cct att ttt gat caa atg ttg      874
Tyr Cys Lys Phe Glu Asp Trp Ile Ile Pro Ile Phe Asp Gln Met Leu
    180                 185                 190
```

```
aag gag caa aag gaa gag aaa gtg ctg tgg aca ccg tct aag tta ata      922
Lys Glu Gln Lys Glu Glu Lys Val Leu Trp Thr Pro Ser Lys Leu Ile
195                 200                 205                 210

gct cga ttg gga aaa gag atc aac aat gaa aac tcc tac ctt tac tgg      970
Ala Arg Leu Gly Lys Glu Ile Asn Asn Glu Asn Ser Tyr Leu Tyr Trp
                215                 220                 225

gca tat aag aac aat att cca gtt tat tgt cca gga tta acc gat ggc     1018
Ala Tyr Lys Asn Asn Ile Pro Val Tyr Cys Pro Gly Leu Thr Asp Gly
            230                 235                 240

tca ctg ggt gac atg ctg tac ttc cat tcc ttc cac aac cct ggt ctg     1066
Ser Leu Gly Asp Met Leu Tyr Phe His Ser Phe His Asn Pro Gly Leu
        245                 250                 255

att gtg gac ata gtg caa gat ata agg gcc atg aat ggt gaa gct gta     1114
Ile Val Asp Ile Val Gln Asp Ile Arg Ala Met Asn Gly Glu Ala Val
    260                 265                 270

cat gca aat cct agc aag acg ggc atg att att tta gga ggc ggc ctt     1162
His Ala Asn Pro Ser Lys Thr Gly Met Ile Ile Leu Gly Gly Gly Leu
275                 280                 285                 290

cca aaa cat cac att tgc aat gcc aat atg atg cgc aat ggt gca gac     1210
Pro Lys His His Ile Cys Asn Ala Asn Met Met Arg Asn Gly Ala Asp
                295                 300                 305

tat gcg gtt ttt att aat act gca caa gaa ttt gat gga agt gat tct     1258
Tyr Ala Val Phe Ile Asn Thr Ala Gln Glu Phe Asp Gly Ser Asp Ser
            310                 315                 320

gga gct cgt cca gat gag gct gtt tca tgg ggg aaa ata cga gga tct     1306
Gly Ala Arg Pro Asp Glu Ala Val Ser Trp Gly Lys Ile Arg Gly Ser
        325                 330                 335

gct aaa act gtt aag gta cat tgt gat gca acg ata gca ttc cct ctg     1354
Ala Lys Thr Val Lys Val His Cys Asp Ala Thr Ile Ala Phe Pro Leu
    340                 345                 350

ctg gtt gct gaa aca ttt gcc tca aga acg tca ccc ctt aat             1396
Leu Val Ala Glu Thr Phe Ala Ser Arg Thr Ser Pro Leu Asn
355                 360                 365

tgataaaggt ccaccgtcaa aagtaaaagg tgtggctggg aagtgtttta ccgcagctcc   1456

acttgtgagt gccaaatgtt ttggtatgta acttataaga ccaaggtcgg ctgtatgtca   1516

tacttgagtt gaggtcaaag ttcatttgca atgcagtgtg tttgaggatc ttgatggacc   1576

agtttgccat tgacttttaa tttgactgtc ttgttattcg caaggtccac ataacaagca   1636

tttttaccat ttagaaacaa tttattagtc ctgaaggaat tgagagtcat gaattcagat   1696

gtaaattatg caatgctaac tatatttttt tggaactgtg gtttctctta gatttgaggt   1756

gttgaaaact gtaatatcta gagcaaataa gactagaaaa gtttatcaac tattactgat   1816

cagttatagt atcttcaata ttttccagaa aaaaaaaaaa aaaaaa                  1862


<210> SEQ ID NO 73
<211> LENGTH: 368
<212> TYPE: PRT
<213> ORGANISM: Medicago sativa

<400> SEQUENCE: 73

Met Ser Glu Thr Lys Gln Glu Asp Asp Thr Ile Met Ser Ser Val His
  1               5                  10                  15

Ser Thr Val Phe Lys Glu Ser Glu Asn Leu Ala Gly Lys Cys Val Gln
             20                  25                  30

Ile Glu Gly Tyr Asp Phe Asn Arg Gly Val Asp Tyr Gln Gln Leu Leu
         35                  40                  45

Lys Ser Met Leu Thr Thr Gly Phe Gln Ala Ser Asn Phe Gly Asp Ala
     50                  55                  60
```

```
Val Lys Val Val Asn Gln Met Leu Asp Trp Arg Leu Val Asp Glu Pro
 65                  70                  75                  80

Ile Asp Glu Asp Cys Asp Glu Asp Lys Lys Asp Leu Glu Tyr Arg Lys
                 85                  90                  95

Ser Val Thr Cys Lys Val Phe Leu Gly Phe Thr Ser Asn Leu Ile Ser
            100                 105                 110

Ser Gly Val Arg Asp Val Val Arg Tyr Leu Cys Gln His His Met Val
        115                 120                 125

His Val Val Val Thr Thr Thr Gly Gly Ile Glu Glu Asp Leu Ile Lys
    130                 135                 140

Cys Leu Ala Pro Thr Tyr Lys Gly Glu Phe Ser Leu Pro Gly Ala Tyr
145                 150                 155                 160

Leu Arg Ser Lys Gly Leu Asn Arg Ile Gly Asn Leu Leu Val Pro Asn
                165                 170                 175

Glu Asn Tyr Cys Lys Phe Glu Asp Trp Ile Ile Pro Ile Phe Asp Gln
            180                 185                 190

Met Leu Lys Glu Gln Lys Glu Glu Lys Val Leu Trp Thr Pro Ser Lys
        195                 200                 205

Leu Ile Ala Arg Leu Gly Lys Glu Ile Asn Asn Glu Asn Ser Tyr Leu
    210                 215                 220

Tyr Trp Ala Tyr Lys Asn Asn Ile Pro Val Tyr Cys Pro Gly Leu Thr
225                 230                 235                 240

Asp Gly Ser Leu Gly Asp Met Leu Tyr Phe His Ser Phe His Asn Pro
                245                 250                 255

Gly Leu Ile Val Asp Ile Val Gln Asp Ile Arg Ala Met Asn Gly Glu
            260                 265                 270

Ala Val His Ala Asn Pro Ser Lys Thr Gly Met Ile Ile Leu Gly Gly
        275                 280                 285

Gly Leu Pro Lys His His Ile Cys Asn Ala Asn Met Met Arg Asn Gly
    290                 295                 300

Ala Asp Tyr Ala Val Phe Ile Asn Thr Ala Gln Glu Phe Asp Gly Ser
305                 310                 315                 320

Asp Ser Gly Ala Arg Pro Asp Glu Ala Val Ser Trp Gly Lys Ile Arg
                325                 330                 335

Gly Ser Ala Lys Thr Val Lys Val His Cys Asp Ala Thr Ile Ala Phe
            340                 345                 350

Pro Leu Leu Val Ala Glu Thr Phe Ala Ser Arg Thr Ser Pro Leu Asn
        355                 360                 365


<210> SEQ ID NO 74
<211> LENGTH: 1363
<212> TYPE: DNA
<213> ORGANISM: Musa acuminata
<220> FEATURE:
<221> NAME/KEY: CDS
<222> LOCATION: (93)..(1220)

<400> SEQUENCE: 74

ggcacgagcg cgcggcgccc gcaacgaata ttgcagagag taagaaggat cctcgccttt      60

gtcaccaaac ccttggtttc cagcgaggcg ac atg gaa ggc ggc gcc gcg gga      113
                                    Met Glu Gly Gly Ala Ala Gly
                                      1               5

ggg cag cga gac cgg gaa acc ctg gac gcg gtg cgg tcg gtg gtg ttt      161
Gly Gln Arg Asp Arg Glu Thr Leu Asp Ala Val Arg Ser Val Val Phe
         10                  15                  20

aag cct tcc gta tcc ttg gag gag aag cgg ttc ccg agg gtc cag ggg      209
```

-continued

```
Lys Pro Ser Val Ser Leu Glu Glu Lys Arg Phe Pro Arg Val Gln Gly
     25                  30                  35

tac gac ttc aac cgg ggt tgt gac ctc atc ggc ctc ctc gat tcc atc      257
Tyr Asp Phe Asn Arg Gly Cys Asp Leu Ile Gly Leu Leu Asp Ser Ile
 40                 45                  50                  55

tcc tct acc ggg ttc caa gct tcc aac ctc ggc gac gcc atc gat gtc      305
Ser Ser Thr Gly Phe Gln Ala Ser Asn Leu Gly Asp Ala Ile Asp Val
                 60                  65                  70

atc aat cag atg att gac tgg agg ctc tcc cat gat gcg ccc acg gaa      353
Ile Asn Gln Met Ile Asp Trp Arg Leu Ser His Asp Ala Pro Thr Glu
             75                  80                  85

gat tgc agc gag gaa gag cgc aat ctg gct tac agg caa tcg gtc acg      401
Asp Cys Ser Glu Glu Glu Arg Asn Leu Ala Tyr Arg Gln Ser Val Thr
         90                  95                 100

tgc aag atc ttt ctg ggc ttc act tcg aac ctt gta tct tct ggc atc      449
Cys Lys Ile Phe Leu Gly Phe Thr Ser Asn Leu Val Ser Ser Gly Ile
    105                 110                 115

agg gag ata att cgg ttt ctt gtg cag cac cga atg gtt gaa gtt tta      497
Arg Glu Ile Ile Arg Phe Leu Val Gln His Arg Met Val Glu Val Leu
120                 125                 130                 135

gtc aca act gct ggc ggc att gaa gaa gat tta atc aaa tgc ctt gct      545
Val Thr Thr Ala Gly Gly Ile Glu Glu Asp Leu Ile Lys Cys Leu Ala
                140                 145                 150

cca aca tat aag ggt gac ttt tct ttg cct gga tcg tat ctg cgt tca      593
Pro Thr Tyr Lys Gly Asp Phe Ser Leu Pro Gly Ser Tyr Leu Arg Ser
            155                 160                 165

aaa gga ttg aat cgg ata gga aac ctt ctt gtc cct aat gac aat tac      641
Lys Gly Leu Asn Arg Ile Gly Asn Leu Leu Val Pro Asn Asp Asn Tyr
        170                 175                 180

tgc aaa ttc gag gac tgg atc atg cca att ctg gac cag atg tta ctt      689
Cys Lys Phe Glu Asp Trp Ile Met Pro Ile Leu Asp Gln Met Leu Leu
    185                 190                 195

gaa cag act aca gag aat gta gtt tgg aca cca tct aaa gtg att gcg      737
Glu Gln Thr Thr Glu Asn Val Val Trp Thr Pro Ser Lys Val Ile Ala
200                 205                 210                 215

cgc ctt gga aaa gaa ata aat gat gaa agt tca tac ctg tac tgg gca      785
Arg Leu Gly Lys Glu Ile Asn Asp Glu Ser Ser Tyr Leu Tyr Trp Ala
                220                 225                 230

tac aag aac aat gtt tct gtc tat tgc ccg gca ttg act gat gga tca      833
Tyr Lys Asn Asn Val Ser Val Tyr Cys Pro Ala Leu Thr Asp Gly Ser
            235                 240                 245

ttg ggg gat atg ttg tac tgc cat tca gtg cgg aat cct ggt tta ctt      881
Leu Gly Asp Met Leu Tyr Cys His Ser Val Arg Asn Pro Gly Leu Leu
        250                 255                 260

att gat att gtg caa gac ata cga gca atg aat gga gaa gct gta cat      929
Ile Asp Ile Val Gln Asp Ile Arg Ala Met Asn Gly Glu Ala Val His
    265                 270                 275

gtg ggt ctg aga aag act ggg gtc ata att ctt ggt ggg ggc ctc cca      977
Val Gly Leu Arg Lys Thr Gly Val Ile Ile Leu Gly Gly Gly Leu Pro
280                 285                 290                 295

aag cac cat ata tgt aat gcc aac atg ttt cgg aat ggt gca gat tat     1025
Lys His His Ile Cys Asn Ala Asn Met Phe Arg Asn Gly Ala Asp Tyr
                300                 305                 310

gct gtt tat gtc aac act gca cag gaa ttt gat gga agt gat tct gga     1073
Ala Val Tyr Val Asn Thr Ala Gln Glu Phe Asp Gly Ser Asp Ser Gly
            315                 320                 325

gca gag cct gat gag gcg att tca tgg gga aag ata aaa ggt tct gcg     1121
Ala Glu Pro Asp Glu Ala Ile Ser Trp Gly Lys Ile Lys Gly Ser Ala
        330                 335                 340

aag act att aaa gtt cat tgt gat gca act att gct ttt cct cta ttg     1169
```

```
Lys Thr Ile Lys Val His Cys Asp Ala Thr Ile Ala Phe Pro Leu Leu
    345                 350                 355

gta gct gca aca ttt gca aga aag ttt cag gaa aga aac aac aaa tta     1217
Val Ala Ala Thr Phe Ala Arg Lys Phe Gln Glu Arg Asn Asn Lys Leu
360                 365                 370                 375

gcc tgatgggggt gcaaaaggtg atcatcttat ttggattcaa ataccttaat          1270
Ala

gtaatctgct aacatctgca gatgctgtat tcttgcaaac caaaaattta atattagata   1330

accgagagcc tacagagggt cctttcaaaa aaa                                1363


<210> SEQ ID NO 75
<211> LENGTH: 376
<212> TYPE: PRT
<213> ORGANISM: Musa acuminata

<400> SEQUENCE: 75

Met Glu Gly Gly Ala Ala Gly Gly Gln Arg Asp Arg Glu Thr Leu Asp
  1               5                  10                  15

Ala Val Arg Ser Val Val Phe Lys Pro Ser Val Ser Leu Glu Glu Lys
             20                  25                  30

Arg Phe Pro Arg Val Gln Gly Tyr Asp Phe Asn Arg Gly Cys Asp Leu
         35                  40                  45

Ile Gly Leu Leu Asp Ser Ile Ser Ser Thr Gly Phe Gln Ala Ser Asn
     50                  55                  60

Leu Gly Asp Ala Ile Asp Val Ile Asn Gln Met Ile Asp Trp Arg Leu
 65                  70                  75                  80

Ser His Asp Ala Pro Thr Glu Asp Cys Ser Glu Glu Glu Arg Asn Leu
                 85                  90                  95

Ala Tyr Arg Gln Ser Val Thr Cys Lys Ile Phe Leu Gly Phe Thr Ser
            100                 105                 110

Asn Leu Val Ser Ser Gly Ile Arg Glu Ile Ile Arg Phe Leu Val Gln
        115                 120                 125

His Arg Met Val Glu Val Leu Val Thr Thr Ala Gly Gly Ile Glu Glu
    130                 135                 140

Asp Leu Ile Lys Cys Leu Ala Pro Thr Tyr Lys Gly Asp Phe Ser Leu
145                 150                 155                 160

Pro Gly Ser Tyr Leu Arg Ser Lys Gly Leu Asn Arg Ile Gly Asn Leu
                165                 170                 175

Leu Val Pro Asn Asp Asn Tyr Cys Lys Phe Glu Asp Trp Ile Met Pro
            180                 185                 190

Ile Leu Asp Gln Met Leu Leu Glu Gln Thr Thr Glu Asn Val Val Trp
        195                 200                 205

Thr Pro Ser Lys Val Ile Ala Arg Leu Gly Lys Glu Ile Asn Asp Glu
    210                 215                 220

Ser Ser Tyr Leu Tyr Trp Ala Tyr Lys Asn Asn Val Ser Val Tyr Cys
225                 230                 235                 240

Pro Ala Leu Thr Asp Gly Ser Leu Gly Asp Met Leu Tyr Cys His Ser
                245                 250                 255

Val Arg Asn Pro Gly Leu Leu Ile Asp Ile Val Gln Asp Ile Arg Ala
            260                 265                 270

Met Asn Gly Glu Ala Val His Val Gly Leu Arg Lys Thr Gly Val Ile
        275                 280                 285

Ile Leu Gly Gly Gly Leu Pro Lys His His Ile Cys Asn Ala Asn Met
    290                 295                 300

Phe Arg Asn Gly Ala Asp Tyr Ala Val Tyr Val Asn Thr Ala Gln Glu
```

```
305                 310                 315                 320

Phe Asp Gly Ser Asp Ser Gly Ala Glu Pro Asp Glu Ala Ile Ser Trp
                325                 330                 335

Gly Lys Ile Lys Gly Ser Ala Lys Thr Ile Lys Val His Cys Asp Ala
            340                 345                 350

Thr Ile Ala Phe Pro Leu Leu Val Ala Ala Thr Phe Ala Arg Lys Phe
        355                 360                 365

Gln Glu Arg Asn Asn Lys Leu Ala
    370                 375


<210> SEQ ID NO 76
<211> LENGTH: 1451
<212> TYPE: DNA
<213> ORGANISM: Populus deltoides
<220> FEATURE:
<221> NAME/KEY: CDS
<222> LOCATION: (8)..(1126)

<400> SEQUENCE: 76

gggattt atg aca ggc aaa aaa caa tgg gag gaa gat ttg cta tca tca       49
        Met Thr Gly Lys Lys Gln Trp Glu Glu Asp Leu Leu Ser Ser
          1               5                  10

gta cgg acc aca gtg ttt aaa gaa tca gaa gct ctt gat ggg aaa tgc       97
Val Arg Thr Thr Val Phe Lys Glu Ser Glu Ala Leu Asp Gly Lys Cys
 15                  20                  25                  30

att aaa att gaa ggt tat gat ttt aat caa gga gtg aac tac tct aag      145
Ile Lys Ile Glu Gly Tyr Asp Phe Asn Gln Gly Val Asn Tyr Ser Lys
                 35                  40                  45

ctt ctc aaa tcc atg gtc tct acc ggg ttt caa gct tcc aac ctt gga      193
Leu Leu Lys Ser Met Val Ser Thr Gly Phe Gln Ala Ser Asn Leu Gly
             50                  55                  60

gat gcc att caa gtt gtt aat aac atg cta gac tgg agg ctt gct gat      241
Asp Ala Ile Gln Val Val Asn Asn Met Leu Asp Trp Arg Leu Ala Asp
         65                  70                  75

gaa gag ata aca gaa gat tgt agt gat gag gag agg gag ttg gcc tat      289
Glu Glu Ile Thr Glu Asp Cys Ser Asp Glu Glu Arg Glu Leu Ala Tyr
     80                  85                  90

aga gag tct gtg aga tgc aaa ctg ttc ttg ggt ttt aca tca aat ctt      337
Arg Glu Ser Val Arg Cys Lys Leu Phe Leu Gly Phe Thr Ser Asn Leu
 95                 100                 105                 110

gtt tct tca ggt gtc aga gat aca att cga tat ctt gtt cag cat cat      385
Val Ser Ser Gly Val Arg Asp Thr Ile Arg Tyr Leu Val Gln His His
                115                 120                 125

atg gtt gat gta gtg gtt aca acg gca ggt ggc ata gaa gaa gat ctt      433
Met Val Asp Val Val Val Thr Thr Ala Gly Gly Ile Glu Glu Asp Leu
            130                 135                 140

ata aaa tgc ctg gca cca aca tac aaa ggt gac ttt tct cta ccc ggg      481
Ile Lys Cys Leu Ala Pro Thr Tyr Lys Gly Asp Phe Ser Leu Pro Gly
        145                 150                 155

gct caa tta cga tca aaa ggg ttg aat cga att ggt aac ttg ttg gta      529
Ala Gln Leu Arg Ser Lys Gly Leu Asn Arg Ile Gly Asn Leu Leu Val
    160                 165                 170

cct aat gac aac tac tgc aaa ttt gag gat tgg atc att cca atc ttt      577
Pro Asn Asp Asn Tyr Cys Lys Phe Glu Asp Trp Ile Ile Pro Ile Phe
175                 180                 185                 190

gac caa atg ttg aag gaa caa att gaa gag aat atc acc tgg aca cct      625
Asp Gln Met Leu Lys Glu Gln Ile Glu Glu Asn Ile Thr Trp Thr Pro
                195                 200                 205

tct aaa tta ata gct cgc atg ggg aaa gaa ata aat aat gag agt tca      673
Ser Lys Leu Ile Ala Arg Met Gly Lys Glu Ile Asn Asn Glu Ser Ser
            210                 215                 220
```

```
tac ctt tat tgg gca tat aag aac gac att cca gta ttc tgt cca ggc      721
Tyr Leu Tyr Trp Ala Tyr Lys Asn Asp Ile Pro Val Phe Cys Pro Gly
        225                 230                 235

tta aca gat ggt tct cta ggg gac atg cta tac ttt cat tcc ttc cac      769
Leu Thr Asp Gly Ser Leu Gly Asp Met Leu Tyr Phe His Ser Phe His
    240                 245                 250

aac cct ggt cta att gtt gcc ata gtc caa gat att aga gcc atg aat      817
Asn Pro Gly Leu Ile Val Ala Ile Val Gln Asp Ile Arg Ala Met Asn
255                 260                 265                 270

ggt gaa gct gtc cac gca agt cct aga aaa act ggt atc atc att ctt      865
Gly Glu Ala Val His Ala Ser Pro Arg Lys Thr Gly Ile Ile Ile Leu
                275                 280                 285

gga ggt ggg ctt cct aag cat cat ata tgc aat gcc aat atg atg cgt      913
Gly Gly Gly Leu Pro Lys His His Ile Cys Asn Ala Asn Met Met Arg
            290                 295                 300

aac ggt gca gat tat gct gta ttc atc aat aca gca caa gaa ttt gat      961
Asn Gly Ala Asp Tyr Ala Val Phe Ile Asn Thr Ala Gln Glu Phe Asp
        305                 310                 315

ggg agt gat tct gga gct cat cct gat gag gct gta tcg tgg ggg aaa     1009
Gly Ser Asp Ser Gly Ala His Pro Asp Glu Ala Val Ser Trp Gly Lys
    320                 325                 330

ata cga ggt tct gct aaa act gtt aag gtc cac tgt gat gca act att     1057
Ile Arg Gly Ser Ala Lys Thr Val Lys Val His Cys Asp Ala Thr Ile
335                 340                 345                 350

gct ttt cct ctc cta gtt gct gaa aca ttt gcc cct agg agg aac aga     1105
Ala Phe Pro Leu Leu Val Ala Glu Thr Phe Ala Pro Arg Arg Asn Arg
                355                 360                 365

ttc tgc agc agt act caa agc tagggctgtg tgcagttctt ggccagaaaa        1156
Phe Cys Ser Ser Thr Gln Ser
            370

ttgattcatt tttatttgta ttatgactga acgatccgca ggatgggtag tgggctccat   1216

tgatgccata aacttctttt tttttcccct cagaattaag ggatccgcca gaacacactg   1276

ctctcagccc caaaccattg ttgcctctac tgggagtagc ataaccaatt gaattgcgct   1336

cctccaagca gcgcctctta gttgcgttat ttattgtaag tagcgcaacc aactaaatta   1396

tgctagttcc cacatttatt gactgctatt ttcaaaagaa aaaaaaaaaa aaaaa        1451


<210> SEQ ID NO 77
<211> LENGTH: 373
<212> TYPE: PRT
<213> ORGANISM: Populus deltoides

<400> SEQUENCE: 77

Met Thr Gly Lys Lys Gln Trp Glu Glu Asp Leu Leu Ser Ser Val Arg
  1               5                  10                  15

Thr Thr Val Phe Lys Glu Ser Glu Ala Leu Asp Gly Lys Cys Ile Lys
             20                  25                  30

Ile Glu Gly Tyr Asp Phe Asn Gln Gly Val Asn Tyr Ser Lys Leu Leu
         35                  40                  45

Lys Ser Met Val Ser Thr Gly Phe Gln Ala Ser Asn Leu Gly Asp Ala
     50                  55                  60

Ile Gln Val Val Asn Asn Met Leu Asp Trp Arg Leu Ala Asp Glu Glu
 65                  70                  75                  80

Ile Thr Glu Asp Cys Ser Asp Glu Glu Arg Glu Leu Ala Tyr Arg Glu
                 85                  90                  95

Ser Val Arg Cys Lys Leu Phe Leu Gly Phe Thr Ser Asn Leu Val Ser
            100                 105                 110
```

```
Ser Gly Val Arg Asp Thr Ile Arg Tyr Leu Val Gln His His Met Val
        115                 120                 125

Asp Val Val Val Thr Thr Ala Gly Gly Ile Glu Glu Asp Leu Ile Lys
    130                 135                 140

Cys Leu Ala Pro Thr Tyr Lys Gly Asp Phe Ser Leu Pro Gly Ala Gln
145                 150                 155                 160

Leu Arg Ser Lys Gly Leu Asn Arg Ile Gly Asn Leu Leu Val Pro Asn
                165                 170                 175

Asp Asn Tyr Cys Lys Phe Glu Asp Trp Ile Ile Pro Ile Phe Asp Gln
            180                 185                 190

Met Leu Lys Glu Gln Ile Glu Glu Asn Ile Thr Trp Thr Pro Ser Lys
        195                 200                 205

Leu Ile Ala Arg Met Gly Lys Glu Ile Asn Asn Glu Ser Ser Tyr Leu
    210                 215                 220

Tyr Trp Ala Tyr Lys Asn Asp Ile Pro Val Phe Cys Pro Gly Leu Thr
225                 230                 235                 240

Asp Gly Ser Leu Gly Asp Met Leu Tyr Phe His Ser Phe His Asn Pro
                245                 250                 255

Gly Leu Ile Val Ala Ile Val Gln Asp Ile Arg Ala Met Asn Gly Glu
            260                 265                 270

Ala Val His Ala Ser Pro Arg Lys Thr Gly Ile Ile Ile Leu Gly Gly
        275                 280                 285

Gly Leu Pro Lys His His Ile Cys Asn Ala Asn Met Met Arg Asn Gly
    290                 295                 300

Ala Asp Tyr Ala Val Phe Ile Asn Thr Ala Gln Glu Phe Asp Gly Ser
305                 310                 315                 320

Asp Ser Gly Ala His Pro Asp Glu Ala Val Ser Trp Gly Lys Ile Arg
                325                 330                 335

Gly Ser Ala Lys Thr Val Lys Val His Cys Asp Ala Thr Ile Ala Phe
            340                 345                 350

Pro Leu Leu Val Ala Glu Thr Phe Ala Pro Arg Arg Asn Arg Phe Cys
        355                 360                 365

Ser Ser Thr Gln Ser
    370


<210> SEQ ID NO 78
<211> LENGTH: 1488
<212> TYPE: DNA
<213> ORGANISM: Arabidopsis thaliana

<400> SEQUENCE: 78

acaataaggc tttaaagccc ataaaaccct taaatatatc aaagcccaaa agaaacgcct      60

tttgcgcttt cccgatcgtg gtcaacttcc tctgttacca aaaaatctgt accgcaaaat     120

cctcgtcgaa gctcgctgct gcaaccatgt ccgacgagga gcatcacttt gagtccagtg     180

acgccggagc gtccaaaacc taccctcaac aagctggaac catccgtaag aatggttaca     240

tcgtcatcaa aaatcgtccc tgcaaggttt cgttctcaaa catttctcca ctctcttcct     300

ctgatcttat tagatctgtt cattacttag attcctcaga ttcttttttt tgtcacctcc     360

acgatgttcg actgatattt gttcttgtca tcattgttaa attcacattt tattgcactt     420

ttgttttagc gaaattatta aattggtcat cttcagtttt gttcgattag ataagtttta     480

ggatttttc ttacacaagt tactggatca gctgctaaat gtcattttgt gtcgcaggtt     540

gttgaggttt caacctcgaa gactggcaag catggtcatg ctaaatgtca ttttgtagct     600

attgatatct tcaccagcaa gaaactcgaa gatattgttc cttcttccca caattgtgat     660
```

gtatgtgaaa aaagctcctt tgatcacttt catttcttgt ttgtttcttt caagtcccat 720
ttgagatttt gtttttgttg aattgggttt caggttcctc atgtcaaccg tactgattat 780
cagctgattg acatttctga agatggatat gtatgtgttc ttaaatagca cttgttcctt 840
tatatggttt agttacttgt tctgttttgt aatcattttg caggtcagtt tgttgactga 900
taacggtagt accaaggatg accttaagct ccctaatgat gacactctgc tccaacaggt 960
taagttttgc atgttcatca cattaaatgt tgctagttaa ttaaaatcaa ctctatgtcg 1020
atttctgaaa atggaagaaa aagtgcagag taatgagtga cctgattgtg ttaatgaaac 1080
agatcaagag tgggtttgat gatggaaaag atctagtggt gagtgtgatg tcagctatgg 1140
gagaggaaca gatcaatgct cttaaggaca tcggtcccaa gtgagactaa caaagcctcc 1200
cctttgttat gagattcttc ttcttcttct gtaggcttcc attactcatc ggagattatc 1260
ttgtttttgg gtgactccta ttttggatat ttaaactttt gttaataatg ccatcttctt 1320
caaccttttc cttctagatg gtttttatac ttcttctaat tgattgattc tttatggttg 1380
tccaagtgtc aaagtgttcc acccatatga ttctaacctt ttgatgagcg aagtctttac 1440
tcgtgcgtta tgtagagacg tagaagcaat accacaaaag agtataat 1488

<210> SEQ ID NO 79
<211> LENGTH: 1566
<212> TYPE: DNA
<213> ORGANISM: Arabidopsis thaliana

<400> SEQUENCE: 79
aggataataa tacagtaacc ctagaaaggt ttcctccacc ttcctcttcc cctcctatat 60
aaaaaaaatc gacatcgctt ttgctcactt ctctctctta ggtttttttt cccttctccc 120
aatctcatct tctccgaaaa cctttcttct ctcaaatttc tgtgaaaaca tgtctgacga 180
cgagcaccac tttgaggcca gcgaatccgg agcttccaag acctatcctc aatcagccgg 240
taacatccgt aaaggtggtc acatcgtcat caaaaaccgt ccctgcaagg tctgatttct 300
atttcatcat caaacatcgt tctcgatctc tttttcctga ttctagatct cgtctctgta 360
tagtagctcc ttgattttgt ttttatcctc ggatttgacc tggttctgtt tagtttgaat 420
ttttcttata gatcgctact tagatgaata tgatgaatct tatcctgtta ttttgatggt 480
ggtacctctc tagattcgtg gaattttggg aaatgaaaat gaaaaatgga tagaaatcaa 540
gcaatatcag acgacgcctt ttgtgatttt gaatctaagt agtctattga ttgatttgat 600
ttaaacgttt atggagaaca tagatttgat tttgatattt tggttttgat taggttgttg 660
aggtttcgac ttccaaaact ggcaagcacg gtcacgccaa atgtcacttt gttgctattg 720
atatcttcac tgctaagaag cttgaagata ttgttccatc ttcccacaat tgtgatgtaa 780
gttactacac aaactatgta gattcatttt cacagtattt gatatgattg tgtgatctga 840
ctcaaatatt gttcctttct cttttttct caggttccac atgtgaaccg tgttgattac 900
cagttgattg atatcactga ggatggcttc gtatgttttt ctttatactc actttcctca 960
tcactccagc tttatttatc tattcttgcc ataacttttg tacttgttta cattataggt 1020
gagccttctc actgacagtg gtggcaccaa ggatgatctc aagcttccca ccgatgatgg 1080
tctcaccgcc caggttattt tcttgtcttt tcatactcgc acacaaatga cttgactttg 1140
tattcatctc tcgaattgtg atattgaaaa cagttgttgt gttttgttaa tgcagatgag 1200
gcttggattc gatgagggaa aggatattgt ggtgtctgtc atgtcttcca tgggagagga 1260
gcagatctgt gccgtcaagg aagttggtgg tggcaagtaa acaagtatca ttcgatatat 1320
tattaccagt ttgacaacgg acgtcaatgt tataagaacc aaaagatgtt tttctttttc 1380
ctaatttaga ccctttgtgt gtgtttcttg ttgcaagaca accatatcta ttggttttgg 1440
attgttggaa aagtttgtgt tgaaacattc aaagtttctt atgagatgtt attcttaaaa 1500
ccactttttg tttgttcact ggatatgttt gttcatgaag cttgttttaa gcaactcttt 1560
acatga 1566

<210> SEQ ID NO 80
<211> LENGTH: 319
<212> TYPE: DNA
<213> ORGANISM: Artificial Sequence
<220> FEATURE:
<223> OTHER INFORMATION: Description of Artificial Sequence: Promoter sequence

<400> SEQUENCE: 80
aagacgttcc aaccacgtct tcaaagcaag tggattgatg tgatatctcc actgacgtaa 60
gggatgacgc acaatcccac tatccttcgc aagacccttc ctctatataa ggaagttcat 120
ttcatttgga gaggacacgc tgaaatcacc agtctctctc tcaagcttgg atcctcgagt 180
actagttcag ggagctcgaa ttgatcctct agagctttcg ttcgtatcat cggtttcgac 240
aacgttcgtc aagttcaatg catcagtttc attgcgcaca caccagaatc ctactgagtt 300
tgagtattat ggcattggg 319

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
gggagggact agtgtgcacg cc 22

<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
gcgaagcggc catggctcga gttttttttt tttttttt 38

<210> SEQ ID NO 83
<211> LENGTH: 521
<212> TYPE: DNA
<213> ORGANISM: Arabidopsis thaliana

<400> SEQUENCE: 83
gggagggact agtgtgcacg ccctgatgaa gctgtgtctt ggggtaaaat taggggttct 60
gctaaaaccg ttaaggtata ctgtgatgct accatagcct tcccattgtt ggttgcagaa 120
acatttgcca caaagagaga ccaaacctgt gagtctaaga cttaagaact gactggttcg 180
tacctctggc ctcatcatcg atgtagtaca agatatcaga gctatgaacg gcgaagctgt 240
ccatgcaaat cctaaaaaga caggcgtttt ggccatggat tcttaaagat cgttgctttt 300
tgattttaca ctggagtgac catataacac tccacattga tgtggctgtg acgcgaattg 360
tcttcttgcg aattgtactt tagtttctct caacctaaaa tgatttgcag attgtgtttt 420
cgtttaaaac acaagagtct tgtagtcaat aatcctttgc cttataaaat tattcagttc 480
caacaaaaaa aaaaaaaaaa ctcgagccat ggccgcttcg c 521

<210> SEQ ID NO 84
<211> LENGTH: 497
<212> TYPE: DNA
<213> ORGANISM: Arabidopsis thaliana

<400> SEQUENCE: 84
ctagtgtgca cgccctgatg aagctgtgtc ttggggtaaa attaggggtt ctgctaaaac 60
cgttaaggta tactgtgatg ctaccatagc cttcccattg ttggttgcag aaacatttgc 120
cacaaagaga gaccaaacct gtgagtctaa gacttaagaa ctgactggtt cgtacctctg 180
gcctcatcat cgatgtagta caagatatca gagctatgaa cggcgaagct gtccatgcaa 240
atcctaaaaa gacaggcgtt ttggccatgg attcttaaag atcgttgctt tttgatttta 300
cactggagtg accatataac actccacatt gatgtggctg tgacgcgaat tgtcttcttg 360
cgaattgtac tttagtttct ctcaacctaa aatgatttgc agattgtgtt ttcgtttaaa 420
acacaagagt cttgtagtca ataatccttt gccttataaa attattcagt tccaacaaaa 480
aaaaaaaaaa aactcga 497

<210> SEQ ID NO 85
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 85
ctcgagaaga ataacatctc ataagaaac 29

<210> SEQ ID NO 86
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 86
gagctcggca agtaaacaag tatcattcg 29

<210> SEQ ID NO 87
<211> LENGTH: 906
<212> TYPE: DNA
<213> ORGANISM: Artificial Sequence
<220> FEATURE:
<223> OTHER INFORMATION: Description of Artificial Sequence: Synthetic
construct

<400> SEQUENCE: 87
cactgaatca aaggccatgg agtcaaagat tcaaatagag gacctaacag aactcgccgt 60
aaagactggc gaacagttca tacagagtct cttacgactc aatgacaaga agaaaatctt 120
cgtcaacatg gtggagcacg acacgcttgt ctacctccaa aaatatcaaa gatacagtct 180
cagaagacca aagggaattg agacttttca acaaagggta atatccggaa acctcctcgg 240
attccattgc ccagctatct gtcactttat tgtgaagata gtggaaaagg aaggtggctc 300
ctacaaatgc catcattgcg ataaaggaaa ggccatcgtt gaagatgcct ctgccgacag 360
tggtcccaaa gatggacccc cacccacgag gagcatcgtg gaaaaagaag acgttccaac 420
cacgtcttca aagcaagtgg attgatgtga taacatggtg gagcacgaca cgcttgtcta 480
cctccaaaaa tatcaaagat acagtctcag aagaccaaag ggaattgaga cttttcaaca 540
aagggtaata tccggaaacc tcctcggatt ccattgccca gctatctgtc actttattgt 600
gaagatagtg gaaaaggaag gtggctccta caaatgccat cattgcgata aaggaaaggc 660
catcgttgaa gatgcctctg ccgacagtgg tcccaaagat ggacccccac ccacgaggag 720
catcgtggaa aaagaagacg ttccaaccac gtcttcaaag caagtggatt gatgtgatat 780
ctccactgac gtaagggatg acgcacaatc ccactatcct tcgcaagacc cttcctctat 840
ataaggaagt tcatttcatt tggagaggac acgctgaaat caccagtctc tctctaagct 900
tggatc 906

<210> SEQ ID NO 88
<211> LENGTH: 205
<212> TYPE: DNA
<213> ORGANISM: Artificial Sequence
<220> FEATURE:
<223> OTHER INFORMATION: Description of Artificial Sequence: Synthetic construct

<400> SEQUENCE: 88
aagaataaca tctcataaga aactttgaat gtttcaacac aaacttttcc aacaatccaa 60
aaccaataga tatggttgtc ttgcaacaag aaacacacac aaagggtcta aattaggaaa 120
aagaaaaaca tcttttggtt cttataacat tgacgtccgt tgtcaaactg gtaataatat 180
atcgaatgat acttgtttac ttgcc 205

<210> SEQ ID NO 89
<211> LENGTH: 662
<212> TYPE: DNA
<213> ORGANISM: Artificial Sequence
<220> FEATURE:
<223> OTHER INFORMATION: Description of Artificial Sequence: Synthetic construct

<400> SEQUENCE: 89
gaattgatcc tctagagctt tcgttcgtat catcggtttc gacaacgttc gtcaagttca 60
atgcatcagt ttcattgcgc acacaccaga atcctactga gttcgagtat tatggcattg 120
ggaaaactgt tttcttgta ccatttgttg tgcttgtaat ttactgtgtt ttttattcgg 180
ttttcgctat cgaactgtga aatggaaatg gatggagaag agttaatgaa tgatatggtc 240
cttttgttca ttctcaaatt aatattattt gttttttctc ttatttgttg tgtgttgaat 300
ttgaaattat aagagatatg caaacatttt gttttgagta aaaatgtgtc aaatcgtggc 360
ctctaatgac cgaagttaat atgaggagta aaacacttgt agttgtacca ttatgcttat 420
tcactaggca acaaatatat tttcagacct agaaaagctg caaatgttac tgaatacaag 480
tatgtcctct tgtgttttag acatttatga actttccttt atgtaatttt ccagaatcct 540
tgtcagattc taatcattgc tttataatta tagttatact catggatttg tagttgagta 600
tgaaaatatt ttttaatgca ttttatgact tgccaattga ttgacaacat gcatcaatcg 660
at 662

<210> SEQ ID NO 90
<211> LENGTH: 37
<212> TYPE: PRT
<213> ORGANISM: Arabidopsis thaliana -continued

<400> SEQUENCE: 90

```
Ala Arg Pro Asp Glu Ala Val Ser Trp Gly Lys Ile Arg Gly Ser Ala
  1               5                  10                  15

Lys Thr Val Lys Val Cys Phe Leu Ile Ser Ser His Pro Asn Leu Tyr
             20                  25                  30

Leu Thr Gln Trp Phe
         35
```

<210> SEQ ID NO 91
<211> LENGTH: 52
<212> TYPE: PRT
<213> ORGANISM: Lycopersicon esculentum

<400> SEQUENCE: 91

```
Gly Ala Arg Pro Asp Glu Ala Val Ser Trp Gly Lys Ile Arg Gly Gly
  1               5                  10                  15

Ala Lys Thr Val Lys Val His Cys Asp Ala Thr Ile Ala Phe Pro Ile
             20                  25                  30

Leu Val Ala Glu Thr Phe Ala Ala Lys Ser Lys Glu Phe Ser Gln Ile
         35                  40                  45

Arg Cys Gln Val
     50
```

<210> SEQ ID NO 92
<211> LENGTH: 193
<212> TYPE: PRT
<213> ORGANISM: Arabidopsis thaliana

<400> SEQUENCE: 92

```
Gly Gly Val Glu Glu Asp Leu Ile Lys Cys Leu Ala Pro Thr Phe Lys
  1               5                  10                  15

Gly Asp Phe Ser Leu Pro Gly Ala Tyr Leu Arg Ser Lys Gly Leu Asn
             20                  25                  30

Arg Ile Gly Asn Leu Leu Val Pro Asn Asp Asn Tyr Cys Lys Phe Glu
         35                  40                  45

Asp Trp Ile Ile Pro Ile Phe Asp Glu Met Leu Lys Glu Gln Lys Glu
     50                  55                  60

Glu Asn Val Leu Trp Thr Pro Ser Lys Leu Leu Ala Arg Leu Gly Lys
 65                  70                  75                  80

Glu Ile Asn Asn Glu Ser Ser Tyr Leu Tyr Trp Ala Tyr Lys Met Asn
                 85                  90                  95

Ile Pro Val Phe Cys Pro Gly Leu Thr Asp Gly Ser Leu Arg Asp Met
            100                 105                 110

Leu Tyr Phe His Ser Phe Arg Thr Ser Gly Leu Ile Ile Asp Val Val
        115                 120                 125

Gln Asp Ile Arg Ala Met Asn Gly Glu Ala Val His Ala Asn Pro Lys
    130                 135                 140

Lys Thr Gly Met Ile Ile Leu Gly Gly Gly Leu Pro Lys His His Ile
145                 150                 155                 160

Cys Asn Ala Asn Met Met Arg Asn Gly Ala Asp Tyr Ala Val Phe Ile
                165                 170                 175

Asn Thr Gly Gln Glu Phe Asp Gly Ser Asp Ser Gly Ala Arg Pro Asp
            180                 185                 190

Glu
```

<210> SEQ ID NO 93

<211> LENGTH: 174
<212> TYPE: PRT
<213> ORGANISM: Dianthus caryophyllus

<400> SEQUENCE: 93

Arg Arg Ser Ile Lys Cys Leu Ala Pro Thr Phe Lys Gly Asp Phe Ala
1 5 10 15

Leu Pro Gly Ala Gln Leu Arg Ser Lys Gly Leu Asn Arg Ile Gly Asn
20 25 30

Leu Leu Val Pro Asn Asp Asn Tyr Cys Lys Phe Glu Asp Trp Ile Ile
35 40 45

Pro Ile Leu Asp Lys Met Leu Glu Glu Gln Ile Ser Glu Lys Ile Leu
50 55 60

Trp Thr Pro Ser Lys Leu Ile Gly Arg Leu Gly Arg Glu Ile Asn Asp
65 70 75 80

Glu Ser Ser Tyr Leu Tyr Trp Ala Phe Lys Asn Asn Ile Pro Val Phe
85 90 95

Cys Pro Gly Leu Thr Asp Gly Ser Leu Gly Asp Met Leu Tyr Phe His
100 105 110

Ser Phe Arg Asn Pro Gly Leu Ile Ile Asp Val Val Gln Asp Ile Arg
115 120 125

Ala Val Asn Gly Glu Ala Val His Ala Ala Pro Arg Lys Thr Gly Met
130 135 140

Ile Ile Leu Gly Gly Gly Leu Pro Lys His His Ile Cys Asn Ala Asn
145 150 155 160

Met Met Arg Asn Gly Ala Asp Tyr Ala Val Phe Ile Asn Thr
165 170

<210> SEQ ID NO 94
<211> LENGTH: 22
<212> TYPE: PRT
<213> ORGANISM: Arabidopsis thaliana

<400> SEQUENCE: 94

Cys Lys Val Val Glu Val Ser Thr Ser Lys Thr Gly Lys His Gly His
1 5 10 15

Ala Lys Cys His Phe Val
20

<210> SEQ ID NO 95
<211> LENGTH: 22
<212> TYPE: PRT
<213> ORGANISM: Arabidopsis thaliana

<400> SEQUENCE: 95

Cys Lys Val Val Glu Val Ser Thr Ser Lys Thr Gly Lys His Gly His
1 5 10 15

Ala Lys Cys His Phe Val
20

<210> SEQ ID NO 96
<211> LENGTH: 22
<212> TYPE: PRT
<213> ORGANISM: Arabidopsis thaliana

<400> SEQUENCE: 96

Cys Lys Val Val Glu Val Ser Thr Ser Lys Thr Gly Lys His Gly His
1 5 10 15

Ala Lys Cys His Phe Val
20

<210> SEQ ID NO 97
<211> LENGTH: 22
<212> TYPE: PRT
<213> ORGANISM: Brassica napus

<400> SEQUENCE: 97

Cys Lys Val Val Glu Val Ser Thr Ser Lys Thr Gly Lys His Gly His
1 5 10 15

Ala Lys Cys His Phe Val
20

<210> SEQ ID NO 98
<211> LENGTH: 22
<212> TYPE: PRT
<213> ORGANISM: Dianthus caryophyllus

<400> SEQUENCE: 98

Cys Lys Val Val Glu Val Ser Thr Ser Lys Thr Gly Lys His Gly His
1 5 10 15

Ala Lys Cys His Phe Val
20

<210> SEQ ID NO 99
<211> LENGTH: 22
<212> TYPE: PRT
<213> ORGANISM: Lycopersicon esculentum

<400> SEQUENCE: 99

Cys Lys Val Val Glu Val Ser Thr Ser Lys Thr Gly Lys His Gly His
1 5 10 15

Ala Lys Cys His Phe Val
20

<210> SEQ ID NO 100
<211> LENGTH: 22
<212> TYPE: PRT
<213> ORGANISM: Lycopersicon esculentum

<400> SEQUENCE: 100

Cys Lys Val Val Glu Val Ser Thr Ser Lys Thr Gly Lys His Gly His
1 5 10 15

Ala Lys Cys His Phe Val
20

<210> SEQ ID NO 101
<211> LENGTH: 22
<212> TYPE: PRT
<213> ORGANISM: Lycopersicon esculentum

<400> SEQUENCE: 101

Cys Lys Val Val Glu Val Ser Thr Ser Lys Thr Gly Lys His Gly His
1 5 10 15

Ala Lys Cys His Phe Val
20

<210> SEQ ID NO 102
<211> LENGTH: 22
<212> TYPE: PRT
<213> ORGANISM: Medicago sativa

<400> SEQUENCE: 102

Cys Lys Val Val Glu Val Ser Thr Ser Lys Thr Gly Lys His Gly His

-continued

```
  1               5                   10                  15

Ala Lys Cys His Phe Val
             20


<210> SEQ ID NO 103
<211> LENGTH: 22
<212> TYPE: PRT
<213> ORGANISM: Medicago sativa

<400> SEQUENCE: 103

Cys Lys Val Val Glu Val Ser Thr Ser Lys Thr Gly Lys His Gly His
  1               5                   10                  15

Ala Lys Cys His Phe Val
             20


<210> SEQ ID NO 104
<211> LENGTH: 22
<212> TYPE: PRT
<213> ORGANISM: Medicago sativa

<400> SEQUENCE: 104

Cys Lys Val Val Glu Val Ser Thr Ser Lys Thr Gly Lys His Gly His
  1               5                   10                  15

Ala Lys Cys His Phe Val
             20


<210> SEQ ID NO 105
<211> LENGTH: 22
<212> TYPE: PRT
<213> ORGANISM: Lactuca sativa

<400> SEQUENCE: 105

Cys Lys Val Val Glu Val Ser Thr Ser Lys Thr Gly Lys His Gly His
  1               5                   10                  15

Ala Lys Cys His Phe Val
             20


<210> SEQ ID NO 106
<211> LENGTH: 22
<212> TYPE: PRT
<213> ORGANISM: Unknown
<220> FEATURE:
<223> OTHER INFORMATION: Description of Unknown: Tree sequence

<400> SEQUENCE: 106

Cys Lys Val Val Glu Val Ser Thr Ser Lys Thr Gly Lys His Gly His
  1               5                   10                  15

Ala Lys Cys His Phe Val
             20


<210> SEQ ID NO 107
<211> LENGTH: 22
<212> TYPE: PRT
<213> ORGANISM: Unknown
<220> FEATURE:
<223> OTHER INFORMATION: Description of Unknown: Tree sequence

<400> SEQUENCE: 107

Cys Lys Val Val Glu Val Ser Thr Ser Lys Thr Gly Lys His Gly His
  1               5                   10                  15

Ala Lys Cys His Phe Val
             20
```

<210> SEQ ID NO 108
<211> LENGTH: 22
<212> TYPE: PRT
<213> ORGANISM: Unknown
<220> FEATURE:
<223> OTHER INFORMATION: Description of Unknown: Tree sequence

<400> SEQUENCE: 108

Cys Lys Val Val Glu Val Ser Thr Ser Lys Thr Gly Lys His Gly His
1 5 10 15

Ala Lys Cys His Phe Val
20

<210> SEQ ID NO 109
<211> LENGTH: 22
<212> TYPE: PRT
<213> ORGANISM: Unknown
<220> FEATURE:
<223> OTHER INFORMATION: Description of Unknown: Tree sequence

<400> SEQUENCE: 109

Cys Lys Val Val Glu Val Ser Thr Ser Lys Thr Gly Lys His Gly His
1 5 10 15

Ala Lys Cys His Phe Val
20

<210> SEQ ID NO 110
<211> LENGTH: 66
<212> TYPE: DNA
<213> ORGANISM: Arabidopsis thaliana

<400> SEQUENCE: 110
tgcaaggttg ttgaggtttc aacctcgaag actggcaagc atggtcatgc taaatgtcat 60
tttgta 66

<210> SEQ ID NO 111
<211> LENGTH: 66
<212> TYPE: DNA
<213> ORGANISM: Arabidopsis thaliana

<400> SEQUENCE: 111
tgcaaggttg ttgaggtttc gacttccaaa actggcaagc acggtcacgc caaatgtcac 60
tttgtt 66

<210> SEQ ID NO 112
<211> LENGTH: 66
<212> TYPE: DNA
<213> ORGANISM: Arabidopsis thaliana

<400> SEQUENCE: 112
tgcaaggtgg ttgaggtatc gacttcgaag actgggaagc atggtcacgc caagtgtcac 60
tttgtt 66

<210> SEQ ID NO 113
<211> LENGTH: 66
<212> TYPE: DNA
<213> ORGANISM: Brassica napus

<400> SEQUENCE: 113
tgcaaggttg ttgaggtttc gacttcgaag actgggaagc acggtcacgc aaagtgtcac 60
tttgtt 66

<210> SEQ ID NO 114
<211> LENGTH: 66
<212> TYPE: DNA
<213> ORGANISM: Dianthus caryophyllus

<400> SEQUENCE: 114
tgcaaggtgg ttgaggtttc tacctccaag actggcaagc acggtcatgc caaatgtcac 60
tttgta 66

<210> SEQ ID NO 115
<211> LENGTH: 66
<212> TYPE: DNA
<213> ORGANISM: Lycopersicon esculentum

<400> SEQUENCE: 115
tgcaaggtgg ttgaagtttc aacctccaag acaggcaagc acggtcatgc taaatgtcac 60
ttcgtg 66

<210> SEQ ID NO 116
<211> LENGTH: 66
<212> TYPE: DNA
<213> ORGANISM: Lycopersicon esculentum

<400> SEQUENCE: 116
tgcaaggttg tggaagtctc tacatccaaa actggcaagc acggtcacgc caaatgtcat 60
ttcgtt 66

<210> SEQ ID NO 117
<211> LENGTH: 66
<212> TYPE: DNA
<213> ORGANISM: Lycopersicon esculentum

<400> SEQUENCE: 117
tgcaaggttg ttgaggtctc cacttccaaa actggcaagc atggacatgc aaaatgtcac 60
tttgtg 66

<210> SEQ ID NO 118
<211> LENGTH: 66
<212> TYPE: DNA
<213> ORGANISM: Medicago sativa

<400> SEQUENCE: 118
tgcaaggtgg ttgaagtttc gacttcgaag accgggaagc atggacatgc caagtgtcat 60
tttgtt 66

<210> SEQ ID NO 119
<211> LENGTH: 66
<212> TYPE: DNA
<213> ORGANISM: Medicago sativa

<400> SEQUENCE: 119
tgcaaggttg ttgaggtttc tacttcaaaa acaggaaaac atggacatgc aaagtgtcac 60
tttgtt 66

<210> SEQ ID NO 120
<211> LENGTH: 66
<212> TYPE: DNA
<213> ORGANISM: Medicago sativa

<400> SEQUENCE: 120
tgcaaggtag ttgaagtttc aacttctaaa actggaaagc atggacatgc aaagtgtcac 60
tttgtt 66

<210> SEQ ID NO 121
<211> LENGTH: 66
<212> TYPE: DNA
<213> ORGANISM: Lactuca sativa

<400> SEQUENCE: 121
tgcaaggttg ttgaagtttc tacctccaag actgggaagc atgggcatgc taagtgtcac 60
tttgtc 66

<210> SEQ ID NO 122
<211> LENGTH: 66
<212> TYPE: DNA
<213> ORGANISM: Unknown
<220> FEATURE:
<223> OTHER INFORMATION: Description of Unknown: Tree sequence

<400> SEQUENCE: 122
tgcaaggtcg tggaggtttc aacctctaaa actggcaagc atggccatgc taaatgtcac 60
tttgtt 66

<210> SEQ ID NO 123
<211> LENGTH: 66
<212> TYPE: DNA
<213> ORGANISM: Unknown
<220> FEATURE:
<223> OTHER INFORMATION: Description of Unknown: Tree sequence

<400> SEQUENCE: 123
tgcaaggttg ttgaggtttc cacctcaaag acaggcaagc acggacatgc taagtgccac 60
tttgtg 66

<210> SEQ ID NO 124
<211> LENGTH: 66
<212> TYPE: DNA
<213> ORGANISM: Unknown
<220> FEATURE:
<223> OTHER INFORMATION: Description of Unknown: Tree sequence

<400> SEQUENCE: 124
tgcaaggttg tggaggtttc tacctctaaa actggcaagc acggccatgc caaatgtcac 60
tttgtt 66

<210> SEQ ID NO 125
<211> LENGTH: 66
<212> TYPE: DNA
<213> ORGANISM: Unknown
<220> FEATURE:
<223> OTHER INFORMATION: Description of Unknown: Tree sequence

<400> SEQUENCE: 125
tgcaaggttg ttgaggtttc aacctcaaag acaggcaagc atggacatgc taagtgccac 60
tttgtg 66

<210> SEQ ID NO 126
<211> LENGTH: 745
<212> TYPE: DNA
<213> ORGANISM: Lycopersicon esculentum
<220> FEATURE:
<221> NAME/KEY: CDS
<222> LOCATION: (55)..(534)

<400> SEQUENCE: 126

```
ttctccacag caaacacaga gaagttcata gcagaagaag agagagattt agct atg       57
                                                            Met
                                                              1

tct gat gaa gaa cac cat ttt gag tcc aaa gct gat gct ggt gcc tca      105
Ser Asp Glu Glu His His Phe Glu Ser Lys Ala Asp Ala Gly Ala Ser
            5                  10                  15

aaa act tac cct caa caa gct ggt act att cgc aag aat ggt tat ata      153
Lys Thr Tyr Pro Gln Gln Ala Gly Thr Ile Arg Lys Asn Gly Tyr Ile
        20                  25                  30

gtt atc aaa ggc aga cct tgc aag gtt gtt gag gtc tcc act tcc aaa      201
Val Ile Lys Gly Arg Pro Cys Lys Val Val Glu Val Ser Thr Ser Lys
    35                  40                  45

act ggc aag cat gga cat gca aaa tgt cac ttt gtg gca atc gac att      249
Thr Gly Lys His Gly His Ala Lys Cys His Phe Val Ala Ile Asp Ile
 50                  55                  60                  65

ttc aat gca aaa aag ctt gaa gat att gtt cct tca tcc cac aat tgt      297
Phe Asn Ala Lys Lys Leu Glu Asp Ile Val Pro Ser Ser His Asn Cys
                70                  75                  80

gat gtg cca cat gtc aat cgt act gac tat cag ctg att gac ata tct      345
Asp Val Pro His Val Asn Arg Thr Asp Tyr Gln Leu Ile Asp Ile Ser
            85                  90                  95

gaa gat ggt ttt gtg tct ctt ctt act gaa aat gga aac acc aaa gac      393
Glu Asp Gly Phe Val Ser Leu Leu Thr Glu Asn Gly Asn Thr Lys Asp
        100                 105                 110

gac ctc aga ctt ccc acc gat gac acc ctg ttg aac cag gtt aaa ggt      441
Asp Leu Arg Leu Pro Thr Asp Asp Thr Leu Leu Asn Gln Val Lys Gly
    115                 120                 125

gga ttt gag gaa gga aag gat ctc gtt ctg tct gtg atg tct gca atg      489
Gly Phe Glu Glu Gly Lys Asp Leu Val Leu Ser Val Met Ser Ala Met
130                 135                 140                 145

ggt gaa gag cag atc tgt gct gtg aag gac att ggt acc aag acc          534
Gly Glu Glu Gln Ile Cys Ala Val Lys Asp Ile Gly Thr Lys Thr
                150                 155                 160

tagttgtgtg cattctgcag cataaataat tgctttttag cgaagacgtt ttatatcttg    594

ttatcgtggt acctttgcaa tctgttttat cgtgaaaaca ccttatatct attggcatgg    654

cttgaatagt tgaaactcta atagtttctg tttggcataa ggcaatgaac tggatttgat    714

agcagaagta atctacatgt cacttttttt t                                   745
```

<210> SEQ ID NO 127
<211> LENGTH: 160
<212> TYPE: PRT
<213> ORGANISM: Lycopersicon esculentum

<400> SEQUENCE: 127

```
Met Ser Asp Glu Glu His His Phe Glu Ser Lys Ala Asp Ala Gly Ala
  1               5                  10                  15

Ser Lys Thr Tyr Pro Gln Gln Ala Gly Thr Ile Arg Lys Asn Gly Tyr
            20                  25                  30

Ile Val Ile Lys Gly Arg Pro Cys Lys Val Val Glu Val Ser Thr Ser
        35                  40                  45

Lys Thr Gly Lys His Gly His Ala Lys Cys His Phe Val Ala Ile Asp
    50                  55                  60

Ile Phe Asn Ala Lys Lys Leu Glu Asp Ile Val Pro Ser Ser His Asn
 65                  70                  75                  80

Cys Asp Val Pro His Val Asn Arg Thr Asp Tyr Gln Leu Ile Asp Ile
                85                  90                  95
```

-continued

```
Ser Glu Asp Gly Phe Val Ser Leu Leu Thr Glu Asn Gly Asn Thr Lys
            100                 105                 110

Asp Asp Leu Arg Leu Pro Thr Asp Asp Thr Leu Leu Asn Gln Val Lys
        115                 120                 125

Gly Gly Phe Glu Glu Gly Lys Asp Leu Val Leu Ser Val Met Ser Ala
    130                 135                 140

Met Gly Glu Glu Gln Ile Cys Ala Val Lys Asp Ile Gly Thr Lys Thr
145                 150                 155                 160


<210> SEQ ID NO 128
<211> LENGTH: 25
<212> TYPE: PRT
<213> ORGANISM: Artificial Sequence
<220> FEATURE:
<223> OTHER INFORMATION: Description of Artificial Sequence: Synthetic
      primer

<400> SEQUENCE: 128

Gly Ala Ala Gly Cys Thr Cys Gly Ala Gly Gly Cys Thr Gly Cys Ala
  1               5                  10                  15

Ala Cys Cys Ala Thr Gly Thr Cys Cys
             20                  25


<210> SEQ ID NO 129
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129

ggggagctct tgttagtctc acttgg                                          26


<210> SEQ ID NO 130
<211> LENGTH: 906
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 130

cactgaatca aaggccatgg agtcaaagat tcaaatagag gacctaacag aactcgccgt      60

aaagactggc gaacagttca tacagagtct cttacgactc aatgacaaga agaaaatctt     120

cgtcaacatg gtggagcacg acacgcttgt ctacctccaa aaatatcaaa gatacagtct     180

cagaagacca aagggaattg agacttttca acaaagggta atatccggaa acctcctcgg     240

attccattgc ccagctatct gtcactttat tgtgaagata gtggaaaagg aaggtggctc     300

ctacaaatgc catcattgcg ataaaggaaa ggccatcgtt gaagatgcct ctgccgacag     360

tggtcccaaa gatggacccc cacccacgag gagcatcgtg gaaaaagaag acgttccaac     420

cacgtcttca aagcaagtgg attgatgtga taacatggtg gagcaccaca cgcttgtcta     480

cctccaaaaa tatcaaagat acagtctcag aagaccaaag ggaattgaga cttttcaaca     540

aagggtaata tccggaaacc tcctcggatt ccattgccca gctatctgtc actttattgt     600

gaagatagtg gaaaaggaag gtggctccta caaatgccat cattgcgata aaggaaaggc     660

catcgttgaa gatgcctctg ccgacagtgg tcccaaagat ggacccccac ccacgaggag     720

catcgtggaa aaagaagacg ttccaaccac gtcttcaaag caagtggatt gatgtgatat     780

ctccactgac gtaagggatg acgcacaatc ccactatcct tcgcaagacc cttcctctat     840
```

ataaggaagt tcatttcatt tggagaggac acgctgaaat caccagtctc tctctaagct 900
tggatc 906

<210> SEQ ID NO 131
<211> LENGTH: 495
<212> TYPE: DNA
<213> ORGANISM: Artificial Sequence
<220> FEATURE:
<223> OTHER INFORMATION: Description of Artificial Sequence: Synthetic construct

<400> SEQUENCE: 131
gctgcaacca tgtccgacga ggagcatcac tttgagtcca gtgacgccgg agcgtccaaa 60
acctaccctc aacaagctgg aaccatccgt aagaatggtt acatcgtcat caaaaatcgt 120
ccctgcaagg ttgttgaggt ttcaacctcg aagactggca agcatggtca tgctaaatgt 180
cattttgtag ctattgatat cttcaccagc aagaaactcg aagatattgt tccttcttcc 240
cacaattgtg atgttcctca tgtcaaccgt actgattatc agctgattga catttctgaa 300
gatggatatg tcagtttgtt gactgataac ggtagtacca aggatgacct taagctccct 360
aatgatgaca ctctgctcca acagatcaag agtgggtttg atgatggaaa agatctagtg 420
gtgagtgtaa tgtcagctat gggagaggaa cagatcaatg ctcttaagga catcggtccc 480
aagtgagact aacaa 495

<210> SEQ ID NO 132
<211> LENGTH: 662
<212> TYPE: DNA
<213> ORGANISM: Artificial Sequence
<220> FEATURE:
<223> OTHER INFORMATION: Description of Artificial Sequence: Synthetic construct

<400> SEQUENCE: 132
gaattgatcc tctagagctt tcgttcgtat catcggtttc gacaacgttc gtcaagttca 60
atgcatcagt ttcattgcgc acacaccaga atcctactga gttcgagtat tatggcattg 120
ggaaaactgt ttttcttgta ccatttgttg tgcttgtaat ttactgtgtt ttttattcgg 180
ttttcgctat cgaactgtga aatggaaatg gatggagaag agttaatgaa tgatatggtc 240
cttttgttca ttctcaaatt aatattattt gttttttctc ttatttgttg tgtgttgaat 300
ttgaaattat aagagatatg caaacatttt gttttgagta aaaatgtgtc aaatcgtggc 360
ctctaatgac cgaagttaat atgaggagta aaacacttgt agttgtacca ttatgcttat 420
tcactaggca acaaatatat tttcagacct agaaaagctg caaatgttac tgaatacaag 480
tatgtcctct tgtgttttag acatttatga actttccttt atgtaatttt ccagaatcct 540
tgtcagattc taatcattgc tttataatta tagttatact catggatttg tagttgagta 600
tgaaaatatt ttttaatgca ttttatgact tgccaattga ttgacaacat gcatcaatcg 660
at 662

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 133

-continued gcgctcgagc tatgtctgat gaagaacacc 30

<210> SEQ ID NO 134
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 134
tttgagctcc agaatgcaca caactagg 28

<210> SEQ ID NO 135
<211> LENGTH: 906
<212> TYPE: DNA
<213> ORGANISM: Artificial Sequence
<220> FEATURE:
<223> OTHER INFORMATION: Description of Artificial Sequence: Synthetic construct

<400> SEQUENCE: 135
cactgaatca aaggccatgg agtcaaagat tcaaatagag gacctaacag aactcgccgt 60
aaagactggc gaacagttca tacagagtct cttacgactc aatgacaaga agaaaatctt 120
cgtcaacatg gtggagcacg acacgcttgt ctacctccaa aaatatcaaa gatacagtct 180
cagaagacca aagggaattg agacttttca acaaagggta atatccggaa acctcctcgg 240
attccattgc ccagctatct gtcactttat tgtgaagata gtggaaaagg aaggtggctc 300
ctacaaatgc catcattgcg ataaaggaaa ggccatcgtt gaagatgcct ctgccgacag 360
tggtcccaaa gatggacccc cacccacgag gagcatcgtg gaaaaagaag acgttccaac 420
cacgtcttca aagcaagtgg attgatgtga taacatggtg gagcacgaca cgcttgtcta 480
cctccaaaaa tatcaaagat acagtctcag aagaccaaag ggaattgaga cttttcaaca 540
aagggtaata tccggaaacc tcctcggatt ccattgccca gctatctgtc actttattgt 600
gaagatagtg gaaaaggaag gtggctccta caaatgccat cattgcgata aaggaaaggc 660
catcgttgaa gatgcctctg ccgacagtgg tcccaaagat ggacccccac ccacgaggag 720
catcgtggaa aaagaagacg ttccaaccac gtcttcaaag caagtggatt gatgtgatat 780
ctccactgac gtaagggatg acgcacaatc ccactatcct tcgcaagacc cttcctctat 840
ataaggaagt tcatttcatt tggagaggac acgctgaaat caccagtctc tctctaagct 900
tggatc 906

<210> SEQ ID NO 136
<211> LENGTH: 499
<212> TYPE: DNA
<213> ORGANISM: Artificial Sequence
<220> FEATURE:
<223> OTHER INFORMATION: Description of Artificial Sequence: Synthetic construct

<400> SEQUENCE: 136
ctatgtctga tgaagaacac cattttgagt ccaaagctga tgctggtgcc tcaaaaactt 60
accctcaaca agctggtact attcgcaaga atggttatat agttatcaaa ggcagacctt 120
gcaaggttgt tgaggtctcc acttccaaaa ctggcaagca tggacatgca aaatgtcact 180
ttgtggcaat cgacattttc aatgcaaaaa agcttgaaga tattgttcct tcatcccaca 240
attgtgatgt gccacatgtc aatcgtactg actatcagct gattgacata tctgaagatg 300
gttttgtgtc tcttcttact gaaaatggaa acaccaaaga cgacctcaga cttcccaccg 360
atgacaccct gttgaaccag gttaaaggtg gatttgagga aggaaaggat ctcgttctgt 420
ctgtgatgtc tgcaatgggt gaagagcaga tctgtgctgt gaaggacatt ggtaccaaga 480
cctagttgtg tgcattctg 499

<210> SEQ ID NO 137
<211> LENGTH: 662
<212> TYPE: DNA
<213> ORGANISM: Artificial Sequence
<220> FEATURE:
<223> OTHER INFORMATION: Description of Artificial Sequence: Synthetic construct

<400> SEQUENCE: 137
gaattgatcc tctagagctt tcgttcgtat catcggtttc gacaacgttc gtcaagttca 60
atgcatcagt ttcattgcgc acacaccaga atcctactga gttcgagtat tatggcattg 120
ggaaaactgt ttttcttgta ccatttgttg tgcttgtaat ttactgtgtt ttttattcgg 180
ttttcgctat cgaactgtga aatggaaatg gatggagaag agttaatgaa tgatatggtc 240
cttttgttca ttctcaaatt aatattattt gttttttctc ttatttgttg tgtgttgaat 300
ttgaaattat aagagatatg caaacatttt gttttgagta aaaatgtgtc aaatcgtggc 360
ctctaatgac cgaagttaat atgaggagta aaacacttgt agttgtacca ttatgcttat 420
tcactaggca acaaatatat tttcagacct agaaaagctg caaatgttac tgaatacaag 480
tatgtcctct tgtgttttag acatttatga actttccttt atgtaatttt ccagaatcct 540
tgtcagattc taatcattgc tttataatta tagttatact catggatttg tagttgagta 600
tgaaaatatt ttttaatgca ttttatgact tgccaattga ttgacaacat gcatcaatcg 660
at 662

<210> SEQ ID NO 138
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
gcatgtcgac atgtctgacg aggagcacc 29

<210> SEQ ID NO 139
<211> LENGTH: 906
<212> TYPE: DNA
<213> ORGANISM: Artificial Sequence
<220> FEATURE:
<223> OTHER INFORMATION: Description of Artificial Sequence: Synthetic construct

<400> SEQUENCE: 139
cactgaatca aaggccatgg agtcaaagat tcaaatagag gacctaacag aactcgccgt 60
aaagactggc gaacagttca tacagagtct cttacgactc aatgacaaga agaaaatctt 120
cgtcaacatg gtggagcacg acacgcttgt ctacctccaa aaatatcaaa gatacagtct 180
cagaagacca aagggaattg agacttttca acaaagggta atatccggaa acctcctcgg 240
attccattgc ccagctatct gtcactttat tgtgaagata gtggaaaagg aaggtggctc 300
ctacaaatgc catcattgcg ataaaggaaa ggccatcgtt gaagatgcct ctgccgacag 360
tggtcccaaa gatggacccc cacccacgag gagcatcgtg gaaaaagaag acgttccaac 420

-continued

```
cacgtcttca aagcaagtgg attgatgtga taacatggtg gagcacgaca cgcttgtcta    480

cctccaaaaa tatcaaagat acagtctcag aagaccaaag ggaattgaga cttttcaaca    540

aagggtaata tccggaaacc tcctcggatt ccattgccca gctatctgtc actttattgt    600

gaagatagtg gaaaaggaag gtggctccta caaatgccat cattgcgata aaggaaaggc    660

catcgttgaa gatgcctctg ccgacagtgg tcccaaagat ggacccccac ccacgaggag    720

catcgtggaa aaagaagacg ttccaaccac gtcttcaaag caagtggatt gatgtgatat    780

ctccactgac gtaagggatg acgcacaatc ccactatcct tcgcaagacc cttcctctat    840

ataaggaagt tcatttcatt tggagaggac acgctgaaat caccagtctc tctctaagct    900

tggatc                                                                906
```

<210> SEQ ID NO 140
<211> LENGTH: 661
<212> TYPE: DNA
<213> ORGANISM: Artificial Sequence
<220> FEATURE:
<223> OTHER INFORMATION: Description of Artificial Sequence: Synthetic construct

<400> SEQUENCE: 140

```
tcgacatgtc tgacgaggag caccacttcg agtccagcga cgccggagct tccaaaacct     60

accctcagca ggctggtaac atccgcaagg gtggtcacat cgtcatcaag ggccgtccct    120

gcaaggttgt tgaggtttcg acttcgaaga ctgggaagca cggtcacgca aagtgtcact    180

ttgttgctat tgacatcttc actgctaaga agctcgagga tattgttccc tcttcccaca    240

attgtgatgt tccccatgtg aaccgtattg actaccagtt gattgatatc tctgagaatg    300

gctttgttag ccttttgacc gacagtggtg gcaccaagga cgacctcaag cttcccaccg    360

atgataatct cagcgctctg atgaagagtg gattcgagga gggaaaggat gtggtggtgt    420

ctgtcatgtc ttccatggga gaggagcaga tctgtgccgt caaggaagtt ggtggtggca    480

agtaaaaccc attctctgag agaggataat cttattacca gtggtcaatg ttataagaac    540

aagaacttgt ttttttcct ttttctaatt tagatcattt gtgttgtgtt tctttgttgc    600

aagacaacca ttatctatta ttggttttgg attgtttaaa aaaaaaaaaa aaaaaaaaaa    660

a                                                                     661
```

<210> SEQ ID NO 141
<211> LENGTH: 662
<212> TYPE: DNA
<213> ORGANISM: Artificial Sequence
<220> FEATURE:
<223> OTHER INFORMATION: Description of Artificial Sequence: Synthetic construct

<400> SEQUENCE: 141

```
gaattgatcc tctagagctt tcgttcgtat catcggtttc gacaacgttc gtcaagttca     60

atgcatcagt ttcattgcgc acacaccaga atcctactga gttcgagtat tatggcattg    120

ggaaaactgt ttttcttgta ccatttgttg tgcttgtaat ttactgtgtt ttttattcgg    180

ttttcgctat cgaactgtga aatggaaatg gatggagaag agttaatgaa tgatatggtc    240

cttttgttca ttctcaaatt aatattattt gttttttctc ttatttgttg tgtgttgaat    300

ttgaaattat aagagatatg caaacatttt gttttgagta aaaatgtgtc aaatcgtggc    360

ctctaatgac cgaagttaat atgaggagta aaacacttgt agttgtacca ttatgcttat    420

tcactaggca acaaatatat tttcagacct agaaaagctg caaatgttac tgaatacaag    480
```

-continued

```
tatgtcctct tgtgttttag acatttatga actttccttt atgtaatttt ccagaatcct    540

tgtcagattc taatcattgc tttataatta tagttatact catggatttg tagttgagta    600

tgaaaatatt ttttaatgca ttttatgact tgccaattga ttgacaacat gcatcaatcg    660

at                                                                   662


<210> SEQ ID NO 142
<211> LENGTH: 325
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 142

ggtgcacgcc ctgatgaagc agtgtcttgg ggtaaaataa ggggatctgc taaaactgtc     60

aaggtgtact gtgatgctac catagccttc cctttgttgg ttgctgaaac atttgcctcc    120

aagagagaac aaagctgtga gcacaagacc taagcccaag aaagcttacg tctcttttat    180

cggtttgttc ttccatcttg ttgttgtacc ctttgtcctg ctttacataa cattcatctc    240

taaaacaata ctacctcctt ttgacaaaaa ataaaaaaaa ttggaaaaat ggtttcacaa    300

gaataaaaaa aaaaaaaaaa aaaaa                                          325


<210> SEQ ID NO 143
<211> LENGTH: 906
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 143

cactgaatca aaggccatgg agtcaaagat tcaaatagag gacctaacag aactcgccgt     60

aaagactggc gaacagttca tacagagtct cttacgactc aatgacaaga agaaaatctt    120

cgtcaacatg gtggagcacg acacgcttgt ctacctccaa aaatatcaaa gatacagtct    180

cagaagacca aagggaattg agacttttca acaaagggta atatccggaa acctcctcgg    240

attccattgc ccagctatct gtcactttat tgtgaagata gtggaaaagg aaggtggctc    300

ctacaaatgc catcattgcg ataaaggaaa ggccatcgtt gaagatgcct ctgccgacag    360

tggtcccaaa gatggacccc cacccacgag gagcatcgtg gaaaaagaag acgttccaac    420

cacgtcttca aagcaagtgg attgatgtga taacatggtg gagcacgaca cgcttgtcta    480

cctccaaaaa tatcaaagat acagtctcag aagaccaaag ggaattgaga cttttcaaca    540

aagggtaata tccggaaacc tcctcggatt ccattgccca gctatctgtc actttattgt    600

gaagatagtg gaaaaggaag gtggctccta caaatgccat cattgcgata aaggaaaggc    660

catcgttgaa gatgcctctg ccgacagtgg tcccaaagat ggacccccac ccacgaggag    720

catcgtggaa aaagaagacg ttccaaccac gtcttcaaag caagtggatt gatgtgatat    780

ctccactgac gtaagggatg acgcacaatc ccactatcct tcgcaagacc cttcctctat    840

ataaggaagt tcatttcatt tggagaggac acgctgaaat caccagtctc tctctaagct    900

tggatc                                                               906


<210> SEQ ID NO 144
<211> LENGTH: 325
<212> TYPE: DNA
<213> ORGANISM: Artificial Sequence
<220> FEATURE:
```

<223> OTHER INFORMATION: Description of Artificial Sequence: Synthetic construct

<400> SEQUENCE: 144

```
ttttttttt ttttttttt tattcttgtg aaaccatttt tccaattttt tttatttttt     60
gtcaaaagga ggtagtattg ttttagagat gaatgttatg taaagcagga caaagggtac    120
aacaacaaga tggaagaaca aaccgataaa agagacgtaa gctttcttgg gcttaggtct    180
tgtgctcaca gctttgttct ctcttggagg caaatgtttc agcaaccaac aaagggaagg    240
ctatggtagc atcacagtac accttgacag ttttagcaga tccccttatt ttaccccaag    300
acactgcttc atcagggcgt gcacc                                         325
```

<210> SEQ ID NO 145
<211> LENGTH: 662
<212> TYPE: DNA
<213> ORGANISM: Artificial Sequence
<220> FEATURE:
<223> OTHER INFORMATION: Description of Artificial Sequence: Synthetic construct

<400> SEQUENCE: 145

```
gaattgatcc tctagagctt tcgttcgtat catcggtttc gacaacgttc gtcaagttca     60
atgcatcagt ttcattgcgc acacaccaga atcctactga gttcgagtat tatggcattg    120
ggaaaactgt ttttcttgta ccatttgttg tgcttgtaat ttactgtgtt ttttattcgg    180
ttttcgctat cgaactgtgc aaatggaaat ggatggagaa gagttaatga atgatatggt    240
ccttttgttc attctcaaat taatattatt tgttttttct cttatttgtt gtgtgttgaa    300
tttgaaatta taagagatat gcaaacattt tgttttgagt aaaaatgtgt caaatcgtgg    360
cctctaatga ccgaagttaa tatgaggagt aaaacacttg tagttgtacc attatgctta    420
ttcactaggc aacaaatata ttttcagacc tagaaaagct gaaatgttac tgaatacaag    480
tatgtcctct tgtgttttag acatttatga actttccttt atgtaatttt ccagaatcct    540
tgtcagattc taatcattgc tttataatta tagttatact catggatttg tagttgagta    600
tgaaaatatt ttttaatgca ttttatgact tgccaattga ttgacaacat gcatcaatcg    660
at                                                                  662
```

<210> SEQ ID NO 146
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 146

```
aagctcgaga tgtcggacga agagcacc                                       28
```

<210> SEQ ID NO 147
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 147

```
gtagagctcc accaatacca tctgcagc                                       28
```

<210> SEQ ID NO 148

<211> LENGTH: 906
<212> TYPE: DNA
<213> ORGANISM: Artificial Sequence
<220> FEATURE:
<223> OTHER INFORMATION: Description of Artificial Sequence: Synthetic
construct

<400> SEQUENCE: 148

```
cactgaatca aaggccatgg agtcaaagat tcaaatagag gacctaacag aactcgccgt     60

aaagactggc gaacagttca tacagagtct cttacgactc aatgacaaga agaaaatctt    120

cgtcaacatg gtggagcacg acacgcttgt ctacctccaa aaatatcaaa gatacagtct    180

cagaagacca aagggaattg agacttttca acaaagggta atatccggaa acctcctcgg    240

attccattgc ccagctatct gtcactttat tgtgaagata gtggaaaagg aaggtggctc    300

ctacaaatgc catcattgcg ataaaggaaa ggccatcgtt gaagatgcct ctgccgacag    360

tggtcccaaa gatggacccc cacccacgag gagcatcgtg gaaaaagaag acgttccaac    420

cacgtcttca aagcaagtgg attgatgtga taacatggtg gagcacgaca cgcttgtcta    480

cctccaaaaa tatcaaagat acagtctcag aagaccaaag ggaattgaga cttttcaaca    540

aagggtaata tccggaaacc tcctcggatt ccattgccca gctatctgtc actttattgt    600

gaagatagtg gaaaaggaag gtggctccta caaatgccat cattgcgata aaggaaaggc    660

catcgttgaa gatgcctctg ccgacagtgg tcccaaagat ggacccccac ccacgaggag    720

catcgtggaa aaagaagacg ttccaaccac gtcttcaaag caagtggatt gatgtgatat    780

ctccactgac gtaagggatg acgcacaatc ccactatcct tcgcaagacc cttcctctat    840

ataaggaagt tcatttcatt tggagaggac acgctgaaat caccagtctc tctctaagct    900

tggatc                                                               906
```

<210> SEQ ID NO 149
<211> LENGTH: 497
<212> TYPE: DNA
<213> ORGANISM: Artificial Sequence
<220> FEATURE:
<223> OTHER INFORMATION: Description of Artificial Sequence: Synthetic
construct

<400> SEQUENCE: 149

```
atgtcggacg aagagcacca cttcgaatcc aaggccgatg ccggagcttc aaagacgtat     60

cctcaacaag ctggtactat tcgtaaaggt ggtcacatcg tcataaaaaa tcgtccttgc    120

aaggtggttg aagtttcaac ttccaagaca ggcaagcacg gtcatgctaa atgtcactcg    180

tggcaattga cattttcact ggaaagaaac ttgaggatat tgttccctct tctcacaatt    240

gtgatgttcc tcatgtgaat aggactgatt atcaacttat tgatatctct gaggatggct    300

ttgtgagtct gttgactgaa aatggtaaca ccaaggatga cttgagactc ccaactgatg    360

atactcttct ggctcaggtc aaagatggtt ttgctgaggg gaaagacctg gttctatcag    420

tgatgtctgc catgggagag gagcagattt gtggtatcaa ggacattggc cctaagtagc    480

tgcagatggt attggtg                                                   497
```

<210> SEQ ID NO 150
<211> LENGTH: 662
<212> TYPE: DNA
<213> ORGANISM: Artificial Sequence
<220> FEATURE:
<223> OTHER INFORMATION: Description of Artificial Sequence: Synthetic
construct

<400> SEQUENCE: 150
gaattgatcc tctagagctt tcgttcgtat catcggtttc gacaacgttc gtcaagttca 60
atgcatcagt ttcattgcgc acacaccaga atcctactga gttcgagtat tatggcattg 120
ggaaaactgt ttttcttgta ccatttgttg tgcttgtaat ttactgtgtt ttttattcgg 180
ttttcgctat cgaactgtga aatggaaatg gatggagaag agttaatgaa tgatatggtc 240
cttttgttca ttctcaaatt aatattattt gttttttctc ttatttgttg tgtgttgaat 300
ttgaaattat aagagatatg caaacatttt gttttgagta aaaatgtgtc aaatcgtggc 360
ctctaatgac cgaagttaat atgaggagta aaacacttgt agttgtacca ttatgcttat 420
tcactaggca acaaatatat tttcagacct agaaaagctg caaatgttac tgaatacaag 480
tatgtcctct tgtgttttag acatttatga actttccttt atgtaatttt ccagaatcct 540
tgtcagattc taatcattgc tttataatta tagttatact catggatttg tagttgagta 600
tgaaaatatt ttttaatgca ttttatgact tgccaattga ttgacaacat gcatcaatcg 660
at 662

<210> SEQ ID NO 151
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
cgactcgagc agccatgtct gacgagg 27

<210> SEQ ID NO 152
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
atcgagctca tcacttgggg ccaatatcc 29

<210> SEQ ID NO 153
<211> LENGTH: 906
<212> TYPE: DNA
<213> ORGANISM: Artificial Sequence
<220> FEATURE:
<223> OTHER INFORMATION: Description of Artificial Sequence: Synthetic construct

<400> SEQUENCE: 153
cactgaatca aaggccatgg agtcaaagat tcaaatagag gacctaacag aactcgccgt 60
aaagactggc gaacagttca tacagagtct cttacgactc aatgacaaga agaaaatctt 120
cgtcaacatg gtggagcacg acacgcttgt ctacctccaa aaatatcaaa gatacagtct 180
cagaagacca aagggaattg agacttttca acaaagggta atatccggaa acctcctcgg 240
attccattgc ccagctatct gtcactttat tgtgaagata gtggaaaagg aaggtggctc 300
ctacaaatgc catcattgcg ataaaggaaa ggccatcgtt gaagatgcct ctgccgacag 360
tggtcccaaa gatggacccc cacccacgag gagcatcgtg gaaaaagaag acgttccaac 420
cacgtcttca aagcaagtgg attgatgtga taacatggtg gagcacgaca cgcttgtcta 480
cctccaaaaa tatcaaagat acagtctcag aagaccaaag ggaattgaga cttttcaaca 540

-continued

```
aagggtaata tccggaaacc tcctcggatt ccattgccca gctatctgtc actttattgt    600

gaagatagtg gaaaaggaag gtggctccta caaatgccat cattgcgata aaggaaaggc    660

catcgttgaa gatgcctctg ccgacagtgg tcccaaagat ggacccccac ccacgaggag    720

catcgtggaa aaagaagacg ttccaaccac gtcttcaaag caagtggatt gatgtgatat    780

ctccactgac gtaagggatg acgcacaatc ccactatcct tcgcaagacc cttcctctat    840

ataaggaagt tcatttcatt tggagaggac acgctgaaat caccagtctc tctctaagct    900

tggatc                                                               906
```

<210> SEQ ID NO 154
<211> LENGTH: 486
<212> TYPE: DNA
<213> ORGANISM: Artificial Sequence
<220> FEATURE:
<223> OTHER INFORMATION: Description of Artificial Sequence: Synthetic construct

<400> SEQUENCE: 154

```
cagccatgtc tgacgaggag catcaatttg agtctaaggc tgatgccgga gcatcaaaaa     60

cttaccctca acaagctggt actattcgta agaacggtta tatcgtcatc aaaggccgtc    120

catgcaaggt tgtggaagtc tctacatcca aaactggcaa gcacggtcac gccaaatgtc    180

atttcgttgc tattgacatc ttcactggga agaagcttga ggatattgtc ccctcttcac    240

acaattgtga tgtgccccat gttaatcgta cagattatca gcttattgac atctctgaag    300

atggatttgt gagtctgctt actgacaatg gtaacaccaa ggatgacctc aggcttccta    360

ctgatgaaaa tctgctttca ctgatcaagg acgggtttgc cgagggtaag gacctcgttg    420

tgtctgttat gtcagctatg ggtgaggaac agattaatgc tttgaaggat attggcccca    480

agtgat                                                               486
```

<210> SEQ ID NO 155
<211> LENGTH: 662
<212> TYPE: DNA
<213> ORGANISM: Artificial Sequence
<220> FEATURE:
<223> OTHER INFORMATION: Description of Artificial Sequence: Synthetic construct

<400> SEQUENCE: 155

```
gaattgatcc tctagagctt tcgttcgtat catcggtttc gacaacgttc gtcaagttca     60

atgcatcagt ttcattgcgc acacaccaga atcctactga gttcgagtat tatggcattg    120

ggaaaactgt ttttcttgta ccatttgttg tgcttgtaat ttactgtgtt ttttattcgg    180

ttttcgctat cgaactgtga aatggaaatg gatggagaag agttaatgaa tgatatggtc    240

cttttgttca ttctcaaatt aatattattt gttttttctc ttatttgttg tgtgttgaat    300

ttgaaattat aagagatatg caaacatttt gttttgagta aaaatgtgtc aaatcgtggc    360

ctctaatgac cgaagttaat atgaggagta aaacacttgt agttgtacca ttatgcttat    420

tcactaggca acaaatatat tttcagacct agaaaagctg caaatgttac tgaatacaag    480

tatgtcctct tgtgttttag acatttatga actttccttt atgtaatttt ccagaatcct    540

tgtcagattc taatcattgc tttataatta tagttatact catggatttg tagttgagta    600

tgaaaatatt ttttaatgca ttttatgact tgccaattga ttgacaacat gcatcaatcg    660

at                                                                   662
```

<210> SEQ ID NO 156

<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 156
cactgctcac tagtttgatg gc 22

<210> SEQ ID NO 157
<211> LENGTH: 38
<212> TYPE: DNA
<213> ORGANISM: Artificial Sequence
<220> FEATURE:
<223> OTHER INFORMATION: Description of Artificial Sequence: Synthetic
primer

<400> SEQUENCE: 157
gcgaagcggc catggctcga gttttttttt ttttttt 38

<210> SEQ ID NO 158
<211> LENGTH: 413
<212> TYPE: DNA
<213> ORGANISM: Lactuca sativa

<400> SEQUENCE: 158
cactgctcac tagtttgatg gcagtgattc tggtgctcga cctgatgaag ctgtctcctg 60
ggggaaaata cgtggttctg ctaaatctgt caaggtgcac tgtgatgcaa ctatcgcgtt 120
ccctttactt gttgcagaaa catttgctgc aaagagagag ggggagatga aaaatgttga 180
gtcaaccaaa gctttggttt aaaaaggtgg aacagtgtag gacagggact catttttgat 240
attttgtttg ctaaaaaatg gtctttggaa gaatattgat gcacacaaac aaggagacaa 300
tgttactgat cttggagagt gtaatgtaaa atgtctaaat aatttcaaag cttctcacaa 360
caaatcaaac tttaaaaaaa aaaaaaaaaa aactcgagcc atggccgctt cgc 413

<210> SEQ ID NO 159
<211> LENGTH: 388
<212> TYPE: DNA
<213> ORGANISM: Lactuca sativa

<400> SEQUENCE: 159
ctagtttgat ggcagtgatt ctggtgctcg acctgatgaa gctgtctcct gggggaaaat 60
acgtggttct gctaaatctg tcaaggtgca ctgtgatgca actatcgcgt tccctttact 120
tgttgcagaa acatttgctg caaagagaga gggggagatg aaaaatgttg agtcaaccaa 180
agctttggtt taaaaaggtg gaacagtgta ggacagggac tcatttttga tattttgttt 240
gctaaaaaat ggtctttgga agaatattga tgcacacaaa caaggagaca atgttactga 300
tcttggagag tgtacatgta aaatgtctaa ataatttcaa agcttctcac aacaaatcaa 360
acttaaaaaa aaaaaaaaaa aaactcga 388

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (3)
<223> OTHER INFORMATION: a, t, c or g
<220> FEATURE:
<221> NAME/KEY: modified_base
<222> LOCATION: (12)
<223> OTHER INFORMATION: a, t, c or g
<220> FEATURE:
<221> NAME/KEY: modified_base
<222> LOCATION: (18)
<223> OTHER INFORMATION: a, t, c or g

<400> SEQUENCE: 160
ggnttraayc gnathggnaa ytt 23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (9)
<223> OTHER INFORMATION: a, t, c or g
<220> FEATURE:
<221> NAME/KEY: modified_base
<222> LOCATION: (21)
<223> OTHER INFORMATION: a, t, c or g

<400> SEQUENCE: 161
tgrtcgganc crtcraaytc ngc 23

<210> SEQ ID NO 162
<211> LENGTH: 108
<212> TYPE: DNA
<213> ORGANISM: Mycosphaerella fijiensis

<400> SEQUENCE: 162
cgccaagcta tttaggtgac actatagaat actcaagcta tgcatccaac gcgttgggag 60
ctctcccata tggtcgacct gcaggcggcc gcgaattcac tagtgatt 108

<210> SEQ ID NO 163
<211> LENGTH: 487
<212> TYPE: DNA
<213> ORGANISM: Mycosphaerella fijiensis
<220> FEATURE:
<221> NAME/KEY: CDS
<222> LOCATION: (1)..(486)

<400> SEQUENCE: 163

```
ggg tta aat cgt att gga aac ttc tta gtg cca aac gac aat tac tgc       48
Gly Leu Asn Arg Ile Gly Asn Phe Leu Val Pro Asn Asp Asn Tyr Cys
  1               5                  10                  15

cgc ttt gaa gac tgg gtg atg cca atc ctc gac aca atg ctc gaa gaa       96
Arg Phe Glu Asp Trp Val Met Pro Ile Leu Asp Thr Met Leu Glu Glu
             20                  25                  30

cag gaa gca tgc aag ggt tcg ggc gaa gca atc cac tgg act ccc agc      144
Gln Glu Ala Cys Lys Gly Ser Gly Glu Ala Ile His Trp Thr Pro Ser
         35                  40                  45

aaa atc atc aac cgg ctt ggc aag gag gtc aac gac gaa tcg tcc gtg      192
Lys Ile Ile Asn Arg Leu Gly Lys Glu Val Asn Asp Glu Ser Ser Val
     50                  55                  60

tac tac tgg gca tgg aag aac gac att cca gtg ttc tgt ccg gcg ctt      240
Tyr Tyr Trp Ala Trp Lys Asn Asp Ile Pro Val Phe Cys Pro Ala Leu
 65                  70                  75                  80

act gat ggc agt ctc gga gac atg ctg tac ttc cac acg ttc aaa tcc      288
Thr Asp Gly Ser Leu Gly Asp Met Leu Tyr Phe His Thr Phe Lys Ser
                 85                  90                  95
```

```
tca ccg cag cag ctt cga gtc gac att gtg gaa gac atc cga aag atc      336
Ser Pro Gln Gln Leu Arg Val Asp Ile Val Glu Asp Ile Arg Lys Ile
            100                 105                 110

aac acc ctc gcc gtc cga gcc aag cgc act ggc atg atc att ctc gga      384
Asn Thr Leu Ala Val Arg Ala Lys Arg Thr Gly Met Ile Ile Leu Gly
        115                 120                 125

ggc ggc att gtc aag cac cac atc gca aat gcc aac ctg atg cgc aat      432
Gly Gly Ile Val Lys His His Ile Ala Asn Ala Asn Leu Met Arg Asn
    130                 135                 140

ggc gcg gaa agc gca gtg tac atc aat acc gcg ccg aat tcg acg gat      480
Gly Ala Glu Ser Ala Val Tyr Ile Asn Thr Ala Pro Asn Ser Thr Asp
145                 150                 155                 160

ccg acc a                                                            487
Pro Thr


<210> SEQ ID NO 164
<211> LENGTH: 162
<212> TYPE: PRT
<213> ORGANISM: Mycosphaerella fijiensis

<400> SEQUENCE: 164

Gly Leu Asn Arg Ile Gly Asn Phe Leu Val Pro Asn Asp Asn Tyr Cys
  1               5                  10                  15

Arg Phe Glu Asp Trp Val Met Pro Ile Leu Asp Thr Met Leu Glu Glu
            20                  25                  30

Gln Glu Ala Cys Lys Gly Ser Gly Glu Ala Ile His Trp Thr Pro Ser
        35                  40                  45

Lys Ile Ile Asn Arg Leu Gly Lys Glu Val Asn Asp Glu Ser Ser Val
     50                  55                  60

Tyr Tyr Trp Ala Trp Lys Asn Asp Ile Pro Val Phe Cys Pro Ala Leu
 65                  70                  75                  80

Thr Asp Gly Ser Leu Gly Asp Met Leu Tyr Phe His Thr Phe Lys Ser
                 85                  90                  95

Ser Pro Gln Gln Leu Arg Val Asp Ile Val Glu Asp Ile Arg Lys Ile
            100                 105                 110

Asn Thr Leu Ala Val Arg Ala Lys Arg Thr Gly Met Ile Ile Leu Gly
        115                 120                 125

Gly Gly Ile Val Lys His His Ile Ala Asn Ala Asn Leu Met Arg Asn
    130                 135                 140

Gly Ala Glu Ser Ala Val Tyr Ile Asn Thr Ala Pro Asn Ser Thr Asp
145                 150                 155                 160

Pro Thr


<210> SEQ ID NO 165
<211> LENGTH: 214
<212> TYPE: DNA
<213> ORGANISM: Mycosphaerella fijiensis

<400> SEQUENCE: 165

aatcgaattc ccgcggccgc catggcggcc gggagcatgc gacgtcgggc ccaattcgcc      60

ctatagtgag tcgtattaca attcactggc cgtcgtttta caacgtcgtg actgggaaaa     120

cctggcggta cccaacttaa tcgccttgca gcacatcccc ctttcgccag ctggcgtaat     180

agcgaagagg cccgcaccga tcgcccttcc aaca                                 214
```

POLYNUCLEOTIDES ENCODING CANOLA DHS AND ANTISENSE POLYNUCLEOTIDES THEREOF

RELATED APPLICATIONS

This application is a divisional application of Ser. No. 10/862,440, filed Jun. 8, 2004, now U.S. Pat. No. 7,358,418, which is a continuation-in-part of Ser. No. 09/725,019, filed Nov. 29, 2000, now U.S. Pat. No. 6,878,860, which is a continuation-in-part of 09/597,771, filed Jun. 19, 2000, now U.S. Pat. No. 6,538,182, which is a continuation in part of 09/348,675, filed Jul. 6, 1999, now abandoned. This application claims priority to and herein incorporates by reference U.S. provisional applications 60/479,968 and 60/479,969 both filed Jun. 20, 2003, and U.S. provisional applications 60/570,833 and 60/570,835, both filed on May 14, 2004.

FIELD OF THE INVENTION

The present invention relates to unique isoforms of eukaryotic initiation Factor 5A ("eIF-5A") and polynucleotides that encode eIF-5A and deoxyhypusine synthase ("DHS"), and polynucleotides that encode DHS, and methods involving modulating the expression of the isoforms eIF-5A and DHS.

DESCRIPTION OF THE PRIOR ART

Senescence is the terminal phase of biological development in the life of a plant. It presages death and occurs at various levels of biological organization including the whole plant, organs, flowers and fruit, tissues and individual cells.

The onset of senescence can be induced by different factors both internal and external. Senescence is a complex, highly regulated developmental stage in the life of a plant or plant tissue, such as fruit, flowers and leaves. Senescence results in the coordinated breakdown of cell membranes and macromolecules and the subsequent mobilization of metabolites to other parts of the plant.

In addition to the programmed senescence which takes place during normal plant development, death of cells and tissues and ensuing remobilization of metabolites occurs as a coordinated response to external, environmental factors. External factors that induce premature initiation of senescence, which is also referred to as necrosis or apoptosis, include environmental stresses such as temperature, drought, poor light or nutrient supply, as well as pathogen attack. Plant tissues exposed to environmental stress also produce ethylene, commonly known as stress ethylene (Buchanan-Wollaston, V., 1997, J. Exp. Botany, 48:181-199; Wright, M., 1974, Plant, 120:63-69). Ethylene is known to cause senescence in some plants.

Senescence is not a passive process, but, rather, is an actively regulated process that involves coordinated expression of specific genes. During senescence, the levels of total RNA decrease and the expression of many genes is switched off (Bate et al., 1991, J. Exper. Botany, 42, 801-11; Hensel et al., 1993, The Plant Cell, 5, 553-64). However, there is increasing evidence that the senescence process depends on de novo transcription of nuclear genes. For example, senescence is blocked by inhibitors of mRNA and protein synthesis and enucleation. Molecular studies using mRNA from senescing leaves and green leaves for in vitro translation experiments show a changed pattern of leaf protein products in senescing leaves (Thomas et al., 1992, J. Plant Physiol., 139, 403-12). With the use of differential screening and subtractive hybridization techniques, many cDNA clones representing senescence-induced genes have been identified from a range of different plants, including both monocots and dicots, such as *Arabidopsis*, maize, cucumber, asparagus, tomato, rice and potato. Identification of genes that are expressed specifically during senescence is hard evidence of the requirement for de novo transcription for senescence to proceed.

The events that take place during senescence appear to be highly coordinated to allow maximum use of the cellular components before necrosis and death occur. Complex interactions involving the perception of specific signals and the induction of cascades of gene expression must occur to regulate this process. Expression of genes encoding senescence related proteins is probably regulated via common activator proteins that are, in turn, activated directly or indirectly by hormonal signals. Little is known about the mechanisms involved in the initial signaling or subsequent co-ordination of the process.

Coordinated gene expression requires factors involved in transcription and translation, including initiation factors. Translation initiation factor genes have been isolated and characterized in a variety of organisms, including plants. Translation initiation factors can control the rate at which mRNA populations are moved out of the nucleus, the rate at which they are associated with a ribosome and to some extent can affect the stability of specific mRNAs. (Zuk, et al., EMBO J. 17:2914-2925 (1998). Indeed, one such translation initiation factor, which is not required for global translation activity, is believed to shuttle specific subsets of mRNAs from the nucleus to the cytoplasm for translation. Jao, et al., J. Cell. Biochem. 86: 590-600, (2002); Wang et al., J Biol Chem 276:17541-17549 (2001); Rosorius et al., J. Cell Sci., 112, 2369-2380 (1999). This translation factor is known as the eukaryotic initiation factor 5A (eIF-5A), and is the only protein known to contain the amino acid hypusine. Park, et al., J Biol Chem 263:15264-15269 (1988).

Eukaryotic translation initiation factor 5A (eIF-5A) is an essential protein factor approximately 17 KDa in size, which is involved in the initiation of eukaryotic cellular protein synthesis. It is characterized by the presence of hypusine [N-(4-amino-2-hydroxybutyl)lysine], a unique modified amino acid, known to be present only in eIF-5A. Hypusine is formed post-translationally via the transfer and hydroxylation of the butylamino group from the polyamine, spermidine, to the side chain amino group of a specific lysine residue in eIF-5A. Activation of eIF-5A involves transfer of the butylamine residue of spermidine to the lysine of eIF-5A, forming hypusine and activating eIF-5A. In eukaryotes, deoxyhypusine synthase (DHS) mediates the post-translational synthesis of hypusine in eIF-5A. The hypusine modification has been shown to be essential for eIF-5A activity in vitro using a methionyl-puromycin assay.

Hypusine is formed on eIF-5A post-translationally through the conversion of a conserved lysine residue by the action of deoxyhypusine synthase (DHS; EC 1.1.1.249) and deoxyhypusine hydroxylase (DHH; EC 1.14.99.29). DHS has been isolated from several plant species, including tomato (GenBank Accession Number AF296077), *Arabidopsis thaliana* (AT-DHS; GenBank Accession Number AF296078), tobacco (Ober and Hartmann, 1999), carnation (GenBank Accession Number AF296079) and banana (GenBank Accession Number AF296080), whereas the gene for DHH has not been recognized.

DHS converts a conserved lysine residue of eIF-5A to deoxyhypusine through the addition of a butylamine group derived from spermidine. This intermediate form of eIF-5A is then hydroxylated by DHH to become hypusine. Park et al., Biol. Signals 6, 115-123 (1997). Both the deoxyhypusine and the hypusine form of eIF-5A are able to bind mRNA in vitro. Liu et al., Biol Signals 6:166-174 (1997). Although the function of eIF-5A is not fully understood, there is some evidence that it may regulate cell division (Park et al., J Biol Chem 263:15264-15269 (1998); Tome et al., Biol Signals 6:150-156, (1997)) and senescence. (Wang et al., J. Biol. Chem. 276(20): 17541-17549 (2001)). See also U.S. Pat. No. 6,538,182 and U.S. application Ser. No. 09/725,019, which are herein incorporated by reference in their entirety. It appears that several organisms are known to have more than one isoform of eIF-5A, which would suit the premise that each isoform is a specific shuttle to specific suites of mRNAs that are involved in such processes as cell division and senescence.

Wang et al. demonstrated that an increased level of DHS mRNA correlates with fruit softening and natural and stress-induced leaf senescence of tomato. Wang et al., J. Biol. Chem. 276(20): 17541-17549 (2001). Furthermore when the expression of DHS was suppressed in transgenic tomato plants by introducing a DHS antisense cDNA fragment under the regulation of a constitutive promoter, the tomato fruit from these transgenic plants exhibited dramatically delayed senescence as evidenced by delayed fruit softening and spoilage. See U.S. Pat. No. 6,538,182 and U.S. application Ser. No. 09/725,019, filed Nov. 29, 2003, incorporated herein by reference in their entirety. Since DHS is known to activate eIF-5A, these data suggest that the hypusine-modified eIF-5A (active eIF-5A) may regulate senescence through selective translation of mRNA species required for senescence. This is further demonstrated through the down-regulation of DHS in *Arabidopsis thaliana* ("AT") by antisense of the full length or 3'UTR cDNA under the control of a constitutive promoter. By down regulating *Arabidopsis thaliana* DHS ("AT-DHS") expression and making it less available for eIF-5A activation, senescence was delayed by approximately 2 weeks (See U.S. Pat. No. 6,538,182). Not only was senescence delayed, but also an increase in seed yield, an increase in stress tolerance and an increase in biomass were observed in the transgenic plants, where the extent of each phenotype was determined by the extent of the down-regulation of DHS. Since tomato and *Arabidopsis thaliana* only have one copy of DHS in their genome, as shown by Southern blot (Wang et al., 2001) and BLAST analysis, in order to target the specific eIF-5A isoform responsible for shuttling of senescence transcripts out of the nucleus, the senescence specific isoform of eIF-5A must be identified and specifically down-regulated through the antisense constructs of senescence-induced eIF-5A (of the 3' UTR) or by taking advantage of the plant's natural ability for down-regulation of an over expressed gene (i.e. creating over-expression through the use of sense polynucleotides).

Plants lack immune systems and thus, have a unique way of dealing with viruses—called co-suppression, which results in sequence-specific degradation of the viral RNA. When a transgene is under a strong constitutive promoter, like the cauliflower mosaic virus double 35S promoter, it appears as a viral transcript to the plant and sequence-specific degradation occurs, but not just of the transgene, but also the endogenous gene. (reviewed in Fagard and Vaucheret, Annual Review. Plant Physiol. Plant Mol. Biol., June; 51:167-194 (2000). There is some evidence that co-suppression may be as effective, if not more effective, than antisense suppression of expression for the down-regulation of an endogenous gene.

SUMMARY OF THE INVENTION

The present invention provides isoforms of eukaryotic initiation Factor 5A ("eIF-5A"): senescence-induced eIF-5A; wounding-induced eIF-5A; and growth eIF-5A as well as polynucleotides that encode these three factors. The present invention provides antisense polynucleotides of the three eIF-5A isoforms. The invention also provide expression vectors comprising sense and antisense polynucleotides of the three eIF-5A isoforms. The present invention also relates to methods involving modulating (increasing/up-regulating or inhibiting) the expression of these factors.

The present invention also relates to deoxyhypusine synthase ("DHS") and polynucleotides that encode DHS. The present invention also provides antisense polynucleotides of DHS. The invention also provide expression vectors comprising sense and antisense polynucleotides of DHS. The present invention also relates to methods involving modulating (increasing/up-regulating or inhibiting) the expression of DHS.

BRIEF DESCRIPTION OF THE DRAWINGS

FIG. 1 shows the alignment of three isoforms of eIF-5A isolated *Arabidopsis thaliana* senescence-induced eIF-5A (line 1)(SEQ ID NO: 58)(previously described in U.S. Pat. No. 6,538,182 and pending application Ser. No. 09/725,019); wounding-induced eIF-5A (line 2)(SEQ II) NO: 59); and growth eIF-5A (line 3)(SEQ ID NO: 60).

FIG. 2 shows the alignment of the coding regions of these three *Arabidopsis thaliana* isoforms. Line 1 is senescence-induced eIF-5A (SEQ ID NO: 61). Line 2 is wounding-induced eIF-5A (SEQ ID NO: 62). Line 3 is growth eIF-5A (SEQ ID NO: 63).

FIG. 3 provides the genomic sequence (SEQ ID NO: 78) of the senescence-induced eIF-5A of *Arabidopsis thaliana.*

FIG. 4 provides the genomic sequence (SEQ ID NO: 79) of the wounding-induced eIF5A of *Arabidopsis thaliana.*

FIG. 5 provides the genomic sequence (SEQ ID NO: 52) of the growth eIF5A of *Arabidopsis thaliana.*

FIG. 6 is a map of binary vector pKYLX71-35S$^2$ (SEQ ID NO: 80).

FIG. 8 shows Western blots of all three isoforms of eIF-5A in different tissues of *Arabidopsis thaliana* wild type of the Columbia ecotype.

FIG. 9 are Western blots for the senescence-induced eIF-5A and the wounding-induced eIF-5A of infected leaves after 72 hours of *Arabidopsis thaliana* wild type of the Columbia ecotype.

FIG. 10 are Northern blots for the three isoforms of eIF-5A in wounded leaves after 72 hours of *Arabidopsis thaliana* wild type of the Columbia ecotype.

FIG. 12 shows an agarose gel with senescence-induced AteIF-5A, wounding-induced AteIF-5A, and growth AteIF-5A genomic sequences in pGEM.

FIG. 17 is a picture of T2 plants transformed with Sense wounding-induced AteIF-5A at 10 days post seeding.

FIG. 34 is a summary of phenotypes displayed in sense growth AteIF-5A plants.

FIG. 39 shows the primers (SEQ ID NOS: 81-82, respectively) used to construct the vector for generating antisense *arabidopsis thaliana* 3' DHS. Amplified Arabidopsis sequences are shown in (SEQ ID NOS: 83-84, respectively)

FIG. 41 shows the sequence for wounding factor eIF-5A (DNA shown in SEQ ID NO: 54, Amino Acid sequence shown in SEQ ID NO: 55) isolated from *arabidopsis* and the location of the antisense construct. The primer sequences are shown in SEQ ID NOS: 85-86, respectively.

FIG. 42 shows the vector construct (nucleotide sequences shown in SEQ ID NOS: 87-89, respectively).

FIG. 42 shows the vector construct (nucleotide sequences shown in SEQ ID NOS 87-89, respectively).

FIG. 43 shows plate counts of leaf discs inoculated with pseudomonas.

FIGS. 45A-45B depict the nucleotide sequence of the tomato leaf DHS cDNA sequence (SEQ ID NO: 1) and the derived amino acid sequence (SEQ ID NO. 2) obtained from a tomato leaf cDNA library.

FIGS. 46A-46D: FIG. 46A depicts the nucleotide sequence of an *Arabidopsis* DHS gene obtained by aligning the tomato DHS sequence with unidentified genomic sequences in the *Arabidopsis* gene bank (SEQ ID NO:5). The gaps between amino acid sequences are predicted introns. FIG. 46B depicts the derived *Arabidopsis* DHS amino acid sequence (SEQ ID NO:6). FIG. 46C depicts the nucleotide sequence (SEQ ID NO: 26) of a 600 base pair *Arabidopsis* DHS cDNA obtained by PCR. FIG. 46D depicts the derived amino acid sequence (SEQ ID NO: 92) of the *Arabidopsis* DHS cDNA fragment.

FIG. 53A is the ethidium bromide stained gel of total RNA. Each lane contained 10 μg RNA. FIG. 53B is an autoradiograph of the Northern blot probed with $^{32}$P-dCTP-labeled full length tomato DHS cDNA. FIG. 53C shows corresponding leakage data measured as conductivity of leaf diffusates.

FIG. 54 is the carnation DHS full-length (1384 base pairs) cDNA clone nucleotide sequence (SEQ ID NO: 9) not including the PolyA tail and 5' end non-coding region. The derived amino acid sequence is shown below the nucleotide sequence (373 amino acids). (SEQ ID NO:10)

FIG. 57 is the nucleotide (top) (SEQ ID NO: 11) and derived amino acid (bottom) (SEQ ID NO: 12) sequence of the tomato fruit senescence-induced eIF-5A gene.

FIG. 58 is the nucleotide (top) (SEQ ID NO: 13) and derived amino acid (bottom) (SEQ ID NO: 14) sequence of the carnation senescence-induced eIF-5A gene.

FIG. 59 is the nucleotide (top) (SEQ ID NO: 15) and derived amino acid (bottom) (SEQ ID NO: 16) sequence of the *Arabidopsis* senescence-induced eIF-5A gene.

FIG. 80 is the nucleotide (top) (SEQ ID NO:30) and derived amino acid (bottom) sequence (SEQ ID NO: 90) of the 3'-end of the *Arabidopsis* senescence-induced DHS gene used in antisense orientation to transform plants.

FIG. 81 is the nucleotide (top) (SEQ ID NO:31) and derived amino acid (bottom) sequence (SEQ ID NO: 91) of the 3'-end of the tomato DHS gene used in antisense orientation to transform plants.

FIG. 82 is the nucleotide (top) (SEQ ID NO:26) and derived amino acid (bottom) sequence (SEQ ID NO: 92) of a 600 base pair *Arabidopsis* DHS probe used to isolate the full-length *Arabidopsis* gene.

FIG. 83 is the nucleotide (top) (SEQ ID NO:27) and derived amino acid (bottom) sequence (SEQ ID NO: 93) of the 483 base pair carnation DHS probe used to isolate the full-length carnation gene.

FIG. 85 shows the alignment of various isoforms of eIF-5A from several plant species. It also provides alignment of the hypusine conserved region. See SEQ ID NOS 4 & 94-125, respectively, in order of appearance.

FIG. 86 provides tomato senescence-induced eIF-5A polynucleotide (SEQ ID NO: 126) and amino acid (SEQ ID NO: 127) sequences.

FIG. 87 provides *Arabidopsis* senescence-induced eIF-5A and the construction of pKYLX71-sense senescence-induced eIF-5A. The primer sequences are shown in SEQ ID NOS128-129, respectively, while the vector sequences are shown in SEQ ID NOS130-132, respectively.

FIGS. 88A-88B provides tomato senescence-induced eIF-5A and the construction of pKYLX71-sense senescence-induced eIF-5A.

FIG. 94 concerned tomato sense polynucleotide senescence-induced eIF-5A.

FIG. 95 provides canola growth eIF-5A amino acid (SEQ ID NO: 67) and polynucleotide (SEQ ID NO: 66) sequences.

FIG. 96 provides canola growth eIF-5A and the construction of pKYLX71-sense growth eIF-5A. The primer sequence is shown in SEQ ID NO: 138, while the vector sequences are shown in SEQ ID NOS 139-141, respectively.

FIGS. 97A-97B provides canola DHS amino acid (SEQ ID NO: 71) and polynucleotide (SEQ ID NO: 70) sequences.

FIG. 98 provides canola DHS and the construction of pKYLX71-sense DHS. The 3'-UTR sequence is shown in SEQ ID NO: 142, while the vector sequences are shown in SEQ ID NOS: 143-145, respectively.

FIG. 101 provides tomato growth eIF-5A amino acid (SEQ ID NO: 65) and polynucleotide (SEQ ID NO: 64) sequences.

FIGS. 102A-102B provides tomato growth eIF-5A and the construction of pKYLX71-sense tomato growth eIF-5A. The primer sequences are shown in SEQ ID NOS 146-147, respectively, while the vector sequences are shown in SEQ ID NOS 148-150, respectively.

FIG. 103 provides tomato wounding-induced eIF-5A amino acid (SEQ ID NO: 57) and polynucleotide (SEQ ID NO: 56) sequences.

FIG. 104*a* and *b* provides tomato wounding-induced eIF-5A and the construction of pKYLX71-sense tomato wounding-induced eIF-5A. The primer sequences are shown in SEQ ID NOS: 151-152, respectively, while the vector sequences are shown in SEQ ID NOS: 153-155, respectively.

FIG. 105 provides portions of lettuce DHS polynucleotide sequences. The primer sequences are shown in SEQ ID NOS: 156-157, respectively, while the Lettuce sequences are shown in SEQ ID NOS: 158-159, respectively.

FIGS. 107A and B provides alfalfa DHS amino acid (SEQ ID NO: 73) and polynucleotide (SEQ ID NO: 72) sequences.

FIGS. 108 A and B provides banana DHS amino acid (SEQ ID NO: 75) and polynucleotide (SEQ ID NO: 74) sequences.

FIGS. 109 A and B provides cottonwood DHS amino acid (SEQ ID NO: 77) and polynucleotide (SEQ ID NO: 76) sequences.

FIG. 110 provides partial *mycosphaerella fijiensis* DHS amino acid and polynucleotide sequences (see SEQ ID NOS: 68, 160, 69 161-164, 163 & 165, 47, 163 and 53, respectively, in order of appearance).

DETAILED DESCRIPTION

Figure 7:
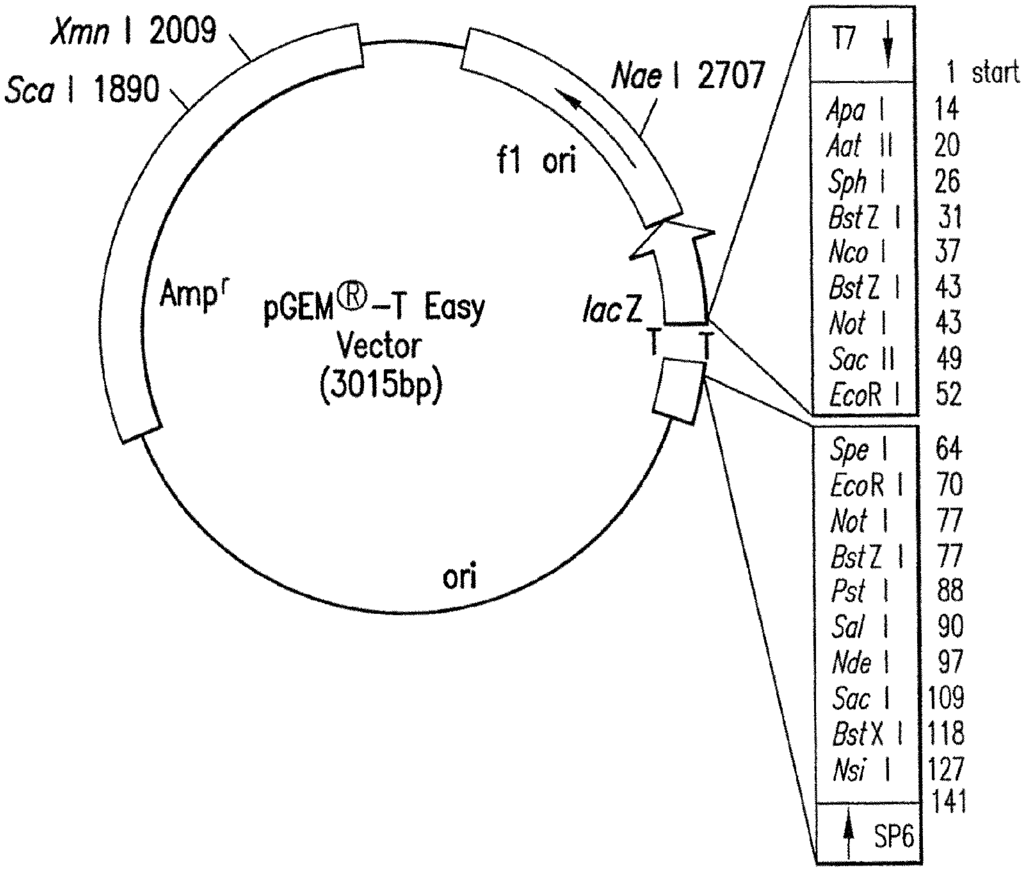
FIG. 7 is a map of binary vector pGEM®-T Easy Vector.

As used herein, the term "plant" refers to either a whole plant, a plant part, a plant cell or a group of plant cells. The type of plant which can be used in the methods of the invention is not limited and includes, for example, ethylene-sensitive and ethylene-insensitive plants; fruit bearing plants such as apricots, apples, oranges, bananas, grapefruit, pears, tomatoes, strawberries, avocados, etc.; vegetables such as carrots, peas, lettuce, cabbage, turnips, potatoes, broccoli, asparagus, etc.; flowers such as carnations, roses, mums, etc.; agronomic crop plants such as corn, rice, soybean, alfalfa and the like, and forest species such as deciduous trees, conifers, evergreens, etc., and in general, any plant that can take up and express the DNA molecules of the present invention. It may include plants of a variety of ploidy levels, including haploid, diploid, tetraploid and polyploid. The plant may be either a monocotyledon or dicotyledon.

A transgenic plant is defined herein as a plant which is genetically modified in some way, including but not limited to a plant which has incorporated heterologous or homologous senescence-induced eIF-5A, wounding-induced eIF-5A, growth eIF-5A or DHS into its genome. The altered genetic material may encode a protein, comprise a regulatory or control sequence, or may be or include an antisense sequence or sense sequence or encode an antisense RNA or sense RNA which is antisense or sense to senescence-induced eIF-5A, wounding-induced eIF-5A, growth eIF-5A or DHS DNA or mRNA sequence or portion thereof of the plant. A "transgene" or "transgenic sequence" is defined as a foreign gene or partial sequence that has been incorporated into a transgenic plant.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, N.Y., 1989. The choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. What is meant herein as high stringency conditions is as follows: the hybridization solution contains 6× S.S.C., 0.01 M EDTA, 1×Denhardt's solution and 0.5% SDS. Hybridization is carried out at about 68° C. for about 3 to 4 hours for fragments of cloned DNA and for about 12 to about 16 hours for total eukaryotic DNA. For lower stringencies the temperature of hybridization is reduced to about 42° C. below the melting temperature ($T_M$) of the duplex. The $T_M$ is known to be a function of the G-C content and duplex length as well as the ionic strength of the solution.

As used herein, the term "substantial sequence identity" or "substantial homology" is used to indicate that a nucleotide sequence or an amino acid sequence exhibits substantial structural or functional equivalence with another nucleotide or amino acid sequence. Any structural or functional differences between sequences having substantial sequence identity or substantial homology will be de minimis; that is, they will not affect the ability of the sequence to function as indicated in the desired application. Differences may be due to inherent variations in codon usage among different species, for example. Structural differences are considered de minimis if there is a significant amount of sequence overlap or similarity between two or more different sequences or if the different sequences exhibit similar physical characteristics even if the sequences differ in length or structure. Such characteristics include, for example, ability to hybridize under defined conditions, or in the case of proteins, immunological crossreactivity, similar enzymatic activity, etc. Each of these characteristics can readily be determined by the skilled practitioner by art known methods.

Additionally, two nucleotide sequences are "substantially complementary" if the sequences have at least about 70 percent, more preferably, 80 percent and most preferably about 90 percent sequence similarity between them. Two amino acid sequences are substantially homologous if they have at least 70% similarity between the active portions of the polypeptides.

As used herein, the phrase "hybridizes to a corresponding portion" of a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridization under appropriate conditions. For example, a 100 nucleotide long antisense molecule from the 3' coding or non-coding region of tomato wounding-induced eIF-5A will recognize and hybridize to an approximately 100 nucleotide portion of a nucleotide sequence within the 3' coding or non-coding region, respectively of AT wounding-induced eIF-5A gene or any other plant wounding-induced eIF-5A gene so long as there is about 70% or more sequence similarity between the two sequences. It is to be understood that the size of the "corresponding portion" will allow for some mismatches in hybridization such that the "corresponding portion" may be smaller or larger than the molecule which hybridizes to it, for example 20-30% larger or smaller, preferably no more than about 12-15% larger or smaller.

The term "functional derivative" of a nucleic acid (or polynucleotide) as used herein means a fragment, variant, homolog, or analog of the gene or nucleotide sequence encoding senescence-induced eIF-5A, wounding-induced eIF-5A, growth eIF-5A or DHS. A functional derivative retains at least a portion of the function of the senescence-induced eIF-5A, wounding-induced eIF-5A, growth eIF-5A or DHS encoding DNA, which permits its utility in accordance with the invention. Such function may include the ability to hybridize under high stringency conditions with native isolated senescence-induced eIF-5A, wounding-induced eIF-5A, growth eIF-5A or DHS or substantially homologous DNA from another plant or an mRNA transcript thereof, and which senescence-induced eIF-5A, wounding-induced eIF-5A, growth eIF-5A or DHS in antisense orientation inhibits expression of senescence-induced eIF-5A, wounding-induced eIF-5A, growth eIF-5A or DHS.

A "fragment" of the gene or DNA sequence refers to any subset of the molecule, e.g., a shorter polynucleotide or oligonucleotide. A "variant" refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. A "homolog" refers to a fragment or variant sequence from a different plant genus or species. An "analog" refers to a non-natural molecule substantially similar to or functioning in relation to either the entire molecule, a variant or a fragment thereof.

By "modulating expression" it is meant that either the expression is inhibited or up-regulated. "Inhibition of expression" refers to the absence or detectable decrease in the level of protein and/or mRNA product from a target gene, such as senescence-induced eIF-5A, wounding-induced eIF-5A, growth eIF-5A or DHS. "Up-regulation" or "over expression" refers to a detectable increase in the level of protein and/or mRNA product from a target gene, such as senescence-induced eIF-5A, wounding-induced eIF-5A, growth eIF-5A or DHS.

Isolated polynucleotides of the present invention include those isolated from natural sources, recombinantly produced or synthesized.

Isolated peptides of the present invention include those isolated from natural sources, recombinantly produced or synthesized. Isolated proteins of the present invention include senescence-induced eIF-5A, wounding-induced eIF-5A, growth eIF-5A or DHS expressed as a fusion protein, preferably comprising eIF-5A or DHS fused with maltose binding protein.

"Functional derivatives" of the senescence-induced eIF-5A, wounding-induced eIF-5A, growth eIF-5A, or DHS peptides of the present invention include fragments, variants, analogs, or chemical derivatives of senescence-induced eIF-5A, wounding-induced eIF-5A, growth eIF-5A or DHS, which retain at least a portion of the activity or immunological cross reactivity with an antibody specific for the eIF-5A isoform or DHS. A fragment of eIF-5A or DHS peptide refers to any subset of the molecule. Variant peptides may be made by direct chemical synthesis, for example, using methods well known in the art. An analog of eIF-5A or DHS peptide refers to a non-natural protein substantially similar to either the entire protein or a fragment thereof. Chemical derivatives of eIF-5A or DHS contain additional chemical moieties not normally a part of the peptide or peptide fragment. Modifications may be introduced into peptides or fragments thereof by reacting targeted amino acid residues of the peptide with an organic derivatizing agent that is capable of reacting with selected side chains or terminal residues.

A eIF-5A or DHS peptide according to the invention may be produced by culturing a cell transformed with a nucleotide sequence of this invention (in the sense orientation), allowing the cell to synthesize the protein and then isolating the protein, either as a free protein or as a fusion protein, depending on the cloning protocol used, from either the culture medium or from cell extracts. Alternatively, the protein can be produced in a cell-free system. Ranu, et al., Meth. Enzymol., 60:459-484, (1979).

Preparation of plasmid DNA, restriction enzyme digestion, agarose gel electrophoresis of DNA, polyacrylamide gel electrophoresis of protein, PCR, RT-PCR, Southern blots, Northern blots, DNA ligation and bacterial transformation were carried out using conventional methods well-known in the art. See, for example, Sambrook, J. et al., Molecular Cloning: A Laboratory Manual, 2nd ed., Cold Spring Harbor Press, Cold Spring Harbor, N.Y., 1989. Techniques of nucleic acid hybridization are disclosed by Sambrook.

Procedures for constructing recombinant nucleotide molecules in accordance with the present invention are disclosed in Sambrook, et al., In: Molecular Cloning: A Laboratory Manual, 2nd ed., Cold Spring Harbor Press, Cold Spring Harbor, N.Y. (1989), and Maniatis, T. et al., Molecular mechanisms in the Control of Gene expression, eds., Nierlich, et al., eds., Acad. Press, N.Y. (1976), which are both incorporated herein in its entirety.

Transgenic plants made in accordance with the present invention may be prepared by DNA transformation using any method of plant transformation known in the art. Plant transformation methods include direct co-cultivation of plants, tissues or cells with *Agrobacterium tumefaciens* or direct infection (Miki, et al., Meth. in Plant Mol. Biol. and Biotechnology, (1993), p. 67-88); direct gene transfer into protoplasts or protoplast uptake (Paszkowski, et al., EMBO J., 12:2717 (1984); electroporation (Fromm, et al., Nature, 319:719 (1986); particle bombardment (Klein et al., BioTechnology, 6:559-563 (1988); injection into meristematic tissues of seedlings and plants (De LaPena, et al., Nature, 325:274-276

(1987); injection into protoplasts of cultured cells and tissues (Reich, et al., BioTechnology, 4:1001-1004 (1986)).

Generally a complete plant is obtained from the transformation process. Plants are regenerated from protoplasts, callus, tissue parts or explants, etc. Plant parts obtained from the regenerated transgenic plants in which the expression of the eIF-5A isoform or DHS is altered, such as leaves, flowers, fruit, seeds and the like are included in the definition of "plant" as used herein. Progeny, variants and mutants of the regenerated plants are also included in the definition of "plant."

eIF-5A Generally

The present invention relates to three different isoforms of eIF-5A: senescence-induced eIF-5A; wounding induced eIF-5A; and growth eIF-5A. The present invention provides various isoforms of eIF-5A isolated from various plant species and methods of isolating the various isoforms eIF-5A. The present invention also provides polynucleotides that encode these various isoforms of eIF-5A of the present invention. The invention also provides antisense polynucleotides of the isoforms of eIF-5A and expression vectors containing such polynucleotides or antisense polynucleotides. In some embodiments, there are provided methods of inhibiting expression of endogenous eIF-5As through the use of expression vectors containing antisense polynucleotides of the isoforms of eIF-5A to transform plants. In some embodiments, there are provided methods of up-regulating endogenous eIF-5A isoforms by providing expression vectors containing polynucleotides of the isoforms of eIF-5A in the sense orientation.

The different isoforms are naturally up or down-regulated depending upon the life stage of the plant or the plant's condition. For example in senescing tissues, the senescence-induced eIF-5A isoform is up-regulated. The senescence-induced eIF-5A is thought to participate in further senescence of the plant or plant tissues by shuttling specific subsets of mRNAs (those involved in the senescence pathway) from the nucleus to the cytoplasm for translation. By down regulating or inhibiting the expression of senescence-induced eIF-5A, senescence can be delayed in the plant and/or plant tissues. Delayed senescence is manifested in the transformed/transgenic plants by having a larger bio-mass, increased shelf life for fruit, increased shelf life of flowers, increased seed size and increased seed yield as compared to non-transformed or wild type plants.

When a plant and/or plant tissues are exposed to a wounding event, such as chilling, dehydration, or mechanical forces, wounding-induced eIF-5A isoform is up-regulated. By down regulating the expression of wounding-induced eIF-5A, an increased resistance to virulent damage arising from pathogen ingression is conferred on the plants as compared to resistance to virulent damage in non-transformed or wild type plants.

When a plant is in the growth phase, growth eIF-5A isoform is up-regulated. By up-regulating growth eIF-5A, the resulting transgenic plants have an increased seed size, increased biomass and increased seed yield.

FIG. 1 shows the alignment of three isoforms of eIF-5A isolated from *Arabidopsis thaliana* ("At"). FIG. 2 shows the alignment of the coding regions of these three isoforms. FIGS. 3-5 provide the genomic sequence of the three isoforms.

Western blots (see FIG. 8) show the expression in these three isoforms at different plant life stages. FIG. 8 reveals that the amount of the senescence-induced factor eIF-5A isoform increases as the ages of the leaves increases. It is not seen in the unopened flower buds, siliques or stems but it is seen in the imbibed seeds. In the imbibed seeds there is cotyledon tissue as well as growing embryo. Thus, senescence-induced eIF-5A is present in the imbibed seeds because the cotyledon tissue is senescing as the embryo is growing. Growth eIF-5A is seen in the imbibed seeds because there the embryo is actively growing. The wounding-induced eIF-5A is seen in the siliques, seeds and stems as the harvesting of these tissues induces some wounding.

Although there is a high degree of homology (about 85%) between the different isoforms and between the isoforms in different plant species, the different isoforms vary from each other in the 3'UTR. One region that is highly conserved between the isoforms and between species as well, is the area that is believed to be the hypusine site. The hypusine site is believed to be the following amino acids: 5'-CKVVEVSTSK-TGKHGHAKCHFV-3' (SEQ ID NO: 32). See FIG. 85 for alignment of various eIF-5A isoforms and of several plant species.

Senescence-Induced eIF-5A

Senescence-induced eIF-5A is expressed in senescing tissues. The present invention relates to the discovery of senescence-induced eIF-5A in *Arabidopsis thaliana*, tomato, and carnation plants. Senescence-induced eIF-5A is up-regulated in senescing tissues and is involved in the induction of senescence related morphological changes in plants and plant tissues. Inhibiting expression of senescence-induced eIF-5A in plants can be used to alter senescence and senescence-related processes in plants. Down-regulation may occur through either the use of antisense constructs or through use of sense constructs to achieve co-suppression. Inhibiting expression of senescence-induced eIF-5A results in various morphological changes in the transgenic plants, including increased plant bio-mass, delayed fruit softening or spoilage, delayed browning of cut flowers or plant tissues, such as lettuce leaves, increased seed yield and increased seed size.

Thus, one embodiment of the present invention is isolated senescence-induced eIF-5A from *Arabidopsis thaliana*. The amino acid sequence is provided in FIG. 59 and is SEQ ID NO: 16. The polynucleotide encoding the amino acid is provided in FIG. 59 and is SEQ ID NO: 15.

Another embodiment of the present invention is isolated senescence-induced eIF-5A from tomato. The amino acid sequence is provided in FIG. 57 and is SEQ ID NO: 12. The polynucleotide encoding the amino acid is provided in FIG. 57 and is SEQ ID NO: 11.

Another embodiment of the present invention is isolated senescence-induced eIF-5A from carnation. The amino acid sequence is provided in FIG. 58 and is SEQ ID NO: 14. The polynucleotide encoding the amino acid is provided in FIG. 58 and is SEQ ID NO: 13

The present invention also provides isolated polynucleotides of senescence-induced eIF-5A that have 90% sequence homology to the above enumerated SEQ ID NOs, and hybridize under high stringency conditions to the complement of the enumerated SEQ ID NOs and which encode senescence-induced eIF-5A.

The present invention also provides antisense polynucleotides of the senescence-induced eIF-5As. The antisense polynucleotides may be of any length as long as they are able to inhibit expression. In some embodiments the antisense polynucleotides comprise the full length coding sequence and in other particularly preferred embodiments the antisense polynucleotides are directed at the 3'UTR since the different isoforms of eIF-5A have a higher degree of variation in the isoforms at the 3'UTR. In some embodiments the antisense polynucleotides are directed at the 5'-non-coding sequence Antisense polynucleotides primarily complementary to 5'-non-coding sequences are known to be effective inhibitors of expression of genes encoding transcription factors. Branch, M. A., Molec. Cell Biol., 13:4284-4290 (1993).

The term "antisense polynucleotide of senescence-induced eIF5A" as used herein and in the claims encompasses not only those antisense polynucleotides that share 100% homology of the complement of an enumerated SEQ ID NO but also includes those antisense polynucleotides that are a functional variants. Functional variants are those variants, either natural or man made, that have at least 80% sequence homology to and hybridizes under high stringency conditions with the corresponding portion of the senescence-induced eIF-5A. Further the variant must have the function as intended by the present invention, that is it is capable of modulating expression of endogenous senescence-induced eIF-5A when introduced into an expression vector and wherein such vector is incorporated into the genome of at least one plant cell. One skilled in the art can appreciate that insubstantial changes can be made in the sequence that would not effect detrimentally the ability of the antisense polynucleotide to bind to the transcript and reduce or inhibition expression of the gene. Thus, the term "antisense polynucleotide" encompasses those polynucleotides that are substantially complementary to the transcript and that still maintain the ability to specifically bind to the transcript and inhibit or reduce gene expression. For a general discussion of antisense see Alberts, et al., Molecular Biology of the Cell, 2nd ed., Garland Publishing, Inc. New York, N.Y., 1989 (in particular pages 195-196, incorporated herein by reference).

One embodiment of the present invention provides expression vectors comprising either the senescence-induced eIF-5A polynucleotides (of the present invention as described above) or antisense polynucleotides of senescence-induced eIF-5A (of the present invention as described above). Vectors can be plasmids, preferably, or may be viral or other vectors known in the art to replicate and express genes encoded thereon in plant cells or bacterial cells. The vector becomes chromosomally integrated such that it can be transcribed to produce the desired antisense polynucleotide of senescence-induced eIF-5A RNA. Such plasmid or viral vectors can be constructed by recombinant DNA technology methods that are standard in the art. For example, the vector may be a plasmid vector containing a replication system functional in a prokaryotic host and an antisense polynucleotide according to the invention. Alternatively, the vector may be a plasmid containing a replication system functional in *Agrobacterium* and an antisense polynucleotide according to the invention. Plasmids that are capable of replicating in *Agrobacterium* are well known in the art. See, Miki, et al., Procedures for Introducing Foreign DNA Into Plants, Methods in Plant Molecular Biology and Biotechnology, Eds. B. R. Glick and J. E. Thompson. CRC Press (1993), PP. 67-83.

The vector further comprises regulatory sequences operatively linked to the polynucleotides to allow expression of such polynucleotides. The regulatory sequences may include a promoter functional in the transformed plant cell. The promoter may be inducible, constitutive, or tissue specific. Such promoters are known by those skilled in the art.

Promoter regulatory elements that are useful in combination with the various isoforms of eIF-5A and DHS of the present invention to generate sense or antisense transcripts of the gene include any plant promoter in general, and more particularly, a constitutive promoter such as the fig wart mosaic virus 35S promoter, the cauliflower mosaic virus promoter, CaMV35S promoter, or the MAS promoter, or a tissue-specific or senescence-induced promoter, such as the carnation petal GST1 promoter or the *Arabidopsis* SAG12 promoter (See, for example, J. C. Palaqui et al., Plant Physiol., 112:1447-1456 (1996); Morton et al., Molecular Breeding, 1: 123-132 (1995); Fobert et al., Plant Journal, 6:567-577 (1994); and Gan et al., Plant Physiol., 113:313 (1997), incorporated herein by reference). Preferably, the promoter used in the present invention is a constitutive promoter. The SAG12 promoter is preferably preferred when using antisense polynucleotides of senescence-induced eIF-5A. See example 23.

Expression levels from a promoter which is useful for the present invention can be tested using conventional expression systems, for example by measuring levels of a reporter gene product, e.g., protein or mRNA in extracts of the leaves, flowers, fruit or other tissues of a transgenic plant into which the promoter/reporter gene have been introduced. An exemplary reporter gene is GUS.

Optionally, the regulatory sequences include a 5' non-translated leader sequence or a polyadenylation signal or enhancers. The present invention further contemplates other regulatory sequences as known by those skilled in the art.

The invention also provides a transgenic plant cell transformed with a vector or combination of vectors of the present invention comprising polynucleotides of senescence-induced eIF-5A in sense or antisense orientation, a transgenic plantlet or mature transgenic plant generated from such a cell, or a plant part, such as a flower, fruit, leaves, seeds, etc. of the transgenic plant.

The present invention also provides methods of inhibiting expression of endogenous senescence-induced eIF-5A. These methods comprise integrating into the genome of at least one cell of a plant, expression vectors of the present invention comprising antisense polynucleotides of senescence-induced eIF-5A. The antisense polynucleotides of senescence-induced eIF-5A are transcribed and inhibit expression of endogenous senescence-induced eIF-5A.

In another method of inhibiting expression of endogenous senescence-induced eIF-5A, an expression vector containing a senescence-induced eIF-5A polynucleotide of the present invention in a sense orientation is integrated into the genome of at least one cell of a plant. The polynucleotide of senescence-induced eIF-5A is transcribed and the resulting co-expression of exogenous senescence-induced eIF-5A causes a down-regulation or inhibition of expression of endogenous senescence-induced eIF-5A.

Wounding-Induced eIF-5A

Wounding-induced eIF-5A is expressed in wounded tissues. The present invention relates to the discovery of wounding-induced eIF-5A in *Arabidopsis thaliana* and tomato. The present inventors have discovered that this isoform is upregulated during a wounding event to the plant. The up-regulation occurs at the transcriptional level. Further, it is up-regulated exclusively at the protein level following virulent infection, which then gives rise to cell death, leading to the inference that wounding-induced eIF-5A is driving cell death in the event of ingression by pathogens. FIG. 9 shows that senescence-induced eIF-5A remains constant in the control plant, the mock treated plant, the Avr treated plant and the Vir treated plant (it is detected as the plants were 4 weeks old). But wounding-induced eIF-5A is up-regulated in the Vir treated plant.

FIG. 10 shows the results of an experiment where leaves of a plant were wounded with a hemostat. Levels of senescence-induced eIF-5A, wounding-induced eIF-5A and growth eIF-5A in *arabidopsis thaliana* ("At") were measured immediately after the wounding, 1 hour, and 9 hours after the wounding. The Northern Blots show that senescence-induced eIF-5A remained constant, but there was a noticeable increase in the levels expression of the wounding-induced eIF-5A. The levels of expression of the growth eIF-5A began to decrease in the event of wounding.

The present inventors have demonstrated that when wounding-induced eIF-5A is up-regulated and a wounding event is imposed upon the plants (such as occurs when the seedlings are transplanted), this wounding results in a very strong suppression of growth eIF-5A. See FIGS. 14-17. The resulting plants have very stunted growth. But when the seeds are soaked in kanomycin and are planted directly into the soil (no need to transplant and thus no transplant wounding), the seeds develop into normal sized plants.

The differences seen between the various test plants all having a sense wounding-induced eIF-5A construct (FIG. 15) incorporated is due to varying degrees of expression of the wounding-induced eIF-5A. One skilled in the art will appreciate that when a gene is introduced (either sense or antisense) one gets varying degrees of either gene up-regulation or down-regulation. The degree of differences depends on where the gene gets incorporated and how many copies get incorporated. By having varying degrees of expression, one can correlate the various phenotypes to the gene expression. Once the desired phenotype is produced, that plant can be picked and used to create the desired progeny. Thus in FIG. 15, the plants that were strongly up-regulated for wounding-induced eIF-5A barely grew after the wounding event (plant tag 10), but the plants that grew a little better (but not as good as wild type) (plant tag 4) were not as strongly up-regulated.

One embodiment of the present invention is isolated wounding-induced eIF-5A from *Arabidopsis thaliana*. The amino acid sequence is provided in FIG. 41 and is SEQ ID NO: 55. The polynucleotide encoding the amino acid is provided in FIG. 41 and is SEQ ID NO: 54.

Another embodiment of the present invention is isolated wounding-induced eIF-5A from tomato. The amino acid sequence is provided in FIG. 103 and is SEQ ID NO: 57. The polynucleotide encoding the amino acid is provided in FIG. 103 and is SEQ ID NO: 56.

The present invention also provides isolated polynucleotides of wounding-induced eIF-5A that have 90% sequence homology to the above enumerated SEQ ID NOs, and hybridize under high stringency conditions to the complement of the enumerated SEQ ID NOs and which encode wounding-induced eIF-5A.

The present invention also provides antisense polynucleotides of the wounding-induced eIF-5As. The antisense polynucleotides may be of any length as long as they are able to inhibit expression. In some embodiments the antisense polynucleotides comprise the full length coding sequence and in other particularly preferred embodiments the antisense polynucleotides are directed at the 3'UTR since the different isoforms of eIF-5A have a higher degree of variation in isoforms at the 3'UTR. In some embodiments the antisense polynucleotides are directed at the 5'-non-coding sequence Antisense polynucleotides primarily complementary to 5'-non-coding sequences are known to be effective inhibitors of expression of genes encoding transcription factors. Branch, M. A., Molec. Cell Biol., 13:4284-4290 (1993).

The term "antisense polynucleotide of wounding-induced eIF5A" as used herein and in the claims encompasses not only those antisense polynucleotides that share 100% homology of the complement of an enumerated SEQ ID NO but also includes those antisense polynucleotides that are a functional variants. Functional variants are those as described above. The variant functions as intended by the present invention, that is it is capable of modulating expression of endogenous wounding-induced eIF-5A when introduced into an expression vector and wherein such vector is incorporated into the genome of at least one plant cell.

One embodiment of the present invention provides expression vectors comprising either wounding-induced eIF-5A polynucleotides (of the present invention as described above) or antisense polynucleotides of wounding-induced eIF-5A (of the present invention as described above). Vectors are as described above.

The invention also provides a transgenic plant cell transformed with a vector or combination of vectors of the present invention comprising polynucleotides of wounding-induced eIF-5A in sense or antisense orientation, a transgenic plantlet or mature transgenic plant generated from such a cell, or a plant part, such as a flower, fruit, leaves, seeds, etc. of the transgenic plant.

The present invention also provides methods of inhibiting expression of endogenous wounding-induced eIF-5A. These methods comprise integrating into the genome of at least one cell of a plant, expression vectors of the present invention comprising antisense polynucleotides of wounding-induced eIF-5A. The antisense polynucleotides of wounding-induced eIF-5A are transcribed and inhibit expression of endogenous wounding-induced eIF-5A.

In another method of inhibiting expression of endogenous wounding-induced eIF-5A, an expression vector containing a wounding-induced eIF-5A polynucleotide of the present invention in a sense orientation is integrated into the genome of at least one cell of a plant. The polynucleotide of wounding-induced eIF-5A is transcribed and the resulting co expression of exogenous wounding-induced eIF-5A causes a down-regulation or inhibition of expression of endogenous wounding-induced eIF-5A.

Figure 44:
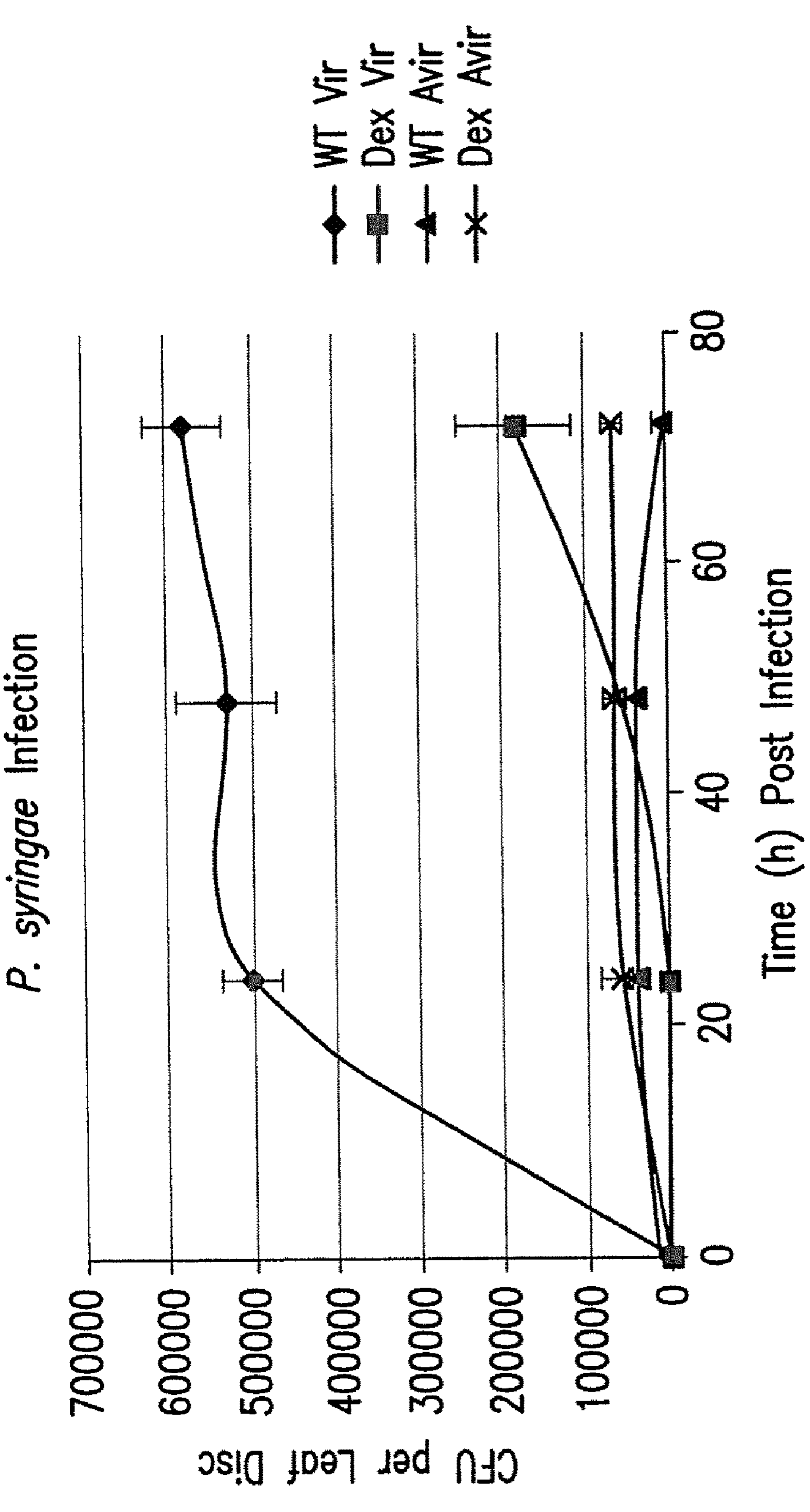
FIG. 44 shows a graph of CFUs in antisense transgenic plants versus wild-type.
Figure 47:
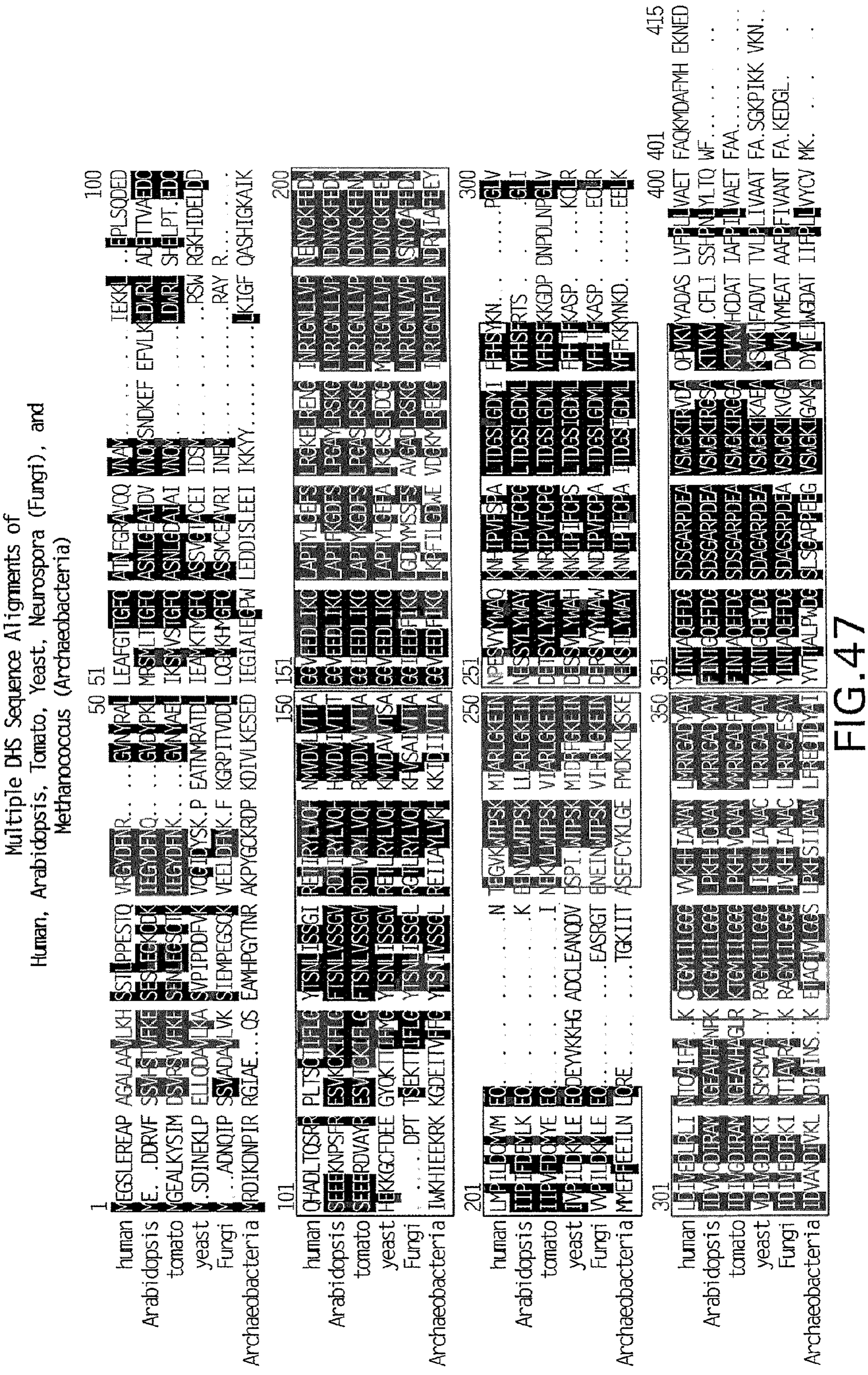
FIG. 47 is an alignment of the derived full length tomato leaf DHS amino acid sequence (SEQ ID NO. 2) and the derived full length *Arabidopsis* (SEQ ID NO: 6) senescence-induced DHS amino acid sequence with sequence of DHS proteins of human (SEQ ID NO: 3), yeast (SEQ ID NO: 45), fungi (SEQ ID NO: 44), and *Archaeobacteria* (SEQ ID NO: 46). Identical amino acids among three or four of the sequences are boxed.
Figure 48:
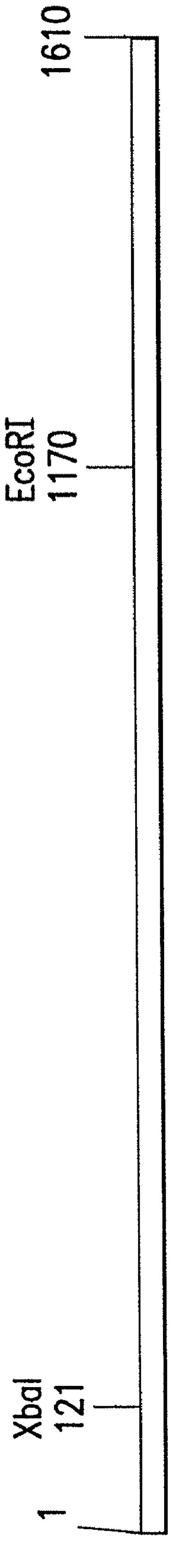
FIG. 48 is a restriction map of the tomato DHS cDNA.

By inhibiting expression of endogenous eIF-5A, resulting transgenic plants have an increased resistance to virulent damage arising from pathogen ingression. See example 16 and FIGS. 43 and 44.

Growth eIF-5A

The present invention also relates to growth eIF-5A. Growth eIF-5A is expressed in growing tissues. When eIF-5A is up-regulated with polynucleotides of growth eIF-5A in sense orientation, three phenotypic changes are noticed: increased seed size, increased biomass, and increased seed yield.

One embodiment of the present invention is isolated growth eIF-5A from *Arabidopsis thaliana*. The amino acid sequences are provided in FIG. 1 and are SEQ ID NO: 58-60, respectively. The polynucleotides encoding the amino acid sequences are provided in FIG. 2 and are SEQ ID NO: 61-63, respectively.

Another embodiment of the present invention is isolated growth eIF-5A from tomato. The amino acid sequence is provided in FIG. 101 and is SEQ ID NO: 65. The polynucleotide encoding the amino acid is provided in FIG. 101 and is SEQ ID NO: 64.

Another embodiment of the present invention is isolated growth eIF-5A from canola. The amino acid sequence is provided in FIG. 95 and is SEQ ID NO: 67. The polynucleotide encoding the amino acid is provided in FIG. 95 and is SEQ ID NO: 66.

The present invention also provides isolated polynucleotides of growth eIF-5A that have 90% sequence homology to the above enumerated SEQ ID NOs, and hybridize under high stringency conditions to the complement of the enumerated SEQ ID NOs and which encode growth eIF-5A.

The present invention also provides antisense polynucleotides of the growth eIF-5As. The antisense polynucleotides may be of any length as long as they are able to inhibit expression. In some embodiments the antisense polynucleotides comprise the full length coding sequence and in other particularly preferred embodiments the antisense polynucleotides are directed at the 3'UTR since the different isoforms of eIF-5A have a higher degree of variation in isoforms at the 3'UTR. In some embodiments the antisense polynucleotides are directed at the 5'-non-coding sequence. Antisense polynucleotides primarily complementary to 5'-non-coding sequences are known to be effective inhibitors of expression of genes encoding transcription factors. Branch, M. A., Molec. Cell Biol., 13:4284-4290 (1993).

The term "antisense polynucleotide of growth eIF5A" as used herein and in the claims encompasses not only those antisense polynucleotides that share 100% homology of the complement of an enumerated SEQ ID NO but also includes those antisense polynucleotides that are a functional variants. Functional variants are those as described above. The variant functions as intended by the present invention, that is it is capable of modulating expression of endogenous growth eIF-5A when introduced into an expression vector and wherein such vector is incorporated into the genome of at least one plant cell. One embodiment of the present invention provides expression vectors comprising either growth eIF-5A polynucleotides (of the present invention as described above) or antisense polynucleotides of growth eIF-5A (of the present invention as described above). Vectors are as described above.

The invention also provides a transgenic plant cell transformed with a vector or combination of vectors of the present invention comprising polynucleotides of growth eIF-5A either in sense or antisense orientation, a transgenic plantlet or mature transgenic plant generated from such a cell, or a plant part, such as a flower, fruit, leaves, seeds, etc. of the transgenic plant.

The present invention also provides methods of inhibiting expression of endogenous growth eIF-5A. These methods comprise integrating into the genome of at least one cell of a plant, expression vectors of the present invention comprising antisense polynucleotides of growth eIF-5A. The antisense polynucleotides of growth eIF-5A are transcribed and inhibit expression of endogenous growth eIF-5A.

In another method of inhibiting expression of endogenous growth eIF-5A, an expression vector containing a growth eIF-5A polynucleotide of the present invention in a sense orientation is integrated into the genome of at least one cell of a plant. The polynucleotide of growth eIF-5A is transcribed and the resulting co-expression of exogenous growth eIF-5A causes a down-regulation or inhibition of expression of endogenous growth eIF-5A.

In another embodiment of the present invention there is provided a method of up-regulating expression of growth eIF-5A. An expression vector containing a growth eIF-5A polynucleotide of the present invention in a sense orientation is integrated into the genome of at least one cell of a plant. The polynucleotide of growth eIF-5A is transcribed and the resulting co-expression of exogenous growth eIF-5A causes the cells to express more growth eIF-5A than non-transgenic cells.

Figure 19:
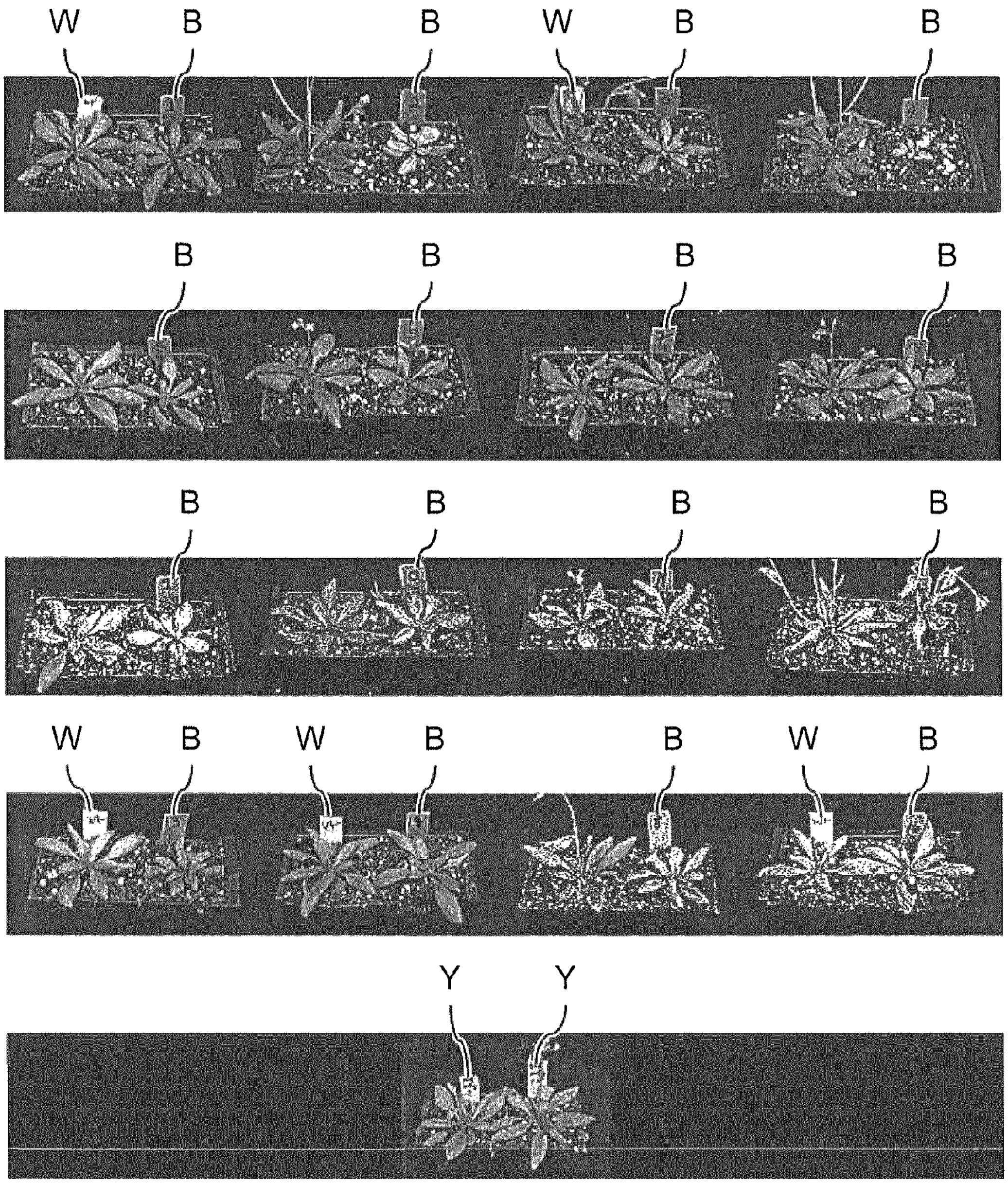
FIG. 19 is a picture of T1 plants transformed with Sense growth AteIF-5A at 4 weeks of age.

FIG. 19 shows that plants that were up-regulated for growth eIF-5A had an increased biomass over that of the control plants. Growth eIF-5A was inserted into *Arabidopsis thaliana* plants in a sense orientation to up-regulate the expression of growth eIF-5A. Sixteen mother lines (1-16) were assayed to determine the general level of growth eIF-5A expression. From each mother line, 8 sister lines were produced (A-H). The level of expression of growth eIF-5A in each mother line was tested and the results shown in FIG. 20. Various degrees of expression are noticed throughout the mother lines. For example, lines 2 and 10 have very high levels of expression whereas lines 11 and 16 have very low or no expression.

Figure 21:
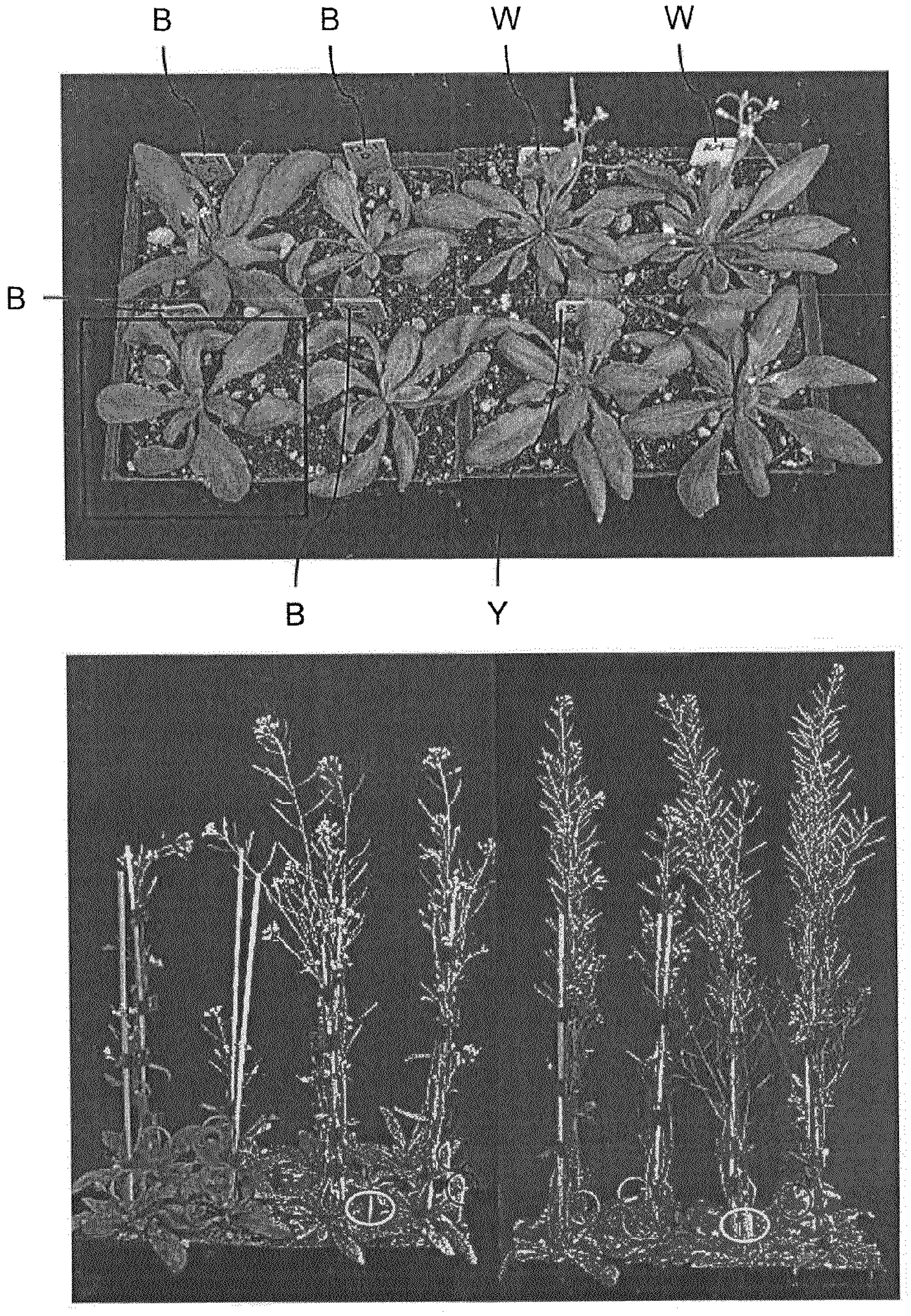
FIG. 21 are T2 plants transformed with Sense growth AteIF-5A (Lines 1A-1D) at 4 weeks of age (top), 5 weeks of age (bottom left) and 6 weeks of age (bottom right).
Figure 22:
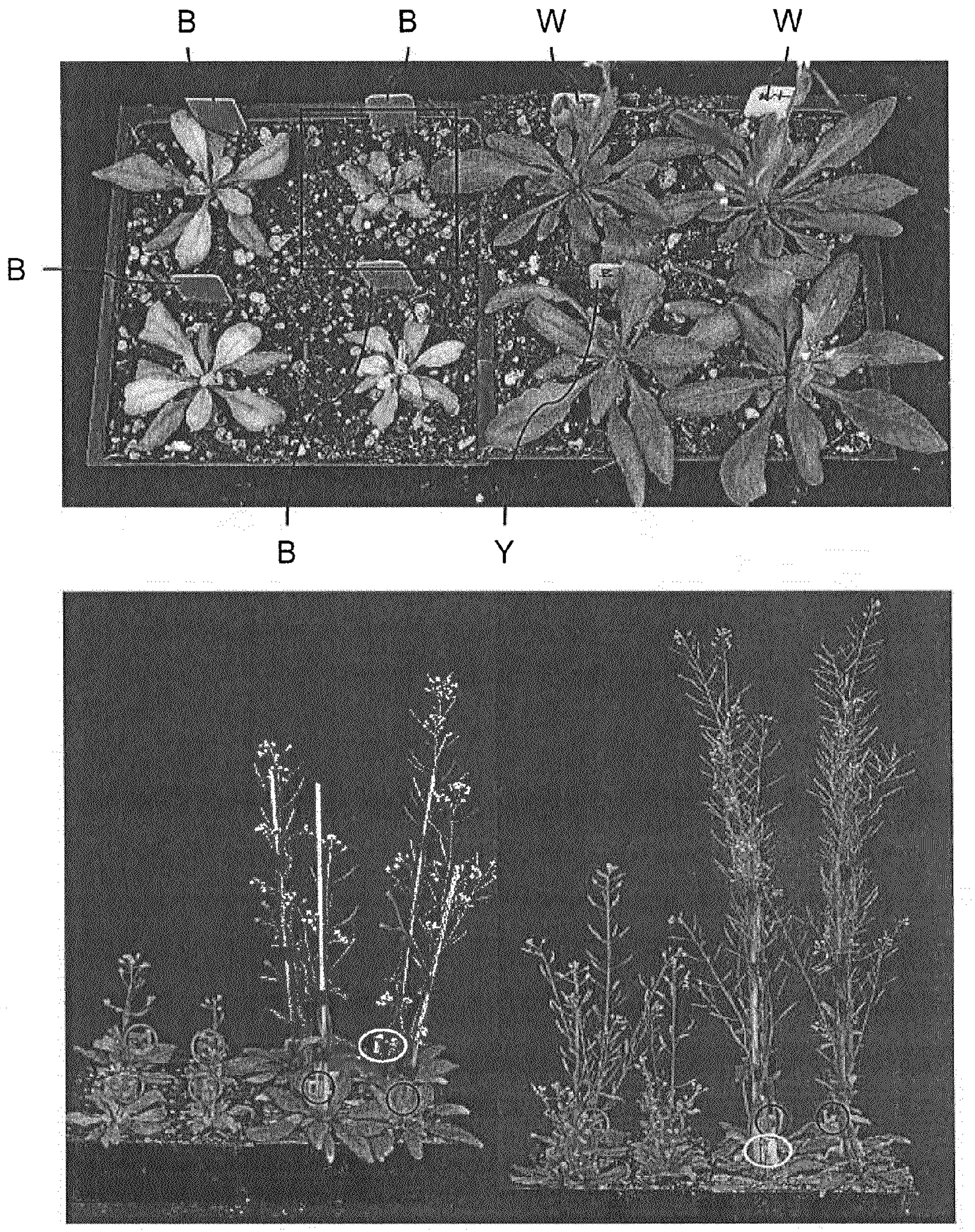
FIG. 22 are T2 plants transformed with Sense growth AteIF-5A (Lines 2A-1D) at 4 weeks of age (top), 5 weeks of age (bottom left) and 6 weeks of age (bottom right).

FIGS. 21 and 22 show the plants from lines 1 and 2. These plants are bigger than the control plants. Because the growth eIF-5A is a cell-division isoform and because it is constitutively expressed, there is increased cell division. A reduction in senescence occurs because the plant is locked into a growth mode and can not make the switch to the senescence pathway.

Figure 23:
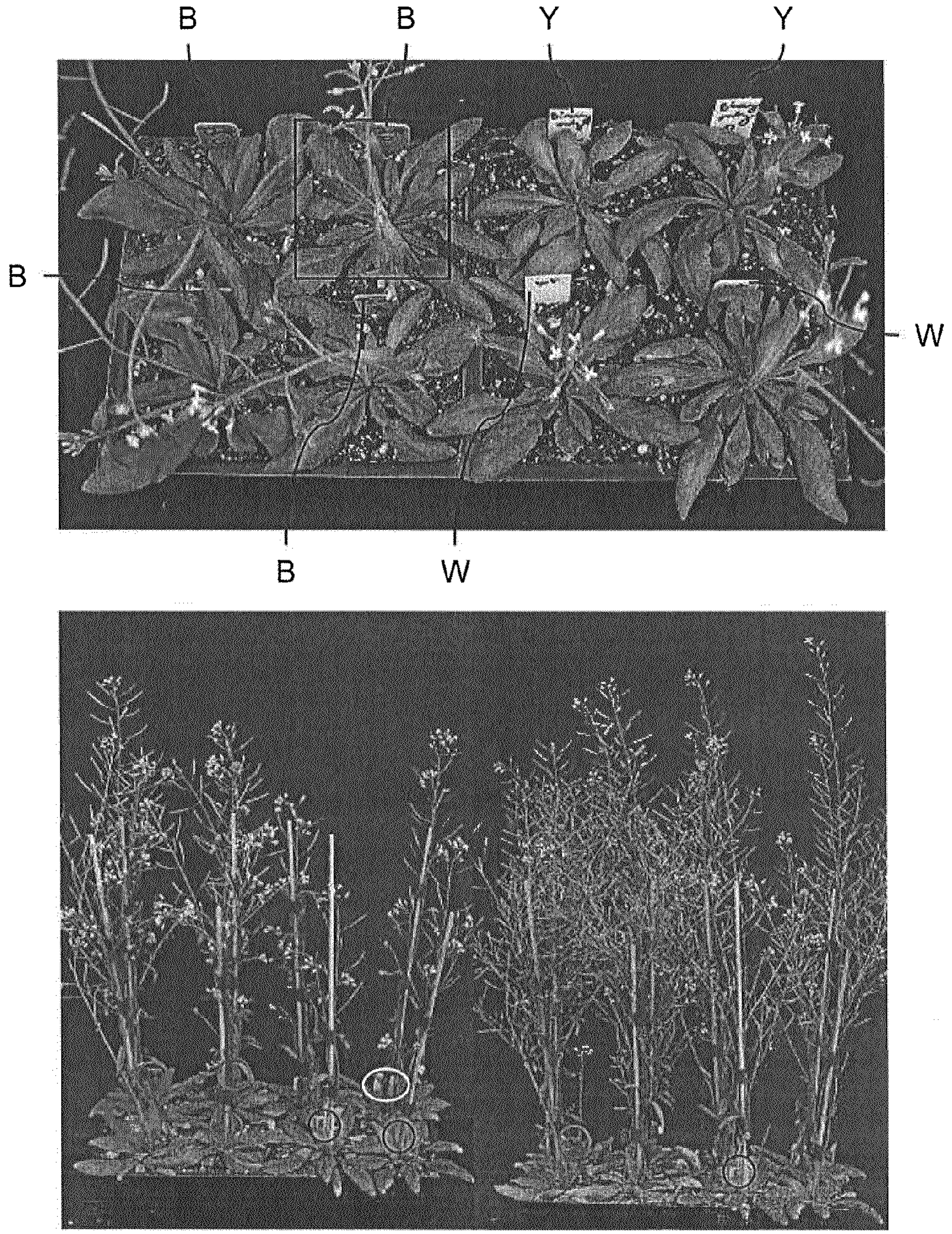
FIG. 23 are T2 plants transformed with Sense growth AteIF-5A (Lines 4A-D) at 4 weeks of age (top), 5 weeks of age (bottom left) and 6 weeks of age (bottom right).
Figure 24:
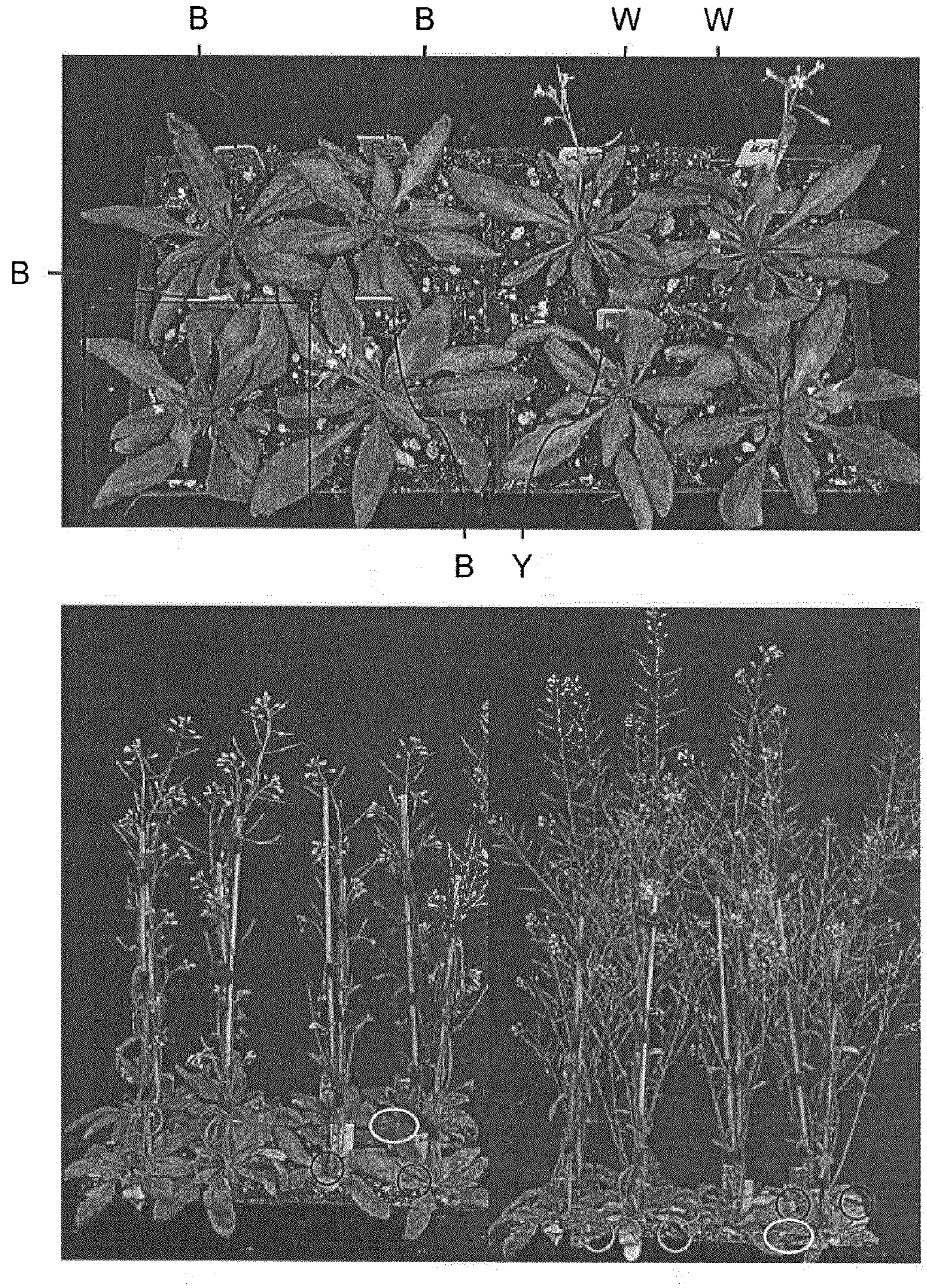
FIG. 24 are T2 plants transformed with Sense growth AteIF-5A (Lines 15A-D) at 4 weeks of age (top), 5 weeks of age (bottom left) and 6 weeks of age (bottom right).

FIGS. 23 and 24 are from lines that had medium level of expression of growth eIF-5A. They appear to have bigger leaves and delayed senescence.

Figure 25:
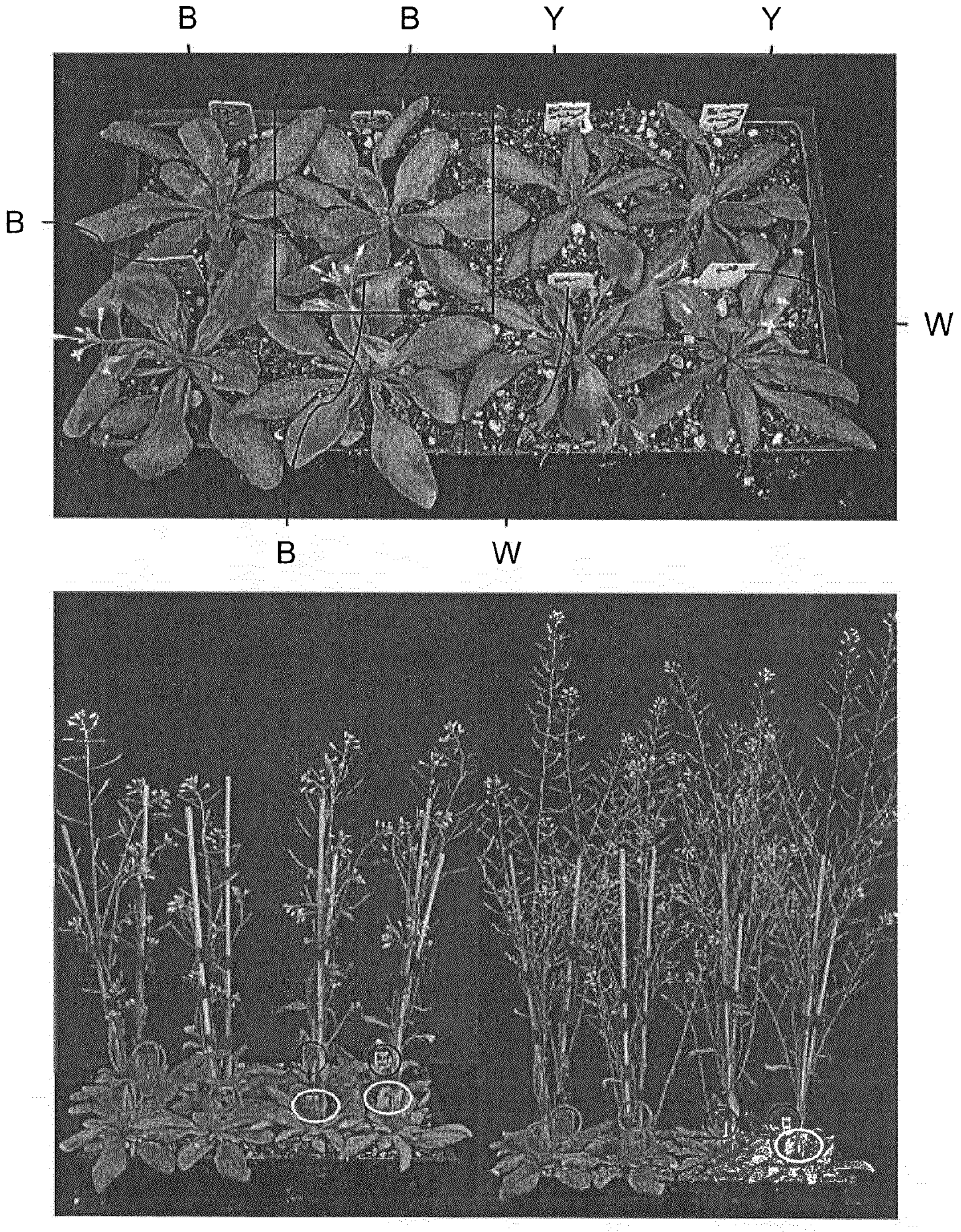
FIG. 25 are T2 plants transformed with Sense growth AteIF-5A (Lines 8A-D) at 4 weeks of age (top), 5 weeks of age (bottom left) and 6 weeks of age (bottom right).
Figure 26:
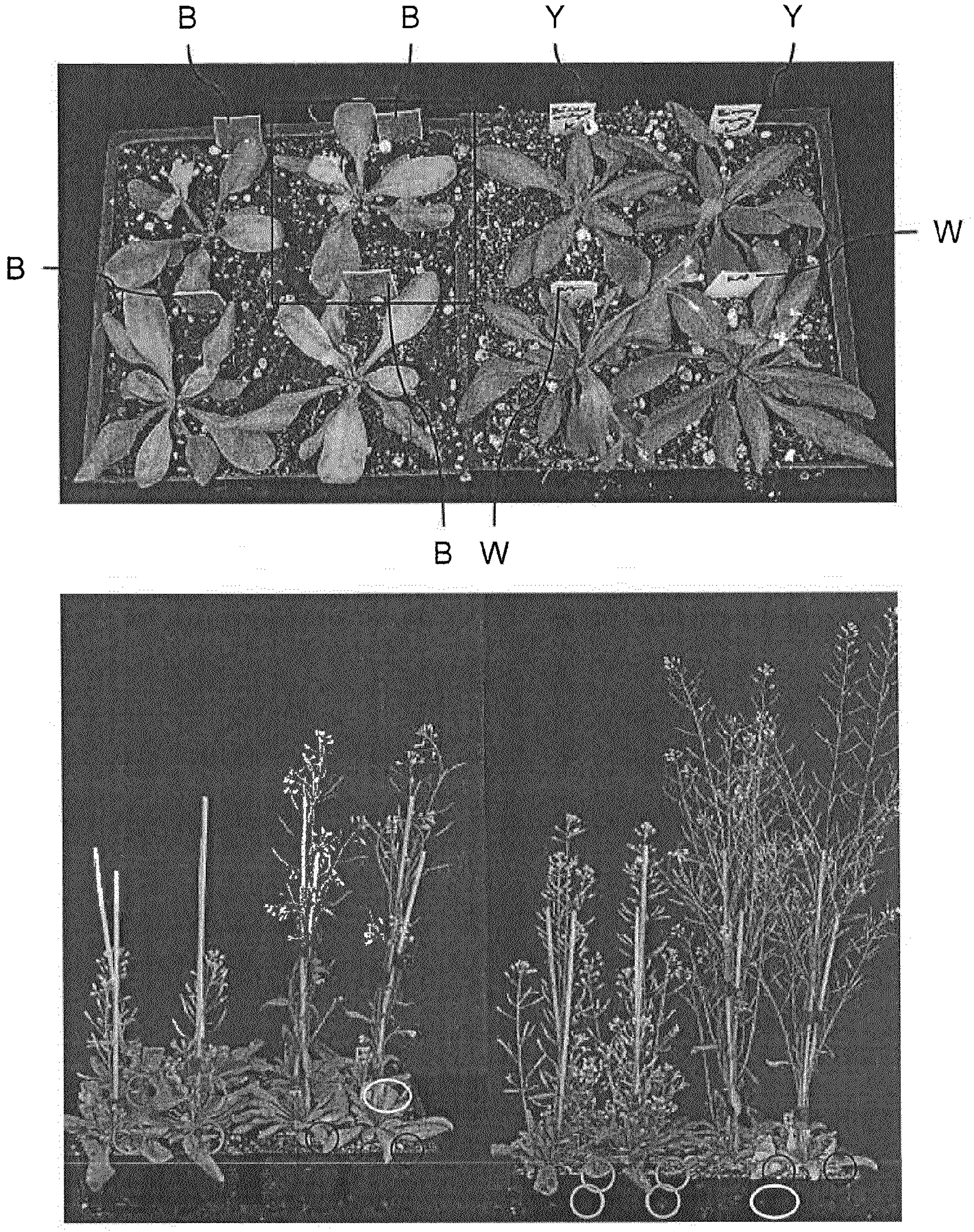
FIG. 26 are T2 plants transformed with Sense growth AteIF-5A (Lines 9E-H) at 4 weeks of age (top), 5 weeks of age (bottom left) and 6 weeks of age (bottom right).

FIGS. 25 and 26 are from lines that had low levels of up-regulation. They have large leaves and large rosettes.

Figure 27:
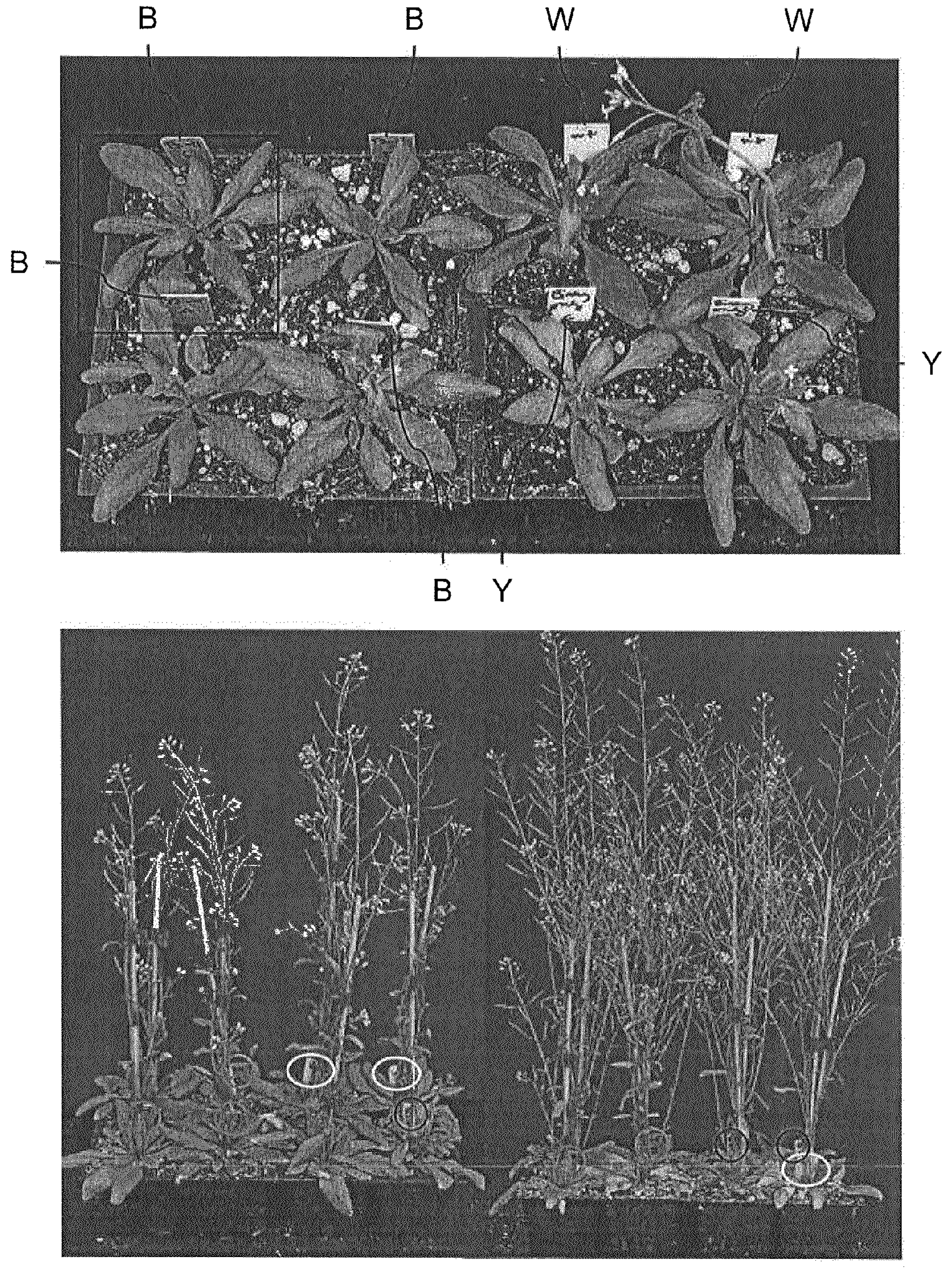
FIG. 27 are T2 plants transformed with Sense growth AteIF-5A (Lines 11A-D) at 4 weeks of age (top), 5 weeks of age (bottom left) and 6 weeks of age (bottom right).
Figure 28:
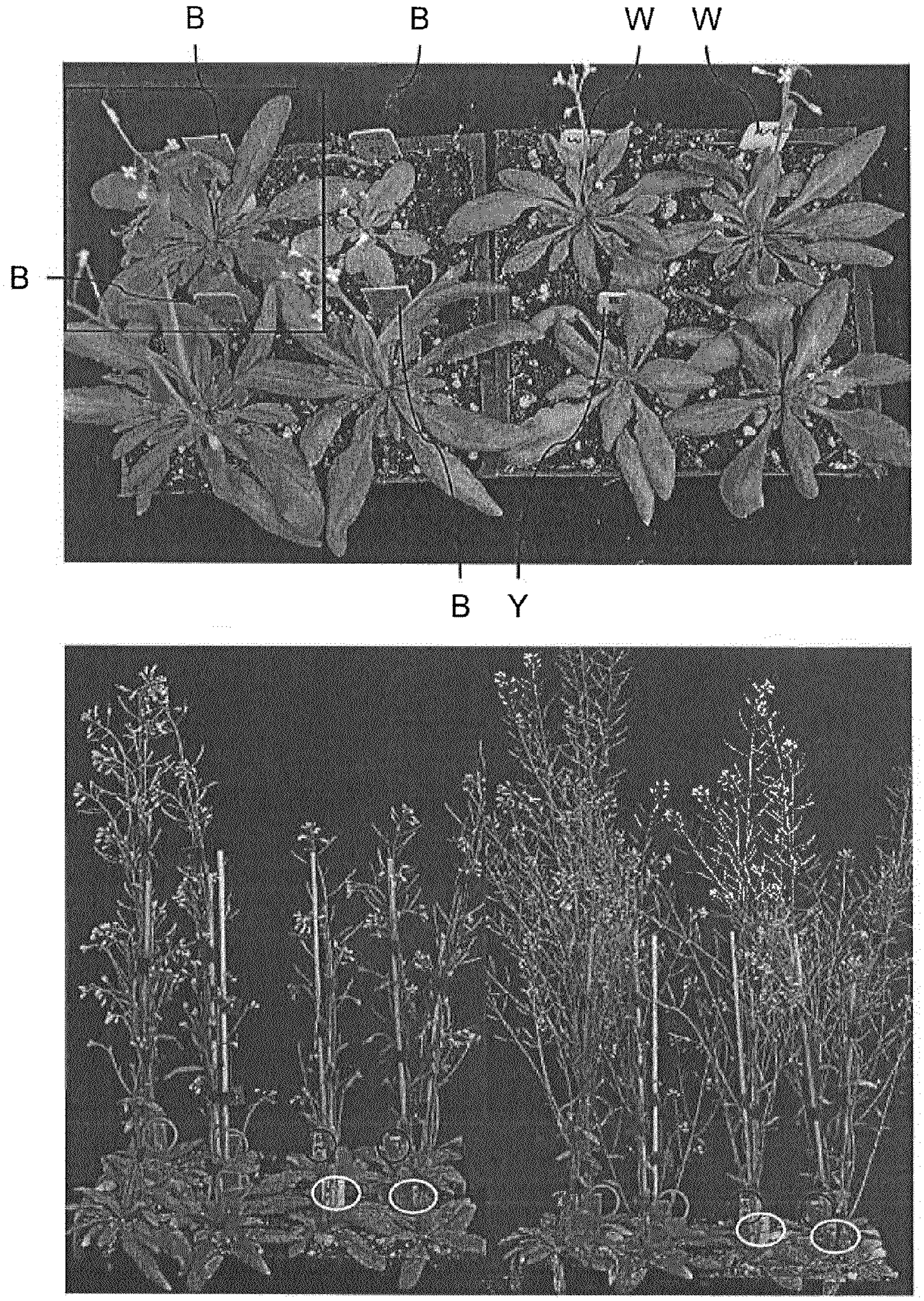
FIG. 28 are T2 plants transformed with Sense growth AteIF-5A (Lines 16A-D) at 4 weeks of age (top), 5 weeks of age (bottom left) and 6 weeks of age (bottom right).

FIGS. 27 and 28 are from lines that have no up-regulation (which may be due to co-suppression of the gene). Since the plant is kanomycin resistant, the gene must be present in order for the plants to grow on the media. It appears that the senescence-induced eIF-5A is also co-suppressed as well thus giving rise to an increase in size.

In addition to increased biomass, there is also increased seed size in plants having growth eIF-5A up-regulated. The seed size of all of the lines was measured. In the lines having the highest levels of growth eIF-5A expression, a greater than 3× increase in seed size is seen. This occurs because up-regulation of growth eIF-5A, increases cell division and thus increases seed size.

The growth eIF-5A (from *Arabidopsis thaliana*) in the above examples was being constitutively expressed, i.e. is being expressed everywhere in the plant through the use of a universal promoter. In contrast, by using a tissue specific promoter, one may direct the up-regulation in particular tissues. For example, by using a seed specific promoter, the growth eIF-5A would only be up-regulated in the seed, allowing the leaves to grow normally, but produce an increase in the amount of seeds. Thus, using a specific promoter, the growth eIF-5A can be up-regulated in the desired plant part to get a desired phenotype.

By up-regulating growth eIF-5A, three phenotypes result—increased biomass, increased seed yield, or increased seed size, but not all three phenotypes are present at the same time (or in the same plant). For example, if a plant exhibits an increase in seed size, a smaller plant will be present. In the plant lines that had the highest up-regulation of growth eIF-5A, the biggest seeds were produced, but the plants were smaller because there was massive cell division going on throughout the whole plant, which was at the expense of cell enlargement (needed for bigger leaves). At lower levels of up-regulation of expression of growth AteIF-5A, one sees an impact on the leaves (bigger) without impacting the seed. Thus, one may use tissue specific expression and pick the phenotype desired. For example, one may place growth eIF-5A under a xylem specific promoter to achieve an increase in the amount of xylem produced. Thus, any desired promoter may be used to achieve the desired tissue-specific up-regulation.

DHS

DHS is necessary for the activation of eIF-5A and is expressed in senescing tissues. The present invention thus provides isolated DHS from *Arabidopsis thaliana*, tomato, carnation, canola, lettuce, alfalfa, banana, cottonwood, and *mycosphaerella.*

Thus one embodiment of the present invention is isolated DRS from *Arabidopsis thaliana*. The amino acid sequence is provided in FIG. 46B and is SEQ ID NO: 6. The polynucleotide encoding the amino acid is provided in FIG. 46A and is SEQ ID NO: 5. The nucleotide sequence in FIG. 46C is shown in SEQ ID NO: 26, while the amino acid sequence in FIG. 46D is shown in SEQ ID NO: 92.

Another embodiment of the present invention is isolated DHS from tomato. The amino acid sequence is provided in FIGS. 45 A and B and is SEQ ID NO: 2. The polynucleotide encoding the amino acid is provided in FIGS. 45 A and B and is SEQ ID NO: 1.

Another embodiment of the present invention is isolated DHS from carnation. The amino acid sequence is provided in FIG. 54 and is SEQ ID NO: 10. The polynucleotide encoding the amino acid is provided in FIG. 54 and is SEQ ID NO: 9.

Another embodiment of the present invention is isolated DHS from canola. The amino acid sequence is provided in FIG. 97 and is SEQ ID NO: 71. The polynucleotide encoding the amino acid is provided in FIG. 97 and is SEQ ID NO: 70.

Another embodiment of the present invention is isolated DHS from lettuce. FIG. 105 provides a portion of lettuce DHS polynucleotide sequence.

Another embodiment of the present invention is isolated DHS from alfalfa. The amino acid sequence is provided in FIGS. 107 A and B and is SEQ ID NO: 73. The polynucleotide encoding the amino acid is provided in FIGS. 107 A and B and is SEQ ID NO: 72.

Another embodiment of the present invention is isolated DHS from banana. The amino acid sequence is provided in FIGS. 108 A and B and is SEQ ID NO: 75. The polynucleotide encoding the amino acid is provided in FIGS. 108 A and B and is SEQ ID NO: 74.

Another embodiment of the present invention is isolated DHS from cottonwood. The amino acid sequence is provided in FIGS. 109 A and B and is SEQ ID NO: 77. The polynucleotide encoding the amino acid is provided in FIGS. 109 A and B and is SEQ ID NO: 76.

Another embodiment of the present invention is isolated DHS from *mycosphaerella*. FIG. 110 provides a portion of lettuce DHS polynucleotide sequence.

The present invention also provides isolated polynucleotides of DHS that have 90% sequence homology to the above enumerated SEQ ID NOs, and hybridize under high stringency conditions to the complement of the enumerated SEQ ID NOs and which encode DHS.

The present invention also provides antisense polynucleotides of DHS. The antisense polynucleotides may be of any length as long as they are able to inhibit expression. In some embodiments the antisense polynucleotides comprise the full length coding sequence, directed at the 3'UTR, or directed at the 5'-non-coding sequence Antisense polynucleotides primarily complementary to 5'-non-coding sequences are known to be effective inhibitors of expression of genes encoding transcription factors. Branch, M. A., Molec. Cell Biol., 13:4284-4290 (1993).

The term “antisense polynucleotide of DHS” as used herein and in the claims encompasses not only those antisense polynucleotides that share 100% homology of the complement of an enumerated SEQ ID NO but also includes those antisense polynucleotides that are a functional variants. Functional variants are as described above. The variant functions as intended by the present invention, that is it is capable of modulating expression of endogenous DHS when introduced into an expression vector and wherein such vector is incorporated into the genome of at least one plant cell.

One embodiment of the present invention provides expression vectors comprising either DHS polynucleotides (of the present invention as described above) or antisense polynucleotides of DHS (of the present invention as described above). Vectors are as described above.

The invention also provides a transgenic plant cell transformed with a vector or combination of vectors of the present invention comprising a polynucleotide of DHS either in the sense or antisense orientation, a transgenic plantlet or mature transgenic plant generated from such a cell, or a plant part, such as a flower, fruit, leaves, seeds, etc. of the transgenic plant.

The present invention also provides methods of inhibiting expression of endogenous DHS. These methods comprise integrating into the genome of at least one cell of a plant, expression vectors of the present invention comprising antisense polynucleotides of DHS. The antisense polynucleotides of DHS are transcribed and inhibit expression of endogenous DHS.

In another method of inhibiting expression of endogenous DHS, an expression vector containing a DHS polynucleotide of the present invention in a sense orientation is integrated into the genome of at least one cell of a plant. The polynucleotide of DHS is transcribed and the resulting co-expression of exogenous DHS causes a down-regulation or inhibition of expression of endogenous DHS.

By inhibiting expression of endogenous DHS, resulting transgenic plants have no or substantially less DHS protein to activate eIF-5A. As discussed earlier, eIF-5A must be activated to render it biologically useful. Thus, by inhibiting or reducing the expression of DHS either by antisense polynucleotides or by co-suppression with sense polynucleotides, the resulting transgenic plants will either have no active eIF-5A or reduced active eIF-5A. These transgenic plants will exhibit an increase in biomass of the plant, increased seed yield and/or increased seed size. Transgenic plants having antisense polynucleotides of DHS show an increase in photosynthesis and also have an increased starch content. See Examples 24 and 25.

Further evidence to support the contention that DHS and eIF-5A play regulatory roles in senescence was provided by treating carnation flowers with inhibitors that are specific for DHS. Spermidine and eIF-5A are the substrates of DHS reaction (Park et al., 1993; Park et al., 1997). Several mono-, di-, and polyamines that have structural features similar to spermidine inhibit DHS activity in vitro (Jakus et al., 1993). Some polyamines, such as spermidine, putrescine, and spermine, have been generally used to extend carnation vase life (Wang and Baker, 1980). Through treatment with different polyamines at different concentrations Wang et al (unpublished b) were able to extend the vase life of carnation flowers by 2 fold. Further studies employing a transient infection system to down-regulate DHS is in progress. Preliminary data indicates that the percent survival rate is almost 4 fold higher at day 8 in cut carnations that were vacuum infiltrated with a transient infection system expressing antisense DHS than untreated flowers (Wang et al., unpublished b).

A further major loss in agriculture besides the loss of growth due to stress is post harvest stress-induced senescence (McCabe et al., 2001). This is especially true for plants that are partially processed such as cut lettuce. A symptom of cutting lettuce is browning which is a result of phenolics production (Matile et al., 1999). A field trial of lettuce with antisense polynucleotides of lettuce eIF-5A (LeIF-5A) or antisense full length DHS demonstrated that the transgenic lettuce was significantly more resistant to browning after cutting than the control lettuce. It appears that even though stress induced senescence due to harvesting has distinct circuitry (Page et al., 2001), the translational control upstream of browning and likely other senescence symptoms is regulated at least in part by DHS and eIF-5A. Downstream of the regulation of senescence are the execution genes. These are the effectors of senescence and cause the metabolic changes that bring on the senescence syndrome. It appears that eIF-5A and DHS when down-regulated are capable of dampening down a whole range of symptoms caused by senescence.

The present invention also relates to antibodies that recognize the three isoforms of eIF-5A (senescence-induced factor eIF-5A); (wounding factor eiF-5A) and (growth factor eIF-5A).

The present invention also provides a method of identifying senescence-induced eIF-5A, wounding-induced eIF-5A, growth eIF-5A and DHS in other plants and fungi. By using the methods described herein and the sequences provided, probes are designed to isolate/identify the desired isoforms or DHS. Since the isoforms of eIF-5A (senescence-induced eIF-5A, wounding-induced eIF-5A, and growth eIF-5A) are often highly homologous in the coding region (see FIG. 2), to ensure identification and even alter amplification of the desired isoform, probes or primers are preferably designed from the beginning of the 5'UTR and at the end of the 3" UTR. (See FIGS. 3, 4 and 5). A preferred set of primers for amplification of wounding-induced eIF-5A or probes for identification of wounding-induced eIF-5A are as follows. The downstream primer is 5' GAG CTC AAG AAT AAC ATC TCA TAA GAAAC3' (SEQ ID NO: 33) The upstream primer is 5' CTC GAG TGC TCA CTT CTC TCT CTT AGG 3' (SEQ ID NO: 34).

Before isolating wounding-induced eIF5A from a plant or plant part, it is best to introduce a wounding event to allow the plant to begin expressing wounding-induced eIF-5A. Any wounding event is acceptable and one such exemplary wound events included crushing the leaves at the central vein. Similarly, before isolating senescence-induced eIF-5A, it best to stress the plant tissue to induce senescence.

Having now generally described the invention, the same will be more readily understood through reference to the following examples, which are provided by way of illustration, and are not intended to be limiting to the present invention.

EXAMPLES

Example 1

Messenger RNA (mRNA) Isolation

Total RNA was isolated from tomato flowers and tomato fruit at various developmental stages and from leaves (untreated or after chilling or sorbitol treatment). The tissue (5 g) was briefly ground in liquid nitrogen. The ground powder was mixed with 30 ml guanidinium buffer (4 M guanidinium isothiocyanate, 2.5 mM NaOAc pH 8.5, 0.8%-mercaptoethanol). The mixture was filtered through four layers of cheesecloth and centrifuged at 10,000 Xg at 4° C. for 30 minutes. The supernatant was then subjected to cesium chloride density gradient centrifugation at 26,000 Xg for 20 hours. The pelleted RNA was rinsed with 75% ethanol, resuspended in 600 µl DEPC-treated water and the RNA precipitated at −70° C. with 0.75 ml 95% ethanol and 30 µl of 3M NaOAc. Ten µg of RNA were fractionated on a 1.2% denaturing formaldehyde agarose gel and transferred to a nylon membrane. Randomly primed $^{32}$P-dCTP-labeled full length DHS cDNA (SEQ ID NO: 1) was used to probe the membrane at 42° C. overnight. The membrane was then washed once in 1×SSC containing 0.1% SDS at room temperature for 15 minutes and three times in 0.2×SSC containing 0.1% SDS at 65° C. for 15 minutes each. The membrane was exposed to x-ray film overnight at −70° C.

PolyA$^+$ mRNA was isolated from total RNA using the PolyA$^+$ tract mRNA Isolation System available from Promega. PolyA$^+$ mRNA was used as a template for cDNA synthesis using the ZAP Express® cDNA synthesis system available from Stratagene (La Jolla, Calif.)

Tomato Leaf cDNA Library Screening

A cDNA library made using mRNA isolated from Match F1 hybrid tomato leaves that had been exposed to 2 M sorbitol for six hours was diluted to approximately $5\times10^6$ PFU/ml. The cDNA library was screened using a $^{32}$P-labeled 600 bp RT-PCR fragment. Three positive cDNA clones were excised and recircularized into a pBK-CMV® (Stratagene) phagemid using the method in the manufacturer's instructions. The full length cDNA was inserted into the pBK-CMV vector.

Plasmid DNA Isolation, DNA Sequencing

The alkaline lysis method described by Sambrook et al., (Supra) was used to isolate plasmid DNA. The full length positive cDNA clone was sequenced using the dideoxy sequencing method. Sanger, et al., Proc. Natl. Acad. Sci. USA, 74:5463-5467. The open reading frame was compiled and analyzed using BLAST search (GenBank, Bethesda, Md.) and alignment of the five most homologous proteins with the derived amino acid sequence of the encoded gene was achieved using a BCM Search Launcher: Multiple Sequence Alignments Pattern-Induced Multiple Alignment Method (See F. Corpet, Nuc. Acids Res., 16:10881-10890, (1987)). Functional motifs present in the derived amino acid sequence were identified by MultiFinder.

Northern Blot Hybridizations of Tomato RNA

Figure 50:
FIG. 50 is a Northern blot of RNA isolated from tomato flowers at different stages of development. The top panel is the ethidium bromide stained gel of total RNA. Each lane contains 10 μg RNA. The bottom panel is an autoradiograph of the Northern blot probed with $^{32}$P-dCTP-labeled full length tomato DHS cDNA.
Figure 51:
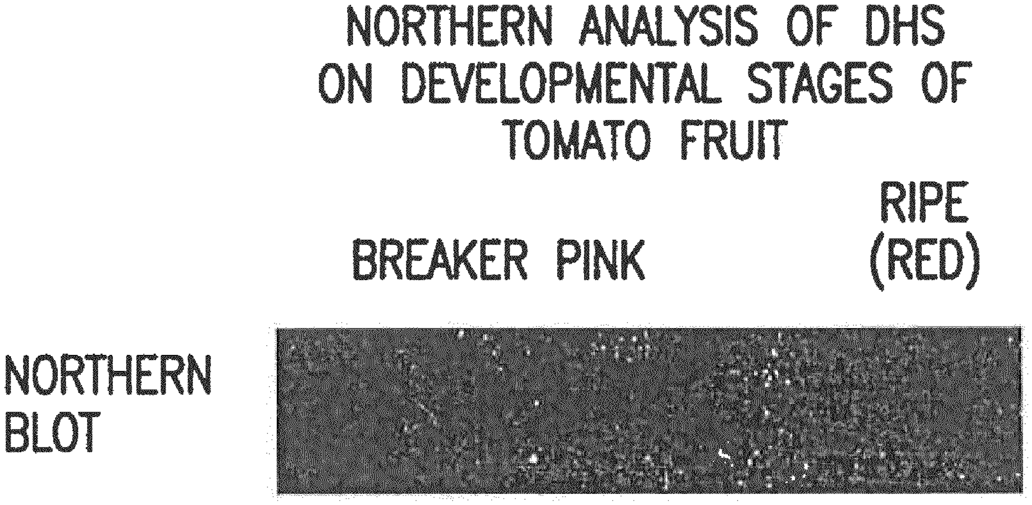
FIG. 51 is a Northern blot of RNA isolated from tomato fruit at various stages of ripening that was probed with $^{32}$P-dCTP-labeled full length tomato DHS cDNA. Each lane contains 10 μg RNA.
Figure 52:
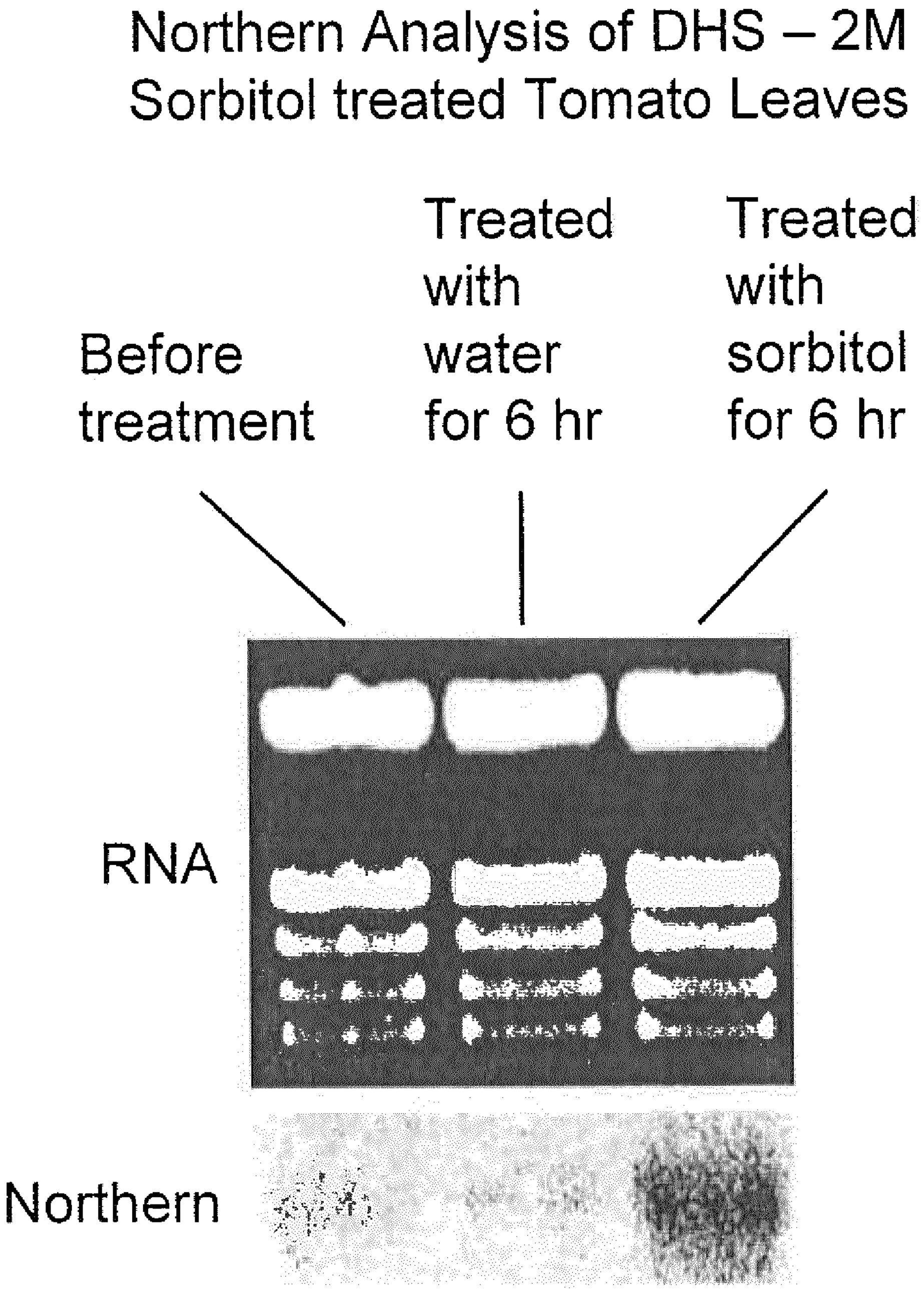
FIG. 52 is a Northern blot of RNA isolated from tomato leaves that had been drought-stressed by treatment with 2 M sorbitol for six hours. Each lane contains 10 μg RNA. The blot was probed with $^{32}$P-dCTP-labeled full length tomato DHS cDNA.

Ten µg of total RNA isolated from tomato flowers at various stages (bud and blossom and senescing petals that are open widely or drying), tomato leaves, and tomato fruit at various stages of ripening (breaker, i.e., green fruit with less than 10% red color, pink, i.e., the entire fruit is orange or pink, and red, either soft or firm) were separated on 1% denatured formaldehyde agarose gels and immobilized on nylon membranes. The full length tomato cDNA labeled with $^{32}$P-dCTP using a random primer kit (Boehringer Mannheim) was used to probe the filters ($7\times10^7$ cpm). The filters were washed once with 1×SSC, 0.1% SDS at room temperature and three times with 0.2×SSC, 0.1% SDS at 65° C. The filters were dried and exposed to X-ray film overnight at −70° C. The results are shown in FIGS. 50-52.

Northern Blot Hybridization of *Arabidopsis* RNA

Figure 55:
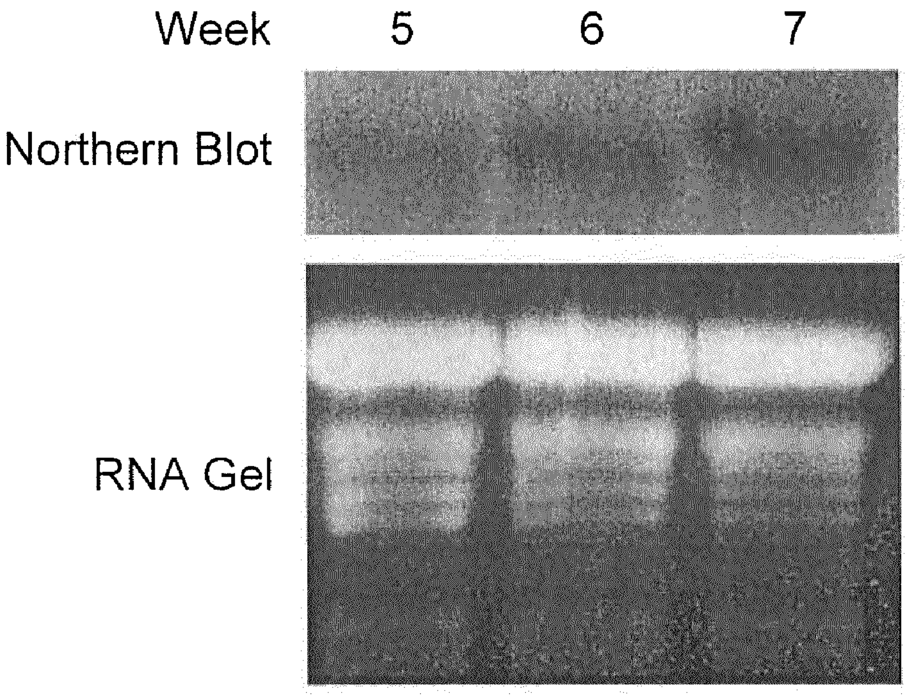
FIG. 55 is a Northern blot of total RNA from senescing *Arabidopsis* leaves probed with $^{32}$P-dCTP-labeled full-length *Arabidopsis* DHS cDNA. The autoradiograph is at the top, the ethidium stained gel below.

Total RNA from leaves of *Arabidopsis* plants at five weeks of age (lane 1), six weeks (lane 2) and seven weeks (lane 3) was isolated as above, separated on 1% denatured formaldehyde agarose gels and immobilized on nylon membranes. The full-length *Arabidopsis* senescence-induced DHS cDNA labeled with $^{32}$P-dCTP using a random primer kit (Boehringer Mannheim) was used to probe the filters ($7\times10^7$ cpm). The filters were washed once with 1×SSC, 0.1% SDS at room temperature and three times with 0.2×SSC, 0.1% SDS at 65° C. The filters were dried and exposed to X-ray film overnight at −70° C. The results are shown in FIG. 55.

Northern Blot Hybridization of Carnation RNA

Figure 56:
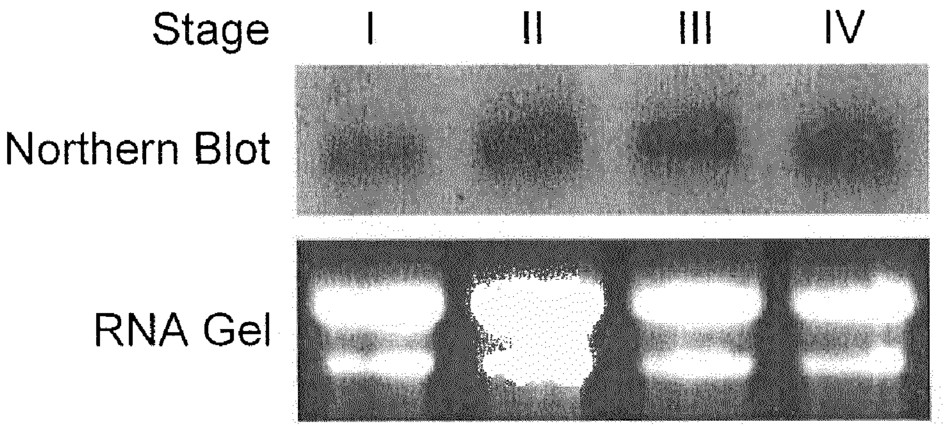
FIG. 56 is a Northern blot of total RNA isolated from petals of carnation flowers at various stages. The blot was probed with $^{32}$P-dCTP-labeled full-length carnation DHS cDNA. The autoradiograph is at the top, the ethidium stained gel below.
Figure 60:
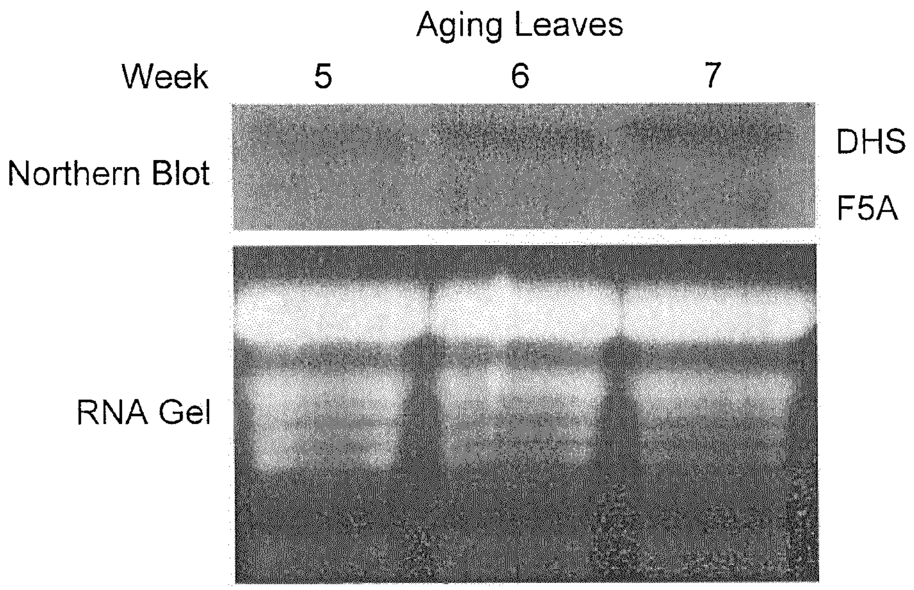
FIG. 60 is a Northern blot of total RNA isolated from leaves of *Arabidopsis* plants at various developmental stages. The blot was probed with $^{32}$P-dCTP-labeled full-length *Arabidopsis* DHS cDNA and full-length senescence-induced eIF-5A. The autoradiograph is at the top, the ethidium stained gel below.
Figure 61:
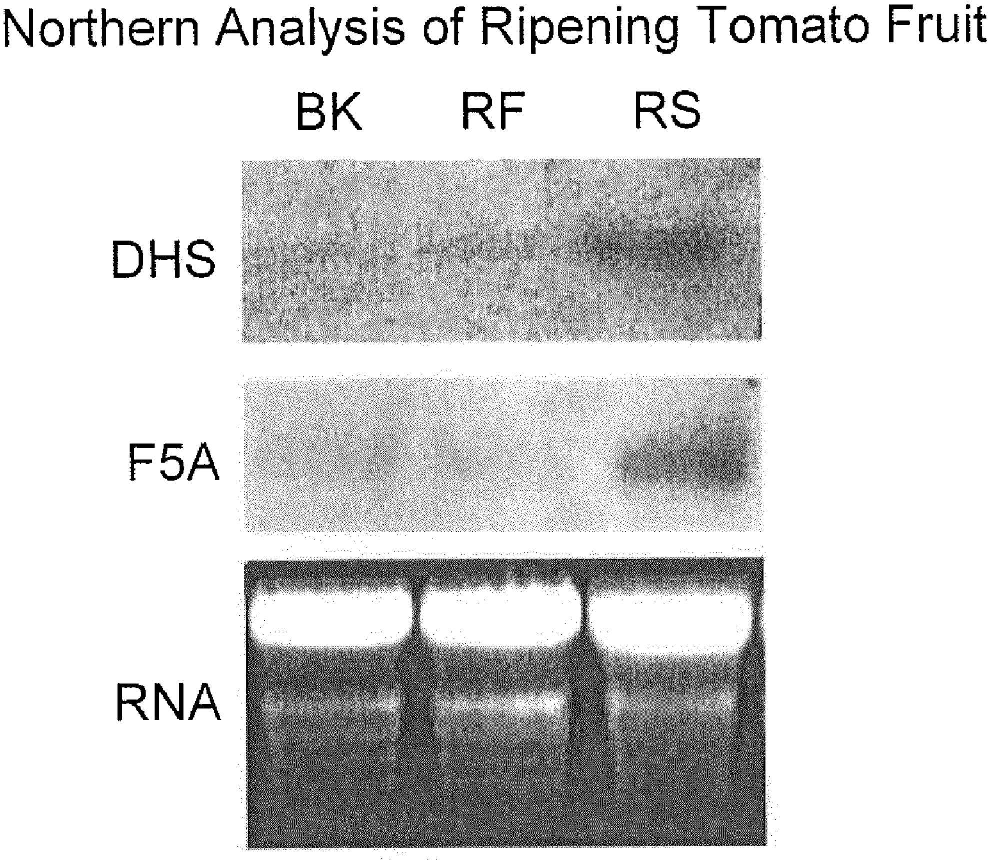
FIG. 61 is a Northern blot of total RNA isolated from tomato fruit at breaker (BK), red-firm (RF) and red-soft ($R^S$) stages of development. The blot was probed with $^{32}$P-dCTP-labeled full-length DHS cDNA and full-length senescence-induced eIF-5A. DHS and eIF-5A are up-regulated in parallel in red-soft fruit coincident with fruit ripening. The autoradiograph is at the top, the ethidium stained gel below.
Figure 62:
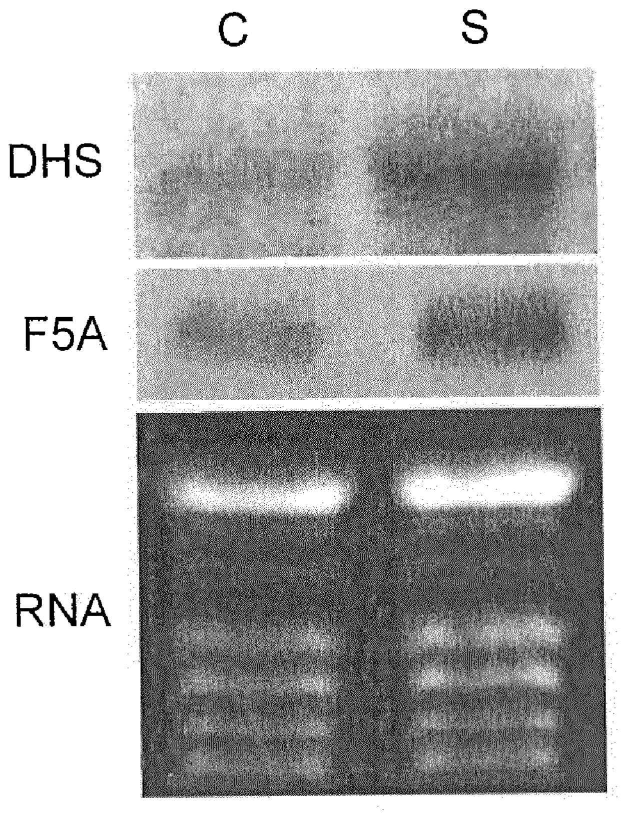
FIG. 62 is a Northern blot of total RNA isolated from leaves of tomato that were treated with sorbitol to induce drought stress. C is control; S is sorbitol treated. The blot was probed with $^{32}$P-dCTP-labeled full-length DHS cDNA and full-length senescence-induced eIF-5A. Both eIF-5A and DHS are up-regulated in response to drought stress. The autoradiograph is at the top, the ethidium stained gel below.
Figure 63:
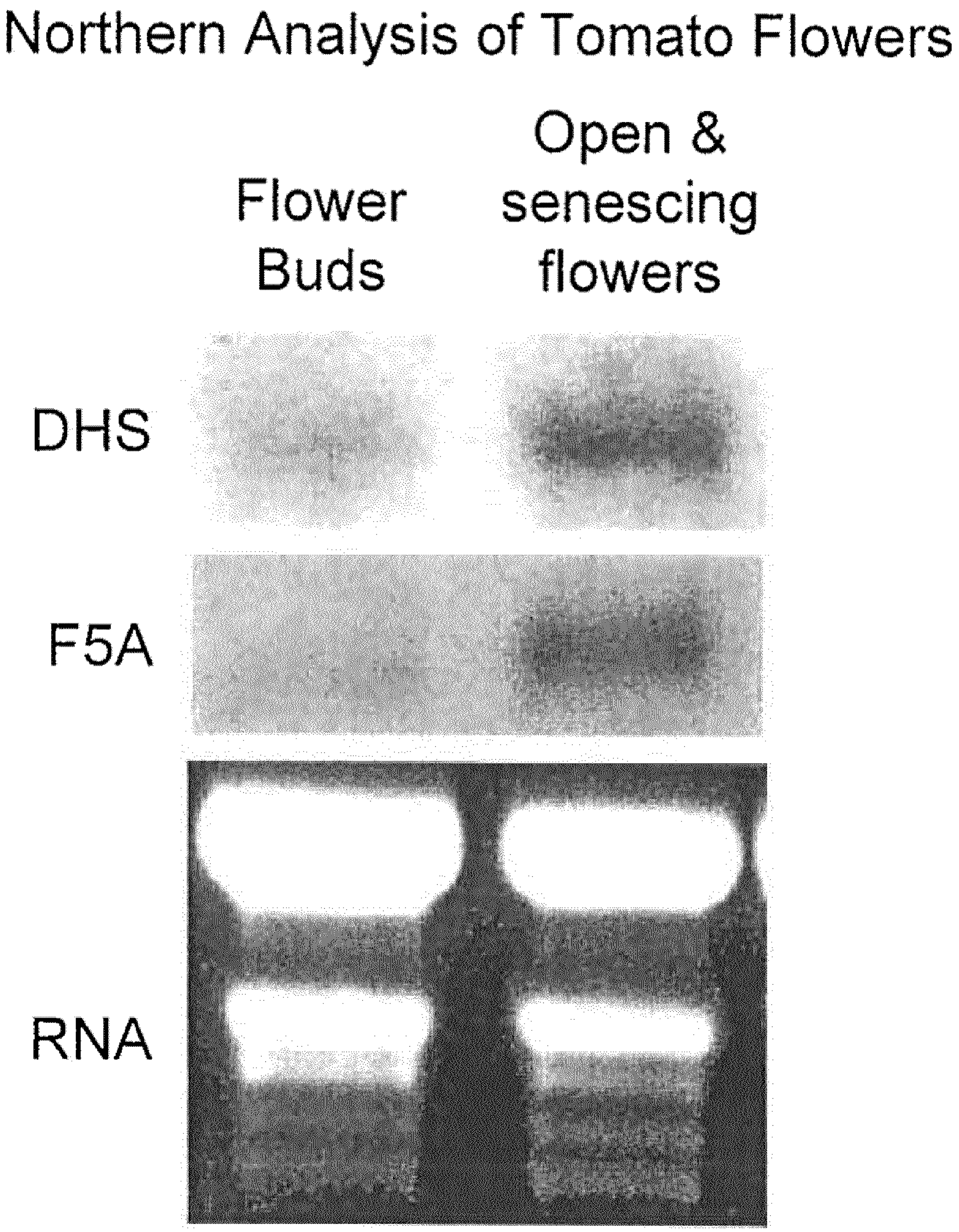
FIG. 63 is a Northern blot of total RNA isolated from flower buds and open senescing flowers of tomato plants. The blot was probed with $^{32}$P-dCTP-labeled full-length senescence-induced DHS cDNA and full-length senescence-induced eIF-5A. Both eIF-5A and DHS are up-regulated in open/senescing flowers. The autoradiograph is at the top, the ethidium stained gel below.
Figure 64:
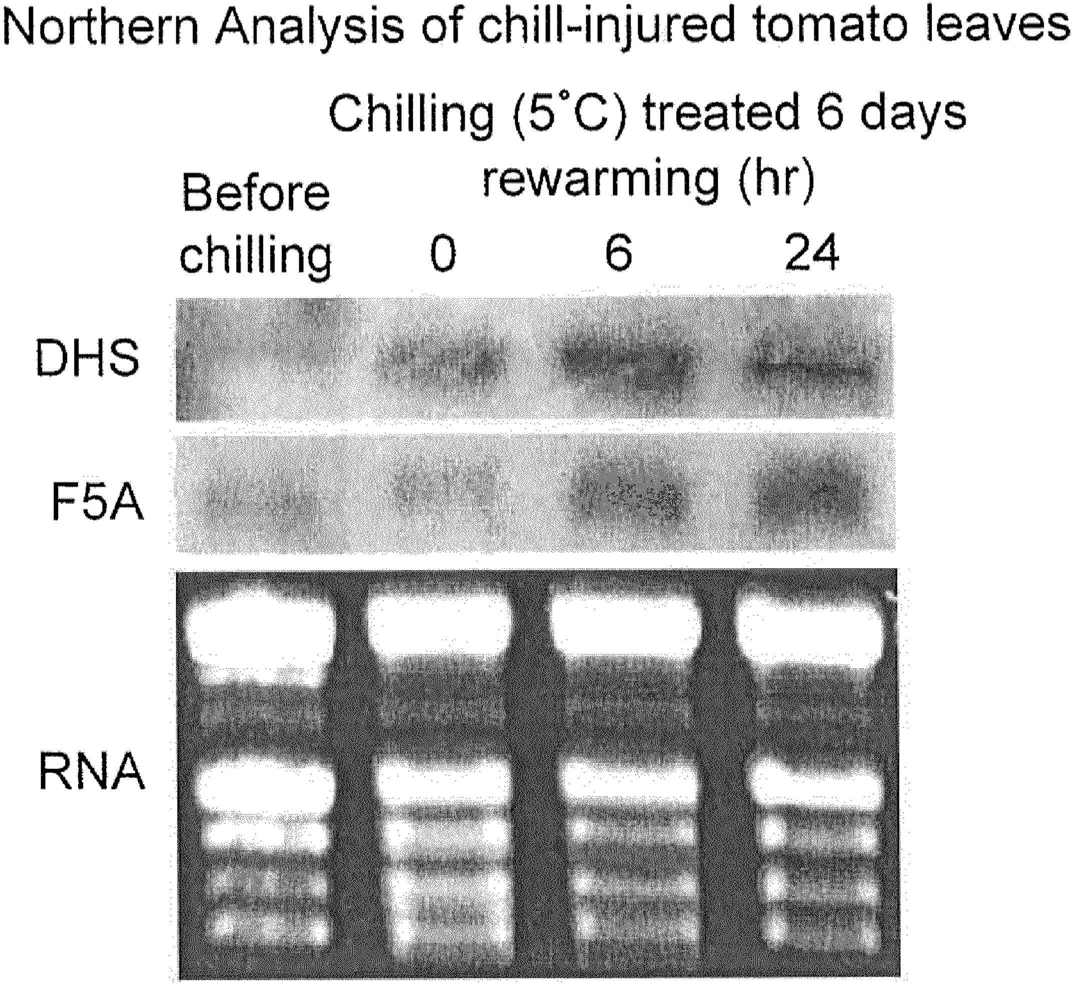
FIG. 64 is a Northern blot of total RNA isolated from chill-injured tomato leaves. The blot was probed with $^{32}$P-dCTP-labeled full-length DHS cDNA and full-length senescence-induced eIF-5A. Both eIF-5A and DHS are up-regulated with the development of chilling injury during rewarming The autoradiograph is at the top, the ethidium stained gel below.
Figure 65:
FIG. 65 is a photograph of 3.1 week old *Arabidopsis* wild-type (left) and transgenic plants expressing the 3'-end of the DHS gene (sequence shown in FIG. 80) in antisense orientation showing increased leaf size in the transgenic plants.
Figure 66:
FIG. 66 is a photograph of 4.6 week old *Arabidopsis* wild-type (left) and transgenic plants expressing the 3'-end of the DHS gene (sequence shown in FIG. 80) in antisense orientation showing increased leaf size in the transgenic plants.
Figure 67:
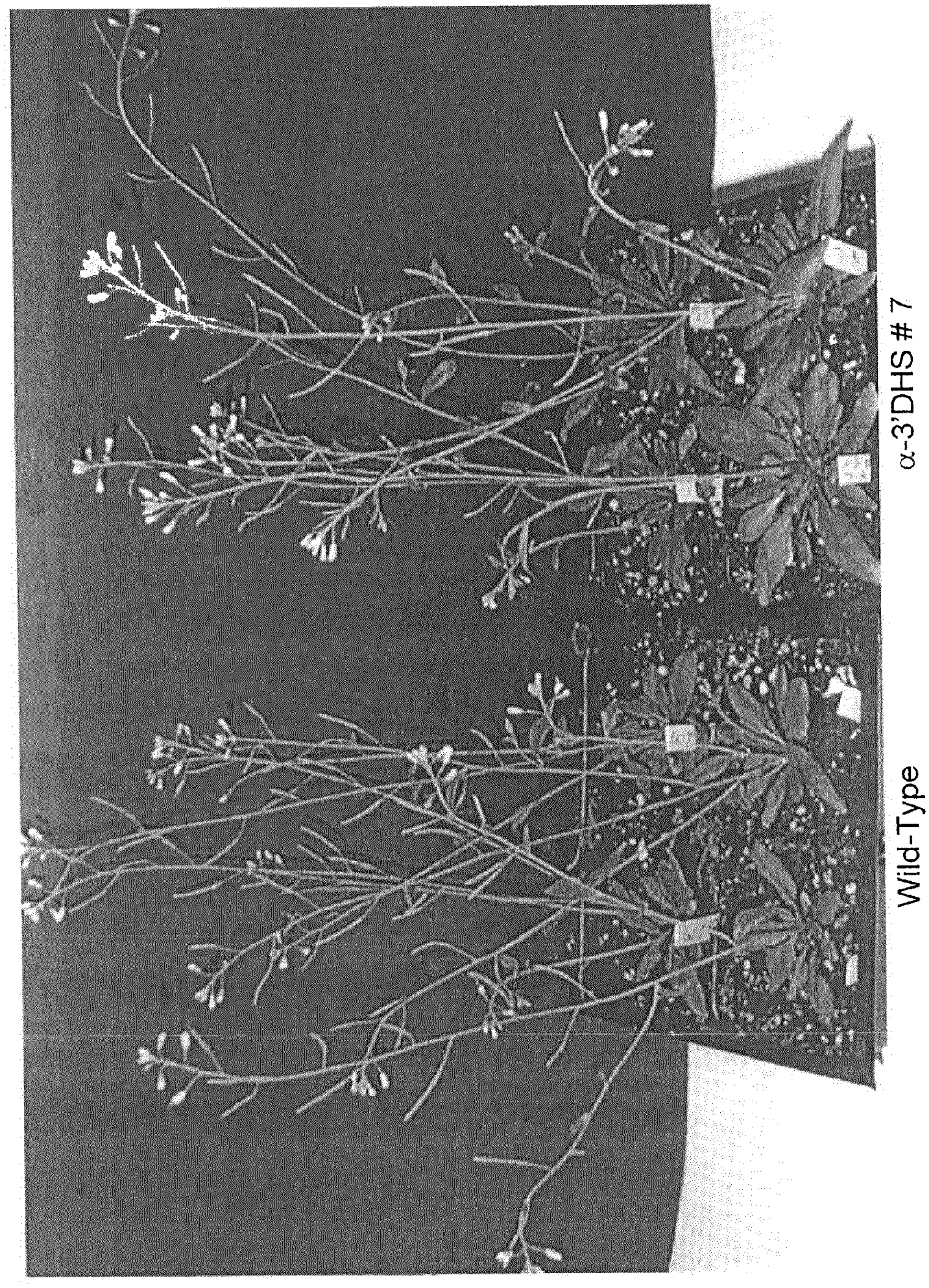
FIG. 67 is a photograph of 5.6 week old *Arabidopsis* wild-type (left) and transgenic plants expressing the 3'-end of the DHS gene (sequence shown in FIG. 80) in antisense orientation showing increased leaf size in the transgenic plants.
Figure 68:
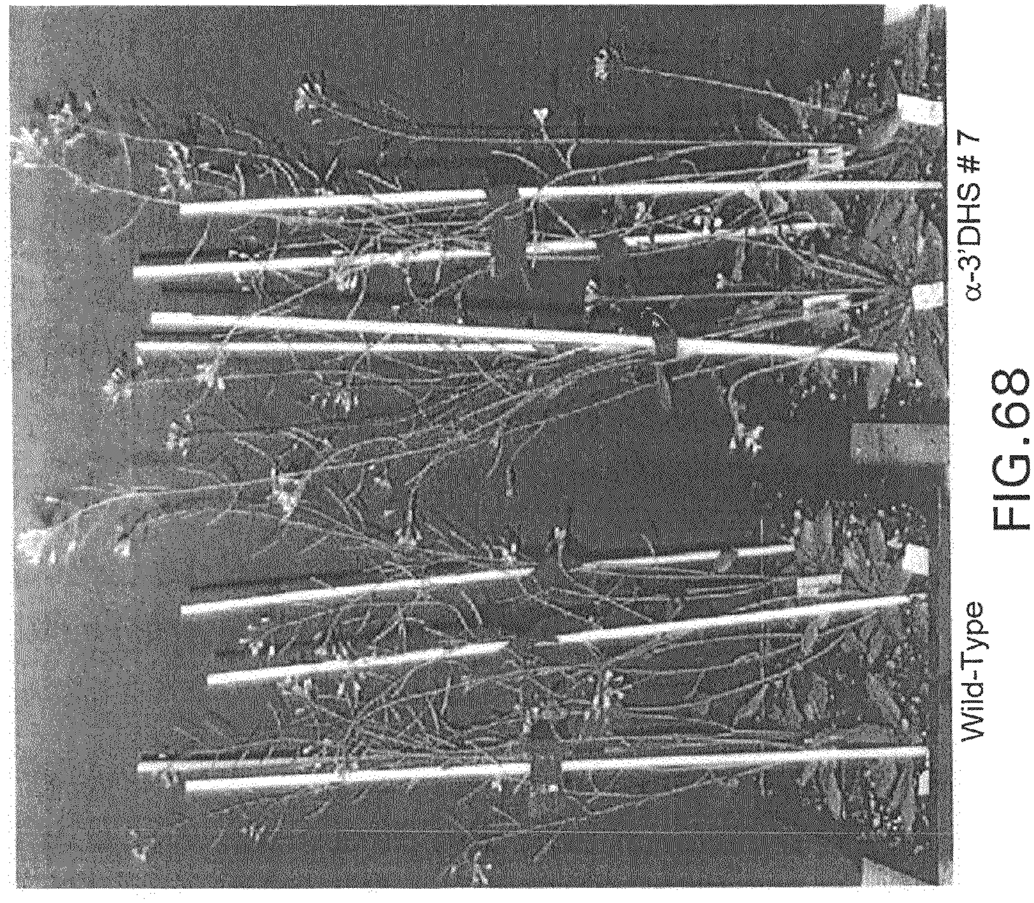
FIG. 68 is a photograph of 6.1 week old *Arabidopsis* wild-type (left) and transgenic plants expressing the 3'-end of the DHS gene (sequence shown in FIG. 80) in antisense orientation showing increased size of transgenic plants.

Total RNA from petals of carnation plants at various stages of flower development, i.e., tight-bud flowers (lane 1), beginning to open (lane 2), fully open flowers (lane 3), flowers with inrolling petals (lane 4), was isolated as above, separated on 1% denatured formaldehyde agarose gels and immobilized on nylon membranes. The full-length carnation senescence-induced DHS cDNA labeled with $^{32}P$-dCTP using a random primer kit (Boehringer Mannheim) was used to probe the filters ($7\times10^7$ cpm). The filters were washed once with 1×SSC, 0.1% SDS at room temperature and three times with 0.2×SSC, 0.1% SDS at 65° C. The filters were dried and exposed to X-ray film overnight at −70° C. The results are shown in FIG. 56.

Example 2

Sorbitol Induction of Tomato Senescence-Induced DHS Gene

Tomato leaves were treated with 2 M sorbitol in a sealed chamber for six hours. RNA was extracted from the sorbitol treated leaves as follows.

Leaves (5 g) were ground in liquid nitrogen. The ground powder was mixed with 30 ml guanidinium buffer (4 M guanidinium isothiocyanate, 2.5 mM NaOAc pH 8.5, 0.8%-mercaptoethanol). The mixture was filtered through four layers of cheesecloth and centrifuged at 10,000×g at 4° C. for 30 minutes. The supernatant was then subjected to cesium chloride density gradient centrifugation at 26,000×g for 20 hours. The pelleted RNA was rinsed with 75% ethanol, resuspended in 600 μl DEPC-treated water and the RNA precipitated at −70° C. with 0.75 ml 95% ethanol and 30 μL of 3M NaOAc. Ten μg of RNA were fractionated on a 1.2% denaturing formaldehyde agarose gel and transferred to a nylon membrane. Randomly primed $^{32}P$-dCTP-labeled full length DHS cDNA (SEQ ID NO: 1) was used to probe the membrane at 42° C. overnight. The membrane was then washed once in 1×SSC containing 0.1% SDS at room temperature for 15 minutes and three times in 0.2×SSC containing 0.1% SDS at 65° C. for 15 minutes each. The membrane was exposed to x-ray film overnight at −70° C.

The results are shown in FIG. 52. As can be seen, transcription of DHS is induced in leaves by sorbitol.

Example 3

Induction of the Tomato DHS gene in Senescing Flowers

Tight flower buds and open, senescing flowers of tomato plants were harvested, and RNA was isolated as in Example 2. Ten μg RNA were fractionated on a 1.2% denaturing formaldehyde agarose gel and transferred to a nylon membrane. Randomly primed $^{32}P$-dCTP-labeled full length DHS cDNA (SEQ ID NO. 1) was used to probe the membrane at 42° C. overnight. The membrane then was washed once in 1×SSC containing 0.1% SDS at room temperature for 15 minutes and then washed three times in 0.2×SSC containing 0.1% SDS at 65° C. for fifteen minutes each. The membrane was exposed to x-ray film overnight at −70° C.

The results are shown in FIG. 50. As can be seen, transcription of DHS is induced in senescing flowers.

Example 4

Induction of the Tomato DHS Gene in Ripening Fruit

RNA was isolated from breaker, pink and ripe fruit as in Example 2. Ten μg RNA were fractionated on a 1.2% denaturing formaldehyde agarose gel and transferred to a nylon membrane. Randomly primed $^{32}P$-dCTP-labeled full length DHS cDNA (SEQ ID NO.1) (FIG. 45) was used to probe the membrane at 42° C. overnight. The membrane then was washed once in 1×SSC containing 0.1% SDS at room temperature for 15 minutes and then washed three times in 0.2×SSC containing 0.1% SDS at 65° C. for fifteen minutes each. The membrane was exposed to x-ray film overnight at −70° C.

The results are shown in FIG. 51. As can be seen, transcription of DHS is strongest in ripe, red fruit just prior to the onset of senescence leading to spoilage.

Example 5

Induction of Tomato Senescence-Induced DHS Gene by Chilling

Tomato plants in pots (7-8 weeks old) were exposed to 6° C. for two days, three days or six days in a growth chamber. The light cycle was set for eight hours of dark and sixteen hours of light. Plants were rewarmed by moving them back into a greenhouse. Plants that were not rewarmed were harvested immediately after removal from the growth chamber. RNA was extracted from the leaves as follows.

Leaves (5 g) were ground in liquid nitrogen. The ground powder was mixed with 30 ml guanidinium buffer (4 M guanidinium isothiocyanate, 2.5 mM NaOAc pH 8.5, 0.8%-mercaptoethanol). The mixture was filtered through four layers of cheesecloth and centrifuged at 10,000 g at 4° C. for 30 minutes. The supernatant was then subjected to cesium chloride density gradient centrifugation at 26,000 g for 20 hours. The pelleted RNA was rinsed with 75% ethanol, resuspended in 600 μl DEPC-treated water and the RNA precipitated at −70° C. with 0.75 ml 95% ethanol and 30 μl of 3M NaOAc. Ten μg of RNA were fractionated on a 1.2% denaturing formaldehyde agarose gel and transferred to a nylon membrane. Randomly primed $^{32}P$-dCTP-labeled full length DHS cDNA (SEQ ID NO: 1) was used to probe the membrane at 42° C. overnight. The membrane was then washed once in 1×SSC containing 0.1% SDS at room temperature for 15 minutes and three times in 0.2×SSC containing 0.1% SDS at 65° C. for 15 minutes each. The membrane was exposed to x-ray film overnight at −70° C.

Figure 53A:
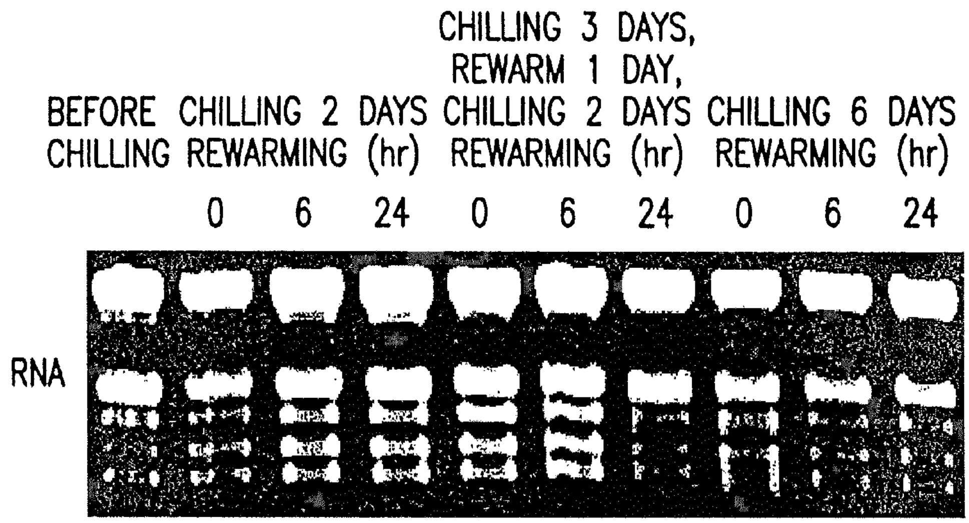
FIGS. 53A-53C is a Northern blot of RNA isolated from tomato leaves that had been exposed to chilling temperature.
Figure 53B:
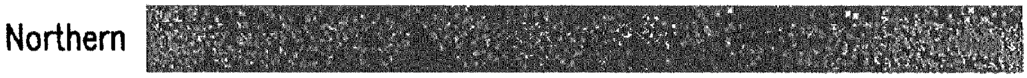
Figure 53C:
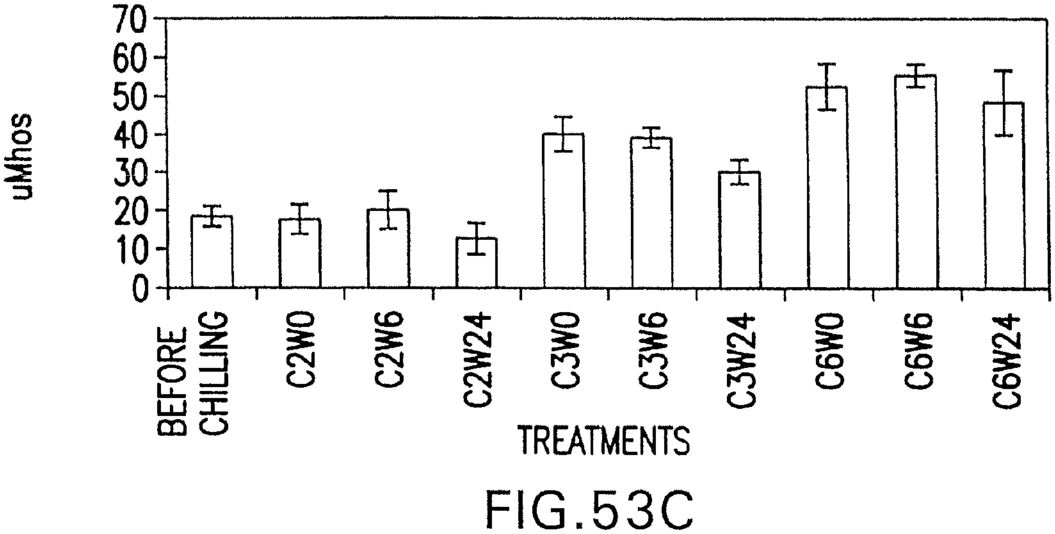

The results are shown in FIG. 53. As can be seen, transcription of DHS is induced in leaves by exposure to chilling temperature and subsequent rewarming, and the enhanced transcription correlates with chilling damage measured as membrane leakiness.

Example 6

Generation of an *Arabidopsis* PCR Product Using Primers Based on Unidentified *Arabidopsis* Genomic Sequence A partial length senescence-induced DHS sequence from an *Arabidopsis* cDNA template was generated by PCR using a pair of oligonucleotide primers designed from *Arabidopsis* genomic sequence. The 5' primer is a 19-mer having the sequence, 5'-GGTGGTGT5TGAGGAAGATC (SEQ ID NO:7); the 3' primer is a 20 mer having the sequence, GGTGCACGCCCTGATGAAGC-3' (SEQ ID NO:8). A polymerase chain reaction using the Expand High Fidelity PCR System (Boehringer Mannheim) and an *Arabidopsis* senescing leaf cDNA library as template was carried out as follows. Reaction components:

| | | |
|---|---|---|
| cDNA | 1 | μl (5 × $10^7$ pfu) |
| dNTP (10 mM each) | 1 | μl |
| $MgCl_2$ (5 mM) + 10x buffer | 5 | μl |
| Primers 1 and 2 (100 μM each) | 2 | μl |
| Expand High Fidelity DNA polymerase | 1.75 | U |
| Reaction volume | 50 | μl |

Reaction parameters:
94° C. for 3 min
94° C./1 min, 58° C./1 min, 72° C./2 min, for 45 cycles
72° C. for 15 min.

Example 7

Isolation of Genomic DNA and Southern Analysis

Genomic DNA was extracted from tomato leaves by grinding 10 grams of tomato leaf tissue to a fine powder in liquid nitrogen. 37.5 ml of a mixture containing 25 ml homogenization buffer [100 mM Tris-HCl, pH 8.0, 100 mm EDTA, 250 mM NaCl, 1% sarkosyl, 1% 2-mercaptoethanol, 10 μg/ml RNase and 12.5 ml phenol] prewarmed to 60° C. was added to the ground tissue. The mixture was shaken for fifteen minutes. An additional 12.5 ml of chloroform/isoamyl alcohol (24:1) was added to the mixture and shaken for another 15 minutes. The mixture was centrifuged and the aqueous phase reextracted with 25 ml phenol/chloroform/isoamylalcohol (25:24:1) and chloroform/isoamylalcohol (24:1). The nucleic acids were recovered by precipitation with 15 ml isopropanol at room temperature. The precipitate was resuspended in 1 ml of water.

Genomic DNA was subjected to restriction enzyme digestion as follows: 10 μg genomic DNA, 40 μl 10× reaction buffer and 100 U restriction enzyme (XbaI, EcoRI, EcoRV or HinDIII) were reacted for five to six hours in a total reaction volume of 400 μl. The mixture was then phenol-extracted and ethanol-precipitated. The digested DNA was subjected to agarose gel electrophoresis on a 0.8% agarose gel at 15 volts for approximately 15 hours. The gel was submerged in denaturation buffer [87.66 g NaCl and 20 g NaOH/Liter] for 30 minutes with gentle agitation, rinsed in distilled water and submerged in neutralization buffer [87.66 g NaCl and 60.55 g tris-HCl, pH 7.5/Liter] for 30 minutes with gentle agitation. The DNA was transferred to a Hybond-$N^+$ nylon membrane by capillary blotting.

Hybridization was performed overnight at 42° C. using $1\times10^6$ cpm/ml of $^{32}P$-dCTP-labeled full length DHS cDNA or 3'-non-coding region of the DHS cDNA clone. Prehybridization and hybridization were carried out in buffer containing 50% formamide, 6×SSC, 5×Denhardt's solution, 0.1% SDS and 100 mg/ml denatured salmon sperm DNA. The membrane was prehybridized for two to four hours; hybridization was carried out overnight.

Figure 49:
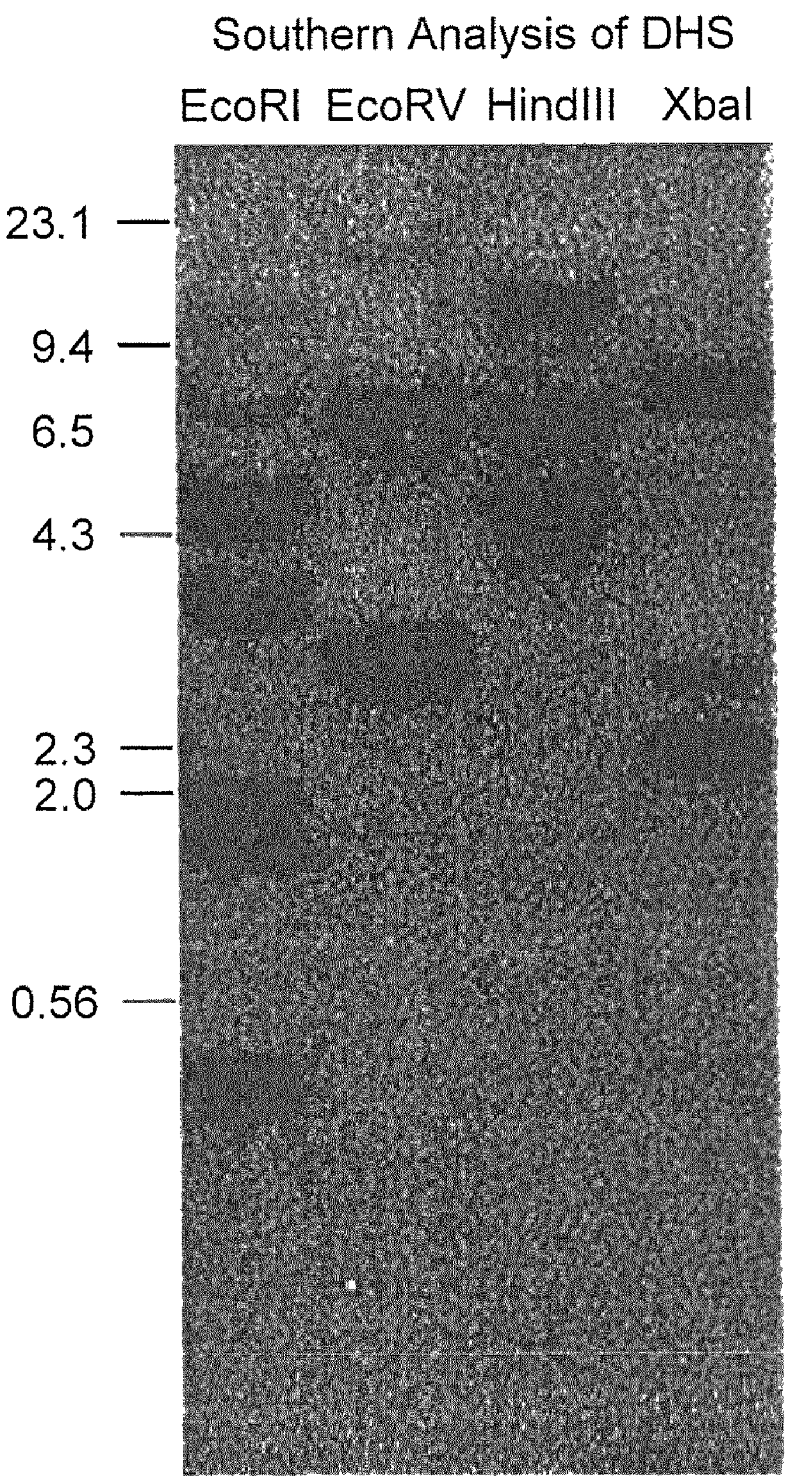
FIG. 49 is a Southern blot of genomic DNA isolated from tomato leaves and probed with $^{32}$P-dCTP-labeled full length tomato DHS cDNA.

After hybridization was complete, membranes were rinsed at room temperature in 2×SSC and 0.1% SDS and then washed in 2×SSC and 0.1% SDS for 15 minutes and 0.2×SSC and 0.1% SDS for 15 minutes. The membrane was then exposed to x-ray film at −80° C. overnight. The results are shown in FIG. 49.

Example 8

Isolation of a Senescence-Induced eIF-5A Gene from *Arabidopsis*

A full-length cDNA clone of the senescence-induced eIF-5A gene expressed in *Arabidopsis* leaves was obtained by PCR using an *Arabidopsis* senescing leaf cDNA library as template. Initially, PCR products corresponding to the 5'- and 3'-ends of the gene were made using a degenerate upstream primer <AAARRYCGMCCYTGCAAGGT> (SEQ ID NO: 17) paired with vector T7 primer <AATACGACTCACTATAG> (SEQ ID NO:18), and a degenerate downstream primer <TCYTTNCCYTCMKCTAAHCC> (SEQ ID NO: 19) paired with vector T3 primer <ATTAACCCTCACTAAAG> (SEQ ID NO: 20). The PCR products were subcloned into pBluescript for sequencing. The full-length cDNA was then obtained using a 5'-specific primer <CTGTTACCAAAAAATCTGTACC> (SEQ ID NO: 21) paired with a 3'-specific primer <AGAAGAAGTATAAAAACCATC> (SEQ ID NO: 22), and subcloned into pBluescript for sequencing.

Example 9

Isolation of a Senescence-Induced eIF-5A Gene from Tomato Fruit

A full-length cDNA clone of the senescence-induced eIF-5A gene expressed in tomato fruit was obtained by PCR using a tomato fruit cDNA library as template. Initially, PCR products corresponding to the 5'- and 3'-ends of the gene were made using a degenerate upstream primer (SEQ ID NO: 17) paired with vector T7 primer (SEQ ID NO: 18), and a degenerate downstream primer (SEQ ID NO: 19) paired with vector T3 primer (SEQ ID NO: 20). The PCR products were subcloned into pBluescript for sequencing. The full-length cDNA was then obtained using a 5'-specific primer <AAAGAATCCTAGAGAGAGAAAGG> (SEQ ID NO: 23) paired with vector T7 primer (SEQ ID NO: 18), and subcloned into pBluescript for sequencing.

Example 10

Isolation of a Senescence-Induced eIF-5A Gene from Carnation

A full-length cDNA clone of the senescence-induced eIF-5A gene expressed in carnation flowers was obtained by PCR using a carnation senescing flower cDNA library as template. Initially, PCR products corresponding to the 5'- and 3'-ends of the gene were made using a degenerate upstream primer (SEQ ID NO: 17) paired with vector T7 primer (SEQ ID NO: 18), and a degenerate downstream primer (SEQ ID NO: 19) paired with vector T3 primer (SEQ ID NO: 20). The PCR products were subcloned into pBluescript for sequencing. The full-length cDNA was then obtained using a 5'-specific primer <TTTTACATCAATCGAAAA> (SEQ ID NO: 24) paired with a 3'-specific primer <ACCAAAACCTGTGTTATAACTCC> (SEQ ID NO: 25), and subcloned into pBluescript for sequencing.

Example 11

Isolation of a Senescence-Induced DHS Gene from *Arabidopsis*

A full-length cDNA clone of the senescence-induced DHS gene expressed in *Arabidopsis* leaves was obtained by screening an *Arabidopsis* senescing leaf cDNA library. The sequence of the probe (SEQ ID NO: 26) that was used for screening is shown in FIG. 82. The probe was obtained by PCR using the senescence leaf cDNA library as a template and primers designed from the unidentified genomic sequence (AB017060) in GenBank. The PCR product was subcloned into pBluescript for sequencing.

Example 12

Isolation of a Senescence-Induced DHS Gene from Carnation

A full-length cDNA clone of the senescence-induced DHS gene expressed in carnation petals was obtained by screening a carnation senescing petal cDNA library. The sequence of the probe (SEQ ID NO: 27) that was used for screening is shown in FIG. 83. The probe was obtained by PCR using the senescence petal cDNA library as a template and degenerate primers (upstream: 5' TTG ARG AAG ATY CAT MAA RTG CCT 3') (SEQ ID NO: 28); downstream: 5'CCA TCA AAY TCY TGK GCR GTG TT 3') (SEQ ID NO: 29). The PCR product was subcloned into pBluescript for sequencing.

Example 13

Transformation of *Arabidopsis* with Full-Length or 3' Region of *Arabidopsis* DHS in Antisense Orientation

*Agrobacteria* were transformed with the binary vector, pKYLX71, containing the full-length senescence-induced *Arabidopsis* DHS cDNA sequence or the 3' end of the DHS gene (SEQ ID NO:30) (FIG. 80), both expressed in the antisense configuration, under the regulation of double 35S promoter. *Arabidopsis* plants were transformed with the transformed *Agrobacteria* by vacuum infiltration, and transformed seeds from resultant $T_0$ plants were selected on ampicillin.

Figure 69:
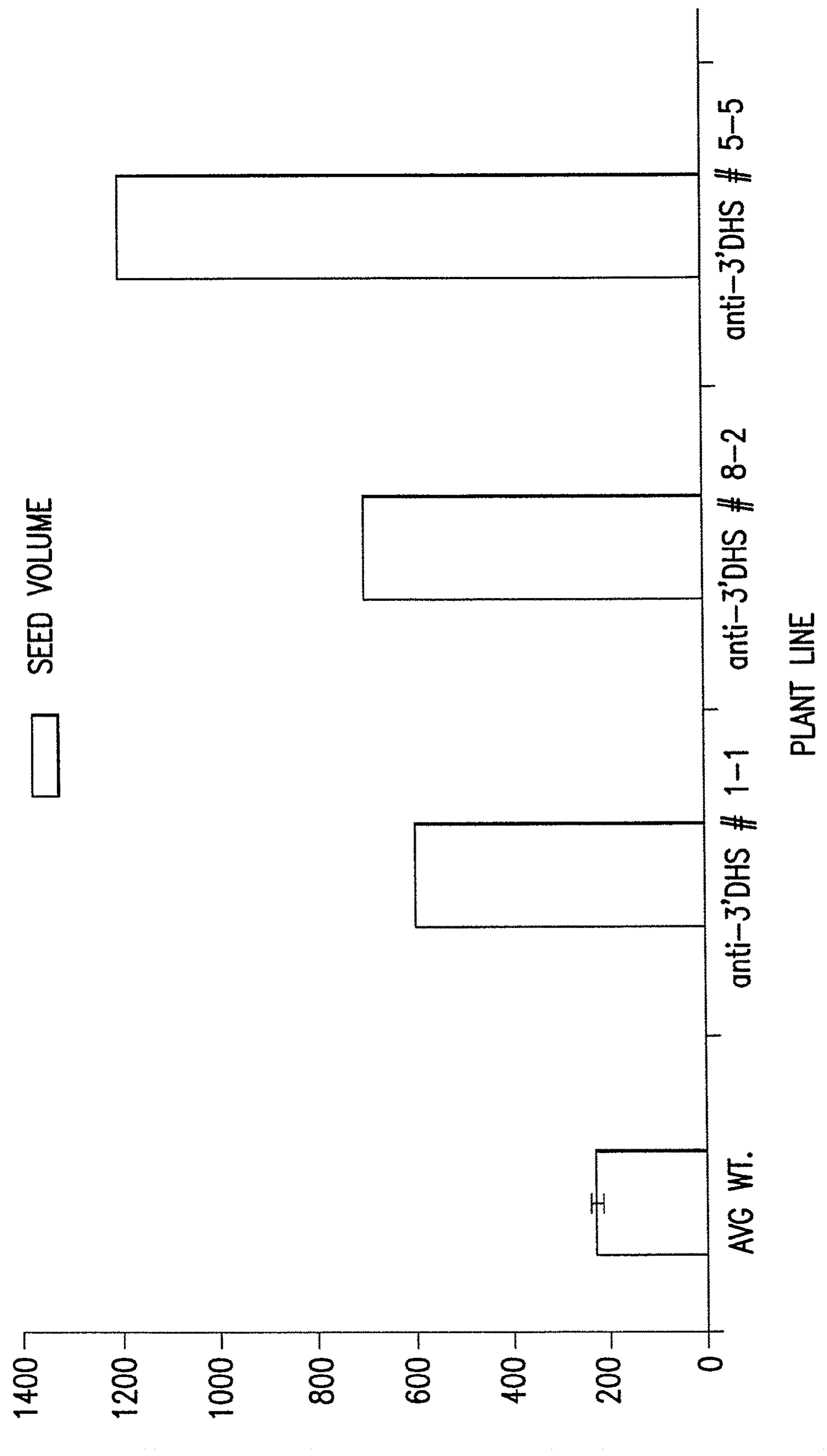
FIG. 69 is a graph showing the increase in seed yield from three $T_1$ transgenic *Arabidopsis* plant lines expressing the DHS gene in antisense orientation. Seed yield is expressed as volume of seed. SE for n=30 is shown for wild-type plants.
Figure 70:
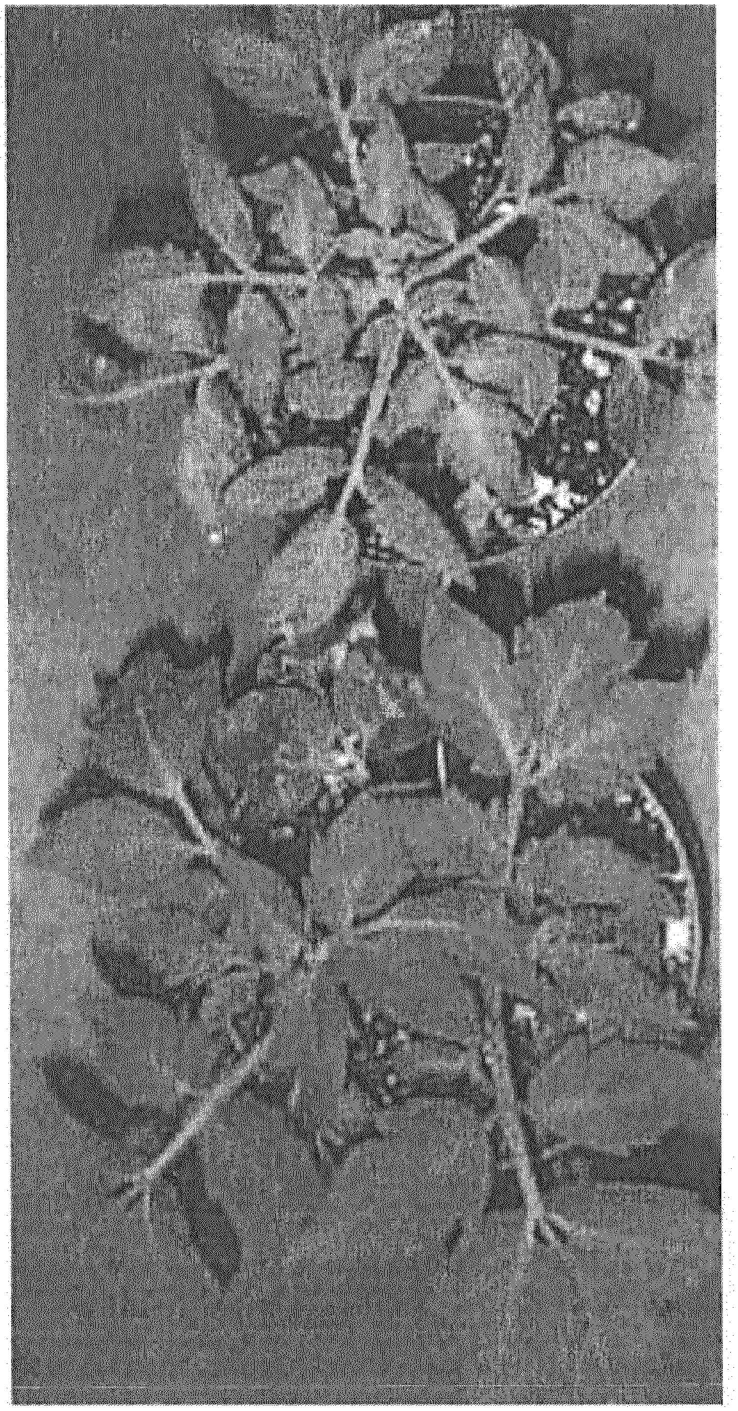
FIG. 70 is a photograph of transgenic tomato plants expressing the 3'-end of the DHS gene (sequence shown in FIG. 80) in antisense orientation (left) and wild-type plants (right) showing increased leaf size and increased plant size in the transgenic plants. The photograph was taken 18 days after transfer of the plantlets to soil.
Figure 71:
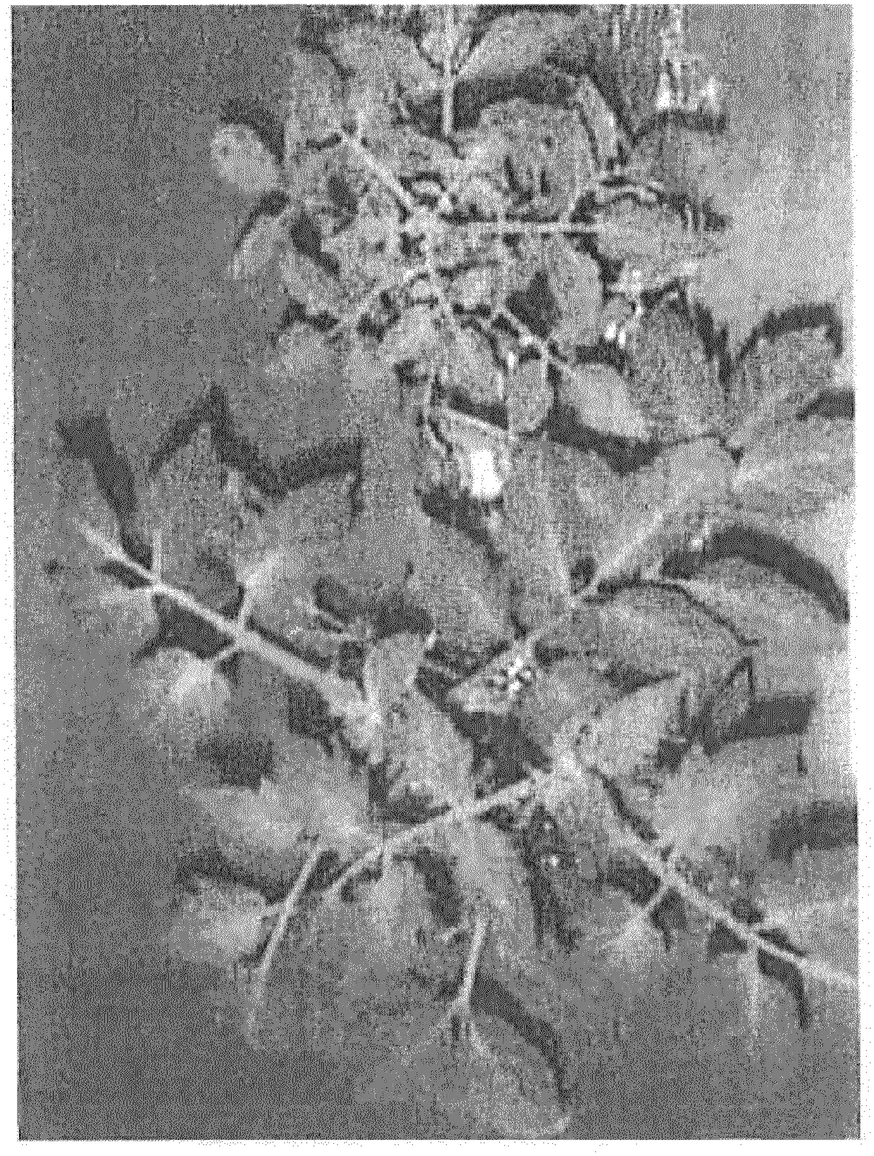
FIG. 71 is a photograph of transgenic tomato plants expressing the 3'-end of the DHS gene (sequence shown in FIG. 36) in antisense orientation (left) and wild-type plants (right) showing increased leaf size and increased plant size in the transgenic plants. The photograph was taken 32 days after transfer of the plantlets to soil.
Figure 72:
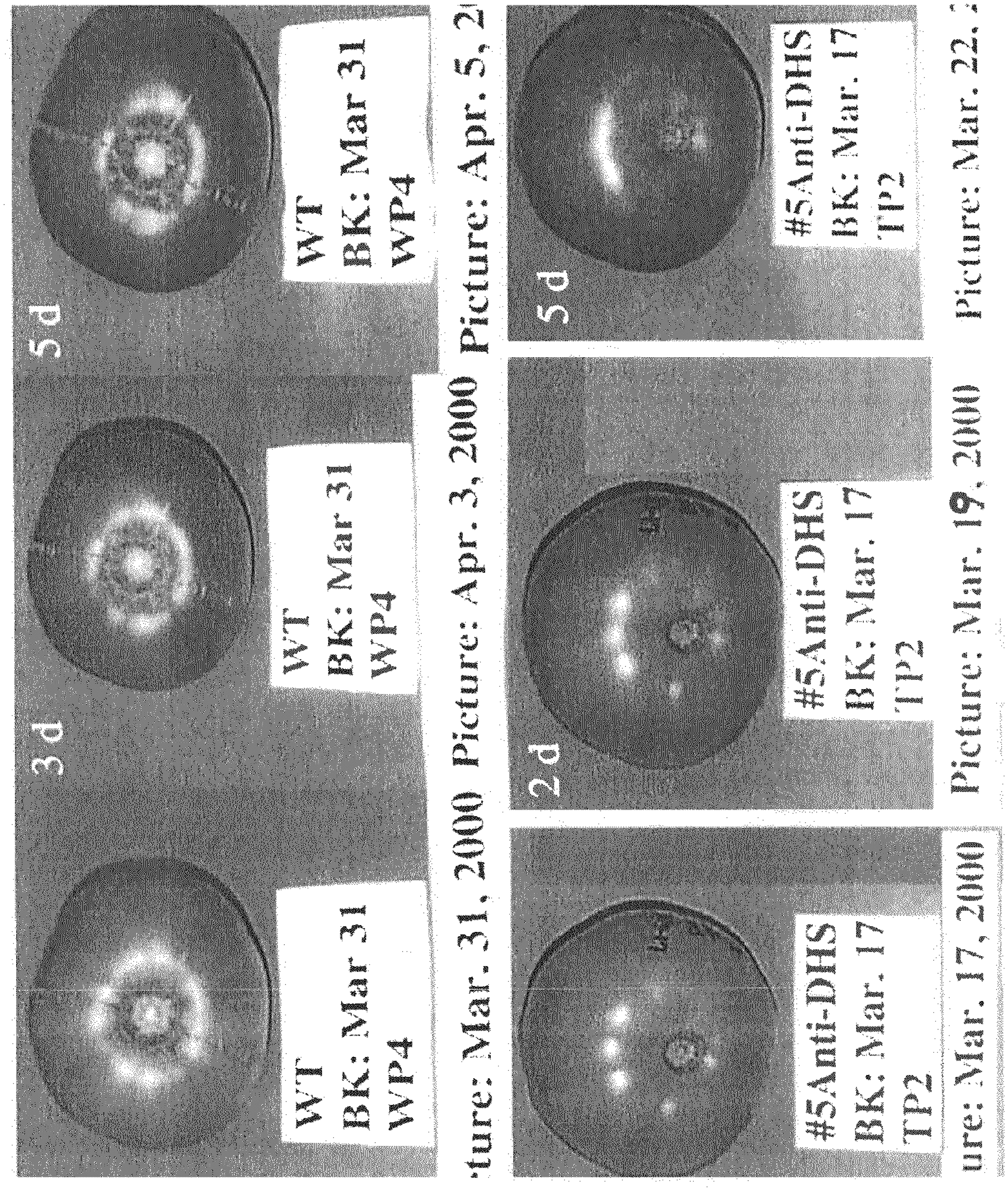
FIGS. 72 through 79 are photographs of tomato fruit from wild-type (top panels) and transgenic plants expressing the full-length DHS gene in antisense orientation (bottom panels). Fruit were harvested at the breaker stage of development and ripened in a growth chamber. Days after harvest are indicated in the upper left corner of each panel.
Figure 73:
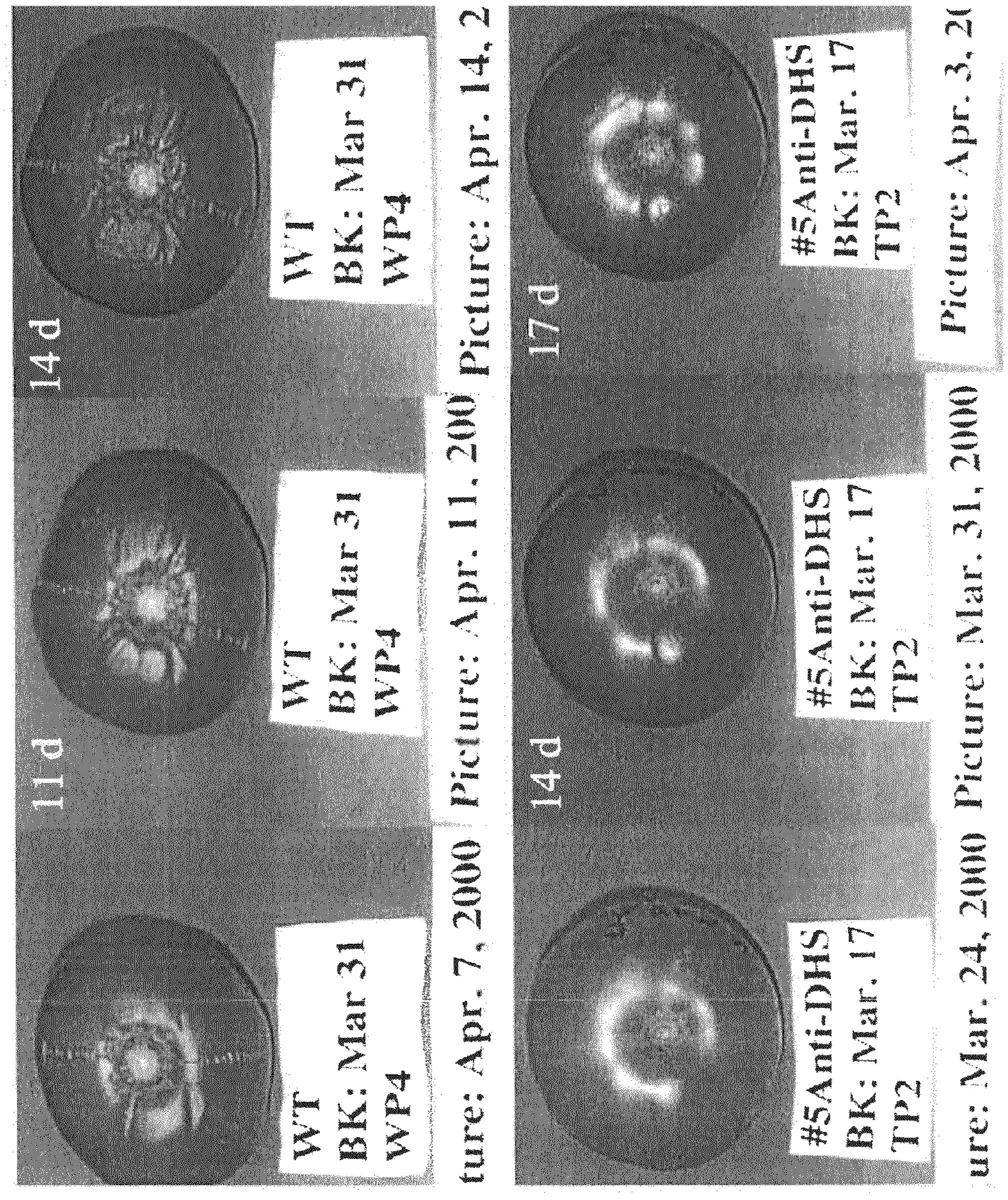
Figure 74:
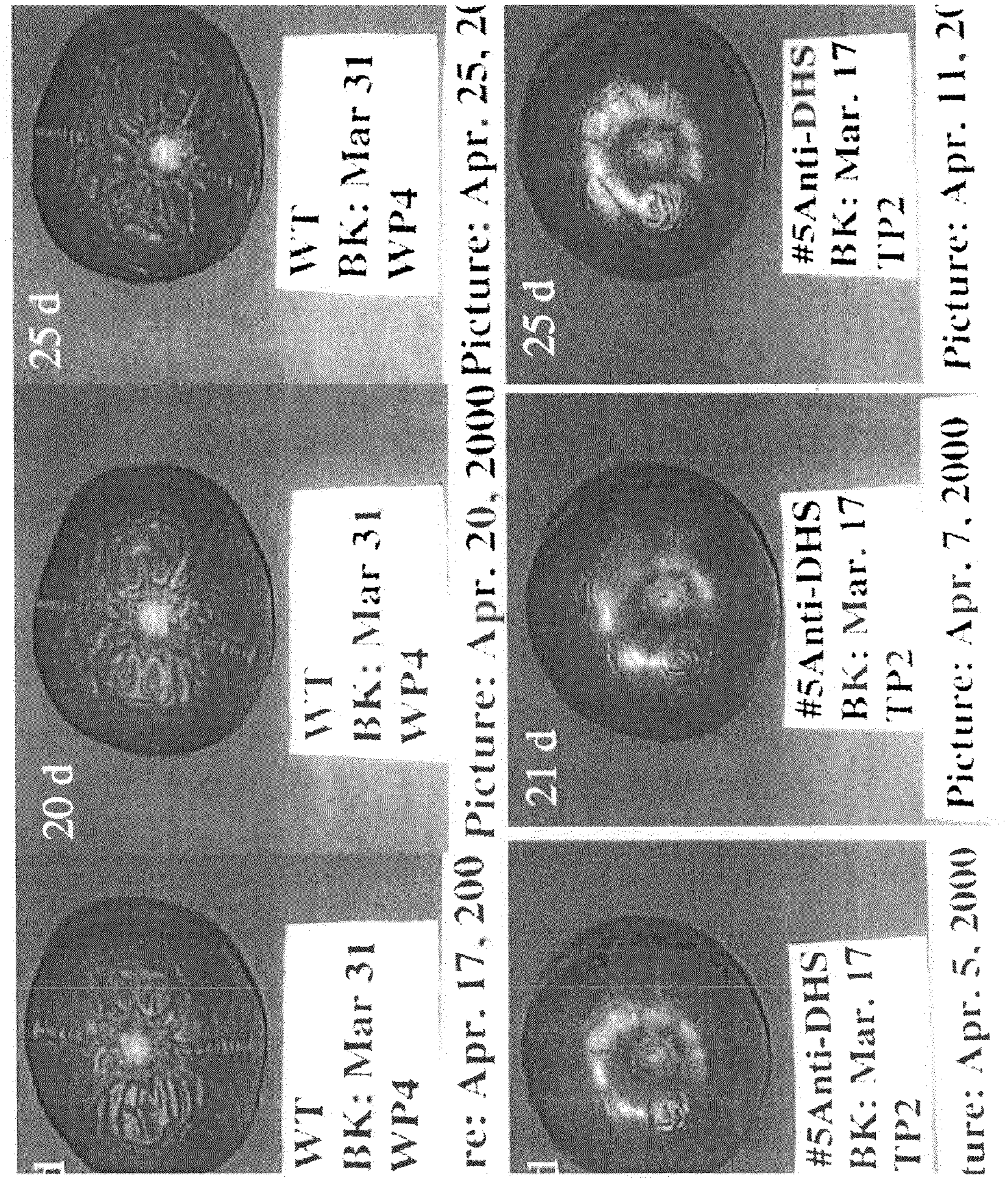
Figure 75:
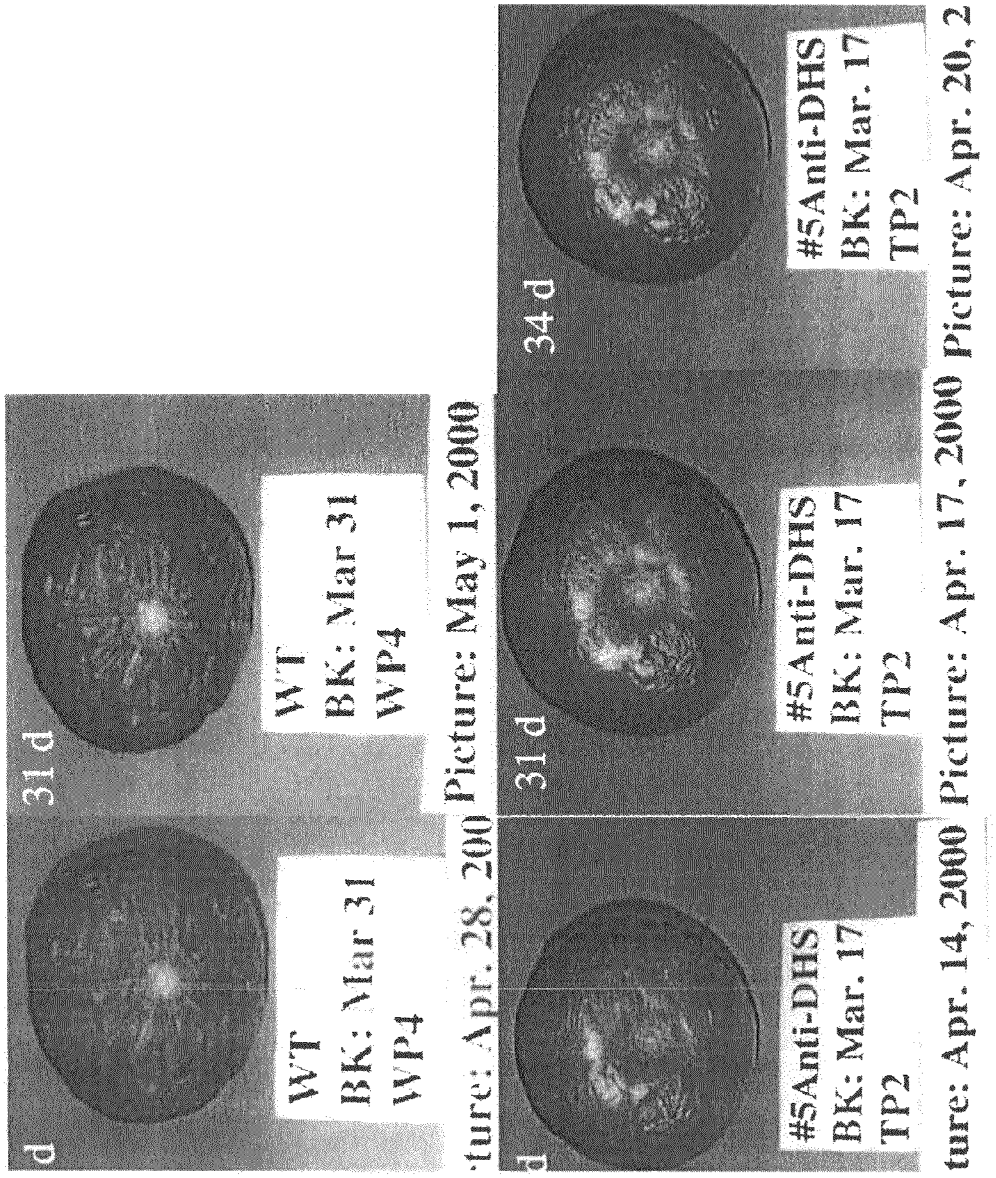
Figure 76:
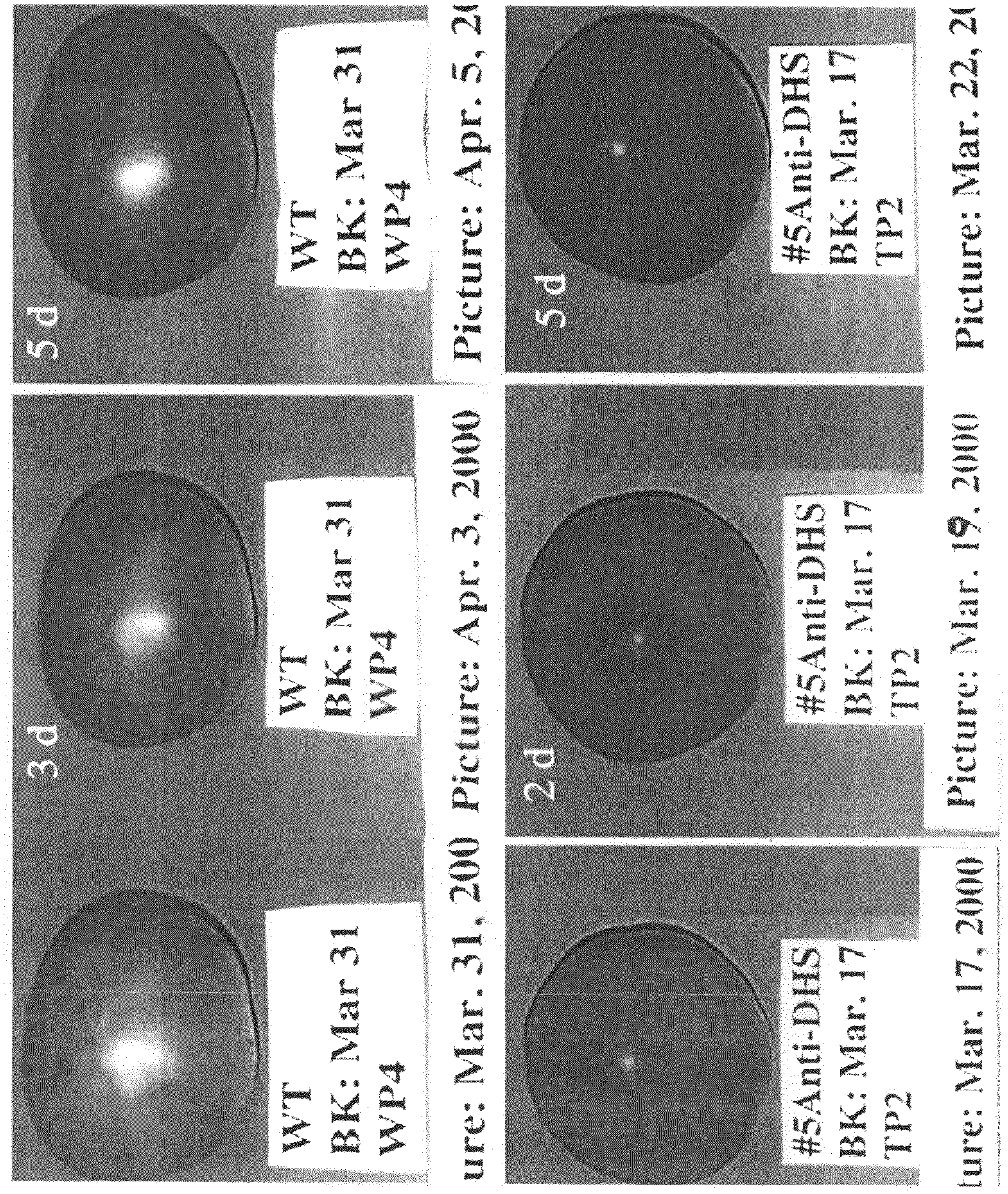
Figure 77:
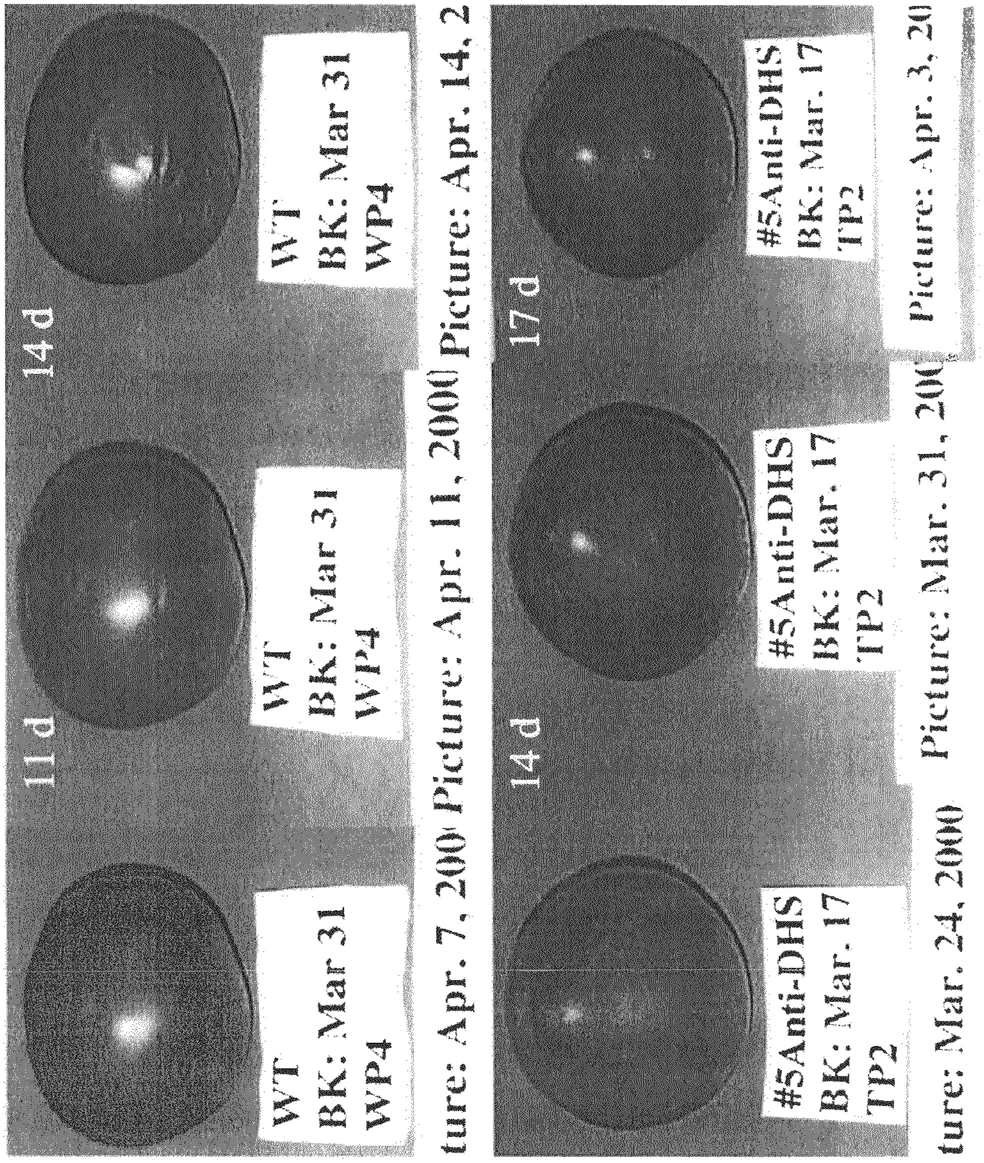
Figure 78:
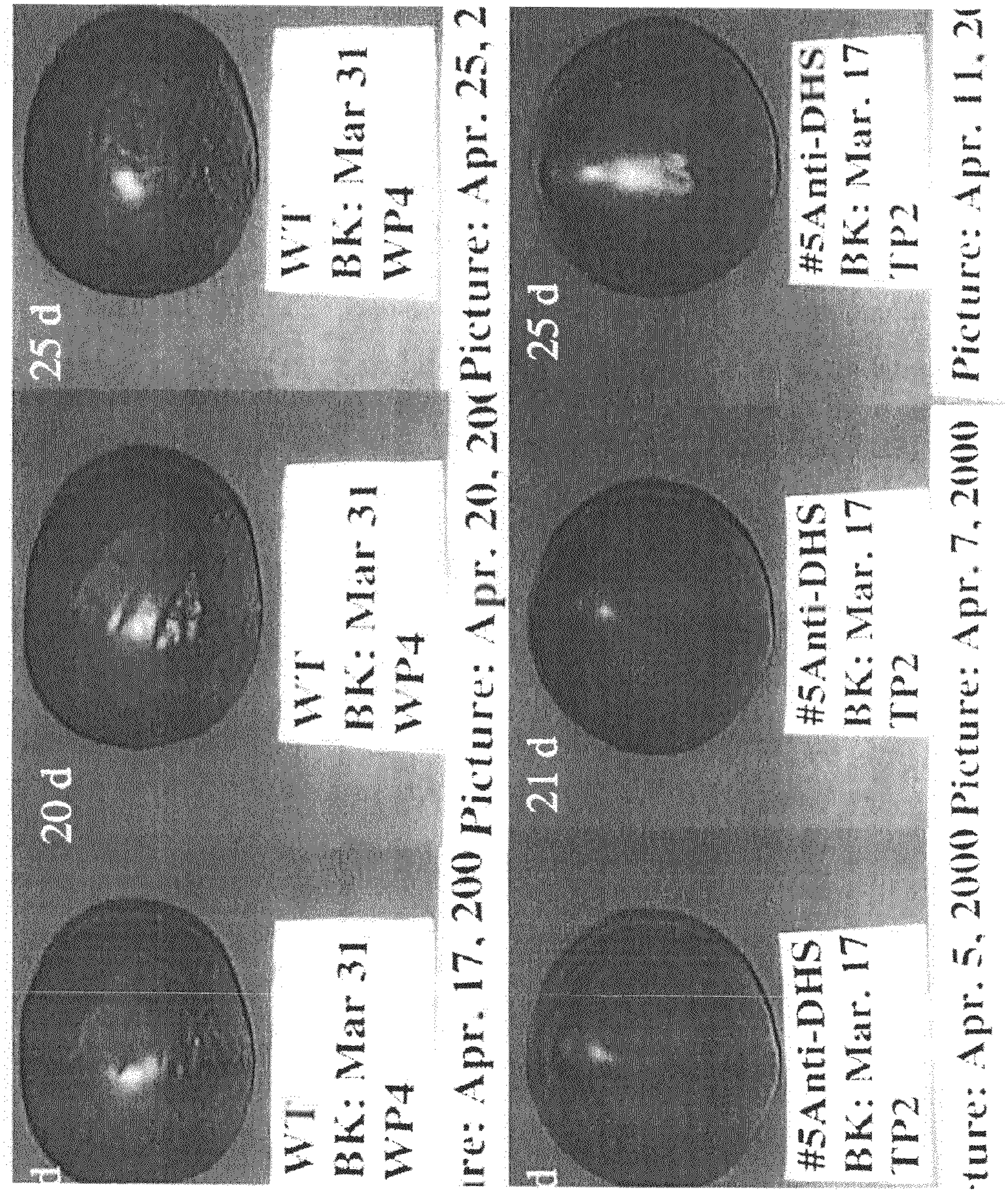
Figure 79:
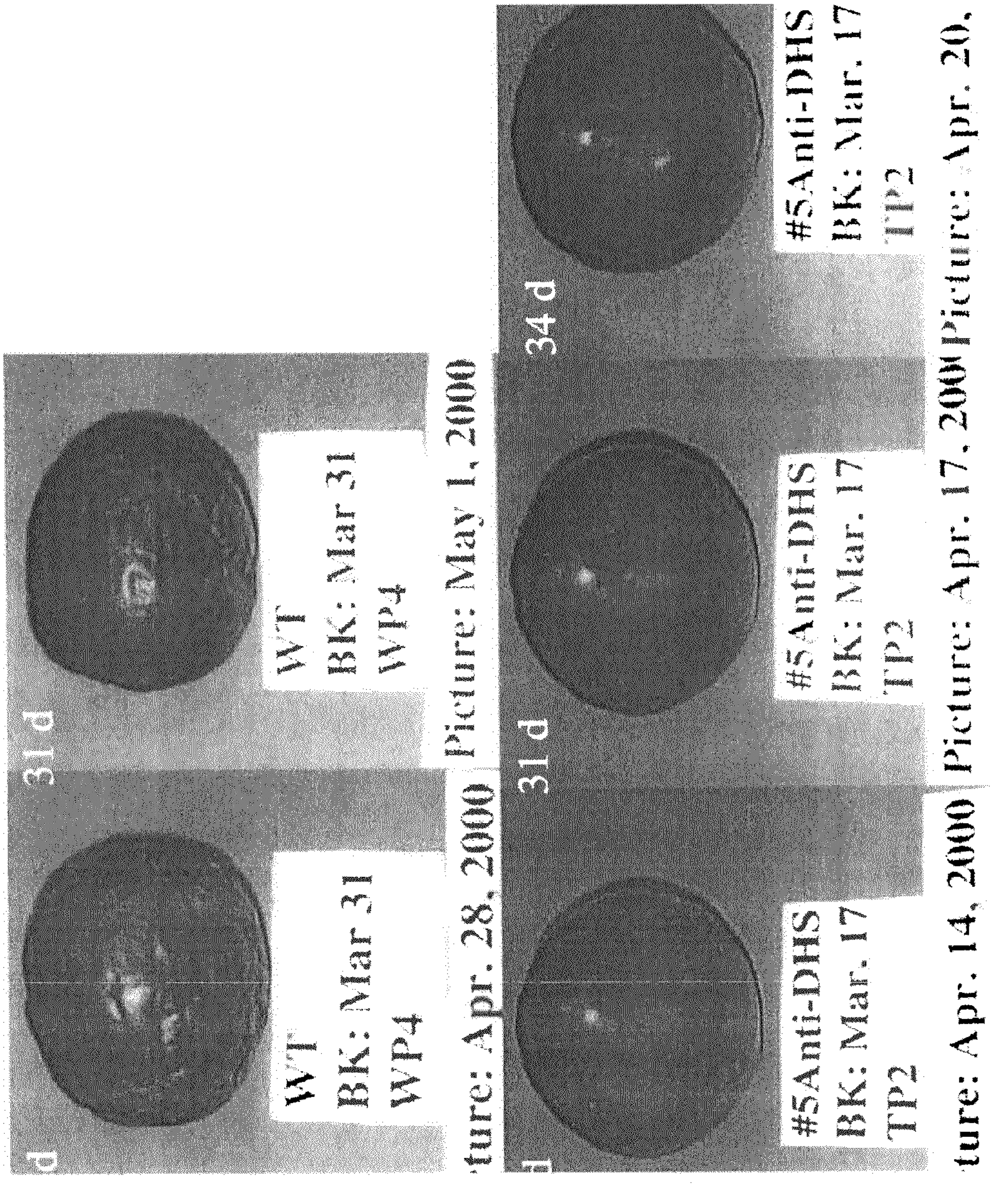

FIGS. 65-68 are photographs of the transformed *Arabidopsis* plants, showing that expression of the DHS gene or 3' end thereof in antisense orientation in the transformed plants results in increased biomass, e.g., larger leaves and increased plant size. FIG. 69 illustrates that the transgenic *Arabidopsis* plants have increased seed yield.

Example 14

Transformation of Tomato Plants with Full-Length or 3' Region of Tomato DHS in Antisense Orientation

*Agrobacteria* were transformed with the binary vector, pKYLX71, containing the full-length senescence-induced tomato DHS cDNA sequence or the 3' end of the DHS gene (SEQ ID NO:31) (FIG. 81), both expressed in the antisense configuration, under the regulation of double 35S promoter. Tomato leaf explants were formed with these *Agrobacteria*, and transformed callus and plantlets were generated and selected by standard tissue culture methods. Transformed plantlets were grown to mature fruit-producing $T_1$ plants under greenhouse conditions.

FIGS. 70-79 are photographs showing that reduced expression of the senescence-induced tomato DHS gene in the transformed plants results in increased biomass, e.g., larger leaf size and larger plants as seen in the transformed *Arabidopsis* plants, as well as delayed softening and spoilage of tomato fruit.

Example 15

Transformation of Tomato Plants with the 3'Region of Tomato DHS in Antisense Orientation

*Agrobacteria* were transformed with the binary vector, pKYLX71, containing the 3' end of the DHS gene (FIG. 81) expressed in the antisense configuration, under the regulation of double 35S promoter. Tomato leaf explants were formed with these *Agrobacteria*, and transformed callus and plantlets were generated and selected by standard tissue culture methods. Transformed plantlets were grown to mature fruit producing $T_1$ plants under green house conditions.

Figure 84A:
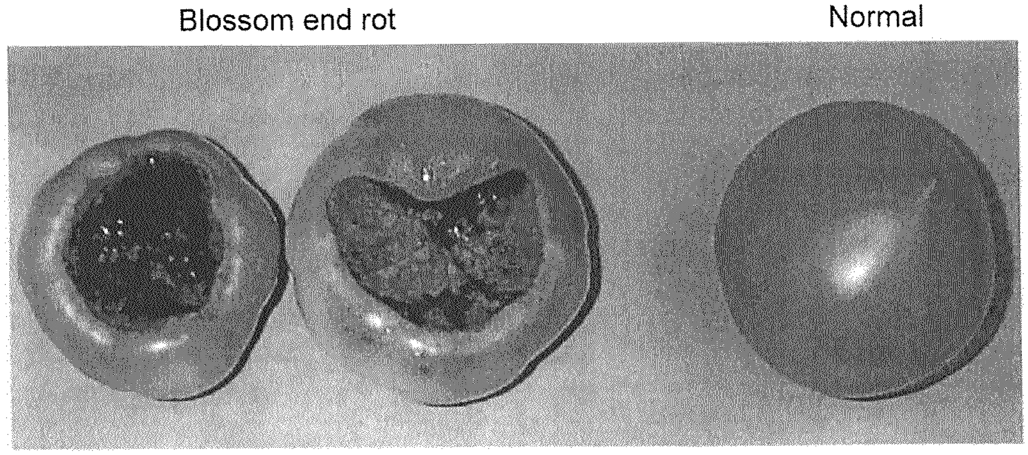
FIGS. 84 (*a*) and (*b*) are photographs of tomato fruits from transgenic tomato plants expressing the 3'-end of the DHS gene (sequence shown in FIG. 81) in antisense orientation (right) and tomato fruits from wild-type plants (left). While the wild-type fruit exhibits blossom end rot, the transgenic fruit does not.
Figure 84B:
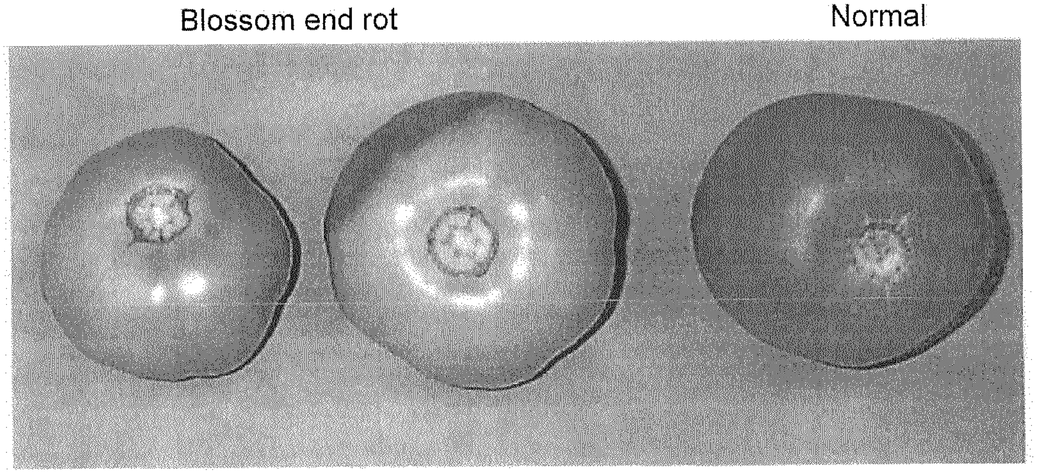
Figure 89B:
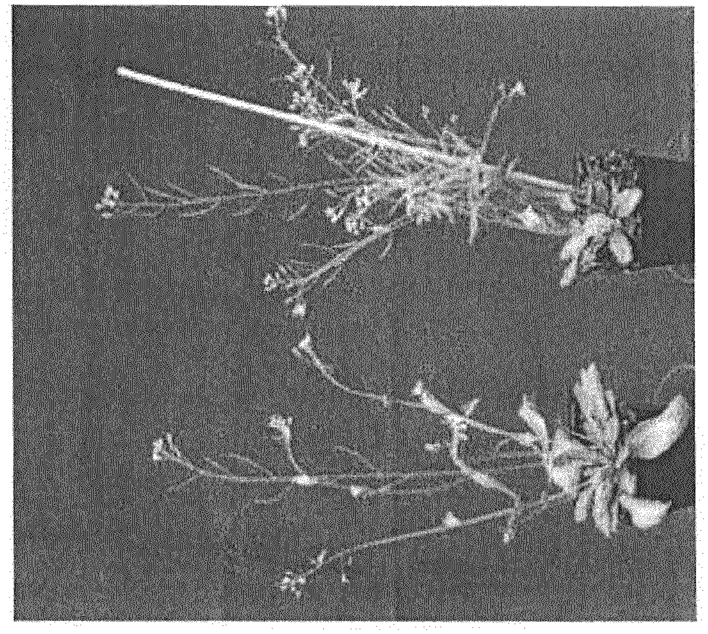
FIGS. 89A-89B provides photographs of a comparison of *Arabidopsis thaliana* control and transgenic plants comprising a sense polynucleotide senescence-induced eIF-5A. The transgenic plant has thicker inflorescence stems over that of the control plant.
Figure 89A:
Figure 90A:
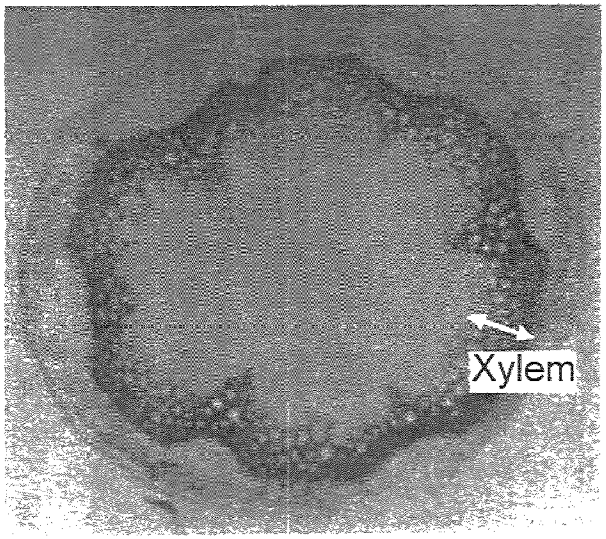
FIGS. 90A-90B and 91A-91B shows that transgenic plants comprising an sense polynucleotide senescence-induced eIF-5A (FIG. 90-*arabidopsis* and FIG. 91-*tomato*) have increased xylogenesis as indicated by the increased xylem in the transgenic plant.
Figure 90B:
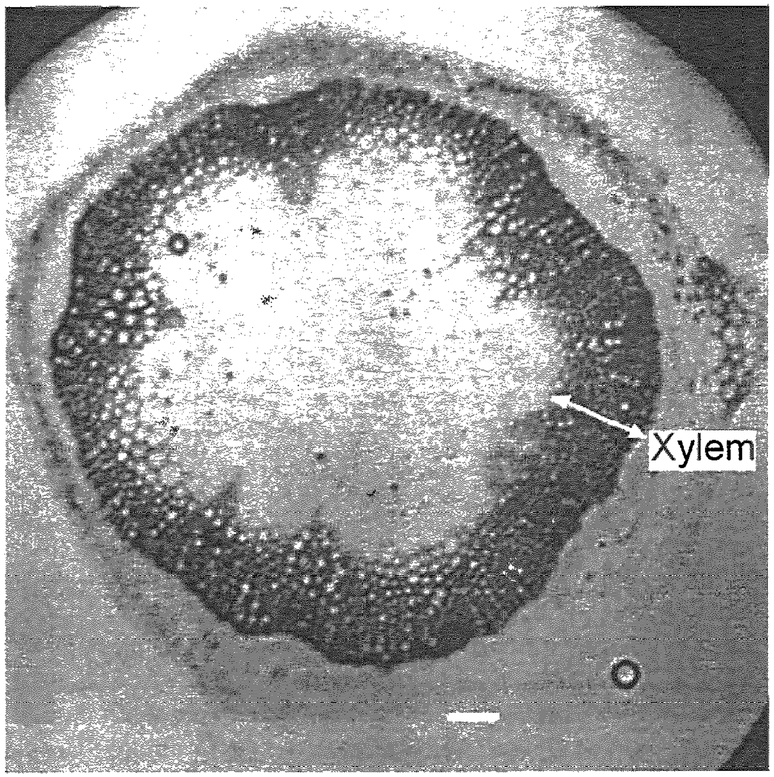
Figure 91A:
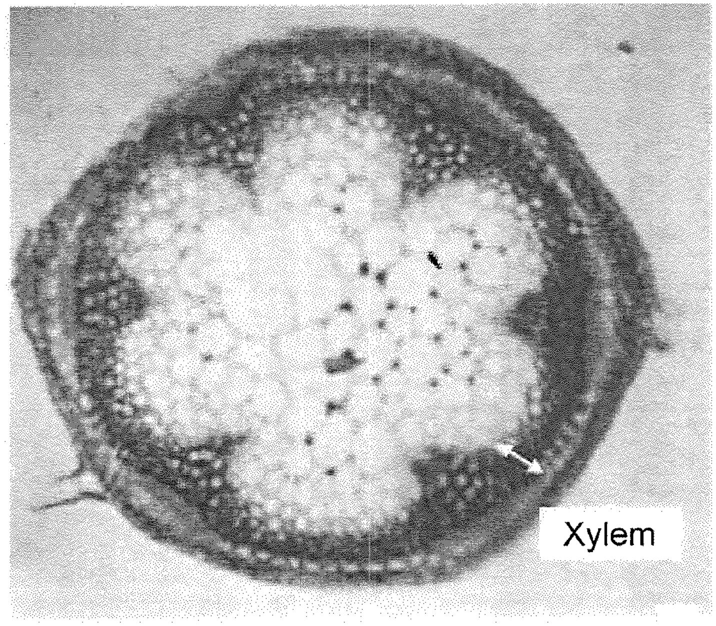
Figure 91B:
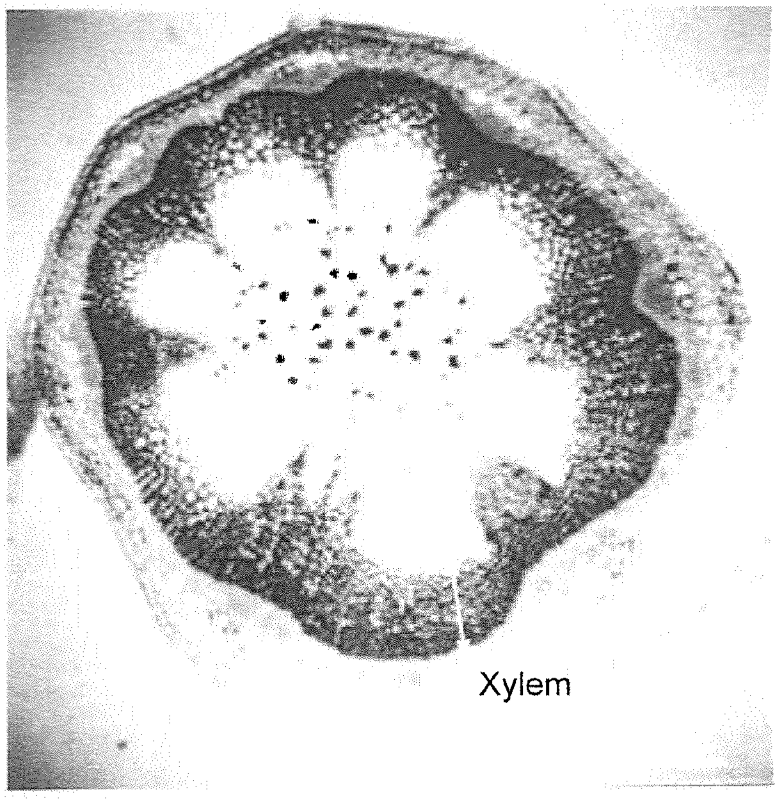
Figure 92A:
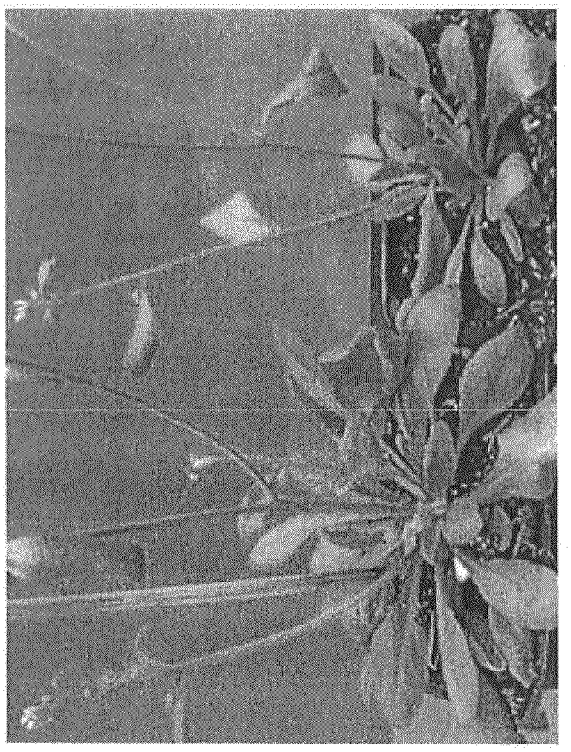
FIGS. 92A-92B provides photographs of a comparison of *Arabidopsis thaliana* control and *Arabidopsis thaliana* transgenic plants comprising a sense polynucleotide senescence-induced eIF-5A. A tomato sense polynucleotide senescence-induced eIF-5A was used in *Arabidopsis thaliana*. The transgenic plant has thicker inflorescence stems over that of the control plant.
Figure 92B:
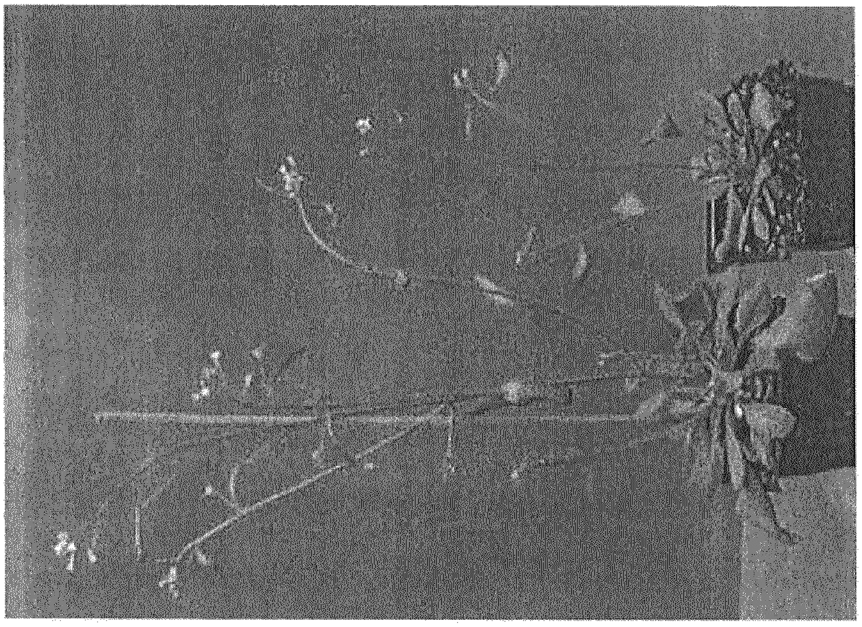
Figure 93:
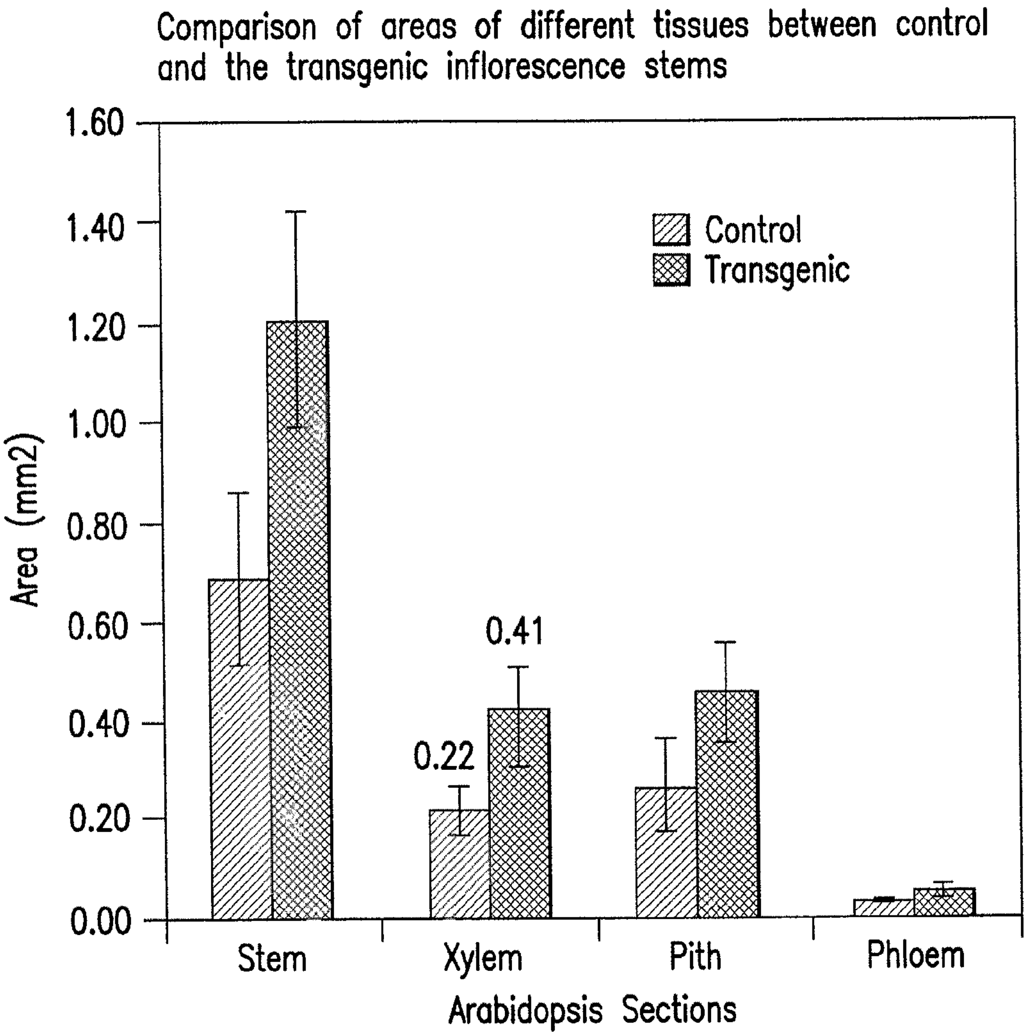
FIGS. 93 and 94 are bar graphs that show increased xylogenesis in transgenic plants comprising a sense polynucleotide senescence-induced eIF-5A.
Figure 94:
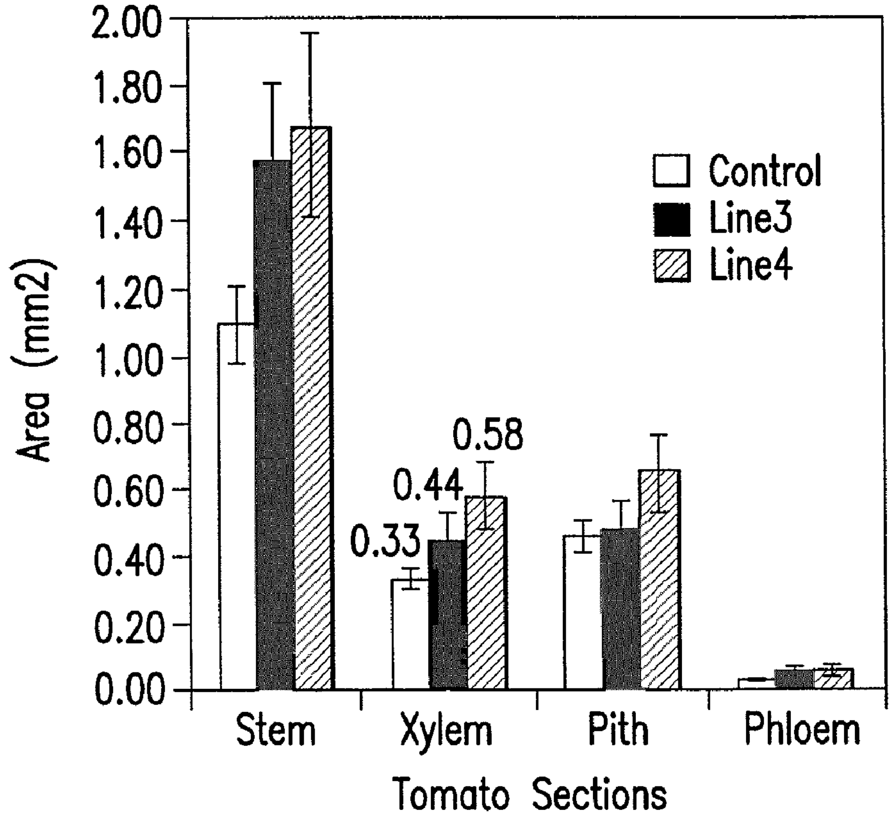
Figure 99:
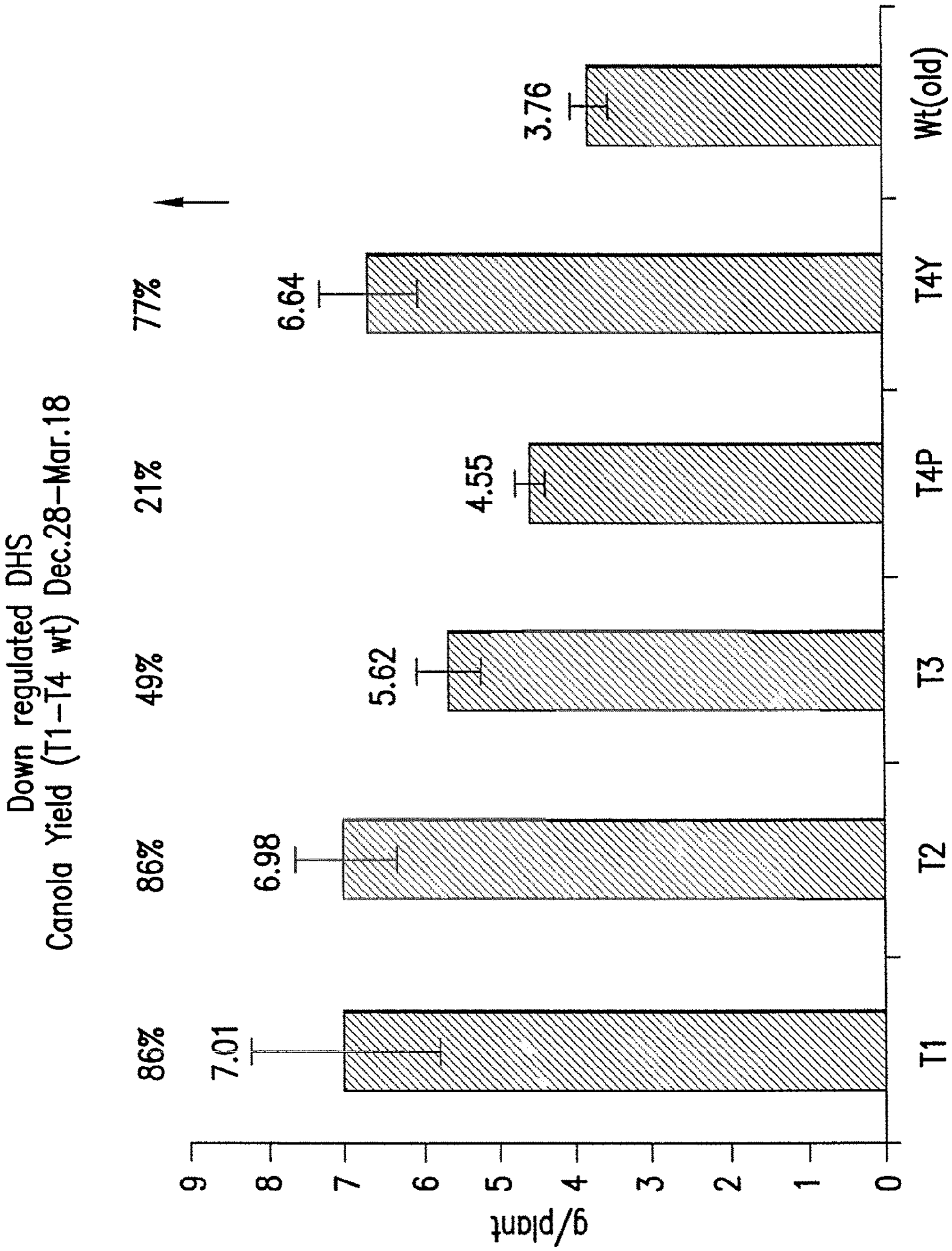
FIG. 99 shows in bar graph form that inhibition of DHS expression increases seed yield in canola.
Figure 100:
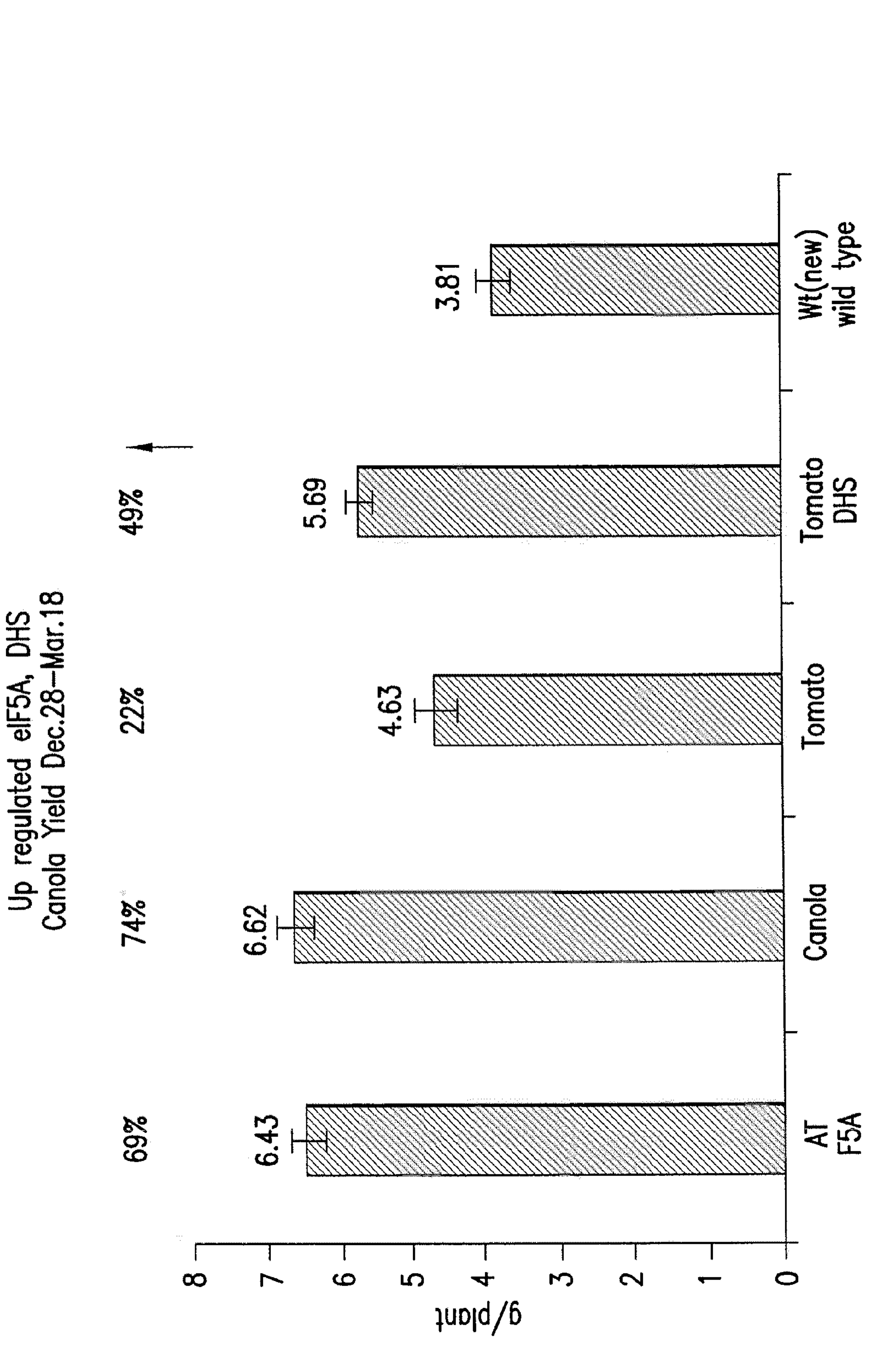
FIG. 100 shows in bar graph form that up regulation of growth isoforms of eIF-5A from left to right *arabidopsis*, canola, tomato, and up regulation of tomato DHS.
Figure 106:
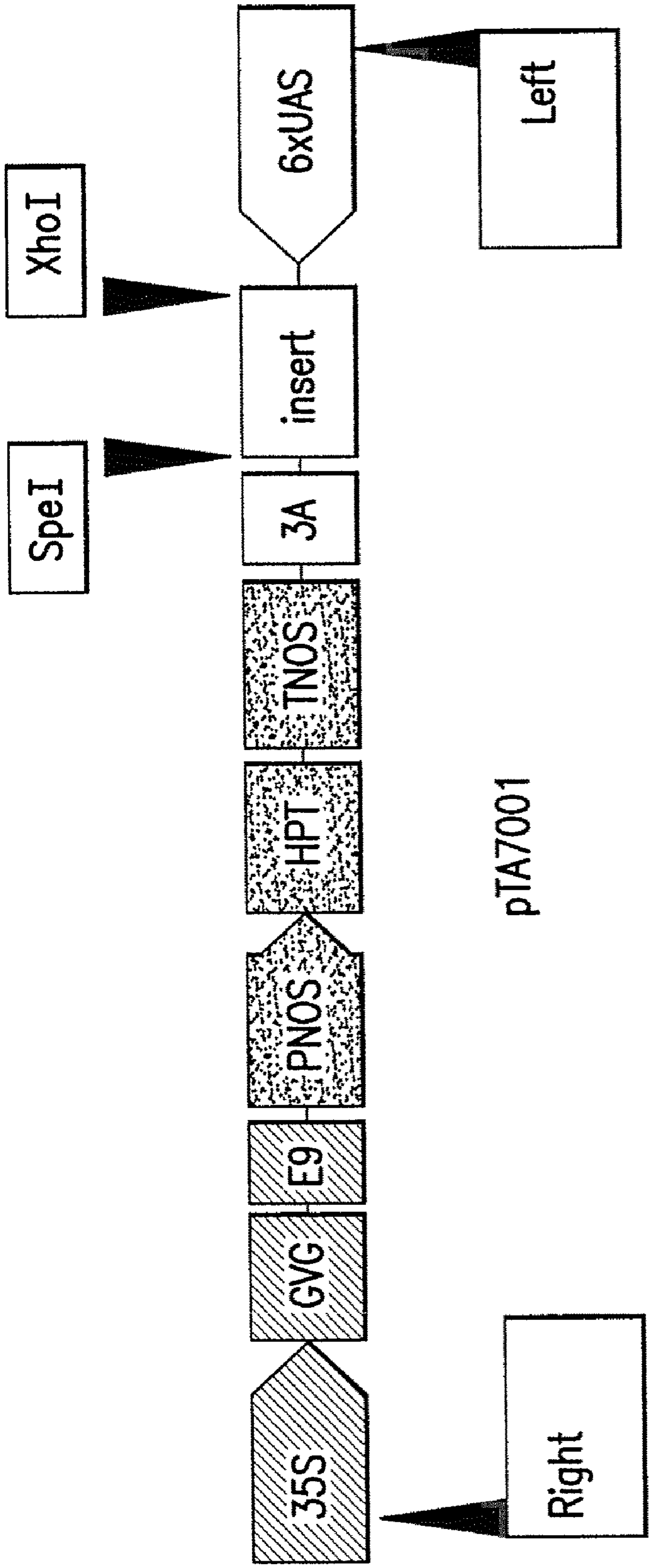

Fruit from these transgenic plants with reduced DHS expression were completely free of blossom end rot under conditions in which about 33% of fruit from control plants developed this disease. Blossom end rot is a physiological disease attributable to nutrient stress that causes the bottom (blossom) end of the fruit to senesce and rot. FIGS. 84A and 84B are photographs showing a control fruit exhibiting blossom end rot and a transgenic fruit that is free of blossom end rot.

The results indicate that reducing the expression of DHS prevents the onset of tissue and cell death arising from physiological disease.

Example 16

Expression of *Arabidopsis thaliana* Translation Initiation Factor 5A (AteIF-5A) Isoforms in Wild Type Columbia—Plant Material Seeds of *Arabidopsis thaliana*, ecotype Columbia, were grown in Promix BX soil (Premier Brands, Brampton, ON, Canada) in 6-inch pots. Freshly seeded pots were maintained at 4° C. for 2 days and then transferred to a growth chamber operating at 22° C. with 16-h light/8-h dark cycles. Lighting at 150 μmol radiation $m^{-2}\cdot s^{-1}$ was provided by cool-white fluorescent bulbs. Whole rosettes were collected one week intervals at 2 weeks to 7 weeks of age, cauline leaves were collected at 5 weeks, stem, siliques, buds, and flowers were collected at 6 weeks and imbibed seeds (24 hours in water) were also collected, flash frozen in liquid nitrogen and stored at −80° C.

Infection of *Arabidopsis thaliana* plants with *Pseudomonas syringae*

Seeds of *Arabidopsis thaliana* ecotype Columbia were sown onto Promix BX soil (Premier Brands, Brampton, ON, Canada) in flats containing 64 growth cells. The seeded flats were maintained at 4° C. for 2 days and transferred to a growth chamber with photoperiod of 9-h light/15-h dark. All plants were treated at 4 weeks of age, though physiologically due to the shortened photoperiod these appear to be slower in development.

Rosette leaves of 4-week-old plants were infected with avirulent (avr) and virulent (vir) strains *Pseudomonas syringae* pv. Tomato DC 3000 obtained from Dr. Robin Cameron (university of Toronto, Toronto, Canada). The abaxial surface of the rosette leaves of each plant was inoculated using 1 ml syringe without a needle. Plants were treated using one of four treatments: no inoculation, mock-inoculation with 10 mM $MgCl_2$, inoculation with avr *P. syringae* strain ($10^6$ cfU/ml 10 mM $MgCl_2$) or inoculation with vir *P. syringae* strain (106 cfU/ml 10 mM $MgCl_2$). Two bacterial counts were made, one immediately after inoculation and the second 3 days later, to ensure that a sufficient amount of bacteria was infiltrated to induce systemic acquired resistance in the avr treatment. The inoculated leaves were harvested at predetermined time points for subsequent analysis.

Plants with reduced DHS or wounding-induced eIF-5A expression were developed using antisense T-DNA insertions for either gene. These plant lines have shown marked resistance to *Pseudomonas syringae* pv Tomato DC 300, with transgenic lines exhibiting up to a 99% decrease in bacterial load, relative to the wild type plants. See FIGS. 43 and 44. Data using crop plants have also indicated enhanced pathogen resistance.

Wounding of *Arabidopsis thaliana* Plants with Hemostat 4-week-old plants grown under normal lighting conditions were wounded by crushing with hemostat along the midvein (approximately 10% of the leaf surface) according to Stotz et al (2000). Tissue was harvested at 0 minutes, 1 hour and 9 hours and immediately frozen in liquid nitrogen and stored at −80° C. for further analysis.

RNA Isolation and Northern Blotting

Total RNA for Northern blot analysis was isolated from *Arabidopsis thaliana* rosette leaves according to Davis et al. (1986). The RNA was fractionated on a 1% agarose gel and transferred to nylon membranes. (Davis et. al., 1986). Immobilized RNA was hybridized overnight at 42° C. with radiolabeled 3'UTR portions of senescence-induced AteIF-5A, wounding-induced AteIF-5A or growth AteIF-5A. The 3'UTRs were labeled with [α-$^{32}$P]-dCTP using a random primer kit (Boehringer Mannheim). The hybridized membranes were washed twice in 2×SSC containing 0.1% SDS at 42° C. for 15 minutes and twice in 1×SSC containing 0.1% SDS at 42° C. for 30 minutes. Hybridization was visualized by autoradiography after an overnight exposure at −80° C.

Antibody Production and Purification

Eukaryotic translation initiation factor 5A (eIF-5A) isoforms of *Arabidopsis thaliana* (At) are highly homologous at the amino acid level, especially at the N-terminal region and the central region of the proteins (FIG. 1). In order to obtain antibodies that will be isoform specific, peptides were designed against regions in the isoforms of AteIF-5A that appeared to be unique to each other. An additional cysteine residue was added to each peptide at the N-terminus for conjugation with KLH. The sequences used were: CNDDTLLQQIKS (SEQ ID NO: 35) for senescence-induced AteIF-5A, CTDDGLTAQMRL (SEQ ID NO: 36) for wounding-induced AteIF5A, and CTDEALLTQLKN (SEQ ID NO: 37) for growth AteIF-5A. When these sequences were submitted to protein BLAST (short nearly exact sequences; limited by *Arabidopsis thaliana*; expected number 20000; word size 2; Matrix PAM90; Gap cost 91) the significant sequences that found in the database were only the matched AteIF-5A and no other. The peptides were synthesized at the University of Western Ontario Peptide Synthesis facility. The carrier protein, Keyhole Limpet Hemocyanin (Sigma), was conjugated to the N-terminal cysteine of the peptide using m-maleimidobenzoyl-N-hydroxysuccinimide ester according to Drenckhahn et al. (1993) and Collawn and Patterson (1999). The rabbits were injected four times at two-week intervals with the linked peptide. Two weeks after the final injection blood is collected by exsanguination of the rabbits and clotting of the collected blood in order to amass the antisera.

Protein Fractionation and Western Blotting

Tissues list above were homogenized (~0.5 g/ml) in buffer (50 mM EPPS, pH 7.4, 0.25M sorbitol, 10 mM EDTA, 2 mM EGTA, 1 mM DTT, 10 mM amino-n-caproic acid, Protease Inhibitor Cocktail for Plant tissues (Sigma)) in an eppendorf tube with a small pestle, or in a large mortar and pestle. The homogenates were centrifuged briefly in the microcentrifuge at maximum speed and the pellet was discarded. The total protein was quantified according to Ghosh et al. (1988). SDS-PAGE was performed on Mini protein Dual Slab cells (Bio-Rad, Mississauga, Ontario), and the gels (12% polyacrlyamide) were stained with Coomassie brilliant blue R250 (Fairbanks et. al. 1971) or transferred to polyvinyldiene difluoride (PVDF) membranes using the semi-dry transfer method (semi-dry transfer cell, Bio-Rad, Hercules, Calif.). The blots were blocked for 30 s in 1 mg/ml polyvinyl alcohol (Miranda et. al., 1993) and for 1 hour in phosphate-buffered saline (PBS) containing 0.1% (v/v) Tween 20 and 5% (w/v) powdered milk. Primary antibody (from bleeds after second injection) was diluted 1:50 in PBS containing 0.1% (v/v) Tween 20 and 1% (w/v) powdered milk. Antigen was visualized using secondary antibody made in goat against rabbit antibody coupled to alkaline phosphatase (Bioshop, Burlington, Ontario) and the phosphatase substrates, NBT and BCIP (BioRad, Mississauga, ON).

Example 17

Production of Transformed *Arabidopsis thaliana* Plants Over Expressing the Three eIF-5A Isoforms Primer Design Eukaryotic translation initiation factor 5A (eIF-5A) isoforms of *Arabidopsis thaliana* (At) are highly homologous in the coding region (FIG. 2). To avoid problems with amplification of the correct genes, primers for senescence-induced AteIF-5A, wounding-induced eIF-5A and growth eIF-5A were designed from the approximate beginning of the 5'UTR and at the end of the 3'UTR as shown in FIGS. 3, 4 and 5 respectively. The 5'UTR and 3'UTR were estimated based on EST information and other sequence information in the GenBank database. The appropriate restriction sites were added to the ends of the primers for ligation in the sense orientation in the pKYLX71 binary vector (FIG. 6). For senescence-induced AteIF-5A the upstream primer is 5' AAGCTT GATCGTGGTCAACTTCCTCTGTTACC 3' (SEQ ID NO: 38) and the downstream primer is 5' GAGCT CAGAAGAAGTATAAAAACCATC 3' (SEQ ID NO: 39). For wounding-induced AteIF-5A the upstream primer is 5' CTC GAGTGCTCACTTCTCTCTCTTAGG 3' (SEQ ID NO: 40) and the downstream primer is 5' GAGCTCA AGAATAACATCTCATAAGAAAC 3' (SEQ ID NO: 41). The upstream primer for growth AteIF-5A is 5' CTC GAGCTAAACTCCATTCGCTGACTTCGC 3' (SEQ ID NO: 42) and the downstream primer is 5' GAGC TCTAGTAAATATAAGAGTGTCTTGC 3' (SEQ ID NO: 43). The restriction sites that were added into the primers were HindIII and SacI for senescence-induced AteIF-5A, XhoI and SacI for wounding-induced AteIF-5A, and XhoI and SacI for growthAteIF-5A as indicated by underlining in the primers listed above.

Isolation of Genomic DNA from *Arabidopsis thaliana*

Genomic DNA was isolated from 3-week-old rosette leaf. The tissue was homogenized in extraction buffer (200 mM Tris pH 7.5, 250 mM NaCl, 25 mM EDTA, 0.5% SDS) and the resulting homogenate was vortexed for 15 seconds. The remaining debris was removed by centrifugation in a microcentrifuge at maximum speed for 1 minute. The supernatant was collected and mixed in a 1:1 ratio with isopropanol, vortexed and left at room temperature for 2 minutes. A pellet was collected by centrifugation in a microcentrifuge at maximum speed for 5 minutes, washed with 70% ethanol and vacuum dried for 2 minutes. The dried pellet was resuspended in water and treated with 1:1 volume of chloroform and vortexed. After centrifugation in a microcentrifuge at maximum speed for 2 minutes the top layer was collected and treated with 20 μl salt (3M sodium acetate) and 2 volumes of ethanol for precipitation at −20° C. for 30 minutes. The purified genomic DNA was then centrifuged at maximum speed for 30 minutes in a microcentrifuge, dried and resuspended in water for PCR.

PCR from Genomic DNA

PCR was performed with the primers described above. The PCR reaction mixture contained 1× Tsg or Taq polymerase reaction buffer, 1 U of Tsg or Taq polymerase, 0.2 mM dNTP, 2 mM $MgCl_2$, and 15 pmols of each specific primer accordingly. The reaction began with a hot start at 95° C. for 10 minutes and first cycle consisted of 1 minute denaturing temperature of 95° C., 2 minutes annealing temperature of 55° C., and a 2 minute extension temperature of 72° C. The following 29 cycles proceeded a touchdown program where the annealing temperature was decreased by 0.5° C. per cycle, and the final cycle had an annealing temperature of 40° C. The final extension of 72° C. was held for 10 minutes. The PCR products were separated by 1% agarose gel electrophoresis, cut out and retrieved by Millipore Ultrafree-DA for DNA Extraction from Agarose spin columns (Millipore Corporation, Bedford, Mass.) according to directions.

Ligation into pGEM®-T Easy

Purified PCR products were ligated into pGEM®-T Easy Vector (FIG. 7) according to directions provided by Promega. Briefly, PCR products were mixed in a 3:1 ratio with pGEM T-Easy Vector, 3 Weiss Units T4 DNA ligase in Rapid Ligation Buffer (30 mM Tris-HCl, 10 mM $MgCl_2$, 10 mM DTT, 1 mM ATP, and 5% polyethylene glycol (MW8000, ACS Grade) pH 7.8) provided in the Promega pGEM®-T Easy Vector System (Promega Corporation, Madison Wis.). The ligation reaction was incubated overnight at 15° C. and transformed into competent *E. coli* DH5-α cell suspension (made competent using RbCl/CaCl; Kushner, 1978). The transformation mixture was first incubated on ice for 30 minutes, heat shocked for 90 seconds at 42° C., and allowed to recover at 37° C. for 1 hour after the addition of 1 ml 2xYT broth. The transformed cells were pelleted, resuspended in a small volume of 2xYT broth and plated on agar plates containing 50 μg/ml ampicillin for selection. Only transformants are able to grow on the ampicillin-containing plates as the pGEM®-T Easy Vector provides ampicillin resistance to the cells. Transformants were selected and screened for the PCR product insert ligated into the pGEM®-T Easy Vector.

Screening for PCR Product Inserts in pGEMO-T Easy Vector through Restriction Enzyme Digestions Colonies that grew on selection media were grown in 5 ml 2xYT broth containing 50 μg/ml ampicillin overnight at 37° C. The recombinant plasmids from the selected colonies were purified using Wizard Prep DNA Purification Kit (Promega). The plasmid DNA was digested with EcoRI for 1 hour at 37° C. and visualized on a 1% agarose gel for verification that the AteIF-5As insert sizes were present. The positive plasmids were then sequenced by the Core Molecular Biology Facility (University of Waterloo, Waterloo, ON) for confirmation that the sequence is suitable for over expression in planta.

Ligation into pKYLX71

The constructs of pGEM:wounding-induced AteIF-5A, and pGEM:growth AteIF-5A were double digested with XhoI and SacI and sub-cloned into the binary vector, pKYLX71 that had also been digested with XhoI and SacI. These enzyme digestions ensured that wounding-induced AteIF-5A and growth AteIF-5A would be inserted in the sense orientation in the binary vector pKYLX71 under the control of the cauliflower mosaic virus double 35S promoter. The ligation reactions used 1 μg of binary vector and 3 μg of either wounding-induced AteIF-5A or growth AteIF-5A. Ligation took place in ligation buffer (30 mM Tris-HCl, 110 mM $MgCl_2$, 10 mM DTT, 1 mM ATP, and 5% polyethylene glycol (MW8000, ACS Grade) pH 7.8) with 3 Weiss units of T4 DNA Ligase (Fermentas). The ligation reaction was incubated overnight at 15° C. and transformed into competent *E. coli* DH5-α cell suspension (made competent using RbCl/CaCl; Kushner, 1978). The transformation mixture was first incubated on ice for 30 minutes; heat shocked for 90 seconds at 42° C. and allowed to recover at 37° C. for 1 hour after the addition of 1 ml 2xYT broth. The transformed cells were pelleted, resuspended in a small volume of 2xYT broth and plated on agar plates containing 50 μg/ml tetracycline for selection. Only transformants are able to grow on the tetracycline-containing plates as the binary vector pKYLX71 provides tetracycline resistance to bacterial cells. Transformants were selected and screened for wounding-induced AteIF-5A or growth AteIF5A insert by PCR and double digestion with XhoI and SacI. Following PCR amplification (same as was done with genomic DNA explained above) and digestion, the products were separated using 1% agarose electrophoresis for conformation of the correct sized insert.

*Agrobacterium* Electroporation and Selection

The constructs pKYLX71:wounding-induced AteIF-5A and pKYLX71:growth AteIF-5A was electroporated into competent *Agrobacterium tumefaciens* GV3010. The preparation of competent *Agrobacterium* cells a single colony was inoculated in 5 ml of 2xYT broth containing 50 μg/ml of rifampicin, and 50 μg/ml gentamycin. This grew overnight at 28° C. in a Form a Scientific Orbital Shaker (Fisher Scientific) at 280 rpm and was used to inoculate 30 ml cultures of 2xYT also with 50 μg/ml of rifampicin, and 50 μg/ml gentamycin at various dilutions (1:500, 1:1000, 1:2000). The newly inoculated cultures grew until $OD_{600}$ was between 0.5 and 0.8 before being cooled and centrifuged down in an SS-34 rotor (Sorvall) at 2000 g for 15 minutes. The pellets were resuspended in 50 ml of ice-cold water and centrifuged at 2000 g for 15 minutes. This washing procedure was repeated for a total of four times to remove the salts and the dead cells from the culture. The final pellet was resuspended in 40 ml ice cold 10% (v/v) glycerol and centrifuged at 2000 g for 15 minutes and repeated once. The pellet was then resuspended in 100 μl ice-cold 10% glycerol and mixed well. Cells were split up into aliquots of 100 μl and stored on ice.

For electroporation of the DNA constructs into the competent *Agrobacterium* cells the 100 μl aliquots were each mixed well with 500 ng of DNA construct. The bacteria:vector mixture was then transferred to a pre-cooled electroporation cuvette and placed in the Gene Pulser (Biorad) adjusted to the following settings: 2.5 kV, 25gF, and 200%. After electroporation 1 ml 2xYT broth was added and the whole suspension was transferred to a culture tube. The electroporated cultures were incubated at 28° C., 280 rpm, for 3 hours to allow them to recover and then 2 ml 2×YT both was added as well as 50 μg/ml of rifampicin, and 50 μg/ml gentamycin. After 2 days of growing in culture the electroporated cells were plated on tetracycline, gentamycin and rifampicin (all at 50 μg/ml) and colonies grew after an addition 2 days. The resulting colonies were screened for pKYLX71:wounding-induced AteIF-5A or pKYLX71:growth AteIF-5A by PCR and double digestion with SacI and XhoI, and visualized by separation on a 1% agarose gel.

Plant Transformation

A positive colony of *Agrobacterium tumefaciens* GV3010 containing either pKYLX71:wounding-induced AteIF-5A or pKYLX71:growth AteIF-5A were used for the transformation of wild type *Arabidopsis thaliana* ecotype Columbia. In preparation of the bacterial slurry used for plant transformation a single colony positive for pKYLX71:wounding-induced AteIF-5A or pKYLX71:growth AteIF-5A construct was inoculated in 5 ml of 2xYT broth containing 50 μg/ml of tetracycline, 50 μg/ml of rifampicin, and 50 μg/ml gentamycin. This grew for 2 days at 28° C. in a Form a Scientific Orbital Shaker (Fisher Scientific) at 280 rpm and was used to inoculate 35 ml (total) 2xYT also with 50 μg/ml of rifampicin, and 50 μg/ml gentamycin. The 35 ml culture was grown overnight at 28° C., 280 rpm, and used to inoculate 535 ml (total) 2xYT with 50 μg/ml of rifampicin, and 50 μg/ml gentamycin. Again the culture was grown overnight at 28° C., 280 rpm, to an $OD_{600}$ of about 2.0.

The cultures were transferred to two 250 ml tubes before centrifugation for 15 minutes at 1945 g at 4° C. in a GSA rotor (Sorvall). The pellets were resuspended in 500 ml of infiltration media (1.1 g MS salts, 25 g sucrose, 0.25 g MES, pH5.7 with KOH, 100 ng/ml benzylaminopurine and 50 μl Vac-In-Stuff (Silwet L-77; Lehle Seeds)) and placed in a large plastic dish in a vacuum desiccator with 4 large rubber stoppers. Five pots containing 8 plants each at the right stage of development were used sequentially for infiltration. Each pot was first inverted over a trash can to remove any loose soil, then was placed (still inverted) into plastic container in the glass desiccator so that the 4 large rubber stoppers acted as stand for the inverted pot thus allowing the bolts to be dipped into the *Agrobacterium* slurry, but not the rosettes. The plants were then subjected to a vacuum (400 mm Hg) in this inverted state for 10 minutes. The vacuum infiltrated plants were then allowed to recover and grown as usual in the growth chamber conditions explained in the plant material section. After several weeks when the siliques were dry and seed matured, the seeds were collected with each pot pooled together.

Selecting plant transformants and Segregation Analysis

To identify primary transformants, seeds from the vacuum-infiltrated plants were surface sterilized in a solution of 1% (v/v) sodium hypochlorite and 0.1% (v/v) Tween 80 for 20 minutes on a rotator (Barnstead/Thermolyne), rinsed four times with sterile water, and resuspended in a sterile 0.8% agar. The resuspended seeds were then planted onto sterile, half-strength Murashige and Skoog (MS) medium (2.2 g/L) supplemented with 1% (w/v) sucrose, 0.5 g/L 2-[N-Morpholino]ethanesulfonic acid (MES), 0.7% (w/v) bacteriological agar and 40 to 50 μg/ml kanamycin (Murashige and Shoog, 1962). Only transformants are able to grow on the kanamycin-containing plates since the binary vector provides the kanamycin resistance gene to the transformant seedlings (FIG. 6). Seedlings that do not harbour the binary vector become yellow and die, as there is no kanamycin resistance gene. Wild-type seedlings were used as controls and plated onto MS medium without kanamycin added to the medium, as well seeds from a homozygous line containing empty pKYLX71 vectors were seeded as controls on kanamycin containing plates. The empty vector control is useful in demonstrating the effect kanamycin has on growth of the seedlings as well as the effect of random integration of the binary vector into the genome of *Arabidopsis thaliana*. A small amount of wild type seed was plated onto a small area of each plate containing MS medium and 40 to 50 μg/ml kanamycin. This was done in order to make sure the medium was selective enough for the transformants and to test the strength of the kanamycin.

The seeded plates were kept at 4° C. for 3 days to synchronize the germination. After 3 days the plates were transferred to growth chambers where they grew for an additional 7 days under 16-h light/8-h dark cycles at 20±2° C. Lighting was maintained at 150 μmol radiation $m^{2} \cdot s^{-1}$ and was provided by cool-white fluorescent bulbs. The efficiency for transformation of *Arabidopsis thaliana* plants with the pKYLX71: wounding-induced AteIF-5A and pKYLX71:growth AteIF-5A vectors was determined.

After a total of 10 days since seeding, the 14 transformants or the 16 transformants for Sense wounding-induced AteIF-5A and Sense growth AteIF-5A respectively were transplanted to Promix BX soil (Premier Brands, Brampton, ON, Canada) in flats containing 32 cells. These transplanted T1 generation plants were then transferred into another growth chamber operating at 22° C. with 16-h light/8-h dark cycles. Lighting at 150 μmol radiation $m^{-2} \cdot s^{-1}$ was provided by cool-white fluorescent bulbs. The T1 generation plants grew to maturity and produced T2 generation seeds. These were harvested and stored at −20° C. until further screening was done. The T1 generation was named 1, 2, 3, etc. All 16 lines of Sense growth AteIF-5A plants survived and produced seeds, but only 9 out of 14 transformants of the Sense wounding-induced AteIF-5A plants survived and produced seeds.

The selection of T2 generation transformants was conducted in the same way as the T1 generation transformants. Line 12 of the Sense growth AteIF-5A plants produced no transformants on the selectable media and was not included in any further work. Lines 1 through to 16 (minus line 12) of the Sense growth AteIF-5A plants each had 8 sublines carried through. These were named A through H so that for example in the T1 line 1, the T2 generation plants were named 1A, 1B, 1C, etc. Lines 1, 2, 3, 4, 5, 7, 9, and 11 of the Sense wounding-induced AteIF-5A plants each had 8 sublines (A-H) carried through. Line 12 T1 plants had only produced about 30 T2 seeds and only 1 subline in the T2 generation will be carried through. T2 plants of Sense wounding-induced AteIF-5A are still growing and being characterized. The T2 plants for the Sense growth AteIF-5A have matured and produced seeds, which were harvested and stored at −20° C. until further analysis.

The selection of the T3 generation transformants of Sense growth AteIF-5A was conducted in the same manner as the T2. Eight lines were chosen based on phenotype analysis as well as the degree of over expression of Sense growth AteIF-5A. The levels of expression were broken down into four categories: high-level expression, medium-level expression, low-level expression, and no expression (due to co-suppression). Two lines were chosen for each of the levels of expression and 12 plants from each line were transplanted. The corresponding lines for these four levels of expression are: 1A, 2D, 4D, 15A, 8D, 9H, 11C and 16C. The T3 generation for Sense growth AteIF-5A plants are still growing and being characterized.

Example 18

Phenotype Analysis of Sense Wounding-Induced AteIF5A and Sense growth AteIF5A: Photographic Record Morphological phenotypes of the Sense wounding-induced AteIF-5A and Sense growth AteIF-5A lines were recorded photographically during segregation, as were the phenotypes of the corresponding control wild type plants (*Arabidopsis thaliana* ecotype Columbia) and plants transformed with an empty binary vector pKYLX71.

Seed Measurements

T3 seeds collected from T2 plants of Sense growth AteIF-5A were measured for total seed yield (both weight and volume), seed size (length and width), and calculated individual weight and volume of produced seed. Total seed yield by weight was measured on a Sartorius analytical digitized scale, and the volume was determined by pouring and packing down the total seed yielded by each plant into a glass 1 ml syringe that was graduated every 100 μl. To determine the seed size by length, width and calculated volume, the seeds were placed on a slide containing a micrometer and viewed on an Olympus BX51 Microscope. Photographs of the seeds on the micrometer were taken with a Spot Insight Color Camera (Diagnostic Instruments Inc.) attached to a Compaq Evo D500 (Compaq Company Corporation; Intel® Pentium 4 CPU 1.7 GHz, 262 MG RAM, running Windows 2000). Using Image-Pro Express Version 4.0 for Windows. Measurements of 10 seeds in each subline were made using the micrometer in the image for size calibration. The measurements were imported into Microsoft Excel, and calculations such as standard error and volume were performed.

Example 19

Biochemical Analysis of Sense Wounding-Induced AteIF5A and Sense Growth AteIF5A-Protein Fractionation and Western Blotting The first cauline leaf from each subline of Sense growth AteIF-5A T2 plants were collected and proteins extracted as described above. Total protein from lines 1A, 2A, up to 16A were fractionated by 12% SDS-PAGE and transferred to a PVDF membrane. The blot was probed with growth αAteIF-5A at a 1:50 dilution. Control total protein was extracted from the first cauline leaf from wild type and empty binary vector control plants.

Example 20

Expression of *Arabidopsis thaliana* Translation Initiation Factor 5A (AteIF-5A) isoforms in Wild Type Columbia Several tissues were collected at different developmental stages and the extracted proteins from these tissues were used for Western blotting. The Western blot in FIG. 8 demonstrates that senescence-induced AteIF-5A is not present in the 2 week old rosette leaves, but is upregulated in the 3 week old rosette leaves and increases in abundance until 5 weeks and declines in abundance, but is still present at 7 weeks. No senescence AteIF-5A was detected in the PEG treated plants or control, but was present in the flower lane (which included senescent flowers) and in the imbibed seed lane reflecting senescence of cotyledonary tissues. When the blot was probed with the wounding-induced αATeIF-5A antibody, faint bands appeared in the siliques, imbibed seed and stem lanes. The band seen in the siliques and stem lanes may be due to the wounding that occurred with collection of the tissue. Since it is difficult to collect the siliques and stem, they were not flash frozen immediately allowing for some up-regulation of the wounding-induced isoform of AteIF-5A. The only band that appeared when the blot was probed with growth αAT-eIF5A was imbibed seeds, keeping with the notion that this is the isoform involved in cell division.

Plants that were treated with either no treatment, mock inoculation with $MgCl_2$, avr *P. syringae* or with vir *P. syringae* were collected at several time points to analyze the expression of the AteIF-5As during pathogen ingress. The avr strain is recognizable by the plant and induces the hypersensitive response that leads to cell death or necrosis in the region of infection, thus disallowing the pathogen to cause disease. Furthermore the localized response eventually becomes a systemic response in order to protect the plant from further ingress. This is known as Systemic Acquired Resistance (SAR), which involves the expression of a suite of genes known as the Pathogenesis Response (PR) genes. On the other hand the vir strain will not be recognized by the plant, and will not induce a hypersensitive response and will lead to disease. The diseased state of *Arabidopsis thaliana* includes yellowing leaves and cell death after a few days post infection. After 72 hours post treatment control plants, mock treated plants, avr treated plants and vir treated plants were collected for western blotting with the three αAteIF-5A antibodies (FIG. 9). At this point both SAR and disease were visible in the avr treated and the vir treated plants respectively. When probed with the senescence-induced αAteIF-5A antibody, a band that was relatively the same in all the samples was observed. Since all of the plants were 4 weeks old this came with no surprise, since the senescence isoform was seen starting at 3 weeks in FIG. 8. When the blot was then probed with the wounding-induced αAteIF-5A antibody, a faint band was detectable in the untreated, mock treated and avr treated plants where there was a strong band detected in the vir treated plants. This upregulation of the wounding isoform may be due to cell death caused by disease (also a type of cellular wounding). The blot probed with growth αAteIF-5A did not show any bands and thus was not included in the figure. As the senescence-induced AteIF-5A did not change in expression during these treatments demonstrates its specificity for natural senescence. The increase in wounding-induced AteIF-5A expression also demonstrates its specificity for death due to wounding. To further investigate this possibility, an experiment was performed with wounding leaves of *Arabidopsis thaliana.*

The wounding experiment showed similar results as the pathogenesis experiment (FIG. 10). Northern blots were used to show the transcriptional change in of senescence-induced AteIF-5A, wounding-induced AteIF-5A and growth AteIF-5A. The probes were specific to each of the AteIF-5As and consisted of the 3' UTR of each. It was observed that like the pathogenesis experiment senescence-induced AteIF-5A expression did not change, as these were 4-week-old plants and samples were only taken over a 9-hour interval. This again is consistent with the fact that senescence-induced AteIF-5A is natural senescence specific isoform. The expression of wounding-induced AteIF-5A however did increase after 9 hours. There is probably some translational control occurring, as the transcript appears fairly constitutive (FIG. 10), but the protein does not appear as highly expressed when not induced (FIG. 9). The transcript for growth AteIF-5A was barely detectable in all the samples, and shows a decline in expression post wounding.

Example 21

Figure 11:
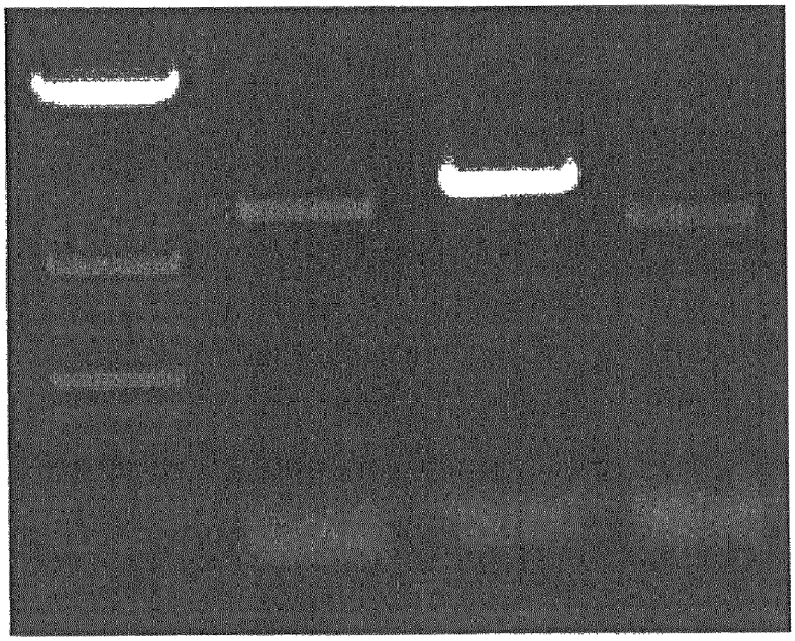
FIG. 11 depicts PCR products from genomic DNA of senescence-induced AteIF-5A, wounding-induced AteIF-5A, and growth AteIF-5A in lanes 1, 2 and 3 respectively.
Figure 13:
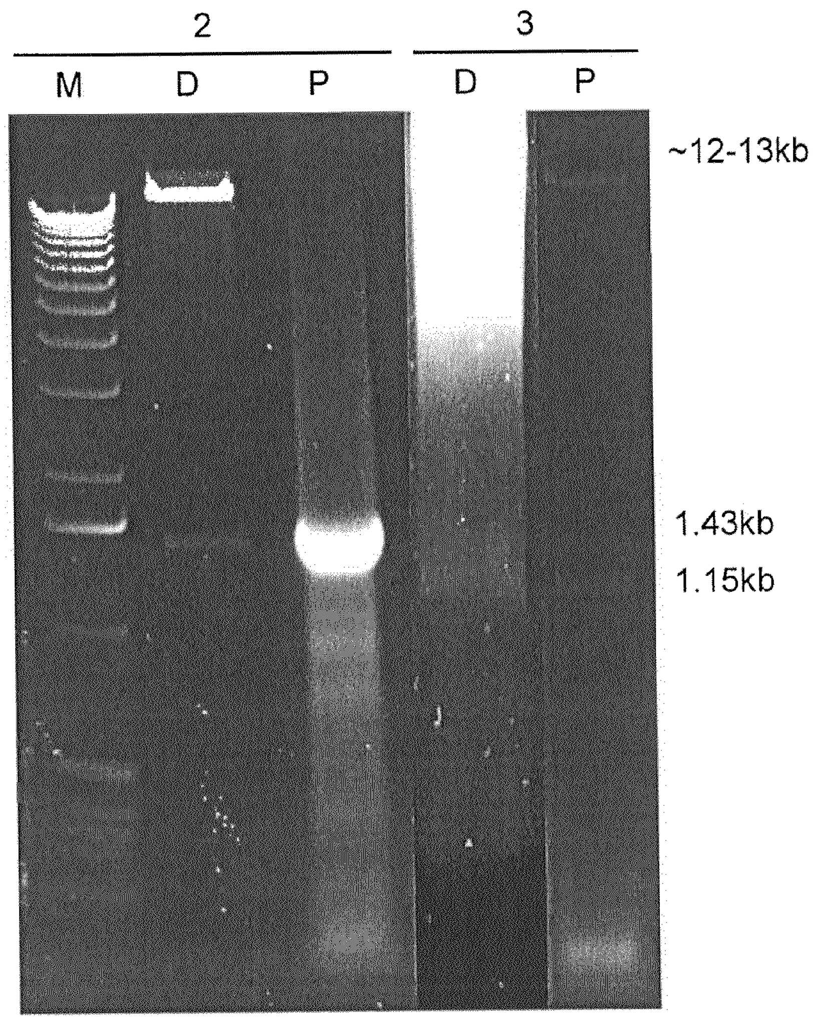
FIG. 13 shows an agarose gel with wounding-induced AteIF-5A, growth AteIF-5A, genomic sequences in pKYLX71.

Production of Transformed *Arabidopsis thaliana* Plants Over Expressing the Three eIF-5A Isoforms The AteIF-5As were isolated from genomic DNA by PCR (FIG. 11). The products were ligated in pGEM (FIG. 12) and the sequence was verified for suitability for over-expression inplanta. Wounding-induced AteIF-5A and growth AteIF-5A were double digested out of pGEM with XhoI and SacI and ligated in the sense orientation behind the cauliflower mosaic virus $35S^2$ promoter in pKYLX71. Positive ligation was confirmed by digestion and PCR (FIG. 13). The pKYLX71: senescence-induced AteIF-5A and the pKYLX71:growth AteIF-5A were then electroporated into *Agrobacterium tumefaciens* GV3010 for transformation via vacuum infiltration of *Arabidopsis thaliana* wild type of the ecotype Columbia. After plant transformation the seeds were collected and transformants selected for on Kanamycin containing MS plates.

*Arabidopsis thaliana* Plants Over Expressing Wounding-Induced AteIF-5A (Sense Wounding-Induced AteIF-5A)

Figure 14:
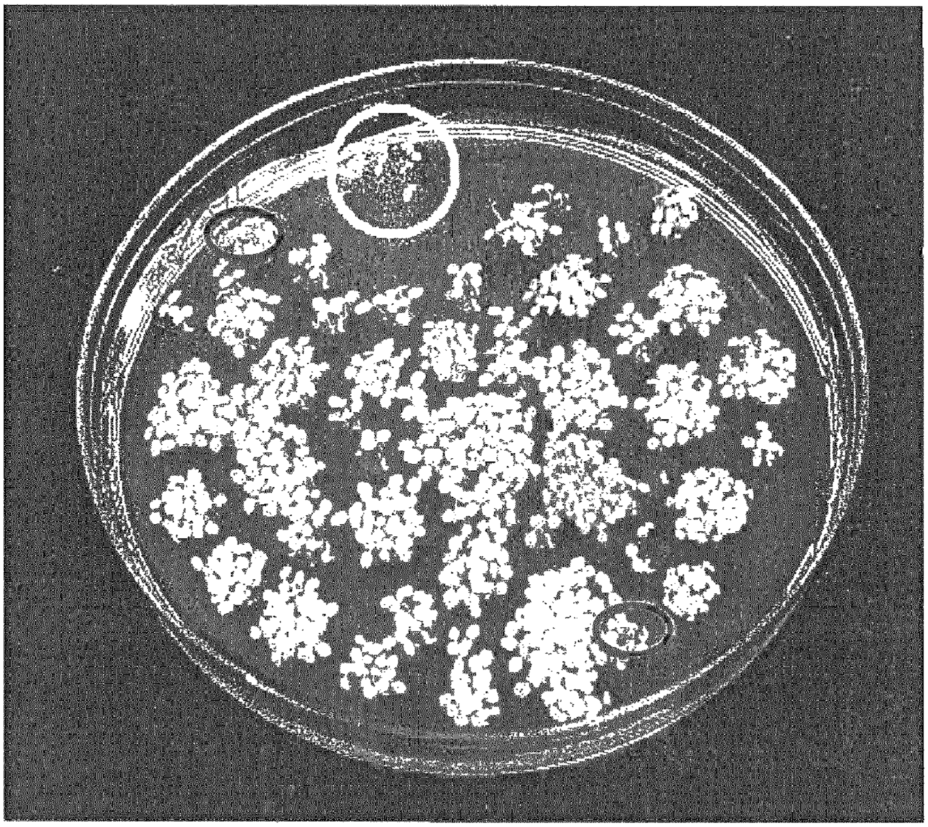
FIG. 14 is a picture of a T1 plate for plants transformed with a construct having sense wounding-induced AteIF-5A.
Figure 15:
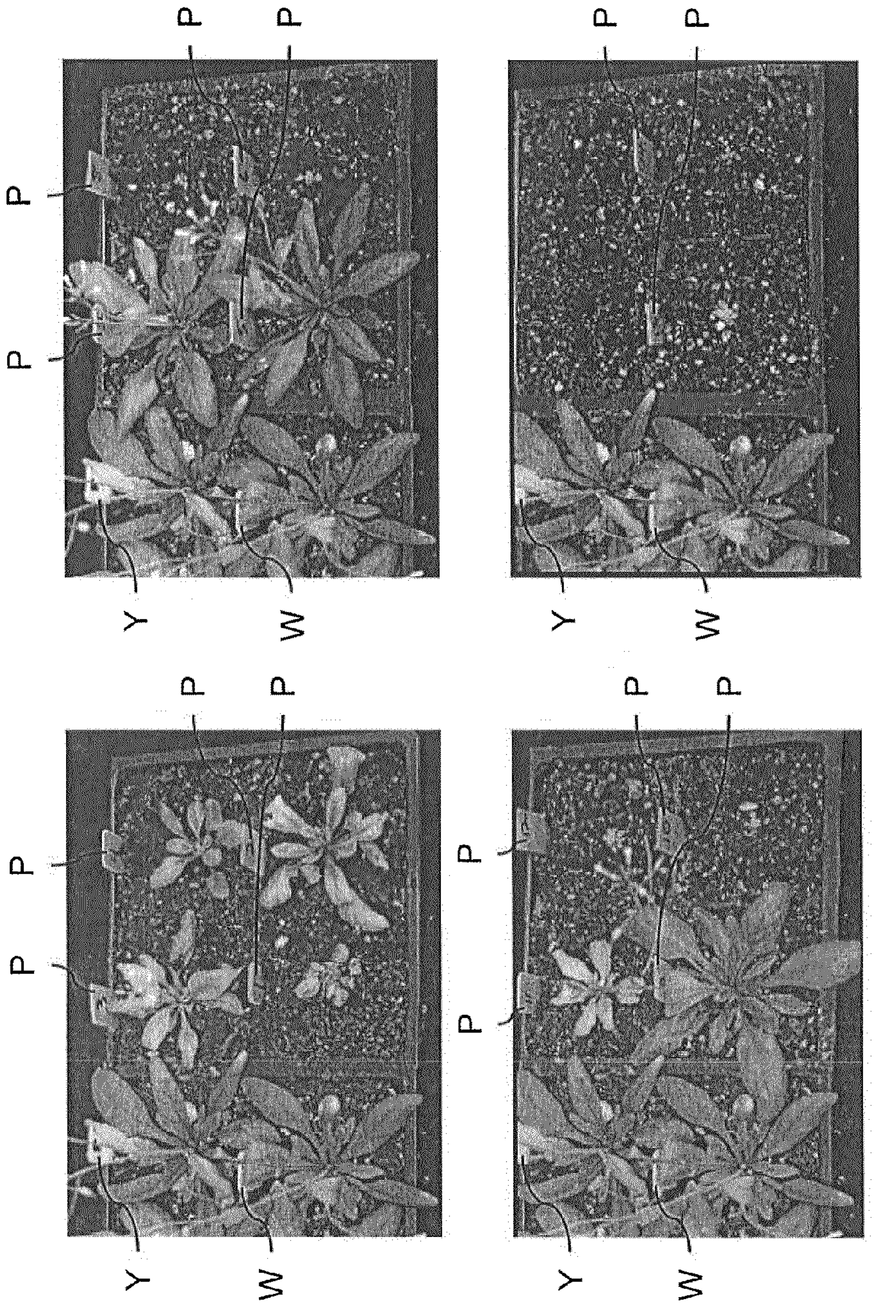
FIG. 15 is a picture of T1 plants transformed with Sense wounding-induced AteIF-5A at 4 weeks of age.
Figure 16:
FIG. 16 is a picture of T1 plants transformed with Sense wounding-induced AteIF-5A at 5.5 weeks of age.

T1 generation plants were seeded on MS plates containing 50 μg/ml Kanamycin and were stored at 4° C. for 3 days and in the growth chamber for 7 days (FIG. 14). There were 14 transformants that were transplanted to soil. A common phenotype in these 14 T1 generation plants was stunted growth. Lines 1, 4, 6, 8, 10, 11, 12, 13, and 14 were severely stunted in their growth and 6, 8, 10, 13 and 14 did not produce any seed. Lines 2 and 3 were moderately stunted whereas lines 5, 7 and 9 grew similarly to wild type plants (FIG. 15 and FIG. 16). Some other phenotypes observed in the T1 generation of Sense wounding-induced AteIF-5A plants included yellow leaves, purple cotyledons, curled up leaves and differences in flower shape. It is interesting to note that the appearance in the stunted growth was not observed until the plants were transplanted to soil. A possible explanation of this would be that during transplant the roots are damaged slightly (a consequence of transplanting that is unavoidable) and were unable to recover. In fact a preliminary experiment where seeds were soaked in a Kanamycin solution and seeded to soil directly no stunted plants were observed (whereas previously 70% of the plants had some degree of stunting), as no root damage would be invoked without transplantation.

Lines 1, 2, 3, 4, 5, 7, 8, 11 and 12 produced T2 seeds and were carried through (FIG. 17). Each T2 line has sublines A-H, except for 12, which only grew one transformant, and are currently being analyzed.

*Arabidopsis thaliana* Plants Over Expressing Growth AteIF-5A (Sense growth AteIF-5A)

Figure 18:
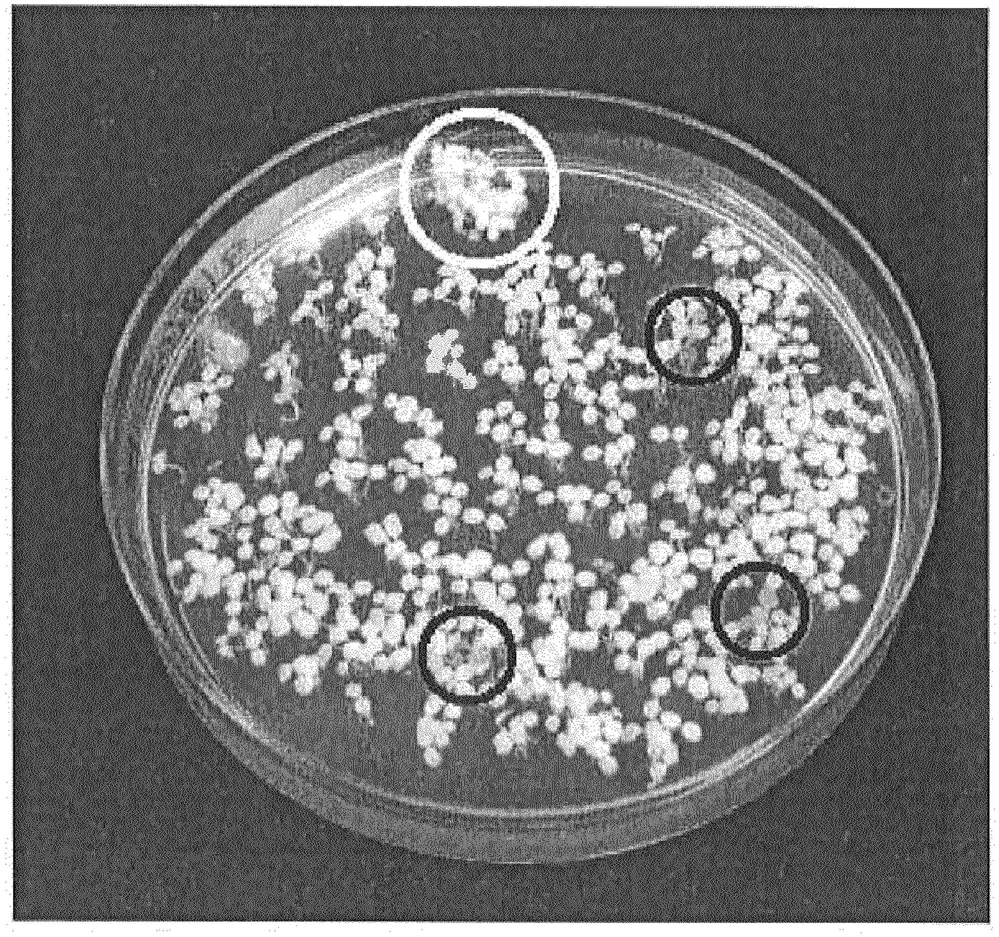
FIG. 18 is a picture of T1 plants transformed with Sense growth AteIF-5A at 10 days post seeding.

The T1 generation seeds of Sense growth AteIF-5A were grown on selective media and 16 transformants grew (FIG. 18). The transformants were photographed over their lifetime. The phenotypes varied from similar to wild type (Lines 1, 2, 5, 6, 7, 8, 10, 11, 12, 13, 14, 15, and 16) to moderately stunted and yellow (Lines 2, 4 and 9; FIG. 19). All the lines were carried through to T2 and each line had 8 sublines labeled A-H. Line 12 did not produce any transformants in T2 and was deemed to be wild type. The T2 generation plants had much more exaggerated phenotypes than that of T1 generation plants. The lines that were carried to T3 will be discussed in detail.

Figure 20:
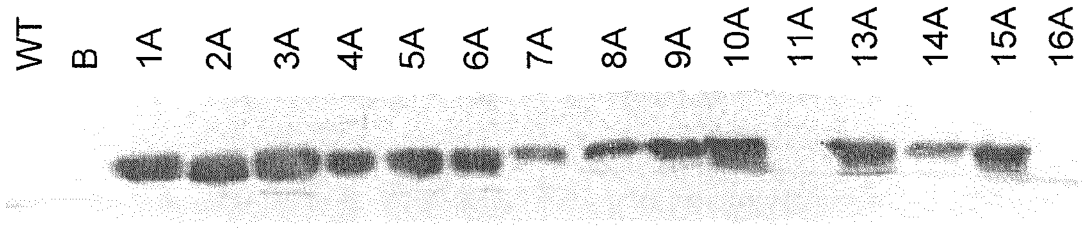
FIG. 20 is a Western blot of T2 plants transformed with Sense growth AteIF-5A lines.

The Sense growth AteIF-5A T2 generation lines were characterized in groups according to the level of expression of the growth AteIF-5A transgene. A Western blot was performed on protein extracted from cauline leaves from each line (FIG. 20). Since most of the sublines A-H demonstrated similar phenotypes within a line, the Western blot was only done with subline A of each line to get a general overview of level of expression of growth AteIF-5A. Protein from the cauline leaves of wild type plants and plants containing the empty binary vector were used as controls on the gels. The level of expression observed in these sublines can be categorized as high (Lines 1, 2, 3, 10, 13), medium (Lines 4, 5, 6, 15), low (Lines 7,8,9,14) or none (Lines 11, 16, wild type and binary control). The blots were also probed with antibodies against senescence-induced AteIF-5A and wounding-induced AteIF-5A. These westerns indicated that the increase in expression in the Sense growth AteIF-5A lines is due to growth AteIF-5A and not a general upregulation of other AteIF-5A isoforms, as no significant amount of either isoform was detected. This also demonstrated that the specificity of the isoform specific antibodies is acceptable.

The Sense growth AteIF-5A lines be carried through to the T3 generation were chosen based on phenotype as well as the level of expression of growth AteIF-5A (See Table 1 for a summary of phenotypes within each line). Two lines from each category of level of expression were chosen. The lines that will be carried through are 1A, 2D, 4D, 15A, 8D, 9H, 11C, and 16C.

Line 1 according to the western blot in FIG. 20, has a high level of growth AteIF-5A expression. These plants had large, dark green rosettes with leaves that were quite round in comparison to wild type plants (FIG. 21). The rosettes of line 1 also had a whorled phenotype, where the leaves all curl in the same direction. These Sense growth AteIF-5A plants bolted slightly later than wild type. Line 2 also demonstrated high level of growth AteIF-5A expression, but differed from line 1 in that these plants were small and yellowed (FIG. 22). Line 2 plants also bolted later than the wild type and binary control plants, as well produced smaller bolts (about half the size) and fewer siliques.

Of the medium level of expression lines, line 4 appeared similar to wild type in leaf/rosette size and in bolt size, though appeared to bolt just a few days before the wild type and binary control plants. The second line with a medium level of expression of growth AteIF-5A is line 15. These plants are, like line 4, very similar to wild type, but the area that the rosette occupied was larger than the controls (FIGS. 23 and 24). The leaves of the rosette also appeared to be rounder at the tips than the controls. The bolts however did not appear to have any distinctive phenotype.

The low expressing Sense growth AteIF-5A lines that will be carried through to T3 are from lines 8 and 9. Line 8 had very large leaves and large rosettes compared to the control plants (FIG. 25). The leaves also appeared to be wider and rounder than the control plants. The time of bolting, bolt size and number seemed to be consistent with the controls. The Sense growth AteIF-5A line 9 had similar leaf shape as in line 8, but was far more yellow and smaller (FIG. 26). As in line 2 (one of the high expressing lines), these plants show stunted growth, shorter bolts, but unlike line 2, line 9 bolted about the same time as the control plants.

The two lines 11 and 16 of the Sense growth AteIF-5A plants according to the western blot (FIG. 20) have no upregulated expression of growth AteIF-5A. This may be due to cosuppression of the transgene as well as the endogenous gene. Though these plants do look similar to the controls (FIG. 27 and FIG. 28), it is believed that the transgene is incorporated into the genome of lines 11 and 16 for several reasons. Firstly, they do have Kanamycin resistance as demonstrated by the selectivity on the Kanamycin containing MS plates. Secondly, the rosette size, leaf size, and bolt size of line 16 (FIG. 28) are at least 50% larger than the controls. But the strongest evidence is in the size and composition of the T3 seeds that they produced.

Figure 29:
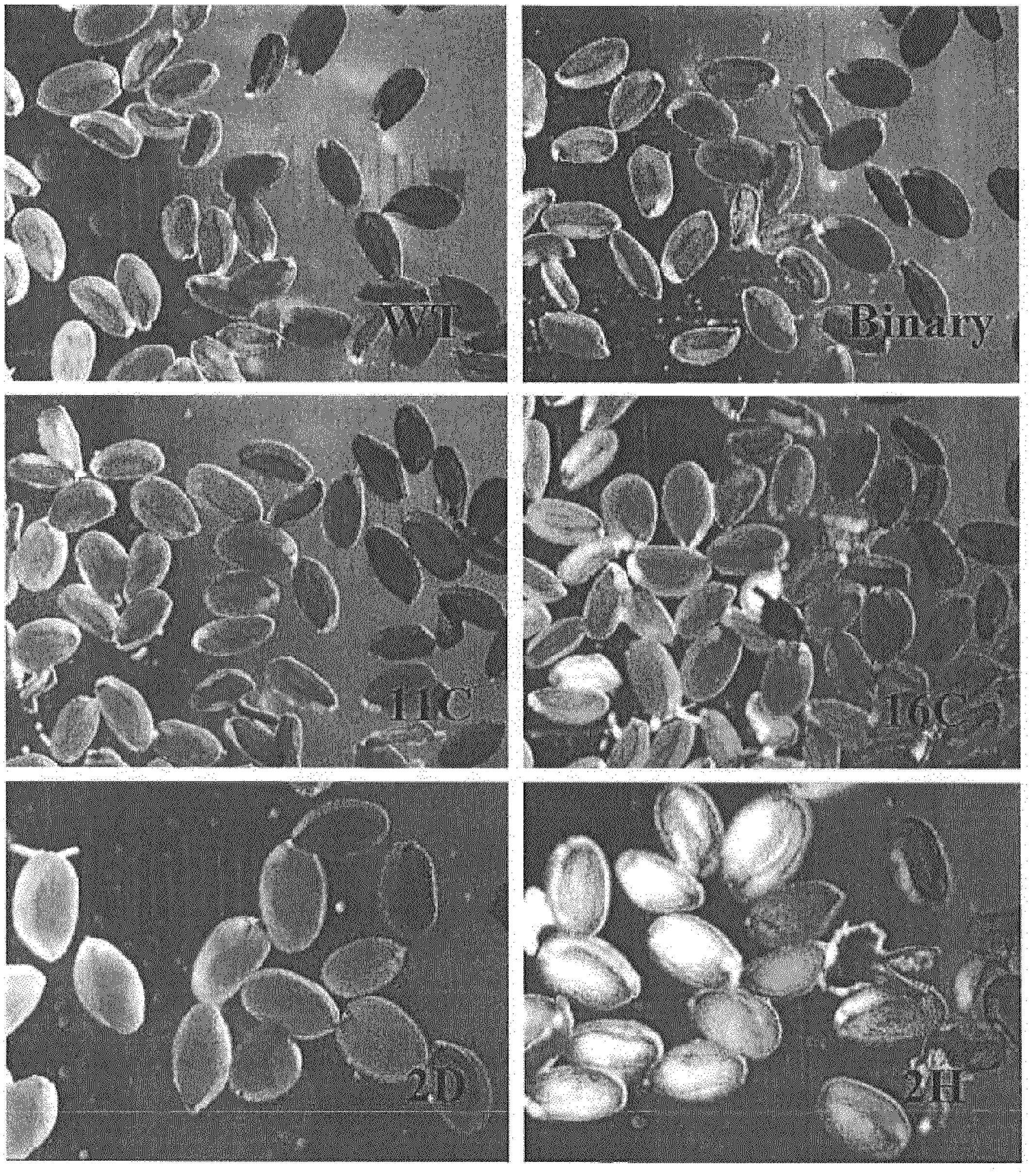
FIG. 29 are photographs of *Arabidopsis thaliana* seeds from various plant lines (including wild type control and plant lines having been transformed with sense growth AteIF-5A.
Figure 30:
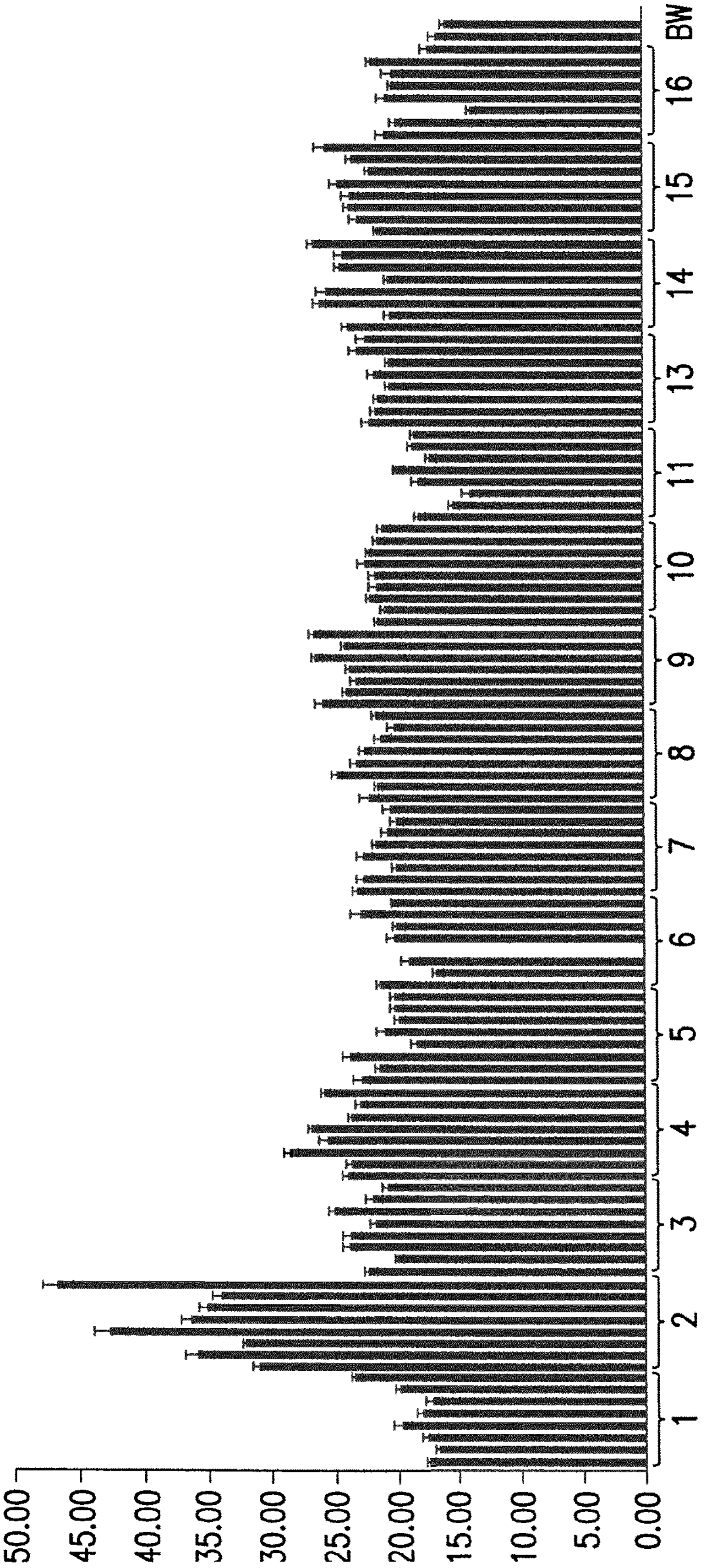
FIG. 30 is a bar graph of average seed size for each plant subline having been transformed with sense growth AteIF-5A.
Figure 31:
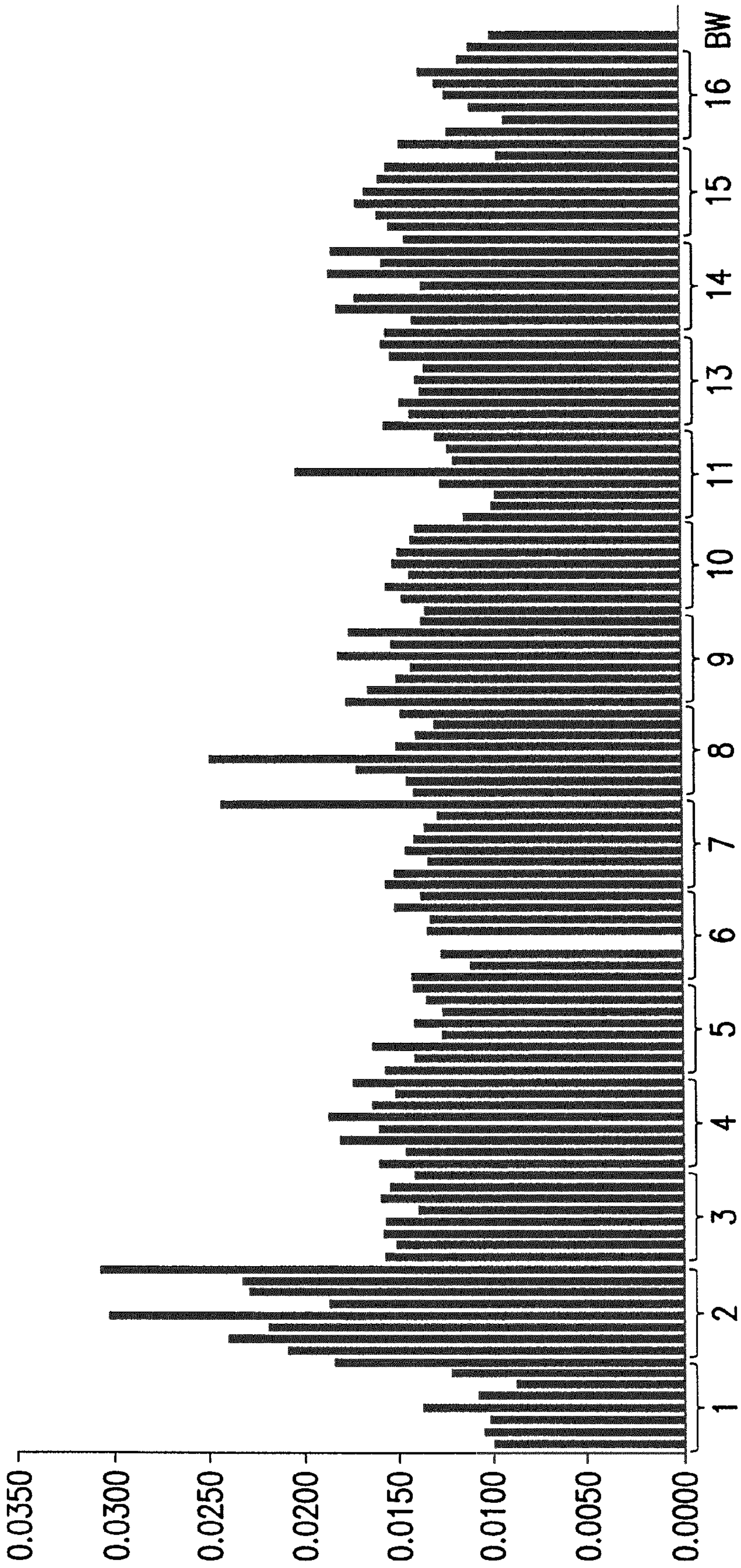
FIG. 31 is a bar graph of individual seed weight for each plant subline having been transformed with sense growth AteIF-5A.
Figure 32:
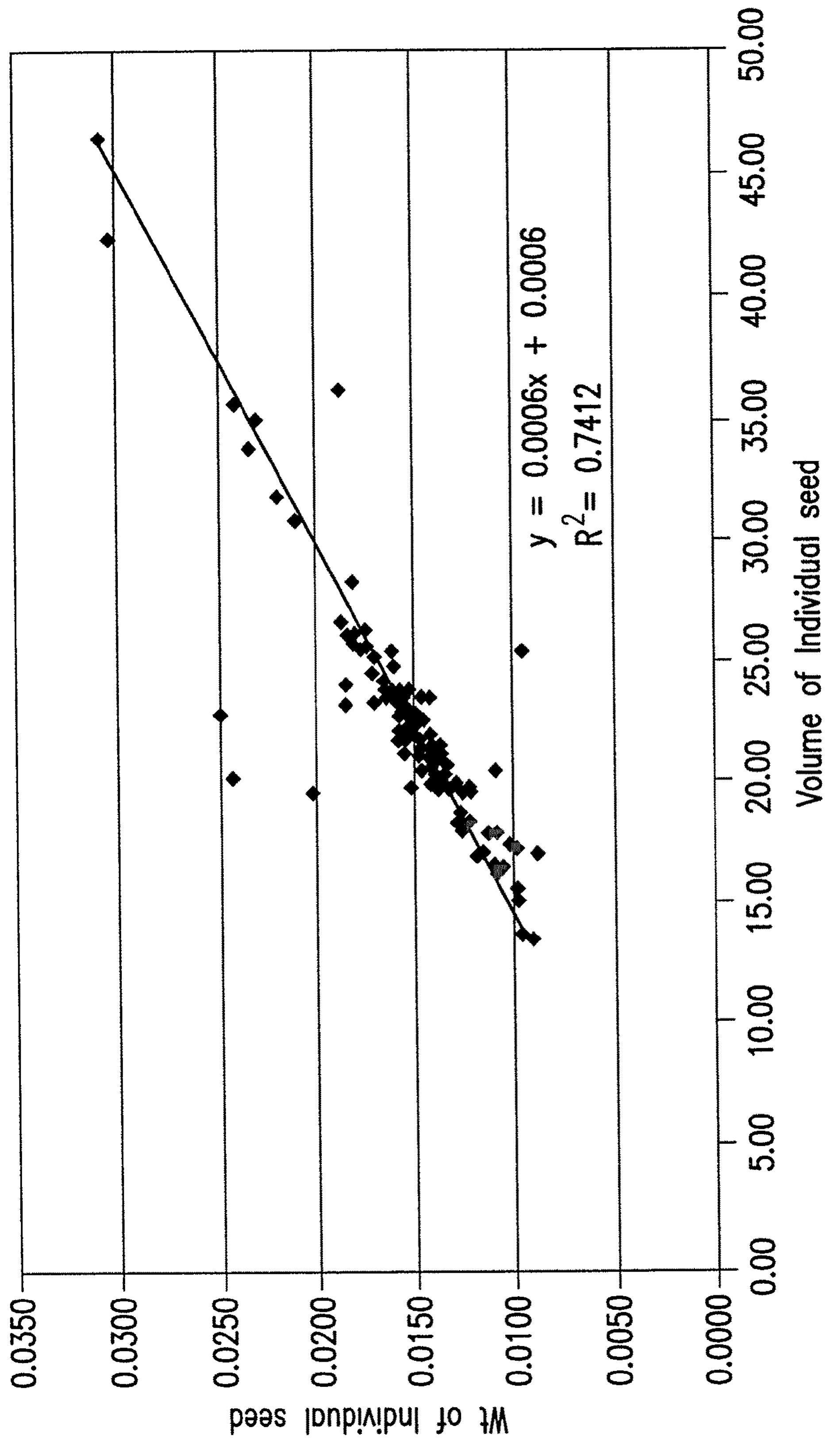
FIG. 32 is a graph showing the proportional relationship between the weight of the individual seeds versus the volume of individual seeds.
Figure 33:
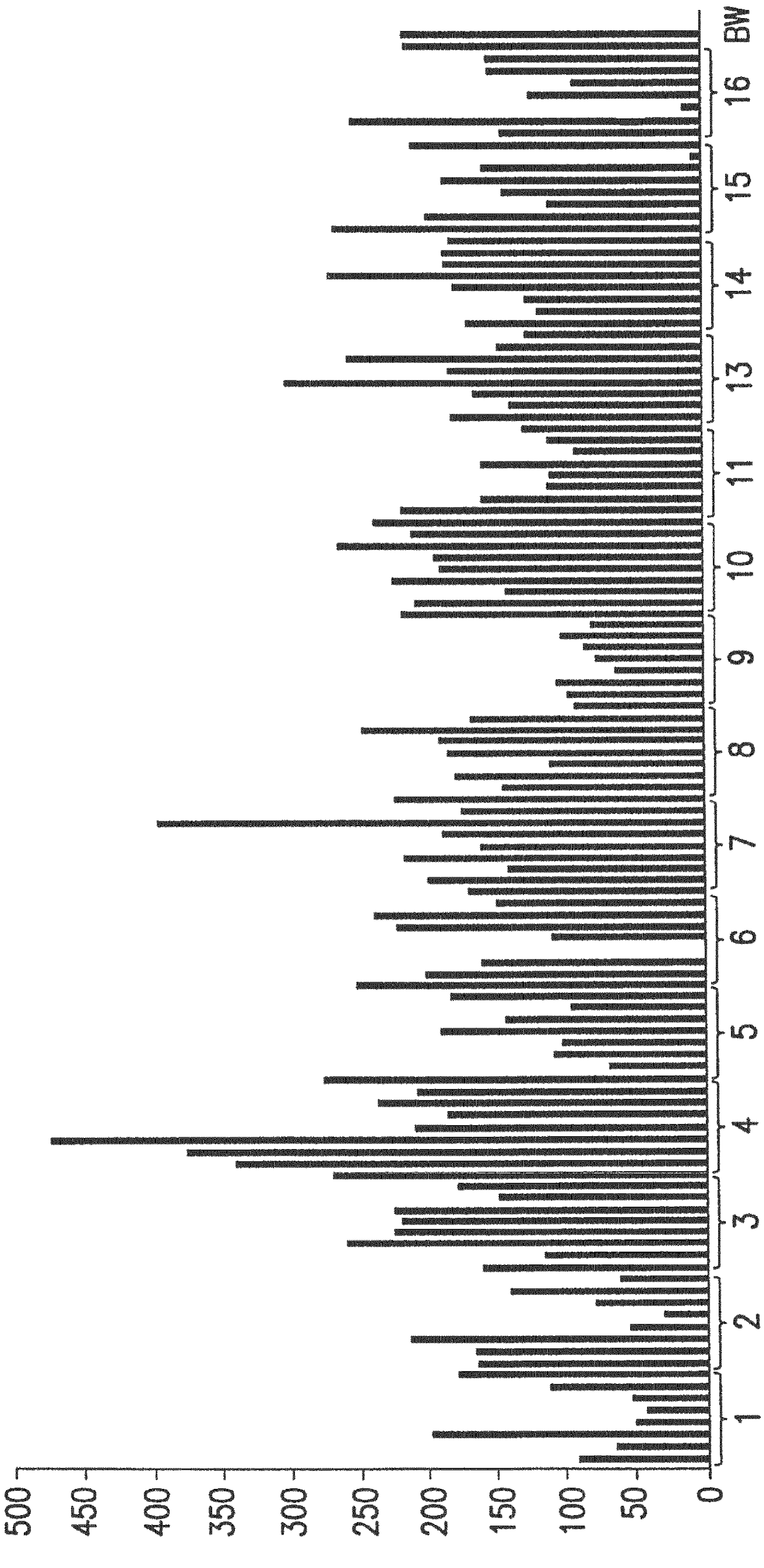
FIG. 33 is a bar graph showing seed yield per plant for each plant subline having been transformed with sense growth AteIF-5A.
Figure 35:
FIG. 35 shows a comparison of transgenic *arabidopsis* plant (transformed with antisense full length senescence-induced eIF-5A) with a wild type plant. The transgenic plant exhibits delayed senescence.
Figure 36:
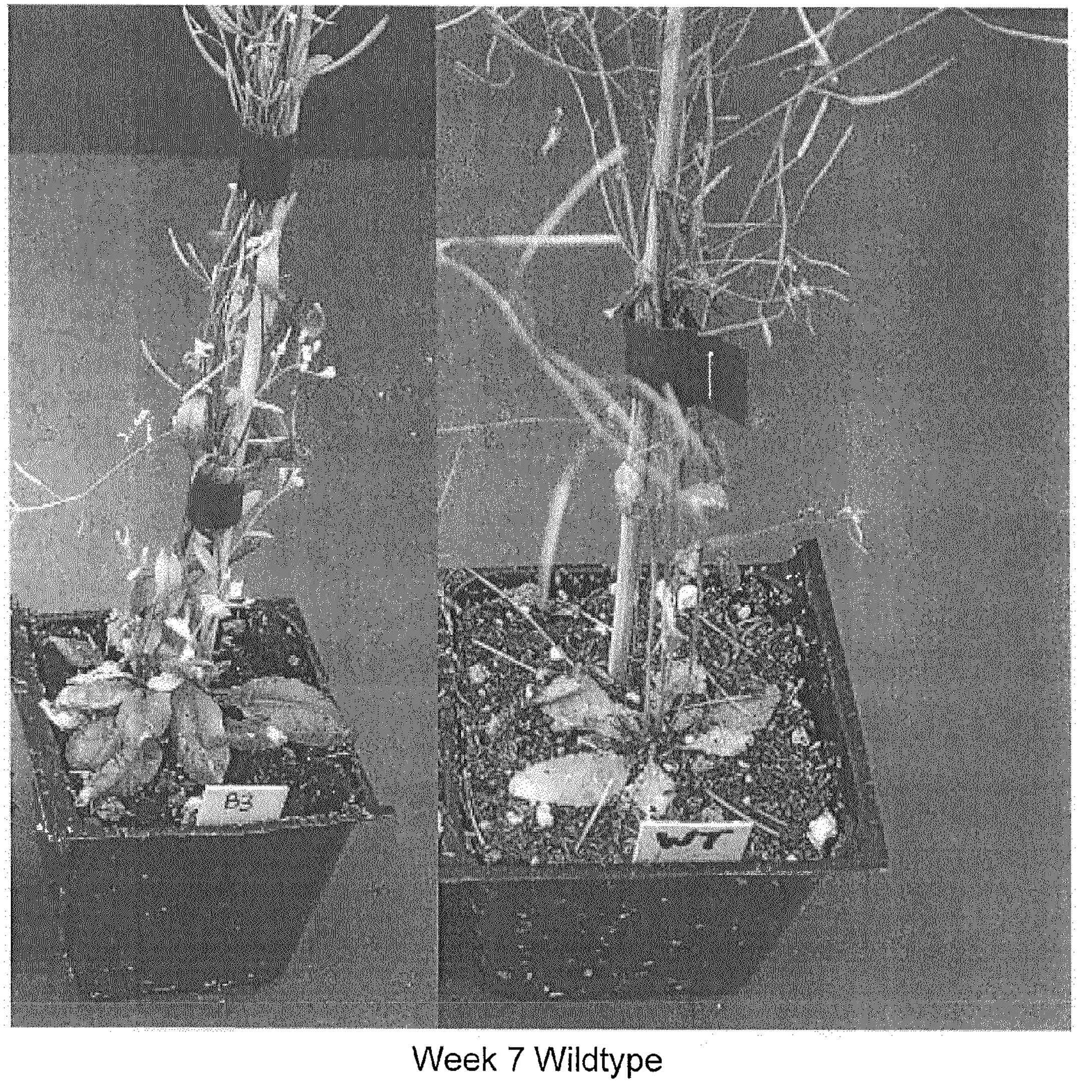
FIGS. 36-38 show photographs of a plant (transformed with antisense growth eIF-5A).
Figure 37:
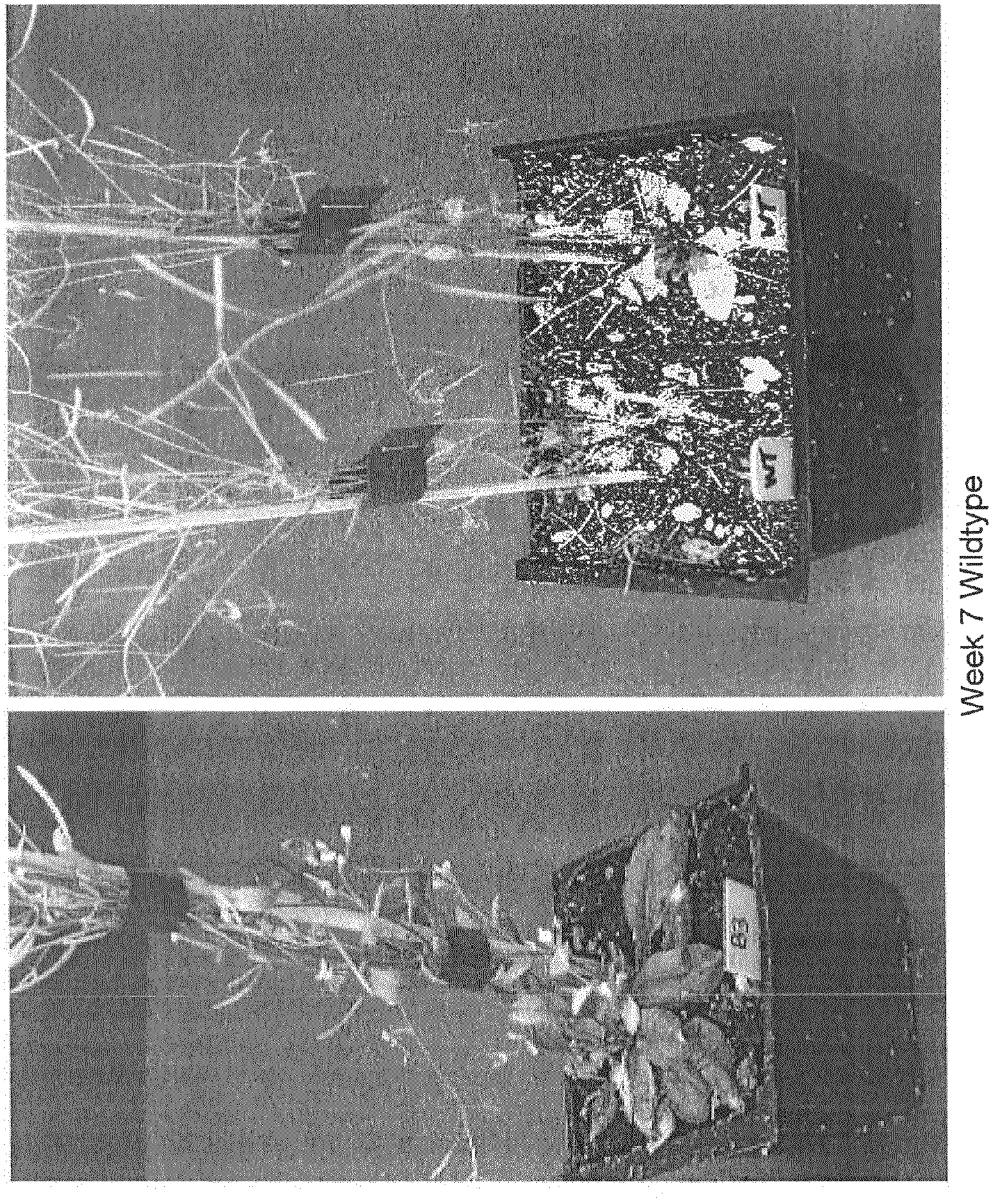
Figure 38:
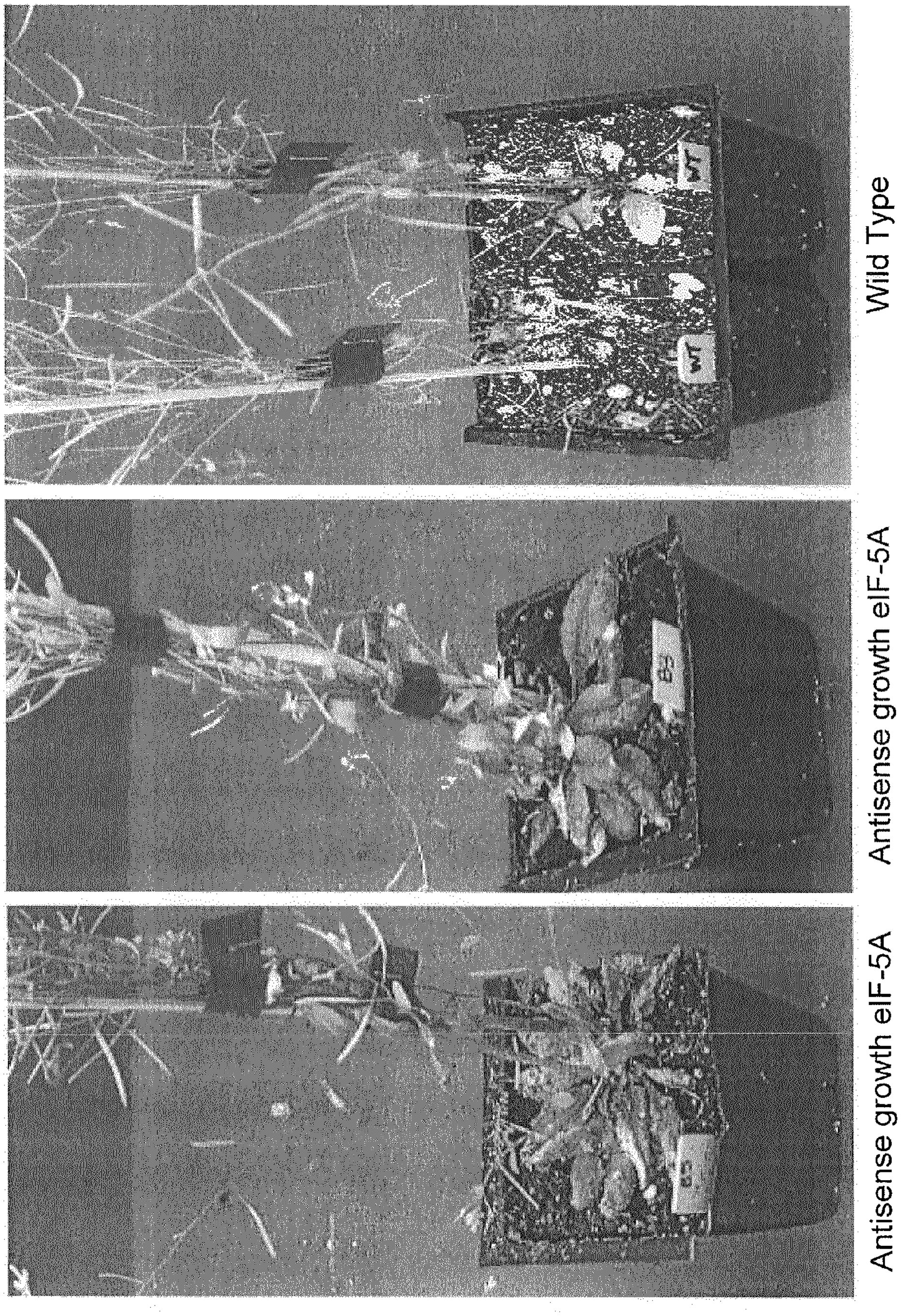
Figure 40:
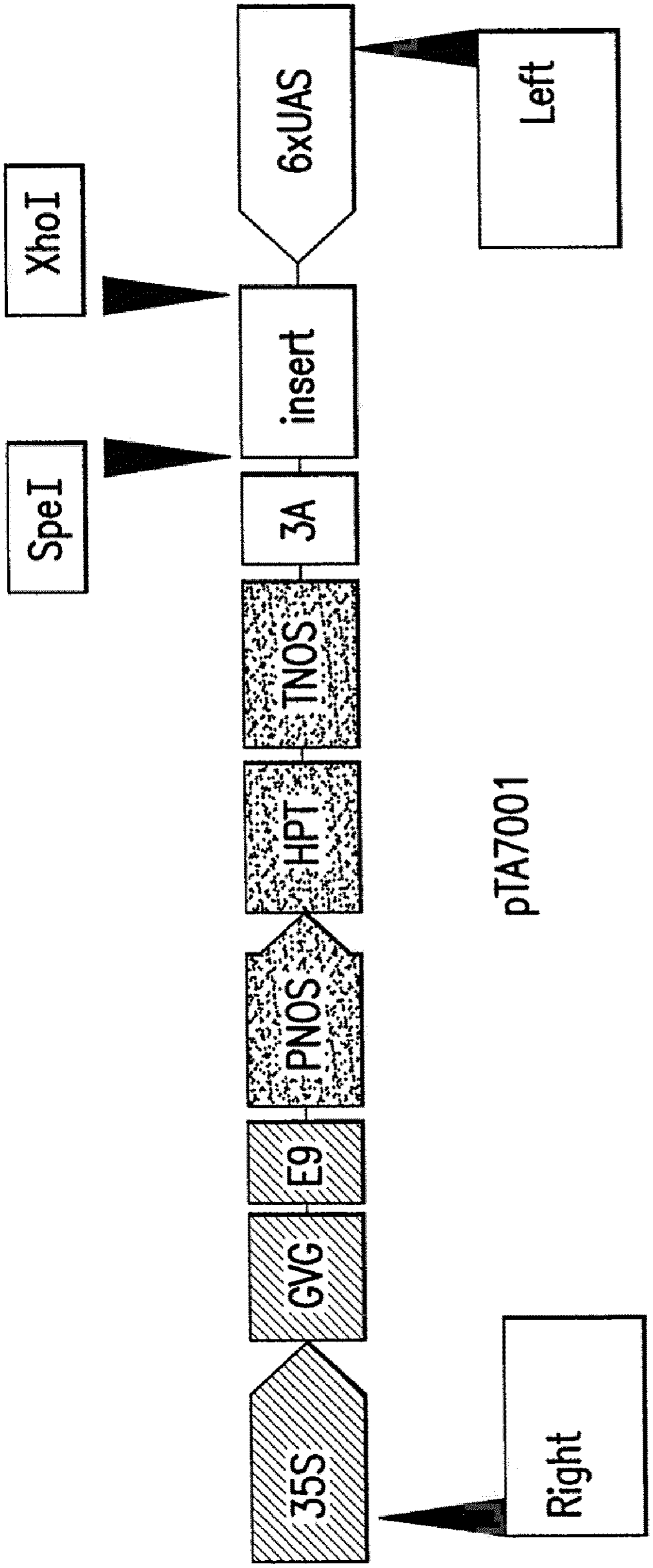
FIG. 40 shows the vector construct.

The T3 seeds were measured from all lines of T2 Sense growth AteIf-5A plants. Photographs were taken of each line (the largest and the smallest highlighted in FIG. 29), and measurements were made in silico with a micrometer in the photographs used for calibration. For each line and for the controls, ten of the largest seeds in the field of view were measured and used for calculations. It was found that the high expression line 2 had seeds that were up to 3 times as large as the wild type and binary controls. Whereas the lines that demonstrated the lowest expression (Lines 11 and 16) had some of the smallest seeds that were only about 88% the size of wild type or binary control seeds. The average seed size for each line was expressed as $nm^3$ (FIG. 30) and was calculated using an equation for the volume of an ellipsoid as seeds from *Arabidopsis thaliana* are approximately ellipsoid. The measured size of the control seeds fell into published guidelines as determined by Boyes et al (2001). From the measured size of individual seeds and the total seed yield (both weight and volume), the average individual seed weight was calculated and plotted (FIG. 31). It appeared that most of the lines that demonstrated a different size than that of the control seeds also had the same trend in individual seed weight. In fact when the seed weight was plotted against the seed size (volume) the relationship was mostly linear with an $R^2$=0.7412.

There were 5 lines that were outliers that had either an increased density (3 of them) or a decreased density (2 of them). One of the lines with the increased density is 8D and will be carried through T3 generation. The total seed yield from all the T2 generation plants were quite variable, with few trends. One notable line however is the medium expressing Sense growth AteIF-5A line 4D, which produced the most seeds (both weight and volume). In fact 4D produced 2.5 fold more than the control plants and will be carried through T3.

T3 seeds were plated on selection media as described previously. Lines 1A, 2D, 4D, 15A, 8D, 9H, 11C and 16C were transplanted to soil. Several other sublines of Sense growth AteIF-5A line 1 did not germinate, as well as line 2H, which had the largest seeds of all the sublines did not germinate. Plants from line 11 (one of the cosuppression lines) were not as healthy as typically found at this age. These seeds were also one of the smallest measured. It appears that these lines are still segregating, as there were still non-Kanamycin resistant plants as well as seeds that did not germinate from all the lines. This is probably a side effect of the transgene and not technique as the control seeds that were treated in the same manner, all germinated.

Example 22

Characterization of *Arabidopsis* Senescence-Induced eIF-5A

Methodology for Obtaining Full-Length *Arabidopsis* Senescence-Induced eIF-5A

Degenerate primers based on several plant eIF-5A genes, in combination with vector primers T3 & T7 were used in order to PCR an eIF-5A gene from an *Arabidopsis* cDNA library. Specifically, the 5' region of the eIF-5A gene was obtained from a PCR reaction utilizing both the T3 primer (located upstream of the F5A gene in the library vector) and one of the downstream (reverse-orientation) degenerate primers. Likewise, the 3' region of the gene was obtained from a PCR reaction utilizing both the T7 primer (located downstream of the eIF-5A gene in the library vector) and one of the upstream (forward-orientation) degenerate primers. The full-length eIF-5A gene was derived from alignment analysis of the 5' region and 3' region of the gene.

There are 2-3 major products for each PCR reaction. These fragments were cloned to pBluescript plasmid and sequenced. The eIF-5A positive PCR fragments were identified based on the mapping analysis against the gene bank. There is only one upstream and downstream positive eIF-5A PCR fragments for *Arabidopsis.*

The specific 5'- and 3'-end primers for the *Arabidopsis* eIF-5A gene were designed according to the 5' and 3' PCR fragment sequencing results. The full-length *Arabidopsis* eIF-5A gene was obtained from a PCR reaction utilizing their specific 5'- and 3'-end primers and the corresponding cDNA library as a template. The full-length gene was further confirmed by sequencing. In the end, we cloned one *Arabidopsis* eIF-5A isoform gene, which was termed senescence-induced eIF-5A.

```
T3 and T7 Primers:
T3:5'- ATT AAC CCT CAC TAA AG -3'  (SEQ ID NO: 20)

T7:5'- AAT ACG ACT CAC TAT AG -3'  (SEQ ID NO: 18)
```

Degenerate Primers for Arabidopsis eIF5A:

```
Forward (upstream) primer:
5'- AAA RRY CGM CCY TGC AAG GT -3' (SEQ ID NO: 17)

Reverse (downstream) primer:
5'- TCY TTN CCY TCM KCT AAH CC -3' (SEQ ID NO: 19)
```

Subcloning *Arabidopsis* Antisense Full-Length Senescence-Induced eIF-5A into pKYLX71 Vector (Containing the SAG12 Promoter)

Specific (Homologous) Primers for Arabidopsis senescence-induced eIF-5A, antisense full-length construct: Forward Full-length senescence-induced eIF-5A primer (30-mer): 5'-CC GAGCTCCTGTTACCAAAAAATCTGTACC-3' (SEQ ID NO: 48) (note: underlined portion is the SacI recognition sequence, used for ligating the 5'-end of the PCR fragment into the SacI site in the Multiple Cloning Site (MCS) of pBluescript). Reverse full-length senescence-induced eIF-5A primer (36-mer): 5'-ACCTCGA GCGGCCGCAGAAGAAGTATAAAAACCATC-3' (SEQ ID NO: 49) (note: underlined portion is the NotI recognition sequence, used for ligation into the MCS of pBluescript).

The orientation of the SacI and NotI sites within the MCS of the pBluescript vector was such that the gene was subcloned in its antisense orientation (i.e. the NotI site is upstream of the SacI site).

Example 23

SAG 12 Promoter was used to Express the Antisense Senescence-Induced *Arabidopsis* Full-length eIF-5A)

Experimental evidence shows that transcription of a set of "senescence-associated genes" or SAGs increases during the onset of senescence (Lohman et al., 1994; Weaver et al., 1998). In fact, senescence appears to begin with the synthesis of new mRNAs and probably down-regulation of other mRNAs, indicating that selective synthesis of proteins is necessary for senescence (Nooden, 1988). That the leaf senescence program is accompanied by changes in gene expression was first demonstrated by Watanabe and Imaseki (1982) using in vitro translation followed by gel electrophoresis to detect changes occurring in translatable mRNA populations. This initial work and subsequent analysis of the in vitro translated proteins revealed the abundance of most mRNAs diminished significantly during the progression of senescence while other translatable mRNAs increased (Watanabe and Imaseki, 1982; Davies and Grierson, 1989; Becker and Apel, 1993; Buchanan-Wollaston, 1994; Smart et al., 1995). Differential screening of cDNA libraries made from mRNAs of senescent leaf tissues also demonstrated that the expression of many genes is down-regulated, whereas the expression of other genes is up-regulated during senescence. SAGs have been identified from a variety of plant species, including *Arabidopsis* (Hensel et al., 1993; Taylor et al., 1993; Lohman et al., 1994; Oh et al., 1996), asparagus (King et al., 1995), barley (Becker and Apel, 1993), *Brassica napus* (Buchanan-Wollaston, 1994), maize (Smart et al., 1995), radish (Azumi and Watanabe, 1991) and tomato (Davies and Grierson, 1989; Drake et al., 1996).

Senescence can be morphologically identified as a characteristically patterned leaf yellowing that begins at the edges of a leaf and reaches the veins last (Weaver et al., 1998). Visible senescence in *Arabidopsis thaliana* rosette leaves appears approximately 21 days after germination with dramatic upregulation of SAG 12 at the time (Noh an Amasino, 1999). SAG 12 is a gene with the closest specificity for natural senescence and is thus termed a senescence marker. With no detectable expression in young leaves, SAG 12 is induced in older leaves after they are 20% yellow but cannot be induced by treatment that does not induce yellowing of leaves (Weaver et al., 1998). Its high degree of specificity for natural senescence can be explained by the fact that the gene product of SAG 12 shows similarity to cysteine proteases and may be involved in protein turnover during senescence (Lohman et al., 1994; Weaver et al., 1998).

Description of Transgenic Plants

Transgenic *Arabidopsis* plants were generated expressing the full-length antisense senescence-induced eIF-5A transgene under the control of the SAG 12 (leaf senescence-specific) promoter, which is activated at the onset of natural leaf senescence, approximately 21 days after germination (Noh and Amasino, 1994), but not in the event of stress-induced senescence. At this point, the transgenic plants express phenotypes characteristic of suppressed full-length senescence-induced eIF-5A expression. Rosette leaves were harvested from 3 to 8-week-old transgenic *Arabidopsis* antisense full-length senescence-induced eIF-5A plants.

Methodology for the Production of Homozygous Transgenic Antisense Senescence-Induced eIF-5A *Arabidopsis thaliana* Plants Under Control of the SAG 12 Promoter Inserting the SAG 12-Antisense-Full-Length Senescence-Induced eIF-5A Construct in pKYLX71

First, the plasmid pKYLX71 was cut with EcoRI and HindIII to remove its double 35S promoter, and resultant sticky ends were filled in with Klenow enzyme to create blunt ends. pKYLX71 without the promoter was then ligated to re-circularize the plasmid.

Secondly, the *Arabidopsis* SAG 12 promoter was amplified from genomic DNA by PCR using primers containing SalI and XbaI, as described below. This promoter sequence was then inserted into the Multiple Cloning Site (MCS) of pBlueScript using the restriction enzymes SalI and XbaI followed by ligation with T4 DNA ligase.

The forward SAG 12 Primer was 5'-GGC C GTCGACGATATCTCTTTTTATATTCAAAC-3' (SEQ ID NO: 50) (underlined portion is SalI recognition site, used for ligating the 5'-end of the PCR fragment into the SalI site in the Multiple Cloning Site (MCS) of pBluescript). The Reverse SAG 12 Primer was 5'-CG TCTAGACATTGTTTTAGGAAAGTTAAATGA-3' (SEQ ID NO: 51) (underlined portion is the XbaI recognition site, used for ligating the 5'-end of the PCR fragment into the SacI site in the Multiple Cloning Site (MCS) of pBluescript).

Thirdly, to create the pBlueScript-SAG 12:antisense-full length-senescence-induced eIF-5A construct, full length senescence-induced eIF-5A was amplified by PCR from the *Arabidopsis* cDNA library using primers with SacI and NotI restriction sites, as outlined below, and subcloned into the pBluescript-SAG 12 described in the previous paragraph. Note that the orientation of the SacI and NotI sites within the MCS of the pBluescript-SAG 12 vector was such that the gene was subcloned in its antisense orientation (i.e. the NotI site is upstream of the SacI site).

The forward full-length senescence-induced eIF-5A Primer was 5'-CC GAGCTCCTGTTACCAAAAAATCTGTACC-3' (SEQ ID NO: 48)(note: underlined portion is the Sad recognition sequence, used for ligating the 5'-end of the PCR fragment into the Sad site in the Multiple Cloning Site (MCS) of pBluescript-SAG 12 vector). The reverse Full-length senescence-induced eIF-5A Primer was 5'-ACCTCGA GCGGCCGCAGAAGAAGTATAAAAACCATC-3'(SEQ ID NO: 49) (note: underlined portion is the NotI recognition sequence, used for ligation into the Multiple Cloning Site (MCS) of pBluescript-SAG 12 vector).

Finally, the desired construct was created in the binary vector, pKYLX71, by digesting pKYLX71 was digested with SacI and XhoI, and also cutting out the SAG 12:full-length senescence-induced eIF-5A cassette from pBluescript with SalI and SacI. The XhoI and SalI sticky ends are partially complementary. Hence, these two sets of digested overhangs (specifically, SacI with SacI, and XhoI with SalI) were able to be ligated together with T4 DNA ligase, creating the final construct (SAG 12:antisense-senescence-induced eIF-5A in pKYLX71).

Transformation and T1 Seed Harvest

The pKYLX71-SAG 12:antisense-eIF-5A construct was proliferated in *E. coli* DHα cells, isolated and electroporated into a competent *Agrobacterium* strain. The bacteria were then used to infiltrate 4.5 week old wildtype *Arabidopsis* plants and the resulting infiltrated plants were designated as "$T_0$" plants, which were then grown to the end of their life-cycle. Seeds were harvested, collected and designated as $T_1$ seeds. 10 plates of $T_1$ seeds were plated and screened for kanamycin resistance (½ MS salt and 50 μg kanamycin/mL) with wildtype as a control; only those seeds containing pKYLX71-SAG 12-antisense-eIF-5A construct survive and grow on kanamycin (K50) media. 24 $T_1$ seedlings were chosen from these plates and placed in soil. The seeds harvested from $T_1$ transgenic plants were labeled as $T_2$ seeds. Each seedling yielded one plant line (#1=1 line containing 1 plant, #2=1 line containing 1 plant, etc.).

Screening and Identification of Phenotypes

Once kanamycin resistant $T_1$ seeds were identified, successive generations of $T_2$, $T_3$ and $T_4$ plants were grown. By screening seeds on K50 media, it was possible to distinguish between those plants which inherited the genetic construct and were homozygous for the construct. A phenotypic expression of stunted growth was observed in one $T_3$ plant line when grown in a pot. However, when the same set of seeds was re-grown in identical conditions, the phenotype was not observed.

From the 24 $T_1$ plants, 4 lines were chosen on the basis of high seed yield (lines T2.14, T2.18, T2.19 and T2.23) and plated on K50 media with wildtype seeds as a control. Approximately 75% of the seeds from each line survived on K50 media and fell into size categories of Small, Medium and Large. From each line, small, medium and large seedlings were removed from plates and planted in soil. Under greenhouse conditions, the Small seedlings did not recover as quickly as their Medium and Large counterparts. At week 6, the Small plants were just beginning to show signs of bolting while the other plants had bolted and flowered. In total, six transgenic $T_2$ plants (from a total of 3 lines×8 plants=96 transgenic plants) demonstrated dramatic delay in bolting and were deemed "Late Bolt" plants. The seed yields of these plants were also dramatically lower than other transgenics.

From the 96 $T_2$ plants, 3 lines were selected to produce $T_3$ plants (T3.19.S8 and T3.14.L7 which were Late Bolts; and, T3.23.S3 which was not a Late Bolt). When planted on K50 media plates, these lines showed homozygous survival. 13 seedlings were transplanted into pots (10 seedlings per pot). From this set of plants, a dramatic dwarf phenotype was observed in T3.14.L7 plant line. $T_4$ seeds were collected, and lower seed yield was observed in that line. A dense growth (dense silique growth, more branches) phenotype was observed in line T3.19.S8, while a phenotype similar to wildtype was observed in line T3.23.S3. Seed sizes from the 3 transgenic lines were compared but no statistically significant differences were determined. Chlorophyll levels were also analyzed but no statistically significant differences from wildtype control were determined.

$T_4$ seeds of lines T3.19.S8, T3.14.L7 and T3.23.S3 were screened on K50 to obtain the next generation of plants and showed evidence of inherited gene construct (uniform green growth on plates) compared with wild-type seed that died. However, when planted in individual flats, the dwarf phenotype was not expressed suggesting that the eIF-F5A antisense transgene had been lost. Finally, seeds collected from all $T_5$ plants were screened on K50 plates and showed evidence of kanamycin resistance. Work is now underway to confirm that the antisense transgene has been lost, and these T4 plants are azygous.

Eight daughter lines were chosen from mother lines T2.14, T2.19 and T2.23 and screened on K50 media with wild-type seeds as a control. Three lines were chosen based on low seed yield: T3.14.L8, T3.14.S8, and T3.23.S1. The other five lines chosen are: T3.18.S7, T3.18.S2, T3.19.S1, T3.19.S5, and T3.23.S6. All the lines screened on K50 media showed homozygous survival, while T3.14.L8, T3.14.S8 and T3.23.S6 showed heterozygous survival. Seedlings from lines T3.14.L8 and T3.14.S8 that survived were white in color with green vascular tissue, while seedlings from T3.23.S6 that survived were entirely dark green in color. These seedlings were selected for transplantation. In total, 28 seedlings from each line were transplanted into cells and grown in greenhouse conditions.

At week 3, all lines started bolting except for lines T3.14.L8 and T3.23.S1 and several plants within lines T3.18.S7, T3.18.S2, T3.19.S1, T3.19.S5, T3.23.S1 and T3.23.S6. An irregular rosette leaf morphology (elongation of $2^{nd}$ pair leaves phenotype) was observed in T3.14.L8 and T3.14.S8 lines. At week 5, additional irregular leaf morphologies of increased number of rosette leaves and crinkle-edged rosette leaves phenotypes were also observed in lines T3.18.S7 and T3.23.S6. Rosettes smaller than wild-type were observed in lines T3.23.S1, T3.19.S1, and T3.19.S5. At week 7, spindly stem and no stem elongation phenotypes were observed in lines T3.18.S7, T3.18.S2, T3.19.S1, T3.19.S5, T3.23.S1 and T3.23.S6. The first and second cauline leaf of each plant was collected at week 5 and 6, respectively, for investigation of senescence eIF-5A protein expression.

Example 24

Determination of Oxygen Output

The leaves were harvested and the areas were measured before they were weighed. The leaves were ground to a fine powder using 1 mL of cold degassed grinding buffer with a mortar and pestle. Then the homogenate was transferred into an eppendorf tube and placed immediately on ice. For tomato leaves, the homogenate isolated required to be filtered through a piece of Miracloth.

50 μl of homogenate from all samples were added into 10 ml test tubes containing 5 ml grinding buffer and 25 μl DCPIP (2,6-dichlorophenol indophenol). The samples were shaken well and then one set of samples were placed for 15 mins under illumination by a pair of lamps and the second set of samples were placed in the dark for 15 mins. After the 15 minute incubation, 50 μL of DCMU (3-(3,4-dichlorophenyl)-1,1dimethylurea) was added to both set of samples in order to stop the reaction and then centrifuged in a microcentrifuge for 2 mins at 14,000 g. The absorbencies of the supernatant collected were read at 590 nm using grinding buffer as a blank.

The molar extinction coefficient for this assay is $16\times10^3$, that is, a change in concentration of 1 mole per liter changes the absorbance of the solution by $16\times10^3$ μmole of DCPIP reduced/h/ml=(difference in absorbance)×[$1/16\times10^3$ (moles/l)]×[reaction volume (ml)/$10^3$ (ml/l)]×[$10^6$ (μmole/mole)]×[60 (min/hr)/reaction time (min)]×[1/sample volume (ml)].

For every 2 moles of DCPIP that are reduced, 1 mole of $O_2$ is generated.

Reference: Allen J. F. and Holmes N. G., 1986 Electron Transport and Redox Titration s in Photosynthesis: Energy Transduction. Edited by M. F. Hipkins & N. R. Baker., IRL Press, Oxford Pp 107-108.

Example 25

Quantitative Determination of Starch

Starch content in tomato stems was determined using a method adapted from Lustinec et al. Quantitative determination of starch, amylose, and amylopectin in plant tissues using glass fiber paper. Anal. Biochem. 132:265-271 (1983). Tomato stem tissue was homogenized in three volumes of water using an Omnimixer (12 reps of 5 sec each), followed by a Polytron homogenizer (30 sec). Homogenate was stored in 10 ml aliquots at −20° C. prior to analysis. For analysis, 10 ml homogenate was thawed and mixed with an equal volume of concentrated perchloric acid ($HClO_4$, 70% w/w) and incubated for 20 min at room temperature to dissolve the starch. Simultaneously, several solutions of potato starch (in the range of 0.1-1.0 mg/ml) were processed alongside the tomato stem sample to generate a standard curve. The homogenate (or potato starch standard solution) was stirred and filtered through Whatman GF/A glass microfiber paper (9.0 cm diameter) using a vacuum flask attached to an aspirator. One ml of filtrate was mixed with 3 ml of iodine solution A (8 mM $I_2$, 17 mM KI, 514 mM NaCl) and incubated for 30 min at 4° C. to form a starch-iodine precipitate. The precipitate was collected on Whatman GF/A glass microfiber paper (9.0 cm diameter) using a vacuum flask attached to an aspirator, and then wash the filtrate with the following solutions: once with 10 mL iodine solution B (83 mM $I_2$, 180 mM KI, 8% perchloric [$HClO_4$] acid); once with 5 mL ethanol-NaCl solution (67% ethanol, 342 mM NaCl); twice with 3 ml ethanol-NaOH solution (67% ethanol, 250 mM NaOH). Once ethanol had evaporated, the microfiber paper was removed from aspirator and inserted into screw-capped glass tube. Sulfuric [$H_2SO_4$] acid (9 mL of 0.75 M solution) was added to the tube and the tube was incubated in a boiling water bath for 30 min. Three 1 mL-aliquots of eluate were pipetted into glass test tubes and mixed with 1 mL of 5% phenol, quickly followed by 5 mL of concentrated $H_2SO_4$. The tubes were vortexed and incubated at room temperature for 30 min to allow the color to develop. Simultaneously, a blank for the spectrophotometer measurements was prepared by mixing 1 mL of 0.75 M $H_2SO_4$ with 1 mL of 5% phenol, and quickly adding 5 mL concentrated $H_2SO_4$; the blank was also incubated at room temperature for 30 min. A spectrophotometer was calibrated at 480 nm using the blank, and the O.D. of all samples and potato starch standards were measured and recorded. A standard curve was prepared using the potato starch solutions, and used to interpolate the quantity of starch in each sample.

Example 26

*Arabidopsis thaliana* (Columbia ecotype) was transformed by the *Arabidopsis thaliana* sense Senescence-induced eIF- 5A (At-eIF) and Tomato sense senescence-induced eIF-5A genes independently. These genes were constitutively expressed in the whole life cycle of the transgenic plants. The inflorescence stems of these plants exhibited a significant increase of xylem development. See FIGS. 89-94.

The seeds of transgenic and control plants were sown on ½ MS medium agar plates, and kept in a growth chamber at 22° C., 80% rh, and 16 h light/day, for 9 days. Then, the seedlings were transferred to 32-well-flats with a commercial soil, and were maintained under the same conditions as above, for 48 days. The main inflorescence stems were selected for microscopic observation. Cross sections were hand-cut from the base of the stems within 2 mm above the rosette. The sections were stained with the phloroglucinol-HCl method. We found that the stem xylem at this age has achieved its maximum development. A comparison was made between transgenic and control plants in the sizes (sectional areas) of xylem. In addition, measurements were done for phloem and pith in both transgenic and control plants.

Measurement of tissue areas was as follows. Cross sections were photographed with a Zeiss microscope, and the micrographs were digitalized using Photoshop®. These images were printed out on paper and different tissues were cut out, and their areas were measured by an area-measuring meter. To calculate the actual area of each tissue, the following formula was used: The actual area=(The area of an individual tissue on paper)/(Magnification)$^2$ It thus appears that senescence-induced eIF-5A is also involved in programmed cell death associated with xylogenesis. Constitutive antisense suppression of senescence-induced AteIF-5A in *Arabidopsis* reduced the thickness of the inflorescence stem as well as the number of xylem cell layers. By contrast, the inflorescence stems of plants in which *Arabidiposis* or tomato senescence-induced eIF-5A was constitutively over-expressed were, on average, 1.7-fold thicker than those of corresponding wild-type plants, and the total xylem area per cross-section of inflorescence stem was 2 fold higher. The over-expressing transgenic plants also had greatly increased rosette leaf biomass and grew faster than wild-type plants, which may reflect enhanced nutrient uptake. The same phenotype was observed when the senescence-induced isoform of eIF-5A from tomato was over-expressed in *Arabidopsis* plants. These results collectively indicate that the senescence-induced isoform of eIF-5A not only regulates leaf and flower senescence, but is also involved in xylogenesis.

Example 27

Suppression of Deoxyhypusine Synthase Delays Browning of Pre-Packaged Cut Lettuce in Ambient Atmosphere Commercially-available pre-packaged salad is commonly stored under conditions of controlled atmosphere, whereby the level of oxygen is greatly reduced below its atmospheric concentration in order to extend the shelf life of the product. The most common symptom of spoiled pre-packaged salad is browning on the cut surfaces of lettuce. Although controlled atmosphere packaging does achieve a delay in browning, it can also result in off-odour and off-flavour. In this study, down-regulation of deoxyhypusine synthase (DHS) was shown to have potential as an alternative strategy for delaying browning on the cut surfaces of lettuce. DHS catalyzes the activation of eukaryotic translation initiation factor 5A (eIF5A), which acts as a nucleocytoplasmic shuttle protein for select populations of mRNAs. DHS appears to play a role in browning of cut lettuce inasmuch as suppression of DHS expression (by antisense technology) resulted in a significant delay in the onset of browning under atmospheric conditions. Specifically, 80% of the cut segments of wildtype lettuce plants showed browning at 6 days after cutting, whereas only 27%, on average, of the cut segments of transgenic plants from 5 segregating lines turned brown over the same period, with some individual plants showing 0% browning. See FIGS. 51 and 53.

Example 28

Suppression of Deoxyhypusine Synthase Expression in Canola Increases Seed Yield Deoxyhypusine synthase (DHS) mediates the first of two enzymatic reactions that convert inactive eukaryotic translation initiation factor-5A (eIF-5A) to an activated form able to facilitate translation. A full-length cDNA clone encoding canola (*Brassica napus* cv Westar) DHS was isolated from a cDNA expression library prepared from senescing leaves. DHS was suppressed in transgenic canola plants by expressing the antisense 3'-UTR of canola DHS cDNA under the regulation of the constitutive cauliflower mosaic virus (CaMV-35S) promoter. Plants expressing this antisense transgene had reduced levels of leaf DHS protein and exhibited delayed natural leaf senescence. Suppression of DHS expression also increased rosette leaf size by 1.5 to 2 fold, and enhanced seed yield by up to 90%. These pleiotropic effects of DHS suppression in canola are in agreement with results obtained previously for *Arabidopsis* (Wang et al., 2003, Plant Mol. Biol. 52: 1223-1235), and indicate that this protein plays a central role in plant development and senescence.

Example 29

Extending the Vase Life of Carnation Flowers by Administering Inhibitors of Deoxyhypusine Synthase and by Antisense Suppression of Deoxyhypusine Synthase A full-length cDNA clone (AF296079) encoding deoxyhypusine synthase (DHS) was isolated from carnation petals. DHS mediates the first of two enzymatic reactions that convert inactive eukaryotic translation initiation factor-5A (eIF-5A) to an activated form able to facilitate translation. Northern analysis revealed that DHS expression is correlated with senescence of carnation flower petals. Treatment of cut carnation flowers with inhibitors of the DHS reaction, including diaminobutane (putrescine), diaminopropane, diaminohexane, diaminooctane and spermidine, extended the vase life of the flowers by up to 83%. In order to evaluate the role of DHS in carnation flower senescence more definitively, expression of the protein was suppressed in transgenic plants by introducing the antisense 3'-UTR of carnation DHS cDNA under regulation of the constitutive cauliflower mosaic virus promoter through *Agrobacterium* transformation. Three lines of transgenic flowers with reduced DHS expression were analyzed and found to have longer vase-life relative to wild-type flowers. Indeed, one of the lines exhibited an increase in vase life of >100%. These findings indicate that DHS plays a central role in flower senescence.

Example 30

The Delayed Bolting Phenotype Induced by Suppression of Deoxyhypusine Synthase in *Arabidopsis* can be Rescued by Treatment with GA3

Deoxyhypusine synthase (DHS) is a ubiquitous enzyme required for post-translational activation of eukaryotic translation initiation factor 5A (eIF-5A) and appears to be essential for normal plant growth and development. DHS was suppressed in *Arabidopsis* by expressing full-length antisense *Arabidopsis* DHS cDNA in transgenic plants under the regulation of the senescence-specific SAG12 promoter. Plants expressing the transgene had reduced levels of leaf DHS protein, and exhibited delayed bolting and a pronounced delay (2 to 5 weeks) in the onset of leaf senescence. The bolts were also shorter, although this did not result in a reduction in biomass or seed yield. Treatment of the transgenic plants with GA3 reversed the delayed bolting phenotype. A similar phenotype was obtained by antisense suppression of DHS under the regulation of GCI, a glucacorticoid-inducible promoter that can be activated by administering dexamethasone (DEX). Again, administering GA3 rescued this phenotype; that is, the GA3-treated transgenic plants bolted normally, the bolts were of normal size and there was no delay in the onset of leaf senescence. These results collectively indicate that DHS, through activation of one or more of the three isoforms of eIF-5A in *Arabidopsis*, influences GA metabolism.

REFERENCES

Azumi, Y and Watanabe, A (1991) Evidence for a senescence-associated gene induced by darkness. Plant Physiol 95: 577-583.

Becker W, Apel K (1993) Differences in gene expression between natural and artificially induced leaf senescence. Planta 189: 74-79

Bevec, D., Jaksche, H., Oft, M., Wohl, T., Himmelspach, M., Pacher, A., Schebesta, M., Koettnitz, K., Dobrovnik, M., Csonga, R., Lottspeich, F., and Hauber, J (1996) Inhibition of HIV-1 replication in lymphocytes by mutants of the Rev cofactor of eIF-5A. Science 271:1858-1860.

Bevec, D, and Hauber, J (1997) Eukaryotic initiation factor 5A activity and HIV-1 Rev function. Biol Signals 6:124-133.

Bleecker, A. B., and Patterson, SE (1997) Last exit: Senescence, abscission, and meristem arrest in *Arabidopsis*. Plant Cell. 9:1169-1179.

Buchanan-Wollaston, V (1997) The molecular biology of leaf senescence. J Exp Bot 48:181-191.

Buchanan-Wollaston V (1994) Isolation of cDNA clones for genes that are expressed during leaf senescence in *Brassica napus*. Plant Physiol 105: 839-846

Chen, K Y, and Liu, A Y C. (1997) Biochemistry and function of hypusine formation on eukaryotic initiation factor 5A. Biol Signals 6:105-109.

Davies K M, and Grierson D (1989) Identification of cDNA clones for tomato (*Lycopersicon esculentum* Mill.) mRNAs that accumulate during fruit ripening and leaf senescence in response to ethylene. Plant Cell 179: 73-80.

Drake R, John I, Farrell A, Cooper W, Schuch W, and Grierson D (1996) Isolation and analysis of cDNAs encoding tomato cysteine proteases expressed during leaf senescence. Plant Mol Biol 30: 755-767

Gan, S and Amasino, R M (1997). Molecular genetic regulation and manipulation of leaf senescence. Plant Physiol 113: 313-319.

Gan, S and Amasino, R M (1995) Inhibition of leaf senescence by autoregulated production of cytokinin. Science 270: 1986-1988.

Hanauske-Abel, H. M., Park, M. H., Hanauske, A.-R., Popowicz, A. M., Lalande, M., and Folk, J. E. Inhibition of G1-S transition by inhibitors of deoxyhypusine hydroxylation. Biochem Biophys Acta 1221: 115-124, 1994.

Henderson, B R, and Percipalle, P. (1997) Interactions between HIV Rev and nuclear import and export factors: the Rev nuclear localization signal mediate specific binding to human importin-beta. J Mol Biol 274: 693-707.

Hensel, L. L., V. Grbic, D. B. Baumgarten, and A. B. Bleecker. (1993). Developmental and age-related processes that influence the longevity and senescence of photosynthetic tissues in *Arabidopsis*. Plant Cell 5:553-564.

Jakus, J., Wolff, E. C., Park, M. H., and Folk, J. E. Features of the spermidine-binding site of deoxyhypusine synthase as derived from inhibition studies: effective inhibition by bis- and mono-guanylated diamines and polyamines. J Biol Chem 268:13151-13159, 1993.

Kang, H A, and Hershey, J W B (1994) Effect of initiation factor eIF-5A depletion on protein synthesis and proliferation of *Saccharomyces cerevisiae*. J Biol Chem 269: 3934-3940.

Katahira, J, Ishizaki, T, Sakai, H, Adachi, A, Yamamoto, K, and Shida, H. (1995) Effects of translation initiation factor eIF-5A on the functioning of human T-cell leukemia virus type I Rex and human immunodeficiency virus Rev inhibited trans dominantly by a Rex mutant deficient in RNA binding. J Virol 69: 3125-3133

Kemper, W M, Berry, K W, and Merrick, W C (1976) Purification and properties of rabbit reticulocyte protein synthesis initiation factors M2Bα and M2Bβ. J Biol Chem 251: 5551-5557.

Lohman, K N, Gan, S, John, M C and Amasino, R (1994) Molecular analysis of natural leaf senescence in *Arabidopsis thaliana*. Phys Plant 92: 322:328.

Lipowsky, G., Bischoff, F. R., Schwarzmaier, P, Kraft, R., Kostka, S., Hartmann, E., Kutay, U., and Gorlich, D. (2000) Exportin 4: a mediator of a novel nuclear export pathway in higher eukaryotes. EMBO J. 19:4362-4371.

Liu, Y P, Nemeroff, M, Yan, Y P, and Chen, K Y. (1997) Interaction of eukaryotic initiation facto 5A with the human immunodeficiency virus type 1 Rev response element RNA and U6 snRNA requires deoxyhypusine or hypusine modification. Biol Signals 6:166-174.

Martinez-Zapater, J M and Salinas, J (1994) *Arabidopsis* Protocols. Humana Press: p. 197.

Mattaj, I. W., and Englmeier, L. (1998) Nucleocytoplasmic transport: The soluble phase.

Annu Rev Biochem 67: 265-306

Mehta, A M, Saftner, R A, Mehta, R A, and Davies, P J (1994) Identification of posttranslationally modified 18-kilodalton protein from rice as eukaryotic translation initiation factor 5A. Plant Physiol 106:1413-1419.

Noh, Y-S and Amasino, R (1999) Identification of a promoter region responsible for the senescence-specific expression of SAG12. Plant Mol Biol 41:181-194.

Noodén, L D, Guaimet, J J and John, I (1997) Senescence mechanisms. Physiol Plant 101: 746-753.

Noodén, L D and Leopold, A C (eds) (1988) The phenomena of senescence and aging. *Senescence and Aging in Plants*. Academic Press: pp. 1-50.

Ober, D and Hartmann, T (1999) Deoxyhypusine synthase from tobacco. J Biol Chem 274: 32040-32047.

Oh S A, Lee S Y, Chung I K, Lee C H, and Nam H G (1996) A senescence-associated gene of *Arabidopsis thaliana* is distinctively regulated during natural and artificially induced leaf senescence. Plant Mol Biol 30: 739-754

Page, D R and Grossniklaus, U (2002) The art and design of genetic screens: *Arabidopsis Thaliana*. Nature Reviews Genetics 3:124-136

Park, M H, Joe, Y A, and Kang K R (1998) Deoxyhypusine synthase activity is essential for cell viability in the yeast *Saccharomyces cerevisiae*. J Biol Chem 16:1677-1683.

Park, M H, Wolff, E C, Lee, Y B and Folk, J E (1994) Antiproliferative effects of inhibitors of deoxyhypusine synthase: inhibition of growth of Chinese hamster ovary cells by guanyl diamines. J Biol Chem 269:27827-27832.

Park, M. H., Wolff E. C., and Folk J. E. (1993) Hypusine: its post-translational formation in eukaryotic initiation factor 5A and its potential role in cellular regulation. BioFactors 4:95-104.

Park, M H, Wolff, E C and Folk, J E (1993) Is hypusine essential for eukaryotic cell proliferation? Trends Biochem Sci 18:475-479.

Park, M H, Wolff, E C, Smit-McBride, Z, Hershey, J W B and Folk, J E (1991) Comparison of the activities of variant forms of eIF-4D: the requirement for hypusine or deoxyhypusine. J Biol Chem 266:7988-7994, 1991.

Park, M H and Wolff, E C (1988) Cell-free synthesis of deoxyhypusine. J Biol Chem 263:15264-15269.

Quirino, B F, Noh, Y-S, Himelblau, E and Amasino, R (2000) Molecular aspects of leaf senescence. Trends Plant Sci 5:278-282.

Rosorius, O., Reichart, B., Kratzer, F., Heger, P., Dabauvalle, M. C. & Hauber, J. (1999) Nuclear pore localization & nucleocytoplasmic transport of eIF-5A: evidence for direct interaction with the export receptor CRM1. J. Cell Sci. 112, 2369-2380.

Ruhl, M., Himmelspach, M., Bahr, G. M., Hammerschmid, F., Jaschke, H., Wolff, B., Aschauer, H., Farrington, G. K., Probst, H., Bevec, D., and Hauber, J. (1993) Eukaryotic initiation factor 5A is a cellular target of the human immunodeficiency virus type 1 Rev activation domain mediating transactivation. J Cell Biol 123:1309-1320.

Schardl, C L, Byrd, A D, Bension, G, Altschuler, M S, Hildebrand, D F and Hunt, A G (1987) Design and construction of a versatile system for the expression of foreign genes in plants. Genes 61: 1-11.

Schnier J, Schwelberger H G, Smit-McBride Z, Kang H A and Hershey J W B (1991) Translation initiation factor 5A and its hypusine modification are essential for cell viability in the yeast *Saccharomyces cerevisiae*. Mol Cell Biol 11:3105-3114

Smart C M, Hosken S E, Thomas H, Greaves J A, Blair B G, Schuch W (1995) The timing of maize leaf senescence and characterization of senescence-related cDNAs. Physiol Plant 93: 673-682

Smart, C M (1994) Gene expression during leaf senescence. New Phytologist 126:419-448.

Taylor C B, Bariola P A, Delcardayre S B, Raines R T, Green R T (1993) RNS2: A senescence-associated RNase of *Arabidopsis* that diverged from the S-RNases before speciation. Proc Natl Acad Sci USA 90: 5118-5122

Tome, M., Fiser, S. M., Payne, C. M., and Gerner, E W. (1997) Excess putrescine accumulation inhibits the formation of modified eukaryotic initiation factor 5A (eIF-5A) and induces apoptosis. Biochem. J. 328: 847-854.

Tome, M., and Gerner, E W. (1997) Cellular eukaryotic initation factor 5A content as a mediator of polyamine effects on growth and apoptosis. Biol Signals 6:150-156.

Walbot V (2000) A green chapter in the book of life. Nature 408: 794-795.

Wang, T-W, Lu, L, Wang, D, and Thompson, J E (2001) Isolation and characterization of senescence-induced cDNAs encoding deoxyhypusine synthase and eucaryotic translation initiation factor 5A from tomato. J Biol Chem 276:17541-17549.

Watanabe, A and Imaseki, H (1982) Changes in translatable mRNA in senescing wheat leaves. Plant Cell Physiol 23:489-497.

Weaver, L. M., Gan, S, Quirino, B and Amasino, R (1998) A comparison of the expression patterns of several senescence-associated genes in response to stress and hormone treatment. Plant Mol Biol 37:455-469.

Xu, A. and Chen, K. Y. (2001) Hypusine is required for a sequence-specific interaction of eukaryotic initiation factor 5A with post-SELEX RNA. J. Biol. Chem. 276:2555-2561.

Zuk, D., and Jacobson, A. (1998) A single amino acid substitution in yeast eIF-5A results in mRNA stabilization. EMBO J. 17:2914-2925.

Boyes, D. C., A. M. Zayed, R. Ascenzi, A. J. McCaskill, N. E. Hoffman, K. R. Davis, and J. Goerlach. 2001. Growth stage-based phenotypic analysis of *Arabidopsis*: A model for high throughput functional genomics in plants. Plant Cell, 13: 1499-1510.

Collawn, J. F., and Y. Patterson. 1999. Production of antipeptide antibodies. In F M Ausubel, R Brent, R E Kingston, D D Moore, J A Smith, J G Seidman, K Struhl, eds, Current Protocols in Molecular Biology on C D. John Wiley & Sons, New York.

Chamot, D. and C. Kuhlemeier. 1992. Differential expression of genes encoding the hypusine-containing translation initiation factor, eIF-5A, in tobacco. Nucleic Acids Res 20: 665-669.

Clemens, M. J., and U.-A. Bommer. 1999. Translational control: The cancer connection. Int. J. of Biochem. Cell Biol. 31: 1-23.

Davis, L. G., M. D. Dibner, and J. B. Battey. 1986. Basic methods in molecular biology. Elsevier Science Publishing Co., Inc, New York, pp. 130-5.

Drenckhahn, D., T. Jons, and F. Schmitz. 1993. Production of polyclonal antibodies against proteins and peptides. In D J Asai, ed, Methods in Cell Biology, Vol 37. Academic Press, New York, pp 7-56.

Dresselhaus, T., C. Simone, and H. Lörz. 1999. A transcript encoding translation factor eIF-5A is stored in unfertilized egg cells of maize. Plant Mol. Biol. 39: 1063-1071.

Fagard, M. and H. Vaucheret. 2000. (Trans) Gene silencing in plants: How many mechanisms? Annu. Rev. Plant Physiol. Mol. Biol. 51: 167-94.

Fairbanks, G., T. L. Steck, and D. F. H. Wallach. 1971. Coomassie blue R250 used in isopropanol-acetic acid. Biochem 10: 2606-2618.

Ghosh, S., S. Gepstein, J. J. Heikkila, and E. B. Dumbroff. 1988. Use of a scanning densitometer or an ELISA plate reader for measurement of nanogram amounts of protein in crude extracts from biological tissues. Anal. Biochem. 169: 227-233.

Jao, D. L.-E., and K. Y. Chen. 2002. Subcellular localization of the hypusin-containing eukaryotic initiation factor 5A by immunofluorescent staining and green fluorescent protein tagging. J. Cell. Biochem. 86: 590-600.

Jakus, J., E. C. Wolff, M. H. Park, and J. E. Folk. 1993. Features of the spermidine-binding site of deoxyhypusine synthase as derived from inhibition studies: effective inhibition by bis- and mono-guanylated diamines and polyamines. J. Biol. Chem. 268, 13151-13159.

Kushner, S. R. 1978. An improved method for transformation of *Escherichia coli* with ColE1 derived plasmids. In: Genetic Engineering: Proceedings of the International Symposium on Genetic Engineering (H. W. Boyer and S, Nicosia, eds.), Elsevier/North-Holland Press, New York. Pp. 17-23.

Liu, Y. P., M. Nemeroff, Y. P. Yan, and K. Y. Chen. 1997. Interaction of eukaryotic initiation factor 5A with the human immunodeficiency virus type 1 Rev response element RNA and U6 snRNA requires deoxyhypusine or hypusine modification. Biol. Signals 6(3), 166-74.

Matile, P., S. Hoertensteiner, and H. Thomas. 1999. Chlorophyll degradation. Annu. Rev. Plant Physiol. Plant Mol. Biol. 50: 67-95.

McCabe, M. S, L. C. Garratt, F. Schepers, W. J. R. M. Jordi, G. M. Stoopen, E. Davelaar, J. H. A. van Rhijn, J. B. Power, and M. R. Davey. 2001. Effects of $P_{SAG12}$-IPT gene expression on development and senescence in transgenic lettuce. Plant Physiol. 127: 505-516.

Miranda, P. V., A. Brandelli, and J. G. Tezon. 1993. Instantaneous blocking for immunoblots. Anal. Biochem. 209: 376-377.

Murashige, T. and F. Skoog. 1962. A revised medium for rapid growth and bioassays with tobacco tissue cultures. Physiol. Plant. 15:473-497.

Nowack, L. N. 2002 personal communications.

Ober, D., and T. Hartmann. 1999. Deoxyhypusine synthase from tobacco. J. Biol. Chem. 274(45): 32040-32047.

Page, T., G. Griffiths, and V. Buchanan-Wollaston. 2001. Molecular and biochemical characterization of postharvest senescence in broccoli. Plant Physiol. 125: 718-727.

Park, J.-H., S. A. Oh, Y. H. Kim, H. R. Woo, and H. G. Nam. 1998. Differential expression of senescence-associated mRNAs during leaf senescence induced by different senescence-inducing factors in *Arabidopsis*. Plant Mol. Biol. 37: 445-454.

Park, M. H., Y. B. Lee, and Y. A. Joe. 1997. Hypusine is essential for eukaryotic cell proliferation. Biol. Signals 6, 115-123.

Park, M. H., E. C. Wolff, and J. E. Folk. 1993. Hypusine: its post-translational formation in eukaryotic initiation factor 5A and its potential role in cellular regulation. BioFactors 4(2), 95-104.

Park, M. H., and E. C. Wolff. 1988. Cell-free synthesis of deoxyhypusine. J. Biol. Chem. 263(30): 15264-15269.

Rosorius, O., B. Reicher, F. Kraetzer, P. Heger, M.-C. Dabauvalle, and J. Hauber. 1999. Nuclear pore localization and nucleocytoplasmic transport of eIF-5A: evidence for direct interaction with the export receptor CRM1. J. Cell Sci. 112: 2369-2380. Stotz 2000.

Tome, M. E., and E. W. Gerner. 1997. Cellular eukaryotic initiation factor 5A content as a mediator of polyamine effects of growth and apoptosis. Biol. Signals 6, 150-156.

Wang, C. Y. and J. E. Baker. 1980. Extending vase life of carnations with minooxyacetic acid, polyamines, E D U, and CCCP. HortSci. 15, 805-806.

Wang, T.-W., L. Lu, C.-G. Zhang, C. A. Taylor, and J. E. Thompson. Unpublished a. Suppression of deoxyhypusine synthase expression in *Arabidopsis thaliana* delays leaf senescence.

Wang, T.-W., W. Wu, C. Taylor, and J. E. Thompson. Unpublished b. Characterization of eukaryotic translation initiation factor-5A cDNA isoforms from tomato.

Wang, T.-W., C.-G. Zhang, L. Lu, L. N. Nowack, and J. E. Thompson. Unpublished c. Extending vase life of carnation by deoxyhypusine synthase inhibitors and transient transfection with antisense deoxyhypusine synthase.

Wang, T.-W., L. Lu, D. Wang, and J. E. Thompson. 2001. Isolation and characterization of senescence-induced cDNAs ecoding deoxyhypusine synthase and eucaryotic translation initiation factor 5A from tomato. J. Biol. Chem. 276(20): 17541-17549.

Zuk, D., and A. Jacobson. 1998. A single amino acid substitution in yeast eIF-5A results in mRNA stabilization. EMBO J. 17(10): 2914-2925.

---

The invention claimed is:

1. An isolated polynucleotide encoding a canola deoxyhypusine synthase (DHS), wherein the canola DHS comprises the amino acid sequence set forth in SEQ ID NO: 71.

2. An isolated polynucleotide encoding a canola deoxyhypusine synthase (DHS), wherein said polynucleotide comprises SEQ ID NO: 70.

3. The isolated polynucleotide according to claim 1, wherein the polynucleotide consists of SEQ ID NO: 70.

4. The isolated polynucleotide according to claim 1, wherein the canola DHS consists of the amino acid sequence set forth in SEQ ID NO: 71.

5. A vector comprising the polynucleotide of claim 1, 2, 3 or 4 and regulatory sequences operatively linked to the polynucleotide to provide transcription of the polynucleotide in a plant.

6. A bacterial cell transformed with the vector according to claim 5.

7. A plant cell transformed with the vector according to claim 5.

8. A plant and progeny thereof, wherein the plant is generated from the plant cell of claim 7 and wherein said plant and progeny thereof comprise said vector.

* * * * *